(12) United States Patent
Finney et al.

(10) Patent No.: US 8,986,954 B2
(45) Date of Patent: Mar. 24, 2015

(54) DNA ENCODING FUNCTION MODIFYING NA$_v$1.7 ANTIBODIES

(71) Applicant: UCB Pharma S.A., Brussels (BE)

(72) Inventors: Helene Margaret Finney, Slough (GB); Terence Seward Baker, Slough (GB); Alastair David Griffiths Lawson, Slough (GB); Karen Margrete Miller, Brussels (BE); Marc Roger de Ryck, Brussels (BE); Christian Gilbert J. Wolff, Brussels (BE)

(73) Assignee: UCB Pharma S.A., Brussels (BE)

( * ) Notice: Subject to any disclaimer, the term of this patent is extended or adjusted under 35 U.S.C. 154(b) by 0 days.

(21) Appl. No.: 14/285,721

(22) Filed: May 23, 2014

(65) Prior Publication Data

US 2014/0342406 A1    Nov. 20, 2014

Related U.S. Application Data

(62) Division of application No. 12/913,145, filed on Oct. 27, 2010, now Pat. No. 8,734,798.

(60) Provisional application No. 61/255,202, filed on Oct. 27, 2009.

(51) Int. Cl.
| | |
|---|---|
| *C07H 21/04* | (2006.01) |
| *C12P 21/08* | (2006.01) |
| *C12N 5/10* | (2006.01) |
| *C07K 16/18* | (2006.01) |
| *C07K 16/28* | (2006.01) |

(52) U.S. Cl.
CPC .............. *C07K 16/28* (2013.01); *C07K 2316/96* (2013.01)
USPC ........ 435/69.1; 435/320.1; 435/326; 435/334; 435/252.3; 530/387.1; 530/388.1; 530/388.22; 536/23.53

(58) Field of Classification Search
None
See application file for complete search history.

(56) References Cited

U.S. PATENT DOCUMENTS

| | | | |
|---|---|---|---|
| 4,741,900 A | 5/1988 | Alvarez et al. |
| 4,816,397 A | 3/1989 | Boss et al. |
| 5,219,996 A | 6/1993 | Bodmer et al. |
| 5,223,409 A | 6/1993 | Ladner et al. |
| 5,403,484 A | 4/1995 | Ladner et al. |
| 5,427,908 A | 6/1995 | Dower et al. |
| 5,516,637 A | 5/1996 | Huang et al. |
| 5,545,806 A | 8/1996 | Lonberg et al. |
| 5,569,825 A | 10/1996 | Lonberg et al. |
| 5,571,698 A | 11/1996 | Ladner et al. |
| 5,580,717 A | 12/1996 | Dower et al. |
| 5,585,089 A | 12/1996 | Queen et al. |
| 5,625,126 A | 4/1997 | Lonberg et al. |
| 5,633,425 A | 5/1997 | Lonberg et al. |
| 5,658,727 A | 8/1997 | Barbas et al. |
| 5,661,016 A | 8/1997 | Lonberg et al. |
| 5,677,425 A | 10/1997 | Bodmer et al. |
| 5,698,426 A | 12/1997 | Huse |
| 5,733,743 A | 3/1998 | Johnson et al. |
| 5,750,753 A | 5/1998 | Kimae et al. |
| 5,770,429 A | 6/1998 | Lonberg et al. |
| 5,780,225 A | 7/1998 | Wigler et al. |
| 5,821,047 A | 10/1998 | Garrard et al. |
| 5,969,108 A | 10/1999 | McCafferty et al. |
| 6,331,415 B1 | 12/2001 | Cabilly et al. |
| 7,456,187 B2 | 11/2008 | Ford et al. |
| 7,521,541 B2 | 4/2009 | Eigenbrot et al. |
| 2004/0191265 A1 | 9/2004 | Schenerman et al. |
| 2007/0041972 A1 | 2/2007 | Rother et al. |
| 2009/0053227 A1 | 2/2009 | Gately |

FOREIGN PATENT DOCUMENTS

| | | |
|---|---|---|
| EP | 0438474 B1 | 5/1996 |
| EP | 0463151 B1 | 6/1996 |
| EP | 0546073 B1 | 9/1997 |
| EP | 0996622 B1 | 5/2000 |
| WO | WO90/02809 A1 | 3/1990 |
| WO | WO91/09967 A1 | 7/1991 |
| WO | WO91/10737 A1 | 7/1991 |
| WO | WO92/01047 A1 | 1/1992 |
| WO | WO92/02551 A1 | 2/1992 |
| WO | WO92/18619 A1 | 10/1992 |
| WO | WO92/22583 A2 | 12/1992 |
| WO | WO93/11236 A1 | 6/1993 |
| WO | WO95/15982 | 6/1995 |
| WO | WO95/20401 | 8/1995 |
| WO | WO97/49805 A3 | 12/1997 |
| WO | WO98/20734 A1 | 5/1998 |
| WO | WO98/25971 A1 | 6/1998 |
| WO | WO99/03859 | 1/1999 |
| WO | WO03/048208 | 6/2003 |
| WO | WO03/050531 A2 | 6/2003 |

(Continued)

OTHER PUBLICATIONS

Adair, J.R., et al., "Therapeutic antibodies", Drug Design Reviews-Online, vol. 2, No. 3, pp. 209-217, 2005.

(Continued)

*Primary Examiner* — Christine J Saoud
*Assistant Examiner* — Jon M Lockard
(74) *Attorney, Agent, or Firm* — Saul Ewing LLP; Doreen Y. Trujillo

(57) ABSTRACT

A Na$_v$1.7 binding entity that after binding functionally modifies the activity of the ion channel, in particular an anti-Na$_v$1.7 antibody or binding fragment thereof, pharmaceutical compositions comprising said antibodies, use of the antibodies and compositions comprising the same, in treatment, for example in the treatment/modulation of pain and processes for generating and preparing said antibodies.

6 Claims, 25 Drawing Sheets

(56) References Cited

FOREIGN PATENT DOCUMENTS

| WO | WO2004/051268 A1 | 6/2004 |
|---|---|---|
| WO | WO2004/106377 A1 | 12/2004 |
| WO | WO2005/003169 A2 | 1/2005 |
| WO | WO2005/003170 A2 | 1/2005 |
| WO | WO2005/003171 A2 | 1/2005 |
| WO | WO2005/113605 A1 | 12/2005 |
| WO | WO2005/117984 A2 | 12/2005 |
| WO | WO2007/041972 A1 | 4/2007 |
| WO | WO2007/109324 A2 | 9/2007 |
| WO | WO2008/038024 A1 | 4/2008 |
| WO | WO2008/090958 A1 | 7/2008 |
| WO | WO2009/033027 A2 | 3/2009 |
| WO | WO2010/035012 A1 | 4/2010 |

OTHER PUBLICATIONS

Alonso, A., et al., "Subthreshold Na1-dependent theta-like rhythmicity in stellate cells of entorhinal cortex layer II", Nature, vol. 342, pp. 175-177, 1989.

Ames, R.S., et al., "Conversion of murine Fabs isolated from a combinatorial phage display library to full length Immunoglobulins", J. Immunol. Methods, vol. 184, No. 2, pp. 177-186, 1995.

Angal, S., et al. "A single amino acid substitution abolishes the heterogeneity of chimeric mouse/human (IgG4) antibody", Molecular Immunology, vol. 30, No. 1, pp. 105-108, 1993.

Anger, T., et al., "Medicinal Chemistry of Neuronal Voltage-Gated Sodium Channel Blockers", J. Med. Chem., vol. 44, No. 2, pp. 115-137, 2001.

Babcook, J., et al., "A Novel Strategy for generating Monoclonal Antibodies from Single, Isolated Lymphocytes Producing Antibodies of Defined Specificities", Proc. Natl. Acad. Sci. USA, vol. 93, No. 15, pp. 7843-7848, 1996.

Barlos, K., et al., "Solid phase synthesis of partially protected and free peptides containing disulphide bonds by simultaneous cysteine oxidation-release from 2-chlorotrityl resin", International Journal of Peptide and Protein Res., vol. 38, No. 6, pp. 562-568, 1991.

Bekele-Arcuri, Z. et al., "Generation and Characterization of Subtype-specific Monoclonal Antibodies to K+ Channel $\alpha$- and $\beta$-subunit Polypeptides," Neuropharmacology, vol. 35, No. 7, pp. 851-865, 1996.

Benes, J., et al.,"Anticonvulsant and Sodium Channel-Blocking Properties of Nove 10, 11 —Dihydro-5H-dibenz[b, t] azepine-5-carboxamide Derivatives," J. Med. Chem., vol. 42, pp. 2582-2587, 1999.

Bird, R.E., et al., "Single-chain antigen-binding proteins", Science, vol. 242, No. 4877, pp. 423-426, 1988.

Black, J.A., et al., "Multiple Sodium Channel Isoforms and Mitogen-Activated Protein Kinases Are Present in Painful Human Neuromas", American Neurological Association, vol. 64, pp. 664-653, 2008.

Black, J.A. et al., "Expression of Nav1.7 DRG neurons extends from peripheral terminals in the skin to central preterminal branches and terminals in the dorsal horn," Molecular Pain, 8:82 (11 pages) (2012).

Bossu, J.L., et al., "Patch-Clamp Study of the Tetrodotoxin-Resistant Sodium Current in Group C Sensory Neurones", Neuroscience Letters, vol. 51, pp. 241-246, 1984.

Brinkmann, U., et al., "Phage Display of Disulfide-Stabilized FV Fragments", J. Immunol. Methods, vol. 182, No. 1, pp. 41-50, 1995.

Burton, D.R., et al., "Human Antibodies from Combinatorial Libraries", Advances in Immunology, vol. 57, pp. 191-280, 1994.

Casset et al., "A peptide mimetic of an anti-CD4 monoclonal antibody by rational design," Biochemical and Biophysical Research Communications, vol. 307, pp. 198-205 (2003).

Chapman, A.P., et al., "Therapeutic antibody fragments with prolonged in vivo half-lives", Nature Biotechnology, vol. 17, pp. 780-783, 1999.

Chapman, A., "PEGylated antibodies and antibody fragments for improved therapy: a review", Advanced Drug Delivery Reviews, vol. 54, pp. 531-545, 2002.

Chen et al., "Selection and Analysis of an Optimized Anti-VEGF Antibody: Crystal Structure of an Affinity-matured Fab in Complex with Antigen," J. Mol. Biol., vol. 293, pp. 865-881 (1999).

Chioni, A-M. et al., "A Novel Polyclonal antibody Specific for the Nay 1.5 Voltage-Gated Na+ Channel 'Neonatal' Splice Form," Journal of Neuroscience Methods, vol. 147, pp. 88-98, 2005.

Chothia, C. and Lesk, A.M., "Canonical Structures for the Hypervariable Regions of Immunoglobulins", J. Mol. Biol., vol. 196, pp. 901-917, 1987.

Cole, S.P.C., et al., "The EBV-hybridoma technique and its application to human lung cancer", Monoclonal Antibodies and Cancer Therapy, vol. 27, (UCLA Symposia on Molecular and Cellular Biology, New Series, R.A. Reisfeld and S. Sell (eds.)), pp. 77-96, Alan R. Liss, Inc., N.Y., 1985.

Cox, J.J., et al., "An SCN9A channelopathy causes congenital inability to experience pain", Nature, vol. 444, No. 7121, pp. 894-898, 2006.

Cummins, T. R., et al., "Electrophysiological Properties of Mutant Nav1.7 Sodium Channels in a Painful Inherited Neuropathy", The Journal of Neuroscience, 24(38), pp. 8232-8236, 2004.

Decanniere, K., et al., "Canonical antigen-binding loop structures in immunoglobulins: more structures, more canonical classes?", J. Mol. Biol., vol. 300, No. 1, pp. 83-91, 2000.

De Genst, E., et al., "Molecular basis for the preferential cleft recognition by dromedary heavy-chain antibodies", PNAS, vol. 103, No. 12, pp. 4586-4591, 2006.

Dellemijn, Paul, "Are opioids effective in relieving neuropathic pain?", International Association for the Study of Pain, 80(3), pp. 453-462, 1999.

De Pascalis et al., "Grafting of "Abbreviated" Complementarity-Determining Regions Containing Specificity Determining Residues Essential for Ligand Contact o Engineer a Less Immunogenic Humanized Monoclonal Antibody," Journal of Immunology, vol. 169, pp. 3076-3084 (2002).

Desmyter, et al., "Crystal structure of a camel single-domain VH antibody fragment in complex with lysozyme", Nat. Struct. Biol., vol. 3, pp. 803-811, 1996.

Dib-Hajj, et al., "Genetics and Molecular Pathophysiology of Nav1,7-Related Pain Syndromes", Advances in Genetics, vol. 63, pp. 85-110, 2008.

Dib-Hajj, et al., "Voltage-Gated Sodium Channels" Therapeutic Targets for Pain, American Academy of Pain Medicine, vol. 10, No. 7, pp. 1260-1269, 2009.

Doyle, D.A., et al., The Structure of the Potassium Channel: Molecular Basis of $K^+$ Conduction and Selectivity, Science, vol. 280, No. 5360, pp. 69-77, 1998.

Dworkin, R. H., "An Overview of Neuropathic Pain: Syndromes, Symptoms, Signs, and Several Mechanisms", The Clinical Journal of Pain, 18; pp. 343-349, 2002.

Frampton, J. E., et al., "Pregabalin—In the Treatment of Painful Diabetic Peripheral Neuropathy", Adis Drug Profile, 64(24), pp. 2813-2820, 2004.

French, C.R., et al., "A Threshold Sodium Channel in Pyramidal Cells in Rat Hippocampus", Neuroscience Letters, vol. 56, pp. 289-294, 1985.

Gilly, W.F., et al., "Threshold channels—a novel type of sodium channel in squid giant axon", Nature, vol. 309, pp. 448-450, 1984.

Gilly, W.F., et al., "Properties of appropriately and inappropriately expressed sodium channels in squid giant axon and its somata", J. Neurosci., vol. 9, No. 4, pp. 1362-1374, 1989.

Goldberg, et al., "Loss-of-function mutations in the $Na_v1.7$ gene underlie congenital indifference to pain in multiple human populations", Clinical Genetics, vol. 71, No. 4; pp. 311-319, 2007.

Gomes, P., et al., "Antigenicity modulation upon peptide cyclization: application to the GH loop of foot-and-mouth disease virus strain C1-Barcelona", Vaccine, 19(25-26), pp. 3459-3466, 2001.

Gonoi, T., et al., "Voltage Clamp Analysis of Tetrodotoxin-sensitive and -insensitive Sodium Channels in Rat Muscle Cells Developing in Vitro[1]", J. Neurosci., vol. 5, No. 9, pp. 2559-2564, 1985.

Gross, M.F., "Aryl sulfonamide tetralin inhibitors of the Kv1.5 ion channel", Bioorganic & Medicinal Chemistry Letters, vol. 19, No. 11, pp. 3063-3066, 2009.

(56) References Cited

OTHER PUBLICATIONS

Gurrath, M., et al., "Conformation/activity studies of rationally designed potent anti-adhesive RGD peptide", Eur. J. Biochem., vol. 210, No. 3, pp. 911-921, 1992.

Hamers-Casterman, C., et al., "Naturally Occurring Antibodies Devoid of Light Chains," Nature, vol. 363, pp. 446-448, 1993.

Harris, R.J., "Processing of C-terminal lysine and arginine residues of proteins isolated from mammalian cell culture", Journal of Chromatography, vol. 705, No. 1, pp. 129-134, 1995.

He, J.X., et al., "An efficient strategy for the large-scale synthesis of head-to-tail cyclic peptides", Letters in Peptide Science, vol. 1, No. 1, pp. 25-30, 1994.

Hill, R.A., et al., "Hydroxyl-substituted sulfonylureas as potent inhibitors of specific [3H]glyburide binding to rat brain synaptosomes", Bioorg Med Chem, vol. 11, No. 9, pp. 2099-2113, 2003.

Holliger P., et al., Engineered antibody fragments and the rise of single domains, Nature Biotech., vol. 23, No. 9, pp. 1126-1136, 2005.

Hoyt, .B., et al., "Benzazepinone Nav1.7 blockers: potential treatments for neuropathic pain", Bioorg. Med. Chem. Lett., vol. 17, No. 22, pp. 6172-6177, 2007.

Ikeda, S.R., et al., "Na+ and $Ca^*$+ currents of acutely isolated adult rat nodose ganglion cells", J. Neurophysiol., vol. 55, pp. 527-539, 1986.

Izumiya, N., et al., "Synthesis of biologically active cyclic peptides", Biopolymers, vol. 20, No. 9, pp. 1785-1791, 1981.

Jiang, Y., et al., "The principle of gating charge movement in a voltage-dependent $K^+$ channe", Nature, vol. 423, No. 33, pp. 42-48, 2003.

Jones, S.W., "Sodium Currents in Dissociated Bull-Frog Sympathetic Neurones", J. Physiol., vol. 389, pp. 605-627, 1987.

Kashmiri, S.V.S., et al., "SDR grafting—a new approach to antibody humanization", Methds, vol. 36, pp. 25-34, 2005.

Kessler, H., et al., "Design of conformationally restricted cyclopeptides for the inhibition of cholate uptake of hepatocytes", Computer-Aided Drug Design, Methods and Applications, (Perun, T. J. & Propst, C. L., eds), pp. 461-484, Marcel Dekker, New York, 1989.

Kettleborough, C.A., et al., "Isolation of tumor cell-specific single-chain Fv from immunized mice using phage-antibody libraries and the reconstruction of whole antibodies from these antibody fragments", Eur. J. Immunol., vol. 24, No. 4, pp. 952-958, 1994.

Klionsky, L., et al., "A Polyclonal Antibody to the Prepore Loop of Transient Receptor Potential Vanilloid Type 1 Blocks Channel Activation," The Journal of Pharmacology and Experimental Therapeutics, vol. 319, No. 1, pp. 192-198, 2006.

Kohler, C. et al. "Continuous cultures of fused cells secreting antibody of predefined specificity", Nature, vol. 256, pp. 495-497 1975.

Kostyuk, P.G., et al., "Ionic currents in the somatic membrane of rat dorsal root ganglion neurons. I. Sodium currents". 1, vol. 6, No. 12, pp. 2423-2430, 1981.

Kozbor, D., et al., "The production of monoclonal antibodies from human lymphocytes", Immunology Today, vol. 4, No. 3, pp. 72-79, 1983.

Lauwereys, M., et al., "Potential enzyme inhibitors derived from dromedary heavy-chain antibodies", EMBO Journal, vol. 17, pp. 3512-3520, 1998.

Leong, S.R., et al., "Adapting pharmacokinetic properties of a humanized anti-interleukin-8 antibody for therapeutic applications using site-specific pegylation", Cytokine, vol. 16, No. 3, pp. 106-119, 2001.

Li, P. and Roller, P.P., "Cyclization Strategies in Peptide Derived Drug Design," Current Topics in Medicinal Chemistry, vol. 2, pp. 325-341, 2002.

Liu, J.L., et al., "Isolation of anti-toxin single domain antibodies from a semi-synthetic spiny dogfish shark display library", BMC Biotechnology, vol. 7:78, 2007.

Llinas, et al., "Electrophysiological properties of in vitro Purkinje cell dendrites in mammalian cerebellar slices", J. Physiol. (Lond.), vol. 305, pp. 197-213, 1980.

Long, S.B., et al., "Crystal Structure of a Mammalian Voltage-Dependent Shaker Family $K^+$ Channel", Science, vol. 309, No. 5736, pp. 897-903, 2005.

MacCallum et al., "Antibody-antigen Interactions: Contact Analysis and Binding Site Topography," J. Mol. Biol., vol. 262, pp. 732-745 (1996).

McGowan, et al., "A Peripherally Acting Nav1.7 Sodium Channel Blocker Reverses Hyperalgesia and Allodynia on Rat Models of inflammatory and Neuropathic Pain", Anesthesia and Analgesia, vol. 109, No. 3, pp. 951-958, (2009).

Meiri, H., et al., "Monoclonal antibodies associated with sodium channel block nerve impulse and stain nodes of Ranvier", Brain Research, vol. 310, pp. 168-173, 1984.

Meiri, H., "Detection of cell surface sodium channels by monoclonal antibodies—could the channels become exposed to the external surface and 'down regulated' by binding to antibodies?", Brain Research, vol. 368, Issue 1, pp. 188-192, Mar. 1986.

Mountain, A., et al., "Engineering antibodies for therapy", Biotechnol. Genet. Eng. Rev., vol. 10, pp. 1-142, 1992.

Muyldermans, S., et al., "Recognition of antigens by single-domain antibody fractions: the superfluous luxury of paired domains", Trends in Biochem. Sci., vol. 26, pp. 230-235, 2001.

Namaka, et al., "A Treatment Algorithm for Neuropathic Pain", Clinical Therapeutics, vol. 26, No. 7, pp. 951-979, 2004.

Nguyen, V.K., et al., "Functional heavy-chain antibodies in Camelidae", Adv. Immunol., vol. 79, pp. 261-296, 2001.

Nygren, P., et al., "Scaffolds for engineering novel binding sites in proteins", Current Opinion in Structural Biology, vol. 7, No. 4, pp. 463-469, 1997.

Orlandi, et al., "Cloning immunoglobulin variable domains for expression by the polymerase chain reaction", PNAS USA, vol. 86, pp. 3833-3837, 1989.

Persic, L., et al., "An integrated vector system for the eukaryotic expression of antibodies or their fragments after selection from phage display libraries", Gene, vol. 187, No. 1, pp. 9-18, 1997.

Pullar, S. et al., "Pharmacotherapy for Neuropathic Pain: Progress and Prospects," Drug News Perspect., vol. 16, No. 9, pp. 622-630, 2003.

Rasband, M.N., et al., "Distinct potassium channels on pain-sensing neurons", PNAS, vol. 98, No. 23, pp. 13373-13378, 2001.

Renfrey S., et al., "The painful reality", Nature Reviews, vol. 2, pp. 175-176, Mar. 2003.

Riechmann, et al., "Reshaping human antibodies for therapy", Nature, vol. 332, pp. 323-324, 1988.

Rudikoff et al., "Single amino acid substitution altering antigen-binding specificity," PNAS, vol. 79, pp. 1979-1983 (1982).

Saerens, D., et al., "Single Domain Antibodies Derived from Dromedary Lymph Node and Peripheral Blood Lymphocytes Sensing Conformational Variants of Prostate-specific Antigen", J. Biol. Chem., vol. 279, No. 50, pp. 51965-51972, 2004.

Saito, Y. et al., "Sodium Channel Mutation in Irritable Bowel Syndrome: Evidence for an Ion Channelopathy," J. Physiol. Gatrointest. Liver Physiol., vol. 296, pp. G211-G218, 2009.

Schmalhofer, W.A., et al., "ProTx-II, a Selective Inhibitor of $Na_v1.7$ Sodium Channels, Blocks Action Potential Propagation in Nociceptors", Mol Pharmacol, vol. 74, pp. 1476-1484, 2008.

Stanfield, R.L., et al., "Crystal Structure of a Shark Single-Domain Antibody V Region in Complex with Lysozyme", Science, vol. 305, No. 5691, pp. 1770-1773, 2004.

Tao, M., et al., "The Differential Ability of Human IgG 1 and IgG4 to Activate Complement Is Determined by the COOH-terminal Sequence of the $C_H2$ Domain", J. Exp. Med, vol. 173, pp. 1025-1028, 1991.

Tao, M., et al., "Structural Features of Human Immunoglobulin G that Determine Isotype-specific Differences in Complement Activation", J. Exp. Med, vol. 178, pp. 661-667, 1993.

Tarnawa, I., et al., "Blockers of voltage-gated sodium channels for the treatment of central nervous system diseases", Recent Patents on CNS Drug Discovery, vol. 2, pp. 57-78, 2007.

Teruya K., et al., "Peptides, Structure and Function, Proceedings of the Eighth American Peptide Symposium," Eds. V.J. Hruby and D.H. Rick, Pierce Chemical Company, Rockford, Illinois, pp. 127-130, 1983.

(56) References Cited

OTHER PUBLICATIONS

Tickle, S., et al., "High-Throughput Screening for High Affinity Antibodies", Journal of the Association for Laboratory Automation, vol. 14, pp. 303-307, 2009.

Toniolo, C., "Conformationally Restricted Peptides Through Short-Range Cyclizations", Int. J. Pept. Protein Res., vol. 35, pp. 287-300, 1990.

Valero, R., et al., "Cyclic Peptides as Confirmationally Restricted Models of Viral Antigens: Applications to Foot-And-Mouth Disease Virus", Biomedical Peptides, Proteins & Nucleic Acids, vol. 1, pp. 133-140, 1995.

Vaughan, et al., "Human antibodies by design", Nature Biotechnology, vol. 16, No. 6, pp. 535-539, 1998.

Verma, R., et al., "Antibody engineering: Comparison of bacterial, yeast, insect and mam Malian expression systems", Journal of Immunological Methods, vol. 216, Nos. 1-2, pp. 165-181, 1998.

Ward, E.S., et al., "Binding activities of a repertoire of single immunoglobulin variable domains secreted from *Escherichia coli*". Nature, vol. 341, No. 6242, pp. 544-546, 1989.

Weiss, R.E., et al., "Functional differences between two classes of sodium channels in developing rat skeletal muscle", Science, vol. 233, pp. 361-364, 1986.

Wu et al., "Humanization of a Murine Monoclonal Antibody by Simultaneous Optimization of Framework and CDR Residues," J. Mol. Biol., vol. 294, pp. 151-162 (1999).

Yang, J., et al., "3-(4-Phenoxyphenyl)pyrazoles: A Novel Class of Sodium Channel Blockers", J. Med. Chem., vol. 47, No. 6, pp. 1547-1552, 2004.

Zuckier, L.S., et al., "Chimeric Human-Mouse IgG Antibodies with Shuffled Constant Region Exons Demonstrate that Multiple Domains Contribute to in Vivo Half-Life", Cancer Research, vol. 58, pp. 3905-3908, 1998.

International Search Report dated Feb. 10, 2011 for PCT/EP2010/066274.

International Search Report dated Jan. 24, 2011 for PCT/EP2010/066276.

International Search Report dated Feb. 7, 2011 for PCT/EP2010/066279.

Co-pending U.S. Appl. No. 13/504,234, filed Jun. 28, 2012.

Co-pending U.S. Appl. No. 13/504,259, filed Jul. 6, 2012.

Co-pending U.S. Appl. No. 13/523,104, filed Jun. 14, 2012.

Figure 2b

Domain A
MAMLPPPGPQSFVHFTKQSLALIEQRIAERKSKEPKEEKKDDDEEAPKPSSDL
EAGKQLPFIYGDIPPGMVSEPLEDLDPYYADKKTFIVLNKGKTIFRFNATPALY
MLSPFSPLRRISIKILVHSLFSMLIMCTILTNCIFMTMNNPPDWTKNVEYTFTGI
YTFESLVKILARGFCVGEFTFLRDPWNWLDFVVIVFAYLTEFVNLGNVSALRT
FRVLRALKTISVIPGLKTIVGALIQSVKKLSDVMILTVFCLSVFALIGLQLFMGN
LKHKCFRNSLENNETLESIMNTLESEEDFRKYFYYLEGSKDALLCGFSTDSGQ
CPEGYTCVKIGRNPDYGYTSFDTFSWAFLALFRLMTQDYWENLYQQTLRAA
GKTYMIFFVVVIFLGSFYLINLILAVVAMAYEEQNQANIEEAKQKELEFQQML
DRLKKEQEEAEAIAAAAAEYTSIRRSRIMGLSESSSETSKLSSKSAKERRNRRK
KKNQKKLSSGEEKGDAEKLSKSESEDSIRRKSFHLGVEGHRRAHEKRLSTPNQ
SPLSIRGSLFSARRSSRTSLFSFKGRGRDIGSETEFADDEHSIFGDNESRRGSLFV
PHRPQERRSSNISQASRSPPMLPVNGKMHSAVDCNGVVSLVDGRSALMLPNG
QLLPEVIIDKATSDDSGTTNQIHKKRRCSSYLLSEDMLNDPNLRQRAMSRASIL
TNTVEELEESRQKCPPWWYRFAHKFLIWNCSPYWIKFKKCIY (SEQ ID NO: 201)

Domain B
FIVMDPFVDLAITICIVLNTLFMAMEHHPMTEEFKNVLAIGNLVFTGIFAAEM
VLKLIAMDPYEYFQVGWNIFDSLIVTLSLVELFLADVEGLSVLRSFRLLRVFKL
AKSWPTLNMLIKIIGNSVGALGNLTLVLAIIVFIFAVVGMQLFGKSYKECVCKI
NDDCTLPRWHMNDFFHSFLIVFRVLCGEWIETMWDCMEVAGQAMCLIVYM
MVMVIGNLVVLNLFLALLLSSFSSDNLTAIEEDPDANNLQIAVTRIKKGINYV
KQTLREFILKAFSKKPKISREIRQAEDLNTKKENYISNHTLAEMSKGHNFLKEK
DKISGFGSSVDKHLMEDSDGQSFIHNPSLTVTVPIAPGESDLENMNAEELSSDS
DSEYSKVRLNRSSSSECSTVDNPLPGEGEEAEAEPMNSDEPEACFTDGCVRRF
SCCQVNIESGKGKIWWNIRKTCYK (SEQ ID NO: 202)

Domain C
IVEHSWFESFIVLMILLSSGALAFEDIYIERKKTIKIILEYADKIFTYIFILEMLLK
WIAYGYKTYFTNAWCWLDFLIVDVSLVTLVANTLGYSDLGPISLRTLRALRP
LRALSRFEGMRVVVNALIGAIPSIMNVLLVCLIFWLIFSIMGVNLFAGKFYECI
NTTDGSRFPASQVPNRSECFALMNVSQNVRWKNLKVNFDNVGLGYLSLLQV
ATFKGWTIIMYAAVDSVNVDKQPKYEYSLYMYIYFVVFIIFGSFFTLNLFIGVII
DNFNQQKKKLGGQDIFMTEEQKKYYNAMKKLGSKKPQKPIPRPGNKIQGCIF
D (SEQ ID NO: 203)

Domain D
LVTNQAFDISIMVLICLNMVTMMVEKEGQSQHMTEVLYWINVVFIILFTGECV
LKLISLRHYYFTVGWNIFDFVVVIISIVGMFLADLIETYFVSPTLFRVIRLARIGR
ILRLVKGAKGIRTLLFALMMSLPALFNIGLLLFLVMFIYAIFGMSNFAYVKKE
DGINDMFNFETFGNSMICLFQITTSAGWDGLLAPILNSKPPDCDPKKVHPGSS
VEGDCGNPSVGIFYFVSYIIISFLVVVNMYIAVILENFSVATEESTEPLSEDDFE
MFYEVWEKFDPDATQFIEFSKLSDFAAALDPPLLIAKPNKVQLIAMDLPMVSG
DRIHCLDILFAFTKRVLGESGEMDSLRSQMEERFMSANPSKVSYEPITTTLKRK
QEDVSATVIQRAYRRYRLRQNVKNISSIYIKDGDRDDDLLNKKDMAFDNVNE
NSSPEKTDATSSTTSPPSYDSVTKPDKEKYEQDRTEKEDKGKDSKESKK (SEQ ID NO: 204)

Figure 2c
Nav1.7 (SEQ ID NO: 205)

```
MAMLPPPGPQSFVHFTKQSLALIEQRIAERKSKEPKEEKKDDDEEAPKPSSDLEAGKQLPFIYGDIPPG
MVSEPLEDLDPYYADKKTFIVLNKGKTIFRFNATPALYMLSPFSPLRRISIKILVHSLFSMLIMCTILT
NCIFMTMNNPPDWTKNVEYTFTGIYTFESLVKILARGFCVGEFTFLRDPWNWLDFVVIVFAYLTEFVNL
GNVSALRTFRVLRALKTISVIPGLKTIVGALIQSVKKLSDVMILTVFCLSVFALIGLQLFMGNLKHKCF
RNSLENNETLESIMNTLESEEDFRKYFYYLEGSKDALLCGFSTDSGQCPEGYTCVKIGRNPDYGYTSFD
TFSWAFLALFRLMTQDYWENLYQQTLRAAGKTYMIFFVVVIFLGSFYLINLILAVVAMAYEEQNQANIE
EAKQKELEFQQMLDRLKKEQEEAEAIAAAAAEYTSIRRSRIMGLSESSSETSKLSSKSAKERRNRRKKK
NQKKLSSGEEKGDAEKLSKSESEDSIRRKSFHLGVEGHRRAHEKRLSTPNQSPLSIRGSLFSARRSSRT
SLFSFKGRGRDIGSETEFADDEHSIFGDNESRRGSLFVPHRPQERRSSNISQASRSPPMLPVNGKMHSA
VDCNGVVSLVDGRSALMLPNGQLLPEVIIDKATSDDSGTTNQIHKKRRCSSYLLSEDMLNDPNLRQRAM
SRASILTNTVEELEESRQKCPPWWYRFAHKFLIWNCSPYWIKFKKCIYFIVMDPFVDLAITICIVLNTL
FMAMEHHPMTEEFKNVLAIGNLVFTGIFAAEMVLKLIAMDPYEYFQVGWNIFDSLIVTLSLVELFLADV
EGLSVLRSFRLLRVFKLAKSWPTLNMLIKIIGNSVGALGNLTLVLAIIVFIFAVVGMQLFGKSYKECVC
KINDDCTLPRWHMNDFFHSFLIVFRVLCGEWIETMWDCMEVAGQAMCLIVYMMVMVIGNLVVLNLFLAL
LLSSFSSDNLTAIEEDPDANNLQIAVTRIKKGINYVKQTLREFILKAFSKKPKISREIRQAEDLNTKKE
NYISNHTLAEMSKGHNFLKEKDKISGFGSSVDKHLMEDSDGQSFIHNPSLTVTVPIAPGESDLENMNAE
ELSSDSDSEYSKVRLNRSSSSECSTVDNPLPGEGEEAEAEPMNSDEPEACFTDGCVRRFSCCQVNIESG
KGKIWWNIRKTCYKIVEHSWFESFIVLMILLSSGALAFEDIYIERKKTIKIILEYADKIFTYIFILEML
LKWIAYGYKTYFTNAWCWLDFLIVDVSLVTLVANTLGYSDLGPISLRTLRALRPLRALSRFEGMRVVVN
ALIGAIPSIMNVLLVCLIFWLIFSIMGVNLFAGKFYECINTTDGSRFPASQVPNRSECFALMNVSQNVR
WKNLKVNFDNVGLGYLSLLQVATFKGWTIIMYAAVDSVNVDKQPKYEYSLYMYIYFVVFIIFGSFFTLN
LFIGVIIDNFNQQKKKLGGQDIFMTEEQKKYYNAMKKLGSKKPQKPIPRPGNKIQGCIFDLVTNQAFDI
SIMVLICLNMVTMMVEKEGQSQHMTEVLYWINVVFIILFTGECVLKLISLRHYYFTVGWNIFDFVVVII
SIVGMFLADLIETYFVSPTLFRVIRLARIGRILRLVKGAKGIRTLLFALMMSLPALFNIGLLLFLVMFI
YAIFGMSNFAYVKKEDGINDMFNPETFGNSMICLFQITTSAGWDGLLAPILNSKPPDCDPKKVHPGSSV
EGDCGNPSVGIFYFVSYIIISFLVVVNMYIAVILENFSVATEESTEPLSEDDFEMFYEVWEKFDPDATQ
FIEFSKLSDFAAALDPPLLIAKPNKVQLIAMDLPMVSGDRIHCLDILFAFTKRVLGESGEMDSLRSQME
ERFMSANPSKVSYEPITTTLKRKQEDVSATVIQRAYRRYRLRQNVKNISSIYIKDGDRDDDLLNKKDMA
FDNVNENSSPEKTDATSSTTSPPSYDSVTKPDKEKYEQDRTEKEDKGKDSKESKK
```

Light DNA
CA167_00914
(SEQ ID NO: 121)

GCCTATGATA TGACCCAGAC TCCAGCCTCT GTGGAGGTAG CTGTGGGAGG CACAGTCACC ATCAATTGCC AGGCCAGTGA GAGCATTGGC
ACTGCATTAG CCTGGTATCA GCAGAAACCA GGGCAGCCTC CCAAGCTCCT GATCTACAAG GCATCCACTC TGGAATCTGG GGTCCCATCG
CGGTTCAAAG GCGGTGGATC TGGGACACAG TTCACTCTCA CCATCAGCGG CCTGCAGTGT GACGATGCTG CCACTTACTA CTGTCAACAG
GGTGAAACTG GATTATACTG TTCGGCGGAG GGACCGAGGT GGTCGTCAAA

Heavy DNA
CA167_00914
(SEQ ID NO: 122)

CAGTCGGTGG AGGAGTCCGG CCTGGGTCCG GTCACGCCTG GGAAGGGGC CCAGGCTCCA CATCTCCAAA ACCTGCACCA TTGTGGGGCC
AATGCAATGA CCTGGGTCCG CCAGGCTCCA CATCTCCAAA ACCTGCACCA TTGTGGGGCC CCCCTGTAAG ATGGTTATAA
TGGGCGAAAG GCCGATTCAC ATGGTTATAA TCCCTGTAAG TGGTGGGCC
TTCTGTGTTC ATGGTTATAA

Light Protein
CA167_00914
(SEQ ID NO: 123)

AYDMTQTPAS VEVAVGGTVT INCQASESIG TALAWYQQKP GQPPKLLIYK ASTLESGVPS RFKGGGSGTQ FTLTISGVQC DDAATYYCQQ
GETANRIDNA FGGGTEVVVK

Heavy Protein
CA167_00914
(SEQ ID NO: 124)

QSVEESGGRL VTPGTPLTLT CTVSGIDLSR NAMTWVRQAP GKGLEYIAYI NTRGDTSYAN WAKGRFTISK TSTTVDLKMT SLITEDTATY
FCVHGYNPCK LWGQGTLVTV S

Light DNA
CA167_00915
(SEQ ID NO: 125)

GCCTATGATA TGACCCAGAC TCCAGCCTCT GTGGAGGTAG CTGTGGGAGG CACAGTCACC ATCAATTGCC AGGCCAGTGA GAGCATTAAC
ACTGCATTAG CCTGGTATCA GCAGAAACCA GGGCAGCCTC CCAAGCTCCT GATCTATGCT GCCTCCACTC TGGCATCCATCG
CGGTTCAAAG GCAGTGGATC TGGGACACAG TTCACTCTCA CCATCAGCGG CGTGCAGTGT GCCGATGCTG CCACTTACTA CTGTCAACAG
GGTTATACTG CAAATAGTGT GGGCGCCTG GGACCGAGGT GGTCGTCAAA

Heavy DNA
CA167_00915
(SEQ ID NO: 126)

CAGTCGGTGG AGGAGTCCGG CCTGGGTCCG GTCGCGCCTG GGAAGGGCC CCAGGCTCCA CATCTCCAAA TGCACAGTCT CTGGAATCGA
AATGCAATGA CCTGGGTCCG CCAGGCTCCA TGGAATACAT CGCATATATT AATACTAGGG GTGGCGATC CTACGCGAAC
TGGGCGAAAG GCCGATTCAC CCCCTGTAAG TGGTGGGCC CGGGACCAGA CGGTCGATCT GAAAATGACC CTTCAGACAC GGCCACCTAT
TTCTGTGTCA ATGGTTATAA CCCCTGTAAG TGGTGGGCC CGGGACCCCT CGTCACCGTC TCG

Light Protein
CA167_00915
(SEQ ID NO: 127)

AYDMTQTPAS VEVAVGGTVT INCQASESIN TALAWYQQKP GQPPKVLIYA ASDLASGVPS RFKGSGSGKQ FTLTISGVQC ADAATYYCQQ
GYTANNIDNA FGGGTEVVVK

Heavy Protein
CA167_00915
(SEQ ID NO: 128)

QSVEESGGRL VAPGTPLTLT CTVSGIDLSR NAMTWVRQAP GKGLEYIAYI NTRGGASYAN WAKGRFTISK TSTTVDLKMT SLTASDTATY
FCVNGYNPCK LWGQGTLVTV S

Figure 5

Light DNA CA167_00930 (SEQ ID NO: 129)
GACATCGTGA TGACCCAGAC TCCATCTTCC GCCCAAGTGC CTGTGGGAGG CACAGTCACC ATCAATTGCC AGTCCAGTCA GAATGTTGTT
AATAACAACT GGTTCTCCTG GTTTCAGCAG AAACCAGGGC AGCCTCCCAA GGTCCTGATC TATTTTGTAT CCAAACTGGC ATCTGGGGTC
CCATCGCGGT TCAAAGGCAG TGGATCTGGG ACACAGTTCA CTCTCACCAT CAGCGACCTG GAGTGTGACG ATGCTGCCAC TTATTATTGT
CAGGCGGTT ATAGTGATAA TATTTATGCG GGTCGTGAA GACCGAGGT GGTCGTCGAA

Heavy DNA CA167_00930 (SEQ ID NO: 130)
CAGTCGGTGG AGGAGTCCGG AGGTCGGCCT GTCACGCCTG GGACACCCCT GGCACTCACC TGCACAGTCT CTGGAATCGA CCTCAGTTAC
TATGCAATAA GCTGGGTCCG CCAGGCTCCA GGGAAGGGGC TGGAATACAT CGGTAGTAGT GGTAGTAGTG GTAAGACATA CTACGCGAGC
TGGGCGAAAG GCCGATTCAC CATCTCCAAA ACCTCGACCA CGGTGGATCT GAAAATGACC AGTCTGACAA CCGAAGACAC GGCCACCTAT
TTCTGTGTCA GGGGTGGTCC TACTTCTAGT CCTAGTTTGT GGGGCCAAGG CACCCTCGTC ACCGTCTCG

Light Protein CA167_00930 (SEQ ID NO: 131)
AQVLTQTPSS TSAAVGGTVT INCQSSQNVV NNNWFSWFQQ KPGQPPKVLI YFVSKLASGV PSRFKGSGSG TQFTLTISDL ECDDAATYYC
GGGYSDNIYA FGGGTEVVE

Heavy Protein CA167_00930 (SEQ ID NO: 132)
QSVEESGGRL VTPGTPLALT CTVSGIDLSY YAISWVRQAP GKGLEYIGII GSSGRTYYAS WAKGRFTISK TSTTVDLKMT SLTTEDTATY
FCVRGGPTSS PSLWGQGTLV TVS

Light DNA CA167_00931 (SEQ ID NO: 133)
GACATCGTGA TGACCCAGAC TCCATCCTCC GTGTCTGCAG CACAGTCACC ATCAATTGCC AGGCCAGTCA GAGTGTTTAT
GGGACCAACC GTTTATCCTG GTATCAGCAG AAACCAGGGC AGCCTCCCAA GCTCCTGATC TATGGTGCAT CCACTCTGAC ATCTGGGGTC
CCATCGCGGT TCAAAGGCAG TGGATCTGGG ACACAGTTCA CTCTCACCAT CAGTGGCGTG CAGTCTGATG GTGCTGCCAC TTACTACTGT
CTAGGCGGTT GGTTTGAAAG GTTTGATTGGG CTTTCGGCGG AGGGACCGAG GTGGTCGTCG AA

Heavy DNA CA167_00931 (SEQ ID NO: 134)
CAGTCGGTGG AGGAGTCCGG GGGTCGCCTG GTCACGCCTG GGACACCCCT GACACTCACC TGTACAGTCT CTGGAATCGA CCTCAGTAGA
AATGCAATGG GCTGGGTCCG CCAGGCTCCA GGGAAGGGGC TGGAATACAT CGGCCATATT GCCAGTCGTG GTAACATATG GTTCAGGAAC
TGGGCGAAAG GCCGATTCAC CGTCTCCAAA ACCTCGACCA CGGTGGATCT AAAAATCACC AGTCCGACAA CCGAGGACAC GGCCACCTAT
TTCTGTGCA GATTTCTTGT AGTATCTGGG GTGGGACTT TTGATCCCTG GGGCCAGGGG ACCCTCGTCA CCGTCTCG

Light Protein CA167_00931 (SEQ ID NO: 135)
DIVMTQTPSS VSAAVGGTVT INCQASQSVY GTNRLSWYQQ KPGQRPKLLI YGASTLTSGV PSRFKGSGSG TQFTLTISGV QCDDAATYYC
LGGWFESSSS LDWAFGGGTE VVVE

Heavy Protein CA167_00931 (SEQ ID NO: 136)
QSVEESGGRL VAPGTPLTLT CTVSGIDLSR NAMGWVRQAP EKGLEYIGHI ASRGNIWFRN WAKGRFTVSK TSTTVDLKIT SPTTEDTATY
FCGRFLVVSG VGIFDPWGQG TLVTVS

Figure 6

Light DNA CA167_00932 (SEQ ID NO: 137)
GCAGCCGTGC TGACCAGAC TCCATCGTCC GTGTCTGCAG CTGTGGGAGG CACAGTCACC ATCAAGTGCC AGTCCAGTCA GAGTGTTTAT
AATAACAACG AATTTCCTG GTATCAGCAG AAACCAGGGC AGCCTCCCAA GCTCCTGATC TATGATGCAT CCAAATTGGC ATCTGGGGTC
CCATCGCGGT TCAGGGCAG TGGATCTGGG ACACAGTTCA CTCTCACCAT CAGCGGCGTG CAGGTGCCAC ATGTTGCCAC TTATTACTGT
CTAGGCGGTT ATAATGATGA TACTAATAGA TGGGCTTTCG GCGGAGGGAC CGAGGTGGTG GTCGAA

Heavy DNA CA167_00932 (SEQ ID NO: 138)
CAGTCGCTGG AGGAGTCCGA GGGTCGCCTG GTCACGCCTG GGACACCCCT GACACTCACC TGCACAGTCT CTGGATTCTC CCTCAGTAGC
TACTGGATGA GCTGGGTCCG CCAGGCTCCA GGGAAGGGGC TGGAGTGGAT CGGAAACATT GGTGGTGGTA GTGGTAGTAC ATTATACGCG
CCCTGGGCAA AAGGCCGATC CACCATCTCC AAAACCTCGA CCACGGTGGA TCTGAAAATC ACCAGTCCAA CAACCGAGGA CACGGCCACC
TATTTCTGTG GCAGATATGT TAAAAATGGT GGTTGGTTATC GGTTGGATCT TTGGGGCCA GGGACCCTGG TCACCGTCTC G

Light Protein CA167_00932 (SEQ ID NO: 139)
AAVLTQTPSS VSAAVGGTVT IKCQSSQSVY NNNEFSWYQQ KPGQPPKLLI YDASKLASGV PSRFSGSGSG TQFTLTISGV QCDDVATYYC
LGGYNDDTNR WAFGGGTEVV VE

Heavy Protein CA167_00932 (SEQ ID NO: 140)
QSLEESGGRL VTPGTPLTLT CTVSGFSLSR YWMSWVRQAP GKGLEWIGNI GGGSGSTLYA PWAKGRSTIS KTSTTVDLKI TSPTTEDTAT
YFCGRYVKNG GGYRLDLWGP GTLVTVS

Light DNA CA167_00933 (SEQ ID NO: 141)
GCCATCGTGA TGACCAGAC TCCATCTTCC GTTTCAACAG CTGTGGGAGA CACAGTCACC ATCAATTGCC AGGCCAGTGA GAGTGTTGCT
TCATCGCGGT GGTTAGCCTG TTAAAGGCAG ACACAGTTCA AAACCAGGGC AGCCTCCCAA GCTCCTGATC TACAAGGCAT CCACTCTGGC ATCTGGGGTC
GCAGGATATA AAAGTAGTAC TACTGATGCT GTTGCTTTCG GCGGAGGGAC CGGCGATGTG GTGTGTGACG ATGTGCCAC TTACTATTGT
CAGTCAGTGA AGAGTCCGA GGGAGTCTC TCAAGCCAA CGGATACCCT GACACTCACC TGCACAGTCT CTGGATTCTC CCTCAGTAGC
TATGCAATAA GGTTAGCCTG CCAGGCTCCA GGGAAGGGGC TGGAATGGAT CGGATTCATT AACACTATTA CTGGTGGCAC AAACTACGCG
AGCTGGGCGA AAAGCCGATC CACCATCACC AGAAACACCA ACGATAACAC GGTGACTCTG AAAATGACCA GTCTGACAGC CGCGGACACG
GCCACGTATT TCTGTGCGAG AAGTGGTGCC TACTTTGACT TGTGGGGCCC AGGCACCCTG GTCACCGTCT CG

Light Protein CA167_00933 (SEQ ID NO: 142)
AIVMTQTPSS KSVPVGDTVT INCQASESVA NNNWLAWFQQ KPGQPPKLLI YKASTLASGV SSRFKGSGSG TQFTLTIGDV VCDDAATYYC
AGYKSSTTDA VAFGGGTEVV VK

Heavy Protein CA167_00933 (SEQ ID NO: 143)
QSVKESEGGL FKPTDTLTLT CTVSGFSLSS YAISWVRQAP GNGLEWIGFI NTITGGTNYA SWAKSRSTIT RNTNDNTVTL KMTSLTAADT
ATYFCARSGA YFDLWGPGTL VTVS

Heavy DNA CA167_00933 (SEQ ID NO: 144)

Figure 7

Light DNA CA167_00983 (SEQ ID NO: 145)
GCCCAAGTGC TGACCCAGAC TGCATCCCCC GTGTCTGCGG CTGTTGGAGG CACAGTCACC ATCAATTGCC AGTCCAGTCA GAGTGTTTAT
AAGAACAACG ACTTAGCCTG GTATCAGCAG AAACCAGGGC AGCCTCCCAA GCTCCTGATC TATTATGCAT CCACTCTGGC ATCTGGGGTC
TCATCGCGGT TCAAAGGCAG TGGATCTGGG ACAGAGTTCA CTCTCACCAT CAGCGACGCG CAGGACGCG ATGCTGCCAC TTACTACTGT
CTAGGTAGTT ATGATTGTAG TAGTGCTGAT TGTAATGCTT TCGGCGGAGG GACCAAGGTG GTCGTCAAA Heavy DNA CA167_00983 (SEQ ID NO: 146)
CAGTCGGTGG AGGAGTCCGG GGGTCGCCTG GTCACGCCTG GGACACCCCT GACACTCACC TGCACAGTCT CTGGATTCTC CCTCAGTAAC
TATGCAATGA GTTGGGTCCG CCAGGCTCCA GGGAAGGGGC TGGAATGGAT CGGAATCATT GGTAAAAGTG GTACGCGAGC CTACGCGAGC
TGGGCGAAAG GCCGATTCAC CATCTCCAGA ACCTCGACCA CGGTCGATCT GGAAATCACC AGTCCGACAA CCGAGGACAC GGCCACCTAT
TTCTGTGTCA GATTGTGCT CTTGTGGGGC CCGGGGACCC TGGTCACCGT CTCG Light Protein CA167_00983 (SEQ ID NO: 147)
AQVLTQTASP VSAAVGGTVT INCQSSQSVY KNNDLAWYQQ KPGQPPKLLI YYASTLASGV SSRFKGSGSG TEFTLTISDA QCDDAATYYC
LGSYDCSSAD CNAFGGGTKV VVK Heavy Protein CA167_00983 (SEQ ID NO: 148)
QSVEESGGRL VTPGTPLTLT CTVSGFSLSN YAMSWVRQAP GKGLEWIGII GKSGSTAYAS WAKGRFTISR TSTTVDLEIT SPTTEDTATY
FCVRFVLLWG PGTLVTVS Light DNA CA167_00984 (SEQ ID NO: 149)
GCCCAAGTGC TGACCCAGAC TCCATCCTCC GTGTCTGCAG CTGTTGGAGG CACAGTCACC ATCAATTGCC AGTCCAGTCA GAGTGTTAAT
AACAACAACT TCTTATCCTG GTATCAGCAG AAACCAGGGC AGCCTCCCAA GCTCCTGATC TACAGGGCTT CCACTCTGGC ATCTGGGGTC
CCATCGCGGT TCAAAGGCAG TGGATCTGGG ACACAGTTCA CTCTCACCAT CAGCGACGTG CAGGACGACG ATGCGCCAC TTACTTCTGT
GCAGGCGGTT ATATAGTGTAA TATTTATGCT TTCGGCGGAGG GACCGAGGT GGTGGTCGAA CAGTCGGTGG AGGAGTCCGG GGGTCGCCTG GTCACGCCTG GGACACCCCT GACACTCACC TGCACAGTCT CTGGATTCTC CCTCAGTGAC
TATATAATAA ACTGGGTCCG CCAGGCTCCA GGGAAGGGGC TGGAATGGAT CGGGATCATG GGTACTAGTG GTACCGCATA CTACGCGAGC
TGGGCGAAAG GCCGATTCAC CATCTCCAAA ACCTCGTCGA TCTGAGAATG TCTGAGAAG ACCAGTCTGA CAACCGAGGA CACGGCCACC
TATTTCTGTG CCAGAGGGGG TGTTGCTACT TCTAATTTCT GGGGCCAAGG CACCCTGGTC ACCGTCTCG Light Protein CA167_00984 (SEQ ID NO: 151)
AQVLTQTPSS VSAAVGGTVT INCQSSQSVN NNNFLSWYQQ KPGQPPKQLI YRASTLASGV PSRFKGSGSG TQFTLTISDV QCDDAATYFC
AGGYSGNIYA FGGGTEVVVE Heavy Protein CA167_00984 (SEQ ID NO: 152)
QSVEESGGRL VTPGTPLTLT CTVSEFSLSD YIINWVRQAP GKGLEWIGIM GTSGTAYYAS WAKGRFTISK TSSTTVDLRM TSLTTEDTAT
YFCARGGVAT SNFWGQGTLV TVS

Figure 8

Light DNA CA167_00985 (SEQ ID NO: 153)
GCCCAAGTGC TGACCCAGAC TGCATCCCCT GTGTCTCTGCAG TGTGTGGGAGG CACAGTCACC ATCAATTGTC AGTCCAGTCA GAGCGTTTAT
GGTAACAATT GGTTAGGCTG GTATCAGCAG AAACCAGGGC AGCCTCCCAA GCTCCTGATC TATTCTGCAT CTACTCTGGC ATCTGGGGTC
CCATCGCGGT TCAGTGCAG ACACAGTTCA CTCTCACCAT CAGCGACCTG GAGTGTGACG ATGGTGCCAC TTACTATTGT
GTAGGCGGGT ATAGTGGTAA TATTCATGTT TTCGGCGGAG GGACCAAGGT GGTGGTCGAA

Heavy DNA CA167_00985 (SEQ ID NO: 154)
CAGTCGGTGG AGGAGTCCGG GGGTCGCCTG GTCACGCCTG GACACCCCT GACACTCACC TGCACAGTCT CTGGATTCTC CCTCAACGAC
TACGACATGA GCTGGGTCCG CCAGGCTCCA GGGAAGGGGC TGGAATGGAT CACAACCATT TATGTTAGTG GTAACACATA CTACGCGACC
TGGGCGAAAG GCCGATTCAC CATCTCCAAA ACCTCGACA CGGTGATCT GAAATGACC AGTCCGACAG CCGAGGACAC GGCCACCTAT
TTCTGTGCCA GAGCCGGTTCC TGGTAGTGGT AAGGGGTTGT GGGGCCCGGG CACCCTCGTC ACCGTCTCG

Light Protein CA167_00985 (SEQ ID NO: 155)
AQVLTQTASP VSAAVGGTVT INCQSSQSVY GNNWLGWYQQ KPGQPPKLLI YSASTLASGV PSRFSGSGSG TQFTLTISDL ECDDGATYYC
VGGYSGNIHV FGGGTKVVE

Heavy Protein CA167_00985 (SEQ ID NO: 156)
QSVEESGGRL VTPGTPLTLT CTVSGFSLND YDMSWVRQAP GKGLEWITTI YVSGNTYYAT WAKGRFTISK TSTTVDLKMT SPTAEDTATY
FCARAVPGSG KGLWGPGTLV TVS

Light DNA CA167_01059 (SEQ ID NO: 157)
GCCCAAGTGC TGACCCAGAC TCCATCCTCC GTGTCTCTGCAG CACAGTCACC ATCAACTGCC AGGCCAGTCA GAGTCTTTAT
AATAAGAAAA ATTTAGCCTG GTATCAGCAG AAACCAGGGC AGCCTCCCAA ACTCCTTATC TATTATGCAT CCACTCTGGC ATCTGGGGTC
TCATCGCGGT TCAAAGGCAG TGGATCTGGG ACACAGTTTA CTCTCACCAT CAGCGGCGTG CAGTGTGACG ATGCTGCCAC TTACTATTGT
CAAGGCGAAT TTAGTTGCAG CAGTGTTGAT TGTGTTGCTT TCGGCGGAGG GACCAAGGTG GTCGTCAAA

Heavy DNA CA167_01059 (SEQ ID NO: 158)
CAGTCGGTGG AGGAGTCCGG GGGTCGCCTG GTAACGCCTG GAGGATCCCT GACACTCACC TGCACAGTCT CTGGAATCGA CCTCAGTAGC
TATGCAATGA CCTGGGTCCG CCAGGCTCCA GGGAAGGGGC TGGAATGGAT CGGAATCATT TATGCTAGTG ATACATACTA CACGAGCTGG
GCGAAAGGCC GATTCACCAT CTCCAAAACC TCGACCACGG TGGATCTCAA AATCACCAGT CCGACAACCG AGGACACGGC CATTTATTTC
TGTGCCAGAG GAGATTCTAC TAGTGGTTTT CATTTGACTT TGTGGGGCCA GGGGACCCTG GTCACCGTCT CG

Light Protein CA167_01059 (SEQ ID NO: 159)
AQVLTQTPSS VSAAVGGTVT INCQASQSLY NKKNLAWYQQ KPGQPPKLLI YYASTLASGV SSRFKGSGSG TQFTLTISGV QCDDAATYYC
QGEFSCSSVD CVAFGGGTKV VVK

Figure 9

Heavy Protein CA167_01059 (SEQ ID NO: 160)
QSLEESGGRL VTPGGSLTLT CTVSGIDLSS YAMTWVRQAP GKGLEWIGII YASDTYYTSW AKGRFTISKT STTVDLKITS PTTEDTAIYF
CARGDSTSGF HLTLWGQGTL VTVS

Light DNA CA167_01060 (SEQ ID NO: 161)
GCCCAAGTGC TGACCCAGAC TCCATCCTCC GTGTCTGCAA CTGTGGGAGG CACAGTCACC ATCAACTGCC AGGCCAGTCA GAGTCTTTAT
AATAAGAAAA ATTTAGCCTG GTATCAACAG AAACCAGGGC AGCCTCCCAA GCTCCTGATC TATTTTGCAT CCACTCTGGC ATCTGGGGTC
TCATCGCGGT TCAAAGGCAG TGGATCTGGG ACACAGTTCA CTCTCACCAT CAGCGACGTG CAGTGTGACG ATGCTGCCAC TTACTATTGT
CAGTCGGAGT TTATTTGCAG CAGTGGTGAT TGTCTTGCTT TCGGCGGAGG GACCAAGGTG GTGGTCAAA

Heavy DNA CA167_01060 (SEQ ID NO: 162)
CAGTCGCTGG AGGAGTCCGG GGGTCGCCTG ATAACGCCTG GAGGATCCCT GACACTCACC TGTACAGTCT CTGGATTCGA CCTCAGTAGC
TATGCAATGA CCTGGGTCCG CCAGGCTCCA GGGAAGGGGC TGGAGTGGAT CGGAATCATT TATGGTACTG AGACCATATA CTACGCGACC
AGGGCGAAAG GCCGATTCAC CATCTCCAAA GCCTCGACAA CGGTGGATCT CAAAATCACC AGTCCGACAA CCGAGGACAC GGCCATTTAT
TTCTGTGCCA GAGGAGATTC TACTAGTGGT TTTCATTTGA CTTTGTGGGG CCCGGCACC CTCGTCACCG TCTCG

Light Protein CA167_01060 (SEQ ID NO: 163)
AQVLTQTPSS VSATVGGTVT INCQASQSLY NKKNLAWYQQ KPGQPPKLLI YFASTLASGV SSRFKGSGSG TQFTLTISDV QCDDAATYYC
QGEFICSSGD CVAFGGGTKV VVK

Heavy Protein CA167_01060 (SEQ ID NO: 164)
QSLEESGGRL ITPGGSLTLT CTVSGFDLSS YAMTWVRQAP GKGLEWIGII YGTETIYYAT RAKGRFTISK ASTTVDLKIT SPTTEDTAIY
FCARGDSTSG FHLTLWGPGT LVTVS

Light DNA CA167_01066 (SEQ ID NO: 165)
GCCCAAGTGC TGACCCAGAC TCCATCCTCC GTGTCTGCAG CTGTGGGAGG CACAGTCACC ATCAATTGCC AGGCCAGTCA GAGTCTTTAT
AATAAGAAAA ATTTGGCCTG GTATCAGCAG AAACCAGGGC AGCCTCCCAA GCTCCTGATG TTCTTTACGT CCACTCTGGC ATCTGGGATC
TCGTCGCGGT TCAAAGGCAG TGGATCTGGG ACACAGTTCA CTCTCACCAT CAGCGGCGTG CAGTGTGACG ATGCTGCCAC TTACTATTGT
CAAGGCGAAT TTAGTTGTAG CAGTGGTGAT TGTCTTTGCTT GTAACTCCTG CGGTCGCCTG TGCACCGTCT GAGAATCACT TATGGTACTG AACTCACATA CCGAGGACAC GGCCATTTAT

Heavy DNA CA167_01066 (SEQ ID NO: 166)
CAGTCGGTGG AGGAGTCCGG CGGTCGCCTG ATAACGCCTG GAGGATCCCT GGAGAGTGGAT CGGAATCATT TATGGTACTG AACTCACATA CCGAGGACAC GGCCATTTAT
TGGGCGAAAG GCCGATTCAC CATCTCCGAA ACCTCGACCA CGGTGGATCT CAAAATCACC AGTCCGACAA CCGAGGACAC GGCCATTTAT
TTCTGTGCCA GAGGAGATGC TACTAGTGGT TTTCATTTGA CGTTGTGGGG CCCGGGGACC CTCGTCACCG TCTCG

Light Protein CA167_01066 (SEQ ID NO: 167)
AQVLTQTPSS VSAAVGGTVI INCQASQSLY NKKNLAWYQQ KPGQPPKLLM FFTSTLASGI SSRFKGSGSG TQFTLTISGV QCDDAATYYC
QGEFSCSSGD CLAFGGGTKV VVK

Figure 10

| | | |
|---|---|---|
| Heavy Protein CA167_01066 (SEQ ID NO: 168) | QSVEESGGRL VTPGGSLILT CTVSGFDLSS YAMTWVRQAP GKGLEWIGII YGTELTYYAT WAKGRFTISE TSTTVDLKLT SPTTEDTAIY FCARGDATSG FHLTLWGPGT LVTVS | |
| Light DNA CA167_01068 (SEQ ID NO: 169) | GCTCAAGTGC TGACCCAGAC TCCAGCCTCC GTGTCTGAAC CCAGAAACCA TCCAGCTCAC CTGTCAGGCA GCCAGCAGTCA GACCATTTAT AGTGGTTTAG CCTGGTATCA GCAGAAACCA GGGCAGCCTC CCAAGCTCCT GATCTACAGG GCATCCACTC TGGCTCATCG CGGTTCAAAG GCAGTGGATC TGGGACAGAG TTCATTCTCA CCATCAGCGA CCTGGAGTGT GGCGATGCTG CCACTTACTA CTGTCAAGTT GGTGGTTATG GTGTTAGTTA TGACCATGCT TTCGGCGGAG GGACCAAGGT GGTCGTCAAA | |
| Heavy DNA CA167_01068 (SEQ ID NO: 170) | CAGGAACAGC TGGAGAGAGTC CGGGGGAGGC CTGGTCCAGC CTGGGGGATCC CTGACACTC ACCTGCACAG CTTCTGGATT CTCCTTCAGT AGCAGTCACT GGATATGTTG GGTCCGCCAG GCTCCAGGGA AGGGGCTGGA ATTGATCGCA TGCATTTATG GTGGTAGTAT TAATATTATT AACTACGCGA GCTGGGCGAA AGGCCGATTC ACCATCTCCA AAACCTCGTC GACCACGGTG ACTCTGCGAA TGACCAGTCT GACAGCCGCG GACACGGCCA CCAATTTCTG TGCGAGAGTA CAGGGTGGTA CAGGGTGTGG TTGGTACTTT GACTTGTGGG GCCCAGGCAC CCTCGTCACC GTCTCG | |
| Light Protein CA167_01068 (SEQ ID NO: 171) | AQVLTQTPAS VSEPVGGTVT IKCQASQTIY SGLAWYQQKP GQPPKLLIYR ASTLASGVSS RFKGSGSGTE FILTISDLEC GDAATYYCQV GGYGVSYDHA FGGGKVVVK | |
| Heavy Protein CA167_01068 (SEQ ID NO: 172) | QEQLEESGGG LVQPEGSLTL TCTASGFSFS SSYWICWVRQ APGKGLELIA CIYGGSINII NYASWAKGRF TISKTSSTTV TLRMTSLTAA DTATNFCARV QGGNSGGWYF DLWGPGTLVT VS | |
| Light DNA CA167_01080 (SEQ ID NO: 173) | GCCCAAGTGC TGACCCAGAC TGCATCGCCC GTGTCTGCAG CTGTGGGAAA CACAGTCACC ATCACTTGCC AGTCCAGTCA GAGTGTTTGG AAGAATAACG ACTTATCCTG GTATCAGCAG AAACTAGGGC AGCCTCCCAA GCTCCTGATC TATTATGCAT CCACTCTGGC ATCTGGGGTC TCATCGCGGT TCAAAGCCAG TGGATCTGGG ACACAGTTCA CTCTCACCAT CAGCGACGTG CAGCGACGTG CAATGTGACG ATGCTGGCAC TTACTACTGT GTAGCAGTT ATGATTGTAG AGGAGTCCGG GGGTCCGCTG GTCACGCCTG GGCGAAGGGAC TGGAGTGGAT CGGTGGATCT GAAAATGACC CCGAGGACAC GGCCACTTAT CAGTCGCTGG AGGAGTCCGG CCTGGGTCCG CCAGGCTCCA GACACCCCT GACACTCACC TGCACAGCCT CTGGAATCGA CCTCAGTAAG TGGGCGAAAG GCCGATTCAC CATCTCCAAA ACCTCGACCA ACGTCGACGA AGTCCGACAA CCGAGGACAC GGCCACTTAT TTCTGTGCCA GAGGTGGTAG TTATTATGAT TTGTGGGGCC AGGGGACCCT GGTCACCGTC TCG | |
| Heavy DNA CA167_01080 (SEQ ID NO: 174) | | |
| Light Protein CA167_01080 (SEQ ID NO: 175) | AQVLTQTASP VSAAVGNTVT ITCQSSQSVW KNNDLSWYQQ KLGQPPKLLI YYASTLASGV SSRFKASGSG TQFTLTISDV QCDDAGTYYC VGSYDCSSAD CNAFGGGTKV VVK | |

Figure 11

Heavy Protein CA167_01080 (SEQ ID NO: 176)
QSLEESGGRL VTPETPLTLT CTASGIDLSK WPMTWVRQAP GKGLEWIGII GRSGSTNYAS WAKGRFTISK TSTTVDLKMT SPTTEDTATY FCARGGSYYD LWGQGTLVTV S

Light DNA CA167_01081 (SEQ ID NO: 177)
GCCGCCGTGC TGACCCAGAC TCCATCTCCC GTGTCTGCAG CTGTGGGAGG CACAGTCAGC ATCAGTTGCC AGTCCAGTCA GAGTGTTGAT AATAACAACT ACTTATCCTG GTATCAGCAG AAACCAGGGC AGCCTCCCAA GCTCCTGATC TATGATGCAT CCGATCTGGC ATCTGGGGTC CCATCGCGGT TCAAAGGCAG TGGATCTGGA ACACAGTTCA CTCTCACCAT CAGCGACGTG CAGCCTGACG ATGCTGCCAC TTACTACTGT GCAGGCGGTT ATATAACTAG TAGTGATATT TTTTATGATT TCGGCGGAGG GACCAAGGTG GTGGTCAAA

Heavy DNA CA167_01081 (SEQ ID NO: 178)
CAGTCGGTGG AGGAGTCCGG GGGTCGCCTG GTCACGCCTG GGACACCCCT GACACTCACC TGCACAGTCT CTGGAATTCTC CCTCAGTACC TATGCAATGA GCTGGGTCCG CCAGGCTCCA GGGAAGGGGC TGGAATGGAT TGGAATCGTT GGAAAGAGTG GTATTATAAA GTACGCGAGC TGGGCGAAAG GCCGATTCAC CATCTCCAAA ACCTCGACCA CGGTGGATCT GAAAATGACC AGTCTGACAA CCGAGGACAC GGCCATTTAT TTCTGTGCCA GACTATGGAG CTTGTGGGGC CAAGGGACCC TCGTCACCGT CTCG

Light Protein CA167_01081 (SEQ ID NO: 179)
AAVLTQTPSP VSAAVGGTVS ISCQSSQSVD NNNYLSWYQQ KPGQPPKLLI YDASDLASGV PSRFKGSGSG TQFTLTISDV QCDDAATYYC AGGYITSSDI FYDFGGGTKV VVK

Heavy Protein CA167_01081 (SEQ ID NO: 180)
QSVEESGGRL VTPGTPLTLT CTVSGFSLST YAMSWVRQAP GKGLEWIGIV GKSGIIKYAS WAKGRFTISK TSTTVDLKMT SLTTEDTAIY FCARLWSLWG QGTLVTVS

Light DNA CA167_01082 (SEQ ID NO: 181)
GACATTGTGA TGACCCAGAC TCCAGCCTCC GTGTCTGAAC CTGTGGGAGG TCCAGCCACC ATCAAGTGCC AGGCCAGTCA GAGCATTAGC AACTGGTTAG CCTGGTATCA GCAGAAACCA GGGCAGCCTC CCAAGCTCCT CATCTACCGG GCATCCACTC TGGCATCTGG GGTCTCATCG CGGTTCAAAG GCAGTGGATC TGGGACAGAG TTCACTCTCA CCATCAGCGA CCTGGAGTGT GCCGATGCTG CCACTTACTA CTGTCAAAGC GATTATGGTA TAGATACTTA TGGAAGTGCT TTCGGCGGAG GGACCAAGGT GGTGGTCAAA

Heavy DNA CA167_01082 (SEQ ID NO: 182)
CAGTCGGCTG AGGAGTCCGG CCTGGGTCCG CCAGGCTCCA GGGAAGGGGC TGGAATGGAT TGGAATCGAT CCTCAGTAGT TATGCAATGA GCTGGGTCCG CCAGGCTCCA GGGAAGGGGC TGGAATGGAT CGTCGTAGTG GTACCACATA CTACGCGAGC TGGGCGAAAG GCCGATTCAC CATCTCCAAA ACCTCGACCA GAAAATCATC AGTCCGACAA CCGAGGACAC GGCCACCTAT TTCTGTGCCA GATGTGATAA TAGTGCTGGT ACGGCATGGA CCCTCGGGGC TGGTCACCGT CTCG

Light Protein CA167_01082 (SEQ ID NO: 183)
DIVMTQTPAS VSEPVGGTVT IKCQASQSIS NWLAWYQQKP GQPPKLLIYR ASTLASGVSS RFKGSGSGTE FTLTISDLEC ADAATYYCQS DYGIDTYGSA FGGGTKVVVK

Figure 12

Heavy Protein CA167_01082 (SEQ ID NO: 184)
QSLEESRGRL VTPGTPLTLT CTVSGIDLSS YAMTWVRQAP GKGLEWIGMV RRSGTTYYAS WAKGRFTISK TSTTVDLKII SPTTEDTATY
FCARCDNSAG DWSYGMDLWG PGTLVTVS

Light DNA CA167_01083 (SEQ ID NO: 185)
GCCCAAGTGC TGACCCAGAC TGCATCGCCC GTGTCTGCAG CTGTGGGAAG CACAGTCACC ATCAATTGCC AGGCCAGTCA GAGTGTTTAT
CAGAACAACT ACTTAGCCTG GTTTCAGCAG AAACCAGGGC AGCCTCCCAA GCTCCTGATC TATTCTGCAT CCACTCTGGC ATCTGGGGTC
TCATCGCGGT TCAAAGGCAG TGGATCTGGG ACACAGTTCA CTCTCACCAT CAGCGACGTG CAGTGTGCCA ATGCTGCCAC TTATTACTGT
CTGGGCGCCT ATGATTGTAG TGGTGTTGAT TGGTGTGCTT TCGGCGGAGG GACCAAGGTG GTCGTCAAA

Heavy DNA CA167_01083 (SEQ ID NO: 186)
CAGTCGGTGG AGGAGTCCGG AGGTCGCCTG GTCACGCCTG GGACACCCCT GACACTCACC TGCACCGTCT CTGGATTCTC CCTCAGTACC
AATGCAATGA TCTGGGTCCG CCAGGCTCCA GGGAAGGGGC TGGAATATAT CGGTGTGATT GCTGTGTAGT GTAGCACATC TTACGCGAGC
TGGGCGAAAG GCCGATTCAC CATCTCCAAA CGGTCGGATCT GAAAATCACC AGTCCGACAA CCGAGGACAC GGCCACCTAT
TTCTGTGCCA GAGGGGGTTG GGTTAGTAGT CCGGAGAGCT TGTGGGGCCA AGGCACCCTC GTCACCGTCT CG

Light Protein CA167_01083 (SEQ ID NO: 187)
AQVLTQTASP VSAAVGSTVT INCQASQSVY QNNYLAWFQQ KPGQPPKRLI YSASTLASGV SSRFKGSGSG TQFTLTISDV QCDDAATYYC
LGAYDCSGVD CSAFGGGTKV VVK

Heavy Protein CA167_01083 (SEQ ID NO: 188)
QSVEESGGRL VTPGTPLTLT CTVSGFSLST NAMIWVRQAP GKGLEYIGVI AGSGSTSYAS WAKGRFTISK TSTTVDLKIT SPTTEDTATY
FCARGGWVSG PESLWGQGTL VTVS

Light DNA CA167_01084 (SEQ ID NO: 189)
GCCCAAGTGC TGACCCAGAC TCCATCTTCC ACGTCTGCAG CTGTGGGAGG CACAGTCACC ATCAGTTGCC AGTCCAGTCC GAGTGTTTAT
GGTAATAACT GGTTAGCCTG GTATCAGAAG AAACCAGGGC AGCCTCCCAA GCTCCTGATC TATTCTGCAT CCACTCTGGC ATCTGGGGTC
TCATCGCGGT TTAAAGGCAG TGGATCTGGG ACACAGTTCA CTCTCACCAT CAGCGACCTG GAGTGTGACG ATGCTGCCAC TTACTACTGT
GCAGGCGGTT ATAGTGGTAA TATTCATGTT TTCGGCGGAG GGACCAAGGT GGTGGTCAAA

Heavy DNA CA167_01084 (SEQ ID NO: 190)
CAGTCGGTGG AGGAGTCCGG GGGTCGCCTG GTCACGCCTG GGACACCCCT GACACTCACC TGCACAGTCT CTGGATTCTC CCTCAATAAC
TACGACATGA CCTGGGTCCG CCAGGCTCCA GGGAAGGGGC TGGAATGGAT CGGAAGTATT TTTGTTAGTG GTAATATATA CTACGCGAGC
TGGGCGAAAG GCCGATTCAC CATCTCCAAA ACCTCGACCA CGGTGGATCT GAAAATGACC AGTCCGACAA CCGAGGACAC GGCCACCTAT
TTCTGTGCCA GAGCAATTCT TGGTAGTAGT AAGGGGTTGT GGGGCCCAGG CACCCTGGTC ACCGTCTCG

Light Protein CA167_01084 (SEQ ID NO: 191)
AQVLTQTPSS TSAAVGGTVT ISCQSSPSVY GNNWLGWYQK KPGQPPKLLI YSASTLASGV SSRFKGSGSG TQFTLTISDL ECDDAATYYC
AGGYSGNIHV FGGGTKVVVK

Figure 13

Heavy Protein CA167_01084 (SEQ ID NO: 192)
QSVEESGGRL VTPGTPLTLT CTVSGFSLNN YDMTWVRQAP GKGLEWIGSI FVSGNIYYAS WAKGRFTISK TSTTVDLKMT SPTTEDTATY FCARAILGSS KGLWGPGTLV TVS

Light DNA CA167_01085 (SEQ ID NO: 193)
GCCTATGATA TGACCCAGAC TCCAGCCTCT GTGGAGGTAG CTGTGGGAGG CACAGTCACC ATCAATTGCC AGGCCAGTCA GAGCATTTAC AGCTATTTAG CCTGGTATCA GCAGAAACCA GGGCAGCCTC CCAAGCTCCT GATTTATTCT GCATCCTATC TAGCATCTGG GGTCCCATCG CGGTTCAGCG GCAGTGGATC TGGGACAGAG TTCACTCTCA CCATCAGCGA CCTGGAGTGT GCCGATGCTG CCACTTATTA CTGTCAACAC GGGTACATTA GTGGTAATGT TGATAATGCT TTCGGCGGAG GGACCAAGGT GGTCGTCAAA
CAGTCGGTGG AGGAGTCCGG GGGTCGCCTG GTCACGCCTG GGACACCCCT CTGGATTCTC CCTCAGCATC TACGACATGA GCTGGGTCCG CCAGGCTCCA GGGAAGGGGC TGGAATGGAT CGGATCCATT TATGTTAGTG GTAATATATA CTACGCGAGC TGGGCGAAAG GCCGATTCAC CATCTCCAAA ACCTCGACCA CGGTGGATCT GAAAATGACC AGTCCGACAA CCGAGGACAC GGCCACCTAT TTCTGTGCCA GAGCGGTTCC TGGTAGTAGT TGGGGCCAGG GACCCTCGTC ACCGTCTCG
AYDMTQTPAS VEVAVGGTVT IKCQASQSIY SYLAWYQQKP GQPPKLLIYS ASYLASGVPS RFSGSGSGTE FTLTISDLEC ADAATYYCQH GYISGNVDNA FGGGTKVVVK

Heavy Protein CA167_01085 (SEQ ID NO: 195)

Heavy DNA CA167_01086 (SEQ ID NO: 196)
QSVEESGGRL VTPGTPLTLT CTVSGFSLSI YDMSWVRQAP GKGLEWIGSI YVSGNIYYAS WAKGRFTISK TSTTVDLKMT SPTTEDTATY FCARAVPGSS KGLWGQGTLV TVS

Light DNA CA167_01086 (SEQ ID NO: 197)
GCGCAAGTGC TGACCCAGAC TCCATCCCCT CGGGGGAGGC GTGTCTGCAG CAAAGTCACC ATCAATTGCC AGTCCAGTCA GAGTATTTAT ACTAACTACT TATCCTGGTA TCAGCAGAAA CCAGGACAGC CTCCCAGGCT CCTGATCTAT TCTGCATCCA CTCTGGCATC TGGGGTCCCA TCGCGGTTCA AAGGCAGTGG AGCTGGGACA CAGTTCACTC TCACAATCAG CGAAGTACAG TGTGACGATG CTGCCACTTA CTACTGTCAA GCCTATTTTA CTGGTGAGAT TTTTCCTTTC GGCGGAGGGA CCAAGGTGGT CGTCAAA
CAGGAGCAAC TGAAGGAGTC CGGGGGAGGC CTGGTAACGC CTGGAGAAAC CCTGACACTC ACCTGCACCG TCTCTGGATT CTCCCTCGAT AACTACCACA TGGGCTGGGT CCGCCAGGCT CCAGGAAAGG GGCTCAATTA CATCGGATTC ATTACTCGTG GTGGTACCAC ATACTACGCG AGCTGGGCGA AGGGCCGATT CACCATCTCC AAAACCTCGA CCAGGTTGGA TCTGATGATC ACCAGTCCGA CAACCGGGGA CACCGCCACC TATTTCTGTG CCAGAGGAAG TGGCCGCTAG TGGCTTTTACT TGTGGGGCCC AGGCACCCTG GTCACCGTCT CG
AQVLTQTPSP VSAAVGKVT INCQSSQSIY TNYLSWYQQK PGQPPRLLIY SASTLASGVP SRFKGSGSGT QFTLTISEVQ CDDAATYYCQ AYFTGEIFPF GGGTKVVVK

Heavy Protein CA167_01086 (SEQ ID NO: 200)
QEQLKESGGG LVTPGGTLTL TCTVSGFSLD NYHMGWVRQA PGKGLNYIGF ITRGGTTYYA SWAKGRFTIS KTSTTVDLMI TSPTTGDTAT YFCARGSGAS GFYLWGPGTL VTVS

DNA ENCODING FUNCTION MODIFYING NA$_v$1.7 ANTIBODIES

CROSS REFERENCE TO RELATED APPLICATIONS

The present application claims priority under 35 U.S.C. §119(a) to provisional application Ser. No. 61/255,202, Filed: Oct. 27, 2009, which is incorporated by reference herein in its entirety.

The present disclosure relates to anti-Na$_v$1.7 antibodies and fragments thereof, with functionally modifying properties, pharmaceutical compositions comprising said antibodies, use of the antibodies and compositions comprising the same, in treatment, for example in the treatment/modulation of pain and processes for generating and preparing said antibodies.

Ion channels are pore-forming proteins that help establish and control cell membrane potential of all living cells by allowing the flow of ions down their electrochemical gradient. They are present in the membranes that surround all biological cells. The human genome contains more than 400 ion channel genes presenting a large diversity and play critical roles in many cellular processes such as secretion, muscular contraction and the generation and propagation of action potentials in cardiac and neuronal tissues.

Ion channels are integral membrane proteins that may adopt large molecular structures based on the assembly of several proteins. Such "multi-subunit" assemblies usually involve an arrangement of identical or homologous proteins closely packed around a water-filled pore through the plane of the membrane or lipid bilayer. The pore-forming subunit(s), usually called the α subunit, may be associated with auxiliary subunits, either membrane bound or cytosolic, that help to control activity and cell surface expression of the ion channel protein. The X-ray structure of various ion channels was recently resolved (Doyle et al. Science 280:69 (1998); Jiang et al., Nature 423:33 (2003); Long et al., Science 309:897 (2005)) and indicate that the organization of the pore structure is largely conserved among ion channel family members. The opening and closing of the ion channel pore, referred as the gating process, may be triggered by various cellular or biochemical processes. The voltage-gated and ligand-gated ion channels are the most prominent members of the ion channel protein family. The activity of voltage-gated ion channels (e.g. calcium, sodium and potassium channels) is controlled by changes in cell membrane potentials whereas the ligand-gated ion channels (e.g. GABA-A receptors, Acethylcholine receptors, . . . ) are controlled by the binding of specific intracellular or extracellular ligands. The gating mechanism is very complex, involving various membrane, pore and cytosolic structures, and differs between classes of ion channels.

Voltage-gated ion channels, sometimes referred to voltage-sensitive ion channels, are a class of transmembrane proteins that provide a basis for cellular excitability in cardiac and neuronal tissues. These channels are activated either by cell hyper- or depolarizations and generate ion fluxes that lead to control of cell membrane potential. Voltage-gated sodium channels are generally responsible for the initiation of action potentials whereas voltage gated potassium channels mediate cell membrane repolarization. The fine tuned interplay between various voltage-gated ion channels is critical for the shaping of cardiac and neuronal action potentials.

The class of voltage-gated sodium channels comprises nine different isoforms (Nav1.1-1.9) and four different sodium channel specific accessory proteins have been described (SCN1b-SCN4b). The distinct functional activities of those isoforms have been described in a variety of neuronal cell types (Llinas et al., J. Physiol. 305:197-213 (1980); Kostyuk et al., Neuroscience 6:2423-2430 (1981); Bossu et al., Neurosci. Lett. 51:241-246 (1984) 1981; Gilly et al., Nature 309:448-450 (1984); French et al., Neurosci. Lett. 56:289-294 (1985); Ikeda et al., J. Neurophysiol. 55:527-539 (1986); Jones et al., J. Physiol. 389:605-627 (1987); Alonso & Llinas, 1989; Gilly et al., J. Neurosci. 9:1362-1374 (1989)) and in skeletal muscle (Gonoi et al., J. Neurosci. 5:2559-2564 (1985); Weiss et al., Science 233:361-364 (1986)). The Nav1.5 and Nav1.4 channels are the major sodium channel isoforms expressed in the cardiac and muscular tissue, respectively whereas Nav1.1, 1.2, 1.3, 1.6, 1.7, 1.8 and 1.9 are specifically expressed in the central and peripheral nervous system. The use of the natural occurring toxin, tetrodotoxin (TTX), allowed to establish a pharmacological classification of the sodium channel isoforms based on their affinity to the toxin. The voltage-gated sodium channels were thus classified as TTX resistant (Nav1.5, 1.8, 1.9) and TTX sensitive.

Certain ion channels have been associated with modulation of pain (see for example PNAS Nov. 6, 2001. vol 98 no. 23 13373-13378 and The Journal of Neuroscience 22, 2004 24(38) 832-836). The ion channel Nav1.7 is believed to have the ability to modulate pain, such as neuropathic pain and thus is a particularly interesting target for therapeutic intervention.

Na$_v$1.7 is a voltage-activated, tetrodotoxin-sensitive sodium channel encoded by the gene SCN9A. Both gain-of-function and loss-of-function mutations of Na$_v$1.7 result in clear pain-related abnormalities in humans.

Originally, gain-of-function mutations in SCN9A were identified by linkage analysis as the cause of erythromelalgia (or primary erythermalgia) and paroxysmal extreme pain disorder (formerly familiar rectal pain). Erythromelalgia is a rare autosomal dominant disorder associated with bouts of burning pain together with heat and redness in the extremities. The complete inability to sense pain by an otherwise healthy individual, devoid of neuropathy, is a very rare phenotype. Very recently, two studies, reported by Cox et al (2006) and by Goldberg et al (2007), describe such a phenotype mapped, as an autosomal-recessive trait, to chromosome 2q24.3, a region containing the gene SCN9A. In both studies, detailed neurological tests revealed that these people are able to distinguish sharp/dull and hot/cold stimuli but have a global absence of pain sensation. All had injuries to lips and/or tongue caused by biting themselves. All had frequent bruises and cuts, and most suffered fractures or osteomyelitis.

This data constitutes strong evidence that SCN9A channelopathy, leading to loss of function of ion channel Na$_v$1.7, is associated with insensitivity to pain, in the absence of neuropathy or of cognitive, emotional or neurological disorders, and clinically validate Na$_v$1.7 as a pain-relevant target. Furthermore, from KO studies and animal pain models, it would appear that Na$_v$1.7 plays a major role in inflammatory pain.

FIG. 2a is a diagrammatic representation of Na$_v$1.7, which comprises four domains A, B, C and D (also referred to as domain I, II, III and IV). Each domain comprises 6 transmembrane protein helixes S1, S2, S3, S4, S5 and S6. The exact amino acid number of each transmembrane protein varies depending on the database entry employed but UniProtKB/Swiss-Prot provides the following information for Nav1.7:

in domain A transmembrane protein S1, S2, S3, S4, S5 and S6 are assigned amino acids 122-145, 154-173, 187-205, 212-231, 248-271 and 379-404, respectively;

in domain B transmembrane protein S1, S2, S3, S4, S5 and S6 are assigned amino acids 739-763, 775-798, 807-826, 833-852, 869-889 and 943-968 respectively;

in domain C transmembrane protein S1, S2, S3, S4, S5 and S6 are assigned amino acids 1188-1211, 1225-1250, 1257-1278, 1283-1304, 1324-1351 and 1431-1457 respectively; and in domain D transmembrane protein S1, S2, S3, S4, S5 and S6 are assigned amino acids 1511-1534, 1546-1569, 1576-1599, 1610-1631, 1647-1669 and 1736-1760, respectively.

There are a number of natural variations of the sequence that are available in public databases, for example see UniProtKB/Swiss-Prot Q15858.

In the present disclosure S1, S2, S3, S4, S5 and S6 refers to the entities described above or a corresponding entity in $Na_v1.7$ including wherein a different amino acid assignment is given to the same and including the corresponding entity in natural or non-natural variants and different isotypes of the same.

Each domain also contains extra-cellular hydrophilic loops E1, E2 and E3. The amino acid sequence of E1 in each domain starts after the transmembrane region S1 and ends at S2. E1 in each domain is distinct from E1 in other domains. The amino acid sequence of E2 in each domain starts after the transmembrane region S3 and ends at S4. E2 in each domain is distinct from E2 in other domains. The amino acid sequence of E3 in each domain starts after the transmembrane region S5 and ends at S6. E3 in each domain is also distinct from E3 in other domains.

Whilst the $Na_v$ and $Ca_v$ ion channels comprise four domains, A, B, C and D, each containing six transmembrane protein helixes, other ion channels, such as $K_v$ ion channels, HCN ion channels and TRP ion channels comprise one domain. As for each domain in the $Na_v$ and $Ca_v$ ion channels, the $K_v$ ion channels, HCN ion channels and TRP ion channels comprise 6 transmembrane protein helixes S1, S2, S3, S4, S5 and S6 and three extra-cellular hydrophilic loops E1, E2 and E3 as described above.

In a $Na_v1.7$ ion channel, the extracellular loops (E loops) are the following amino acid residues of SEQ ID NO:205 in FIG. 2c:

| $Na_v1.7$ Domain | E1 amino acids | E2 amino acids | E3 amino acids |
| --- | --- | --- | --- |
| A | 146-153 | 206-211 | 272-378 |
| B | 764-774 | 827-832 | 890-942 |
| C | 1212-1224 | 1279-1282 | 1352-1430 |
| D | 1535-1545 | 1600-1609 | 1670-1735 |

The extracellular loops in some domains of $Na_v1.7$ share similarities with extracellular loops found in other ion channels.

$Na_v1.7$ is expressed in the peripheral nervous system i.e. in nociceptive dorsal root ganglions (DRG), most notably in nociceptive small-diameter DRG neurons, with little representation in the brain. $Na_v1.7$ distribution (e.g. sensory ending) and physiology predispose it to a major role in transmitting painful stimuli.

The expression of $Na_v1.7$ in the peripheral nervous system makes it a very attractive target for the generation of function blocking antibodies which represent an innovative approach for valuable treatment for pain with no side-effects or minimizing side effects to a tolerable level.

Neuropathic pain is a highly prevalent condition. In the United States, it is estimated to affect between 0.6 and 1.5% of the population, or 1.8 to 4.5 million people. (Pullar and Palmer, 2003). At least 1.4 million people each year are diagnosed with painful diabetic neuropathy (PDN), post-herpetic neuropathy (PHN) or trigeminal neuralgia (TN)—three major causes of neuropathic pain. Other causes of neuropathic pain include spinal cord injuries, multiple sclerosis, phantom limb pain, post-stroke pain and HIV-associated pain. If patients with neuropathic-related chronic back pain, osteoarthritis and cancer were included, the total number would at least double. Nonsteroidal anti-inflammatory drugs (NSAIDs) although frequently used, are not very effective in the treatment of neuropathic pain. Moreover, their chronic use may lead to serious gastric damage. On the other hand, the use of opioids (morphine and derivatives) is restricted to the most severe form of neuropathic pain, i.e., cancer-related neuropathy, because serious side-effects are associated with chronic treatment, such as nausea, emesis, respiratory depression, constipation and tolerance, and the potential for addiction and abuse. The latter have prevented the use of opioids in other neuropathies (Dellemijn, 1999; Namaka et al., 2004). Anti-epileptic drugs (AEDs) are known to attenuate abnormal neural hyperexcitability in the brain. In view of neural hyperexcitability playing a crucial role in neuropathic pain, it is understandable that AEDs were aimed at the treatment of chronic neuropathic pain (Renfrey, Downton and Featherstone, 2003). The most recent and important examples are gabapentin (Neurontin) and pregabalin (Lyrica, Frampton and Scott, 2004). However, even gabapentin, the gold standard for the treatment of neuropathic pain, reduces pain at best by 50% in about 40% of patients (Dworkin, 2002). Further, in contrast to opioids, gabapentin is not used in the treatment of cancer-related neuropathic pain.

As stated above, $Na_v1.7$ 'loss of function' mutation in human leads to insensitivity to pain (Cox et al., 2006). Moreover, $Na_v1.7$ 'gain of function' mutation in human leads to the pain phenotypes erythromelalgia and paroxysmal extreme pain disorder (Dib-Hajj, Yang, Waxman, 2008). Additionally, a peripherally acting small molecule blocking $Na_v1.7$ reverses hyperalgesia and allodynia in rat models of inflammatory and neuropathic pain (McGowan et al., 2009). Therefore a peripherally acting $Na_v1.7$ blocking antibody should be beneficial for pain therapy.

To date potent chemical inhibitors of ion channels have been identified but generally these are characterised by a poor selectivity against other ion channel isoforms. Given the ubiquitous distribution of ion channels in living organisms these non-selective inhibitors have been of limited utility.

Whilst antibodies are clearly desirable, due to their exquisite specificity, it has not been wholly straightforward to generate functionally modifying antibodies, in part, because clonal antibodies are ultimately required for therapeutic applications and some researchers' in the field have indicated that polyclonal antibodies are required for effecting modification of the function of ion channels. Klionsky et al., 2006 (The Journal of Pharmacology and Experimental Therapeutics Vol 319 No. 1 page 192-198) states on page 198:

"Since no rabbit, mouse or fully human monoclonal antibodies generated against the prepore region of human TRPV1 . . . were effective in blocking channel activation we hypothesise that it may not be possible to lock the channel conformation through high-affinity binders to small epitopes in this region".

$Na_v1.7$ seems to have been a particularly challenging target in respect of generating functionally modifying antibodies. However, the present inventors have now found that the activity of $Na_v1.7$ ion channels can be altered employing functionally modifying antibodies, for example a clonal population of antibodies. To date whilst antibodies to ion channels have been generated it is believed that no functionally modifying antibodies to $Na_v1.7$ have been disclosed.

SUMMARY OF THE INVENTION

Thus the invention provides an anti-Na$_v$1.7 antibody or binding fragment thereof which after binding the ion channel is functionally modifying thereto.

BRIEF DESCRIPTION OF THE DRAWINGS

FIG. 2b shows the amino acid sequence for domain A (SEQ ID NO:201), B (SEQ ID NO:202), C (SEQ ID NO:203) and D (SEQ ID NO:204) of Na$_v$1.7.

FIG. 2c shows the full amino acid sequence of Nav1.7 (SEQ ID NO:205).

FIGS. 4-13 show the amino acid and DNA sequence of certain anti-Na$_v$1.7 antibodies.

DETAILED DESCRIPTION OF THE INVENTION

Figure 1:
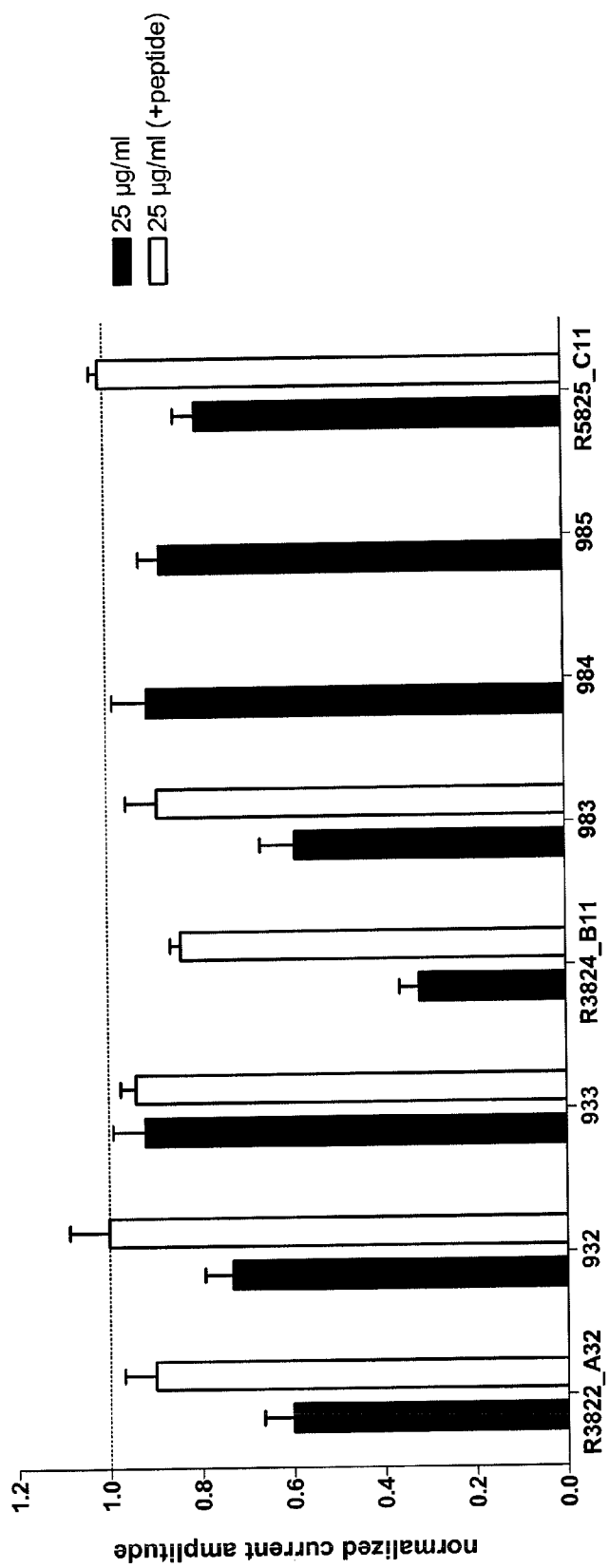
FIG. 1 shows the functional effects of certain monoclonal antibodies on human Na$_v$1.7 current in HEK cells.
Figure 2A:
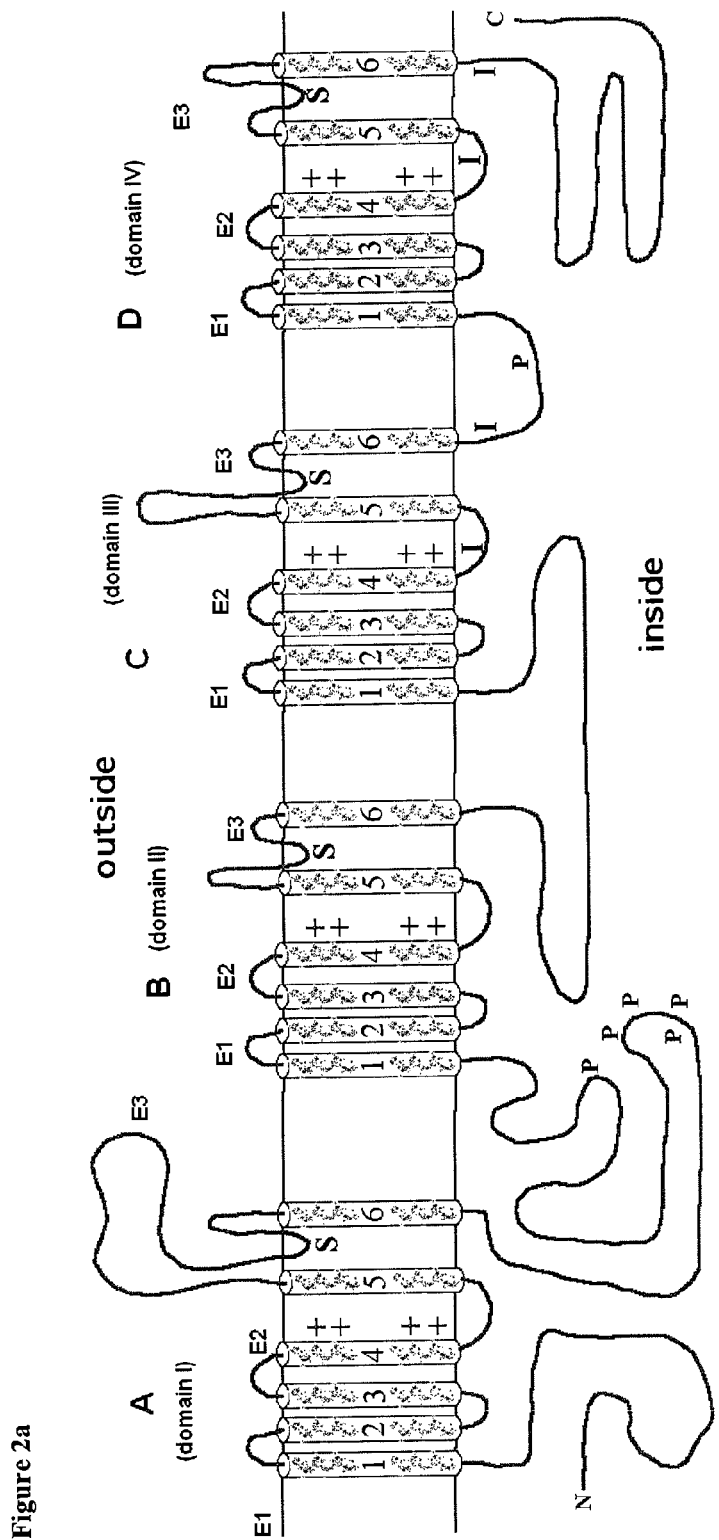
FIG. 2a shows a diagrammatic representation of Na$_v$1.7.

In one aspect the present disclosure provides a Na$_v$1.7 binding entity that functionally modifies the activity of the ion channel, including an antibody, an antibody fragment, a protein or proteinaceous scaffold, a nucleic acid or nucleotide, a small molecule such as a synthetic molecule or the like, in particular an antibody, an antibody fragment, a protein or proteinaceous scaffold, a nucleic acid or nucleotide.

In one embodiment the invention provides an anti-Na$_v$1.7 antibody or binding fragment thereof which after binding to Na$_v$1.7 is functionally modifying thereto.

Functionally modifying antibody as employed herein is intended to refer to an antibody or fragment (such as a binding fragment) that changes the activity of the ion channel, for example by reducing an activity by at least 5%, for example 10 or 15% such as 20% in at least one in vitro or in vivo assay. Suitable in vitro assays include a patch clamp assay or other assay as described herein. In one embodiment the functionally modifying antibody reduces the amplitude of current through a patch clamp assay by 5%, 10%, 15%, 20%, 30%, 40%, 50%, 60%, 70% or more percent. In one example the patch clamp assay is conducted using recombinant human Nav1.7 channels expressed in HEK cells as described in the examples herein and the amplitude of current through the patch clamp assay determined.

An antibody that provides a functional modification to the ion channel and a functionally modifying antibody are terms used interchangeably herein.

In one embodiment the functional modification is, for example sufficient to block, close or inhibit the pore of the ion channel. This functional modification may be effected by any mechanism including, physically blocking the pore, causing a conformational change in the ion channel which for example blocks the pore or eliciting the ion channel to adopt a non-functional state (resting or inactivated state) and/or maintaining the ion channel in a non-functional state (allosteric modulation).

In one embodiment the functional modification is sufficient to reduce the cell surface levels of the ion channel protein. This functional modification may be effected by any mechanism including but not limited to, antibody induced internalization or endocytosis or increased cycling of the ion channel, leading to a reduce number of functional ion channel proteins at the cell surface.

The mechanisms proposed supra for functional modification of the ion channel are examples and are not intended to be limiting in respect of ways the a functionally modifying antibody may generate a functionally modifying effect in the ion channel.

Alignment of Nav 1.7 with other available family members, i.e Nav1.1, Nav 1.2, Nav 1.3, Nav 1.4, Nav 1.5, Nav 1.6, Nav 1.8 and Nav 1.9 allows the identification of differences in the sequence of Na$_v$1.7 extracellular domains vs the extracellular domains of the other ion channels. Points of particular difference include: amino acid residues: 146, 276, 279, 280, 281, 286, 287, 290, 291, 292, 293, 295, 296, 299, 300, 301, 305, 317, 319, 329, 333, 773, 1218, 1224, 1357, 1360, 1361, 1363, 1365, 1367, 1371, 1376, 1377, 1379, 1385, 1394, 1409, 1410, 1419, 1420, 1423, 1536, 1537, 1538, 1542, 1545, 1601, 1673, 1676, 1711, 1718, 1719, 1720 and 1727.

In one embodiment the antibody or fragment binds an extra-cellular (or extra-cellular accessible region) of domain A in the ion channel.

In one embodiment the antibody or fragment binds an extra-cellular (or extra-cellular accessible region) of domain B in the ion channel.

In one embodiment the antibody or fragment binds an extra-cellular (or extra-cellular accessible region) of domain C in the ion channel.

In one embodiment the antibody or fragment is binds an extra-cellular (or extra-cellular accessible region) of domain D in the ion channel.

In one embodiment the antibody or fragment binds in an E1 region of the ion channel, for example binds part or all of the E1 region of domain A, B, C or D, such as domain B.

In one embodiment the antibody or fragment binds in the E3 region of the ion channel, for example part of the E3 region of domain A, B, C or D, such as domain A.

An anti-Na$_v$1.7 antibody is an antibody that binds specifically to Na$_v$1.7. Specific binding is intended to refer to the fact that the antibody is selective for Na$_v$1.7 and can distinguish it from other ion channels and proteins, for example other ion channels in the same family. A selective antibody is one that, for example can be used to affinity purify Na$_v$1.7 including from other ion channels.

In one embodiment the anti-Na$_v$1.7 antibody is specific to mammalian Na$_v$1.7, for example human Na$_v$1.7.

In one embodiment the anti-Na$_v$1.7 antibody cross-reacts with human Na$_v$1.7 and rat Na$_v$1.7.

In one embodiment the anti-Na$_v$1.7 antibody cross-reacts with human Na$_v$1.7 and mouse Na$_v$1.7.

In one embodiment the functionally modifying antibody or fragment is a clonal population of antibodies, for example a monoclonal population. It has been suggested in the literature that polyclonal antibodies are required to obtain functional modification of ion channels. Therefore, it is particularly surprising that the present disclosure provides monoclonal antibodies which are functionally modifying to Na$_v$1.7.

Monoclonal as employed herein is intended to refer antibodies or fragments derived from a single cell, for example by employing hybridoma technology or single lymphocyte antibody methods by cloning and expressing immunoglobulin variable region cDNAs generated from single lymphocytes selected for the production of specific antibodies by, for example, the methods described by Babcook, J. et al., *Proc. Natl. Acad. Sci. USA*, 1996, 93(15), 7843-7848, WO 92/02551, WO2004/051268 and WO2004/106377.

A clonal population is intended to refer to a population of antibodies or fragments with the same properties, characteristics including the same amino acid sequence and specificity.

In one embodiment the antibody is a whole antibody.

In one embodiment the antibody or fragment thereof is multivalent and/or bi-specific. Multivalent as employed herein is intended to refer multiple binding sites (for example at least two binding sites) in the antibody or fragment entity. Multivalent entities, in the context of the present specification, have at least two binding sites with the same specificity. Mutivalent antibodies with binding sites that bind the same epitope will not be considered bi-specific unless the entity comprises a third binding site with different specificity to a first and second binding site.

In an entity with multiple binding sites where each binding site binds a different epitope on the same or different target antigen, then the antibody or fragment entity will be considered bispecific, within the meaning of the present disclosure.

Binding site as employed herein is intended to refer to an area of the antibody or fragment, which specifically binds a target antigen. A heavy chain variable domain and light chain variable domain pairing will be considered an example of a binding site herein.

In one embodiment an antibody fragment according to the disclosure is monovalent. That is to say, has only one binding site.

In one embodiment the antibody is a fragment, for example a single domain antibody, a single chain Fv, a Fab, a Fab' or a pairing of a full length heavy and light chain.

The antibody of the disclosure and fragments thereof, of use in the present invention, can be from any species but are preferably derived from a monoclonal antibody, a human antibody, or are humanised fragments. An antibody fragment for use in the present invention can be derived from any class (e.g. IgG, IgE, IgM, IgD or IgA) or subclass of immunoglobulin molecule and may be obtained from any species including for example mouse, rat, shark, rabbit, pig, hamster, camel, llama, goat or human.

The residues in antibody variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al. (supra)"). This numbering system is used in the present specification except where otherwise indicated.

The Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence.

The CDRs of the heavy chain variable domain are located at residues 31-35 (CDR-H1), residues 50-65 (CDR-H2) and residues 95-102 (CDR-H3) according to the Kabat numbering system. Kabat numbering will be employed herein.

An alternative number system, not used herein, is Chothia (Chothia, C. and Lesk, A. M. J. Mol. Biol., 196, 901-917 (1987)), where the loop equivalent to CDR-H1 extends from residue 26 to residue 32. A combination of Chothia and Kabat numbering for 'CDR-H1', would for example comprises residues 26 to 35.

The CDRs of the light chain variable domain are located at residues 24-34 (CDR-L1), residues 50-56 (CDR-L2) and residues 89-97 (CDR-L3) according to the Kabat numbering system.

Below is provided the CDRs for various rabbit antibodies:

| | | | |
|---|---|---|---|
| CA167 00914 | CDR-L1 | QASESIGTALA | Seq Id No: 1 |
| | CDR-L2 | KASTLES | Seq Id No: 2 |
| | CDR-L3 | QQGETANRIDNA | Seq Id No: 3 |
| | CDR-H1 | RNAMT | Seq Id No: 4 |
| | CDR-H2 | YINTRGDTSYANWAKG | Seq Id No: 5 |
| | CDR-H3 | GYNPCKL | Seq Id No: 6 |
| CA167 00915 | CDR-L1 | QASESINTALA | Seq Id No: 7 |
| | CDR-L2 | AASDLAS | Seq Id No: 8 |
| | CDR-L3 | QQGYTANNIDNA | Seq Id No: 9 |
| | CDR-H1 | RNAMT | Seq Id No: 4 |
| | CDR-H2 | YINTRGGASYANWAKG | Seq Id No: 11 |
| | CDR-H3 | GYNPCKL | Seq Id No: 6 |
| CA167 00930 | CDR-L1 | QSSQNVVNNNWFS | Seq Id No: 13 |
| | CDR-L2 | FVSKLAS | Seq Id No: 14 |
| | CDR-L3 | GGGYSDNIYA | Seq Id No: 15 |
| | CDR-H1 | YYAIS | Seq Id No: 16 |
| | CDR-H2 | IIGSSGRTYYASWAKG | Seq Id No: 17 |
| | CDR-H3 | GGPTSSPSL | Seq Id No: 18 |
| CA167 00931 | CDR-L1 | QASQSVYGTNRLS | Seq Id No: 19 |
| | CDR-L2 | GASTLTS | Seq Id No: 20 |
| | CDR-L3 | LGGWFESSSSLDWA | Seq Id No: 21 |
| | CDR-H1 | RNAMG | Seq Id No: 22 |
| | CDR-H2 | HIASRGNINFRNWAKG | Seq Id No: 23 |
| | CDR-H3 | FLVVSGVGTFDP | Seq Id No: 24 |
| CA167 00932 | CDR-L1 | QSSQSVYNNNEFS | Seq Id No: 25 |
| | CDR-L2 | DASKLAS | Seq Id No: 26 |
| | CDR-L3 | LGGYNDDTNRWA | Seq Id No: 27 |
| | CDR-H1 | RYWMS | Seq Id No: 28 |
| | CDR-H2 | NIGGGSGSTLYAPWAKG | Seq Id No: 29 |
| | CDR-H3 | YVKNGGGYRLDL | Seq Id No: 30 |
| CA167 00933 | CDR-L1 | QASESVANNNWLA | Seq Id No: 31 |
| | CDR-L2 | KASTLAS | Seq Id No: 32 |
| | CDR-L3 | AGYKSSTTDAVA | Seq Id No: 33 |
| | CDR-H1 | SYAIS | Seq Id No: 34 |
| | CDR-H2 | FINTITGGTNYASWAKS | Seq Id No: 35 |
| | CDR-H3 | SGAYFDL | Seq Id No: 36 |

-continued

| | | | |
|---|---|---|---|
| CA167 00983 | CDR-L1 | QSSQSVYKNNDLA | Seq Id No: 37 |
| | CDR-L2 | YASTLAS | Seq Id No: 38 |
| | CDR-L3 | LGSYDCSSADCNA | Seq Id No: 39 |
| | CDR-H1 | NYAMS | Seq Id No: 40 |
| | CDR-H2 | IIGKSGSTAYASWAKG | Seq Id No: 41 |
| | CDR-H3 | FVLL | Seq Id No: 42 |
| CA167 00984 | CDR-L1 | QSSQSVNNNNFLS | Seq Id No: 43 |
| | CDR-L2 | RASTLAS | Seq Id No: 44 |
| | CDR-L3 | AGGYSGNIYA | Seq Id No: 45 |
| | CDR-H1 | DYIIN | Seq Id No: 46 |
| | CDR-H2 | IMGTSGTAYYASWAKG | Seq Id No: 47 |
| | CDR-H3 | GGVATSNF | Seq Id No: 48 |
| CA167 00985 | CDR-L1 | QSSQSVYGNNWLG | Seq Id No: 49 |
| | CDR-L2 | SASTLAS | Seq Id No: 50 |
| | CDR-L3 | VGGYSGNIHV | Seq Id No: 51 |
| | CDR-H1 | DYDMS | Seq Id No: 52 |
| | CDR-H2 | TIYVSGNTYYATWAKG | Seq Id No: 53 |
| | CDR-H3 | AVPGSGKGL | Seq Id No: 54 |
| CA167 01059 | CDR-L1 | QASQSLYNKKNLA | Seq Id No: 55 |
| | CDR-L2 | YASTLAS | Seq Id No: 38 |
| | CDR-L3 | QGEFSCSSVDCVA | Seq Id No: 57 |
| | CDR-H1 | SYAMT | Seq Id No: 58 |
| | CDR-H2 | IIYASDTYYTSWAKG | Seq Id No: 59 |
| | CDR-H3 | GDSTSGFHLTL | Seq Id No: 60 |
| CA 167 01060 | CDR-L1 | QASQSLYNKKNLA | Seq Id No: 55 |
| | CDR-L2 | FASTLAS | Seq Id No: 62 |
| | CDR-L3 | QGEFICSSGDCVA | Seq Id No: 63 |
| | CDR-H1 | SYAMT | Seq Id No: 58 |
| | CDR-H2 | IIYGTETIYYATRAKG | Seq Id No: 65 |
| | CDR-H3 | GDSTSGFHLTL | Seq Id No: 60 |
| CA167 01060 | CDR-L1 | QASQSLYNKKNLA | Seq Id No: 55 |
| | CDR-L2 | FASTLAS | Seq Id No: 62 |
| | CDR-L3 | QGEFICSSGDCVA | Seq Id No: 63 |
| | CDR-H1 | SYAMT | Seq Id No: 58 |
| | CDR-H2 | IIYGTETIYYATRAKG | Seq Id No: 65 |
| | CDR-H3 | GDSTSGFHLTL | Seq Id No: 60 |
| CA167 01066 | CDR-L1 | QASQSLYNKKNLA | Seq Id No: 55 |
| | CDR-L2 | FTSTLAS | Seq Id No: 68 |
| | CDR-L3 | QGEFSCSSGDCLA | Seq Id No: 69 |
| | CDR-H1 | SYAMT | Seq Id No: 58 |
| | CDR-H2 | IIYGTELTYYATWAKG | Seq Id No: 71 |
| | CDR-H3 | GDATSGFHLTL | Seq Id No: 72 |
| CA167 01068 | CDR-L1 | QASQTIYSGLA | Seq Id No: 73 |
| | CDR-L2 | RASTLAS | Seq Id No: 44 |
| | CDR-L3 | QVGGYGVSYDHA | Seq Id No: 75 |
| | CDR-H1 | SSYWIC | Seq Id No: 76 |
| | CDR-H2 | CIYGGSINIINYASWAKG | Seq Id No: 77 |
| | CDR-H3 | VQGGNSGGWYFDL | Seq Id No: 78 |
| CA167 01080 | CDR-L1 | QSSQSVWKNNDLS | Seq Id No: 79 |
| | CDR-L2 | YASTLAS | Seq Id No: 38 |
| | CDR-L3 | VGSYDCSSADCNA | Seq Id No: 81 |
| | CDR-H1 | KWPMT | Seq Id No: 82 |
| | CDR-H2 | IIGRSGSTNYASWAKG | Seq Id No: 83 |
| | CDR-H3 | GGSYYDL | Seq Id No: 84 |
| CA167 01081 | CDR-L1 | QSSQSVDNNNYLS | Seq Id No: 85 |
| | CDR-L2 | DASDLAS | Seq Id No: 86 |
| | CDR-L3 | AGGYITSSDIFYD | Seq Id No: 87 |
| | CDR-H1 | TYAMS | Seq Id No: 88 |
| | CDR-H2 | IVGKSGIIKYASWAKG | Seq Id No: 89 |
| | CDR-H3 | LWSL | Seq Id No: 90 |
| CA167 01082 | CDR-L1 | QASQSISNWLA | Seq Id No: 91 |
| | CDR-L2 | RASTLAS | Seq Id No: 44 |
| | CDR-L3 | QSDYGIDTYGSA | Seq Id No: 93 |
| | CDR-H1 | SYAMT | Seq Id No: 58 |
| | CDR-H2 | MVRRSGTTYYASWAKG | Seq Id No: 95 |
| | CDR-H3 | CDNSAGDWSYGMDL | Seq Id No: 96 |
| CA167 01083 | CDR-L1 | QASQSVYQNNYLA | Seq Id No: 97 |
| | CDR-L2 | SASTLAS | Seq Id No: 50 |
| | CDR-L3 | LGAYDCSGVDCSA | Seq Id No: 99 |
| | CDR-H1 | TNAMI | Seq Id No: 100 |
| | CDR-H2 | VIAGSGSTSYASWAKG | Seq Id No: 101 |
| | CDR-H3 | GGWVSGPESL | Seq Id No: 102 |
| CA167 01084 | CDR-L1 | QSSPSVYGNNWLG | Seq Id No: 103 |
| | CDR-L2 | SASTLAS | Seq Id No: 50 |
| | CDR-L3 | AGGYSGNIHV | Seq Id No: 105 |
| | CDR-H1 | NYDMT | Seq Id No: 106 |
| | CDR-H2 | SIFVSGNIYYASWAKG | Seq Id No: 107 |
| | CDR-H3 | AILGSSKGL | Seq Id No: 108 |

-continued

| | | | |
|---|---|---|---|
| CA167 01085 | CDR-L1 | QASQSIYSYLA | Seq Id No: 109 |
| | CDR-L2 | SASYLAS | Seq Id No: 110 |
| | CDR-L3 | QHGYISGNVDNA | Seq Id No: 111 |
| | CDR-H1 | IYDMS | Seq Id No: 112 |
| | CDR-H2 | SIYVSGNIYYASWAKG | Seq Id No: 113 |
| | CDR-H3 | AVPGSSKGL | Seq Id No: 114 |
| CA167 01086 | CDR-L1 | QSSQSIYTNYLS | Seq Id No: 115 |
| | CDR-L2 | SASTLAS | Seq Id No: 50 |
| | CDR-L3 | QAYFTGEIFP | Seq Id No: 117 |
| | CDR-H1 | NYHMG | Seq Id No: 118 |
| | CDR-H2 | FITRGGTTYYASWAKG | Seq Id No: 119 |
| | CDR-H3 | GSGASGFYL | Seq Id No: 120 |

In one embodiment the disclosure herein extends to an antibody comprising 1, 2, 3, 4, 5, or 6 CDR sequences disclosed in this specification.

In one embodiment the disclosure extends to an antibody comprising a single variable domain or a pair of variable domain from a sequence or sequences herein.

In one embodiment the variable domain of the heavy chain comprises at least one of a CDR having the sequence given in the table listed above, for example where the CDR is in its "natural position".

The natural position of a CDR such as H1, H2, H3, L1, L2 or L3 is given above in the tables.

In one example an antibody of the present invention comprises a heavy chain wherein at least two of CDR-H1, CDR-H2 and CDR-H3 of the variable domain of the heavy chain are selected from sequences given in the tables above, for example the CDRs are in their natural position and optionally in their natural pairing. Natural pairing as employed herein is intended to refer to CDRs from the same antibody (i.e from one table above).

In one embodiment an antibody according to the present invention comprises a heavy chain, wherein the variable domain comprises the sequence given in:
SEQ ID NO:4 for CDR-H1,
SEQ ID NO:5 for CDR-H2 and
SEQ ID NO: 6 for CDR-H3,
or
SEQ ID NO:4 for CDR-H1,
SEQ ID NO:11 for CDR-H2 and
SEQ ID NO:6 for CDR-H3,
or
SEQ ID NO:16 for CDR-H1,
SEQ ID NO:17 for CDR-H2 and
SEQ ID NO:18 for CDR-H3,
or,
SEQ ID NO:22 for CDR-H1,
SEQ ID NO:23 for CDR-H2 and
SEQ ID NO:24 for CDR-H3,
or
SEQ ID NO:28 for CDR-H1,
SEQ ID NO:29 for CDR-H2 and
SEQ ID NO:30 for CDR-H3,
or
SEQ ID NO:34 for CDR-H1,
SEQ ID NO:35 for CDR-H2 and
SEQ ID NO:36 for CDR-H3,
or
SEQ ID NO:40 for CDR-H1,
SEQ ID NO:41 for CDR-H2 and
SEQ ID NO:42 for CDR-H3,
or SEQ ID NO:46 for CDR-H1,
SEQ ID NO:47 for CDR-H2 and
SEQ ID NO:48 for CDR-H3,
or
SEQ ID NO:52 for CDR-H1,
SEQ ID NO:53 for CDR-H2 and
SEQ ID NO:54 for CDR-H3,
or
SEQ ID NO:58 for CDR-H1,
SEQ ID NO:59 for CDR-H2 and
SEQ ID NO:60 for CDR-H3,
or
SEQ ID NO:58 for CDR-H1,
SEQ ID NO:65 for CDR-H2 and
SEQ ID NO:60 for CDR-H3,
or
SEQ ID NO:58 for CDR-H1,
SEQ ID NO:71 for CDR-H2 and
SEQ ID NO:72 for CDR-H3,
or
SEQ ID NO:76 for CDR-H1,
SEQ ID NO:77 for CDR-H2 and
SEQ ID NO:78 for CDR-H3,
or
SEQ ID NO:82 for CDR-H1,
SEQ ID NO:83 for CDR-H2 and
SEQ ID NO:84 for CDR-H3,
or
SEQ ID NO:88 for CDR-H1,
SEQ ID NO:89 for CDR-H2 and
SEQ ID NO:90 for CDR-H3,
or
SEQ ID NO: 58 for CDR-H1,
SEQ ID NO:95 for CDR-H2 and
SEQ ID NO:96 for CDR-H3,
or
SEQ ID NO:100 for CDR-H1,
SEQ ID NO:101 for CDR-H2 and
SEQ ID NO:102 for CDR-H3,
or
SEQ ID NO:106 for CDR-H1,
SEQ ID NO:107 for CDR-H2 and
SEQ ID NO:108 for CDR-H3,
or
SEQ ID NO:112 for CDR-H1,
SEQ ID NO:113 for CDR-H2 and
SEQ ID NO:114 for CDR-H3,
or
SEQ ID NO:118 for CDR-H1,
SEQ ID NO:119 for CDR-H2 and
SEQ ID NO:120 for CDR-H3
or a sequence having at least 60%, 70%, 80% such as at least 90%, 95% or 98% identity or similarity thereto.

In one embodiment an antibody according to the present invention comprises a heavy chain wherein the variable domain of the heavy chain comprises a variable domain as disclosed herein, for example from any heavy chain described.

In another embodiment, the antibody of the present invention comprises a heavy chain, wherein the variable domain of the heavy chain comprises a sequence having at least 60%, 70%, 80% identity or similarity, such as at least 90%, 95% or 98% identity or similarity to a heavy chain variable region disclosed herein.

"Identity", as used herein, indicates that at any particular position in the aligned sequences, the amino acid residue is identical between the sequences. "Similarity", as used herein, indicates that, at any particular position in the aligned sequences, the amino acid residue is of a similar type between the sequences. For example, leucine may be substituted for isoleucine or valine. Other amino acids which can often be substituted for one another include but are not limited to:
 phenylalanine, tyrosine and tryptophan (amino acids having aromatic side chains);
 lysine, arginine and histidine (amino acids having basic side chains);
 aspartate and glutamate (amino acids having acidic side chains);
 asparagine and glutamine (amino acids having amide side chains); and
 cysteine and methionine (amino acids having sulphur-containing side chains).

Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

The present invention also provides an anti-$Na_v1.7$ antibody which selectively inhibits function of $Na_v1.7$, comprising a light chain which comprises at least one of a CDR having the sequence given in a table listed above, for example the CDR is in its "natural position".

In one embodiment the antibody of the present invention comprises a light chain, wherein at least two of CDR-L1, CDR-L2 and CDR-L3 of the variable domain of the light chain are selected from sequences given in the tables above, for example the CDRs are in their natural position and optionally in their natural pairing. Natural pairing as employed herein is intended to refer to CDRs from the same antibody (i.e. from one table above).

For the avoidance of doubt, it is understood that all permutations are included.

In one example the antibody of the present invention comprises a light chain, wherein the variable domain comprises the sequence given in
SEQ ID NO:1 for CDR-L1,
SEQ ID NO:2 for CDR-L2 and
SEQ ID NO:3 for CDR-L3,
or
SEQ ID NO:7 for CDR-L1,
SEQ ID NO:8 for CDR-L2 and
SEQ ID NO:9 for CDR-L3,
or
SEQ ID NO:13 for CDR-L1,
SEQ ID NO:14 for CDR-L2 and
SEQ ID NO:15 for CDR-L3,
or,
SEQ ID NO:19 for CDR-L1,
SEQ ID NO:20 for CDR-L2 and
SEQ ID NO:21 for CDR-L3,
or
SEQ ID NO:25 for CDR-L1,
SEQ ID NO:26 for CDR-L2 and
SEQ ID NO:27 for CDR-L3,
or
SEQ ID NO:31 for CDR-L1,
SEQ ID NO:32 for CDR-L2 and
SEQ ID NO:33 for CDR-L3,
or SEQ ID NO:37 for CDR-L1,
SEQ ID NO:38 for CDR-L2 and
SEQ ID NO:39 for CDR-L3,
or
SEQ ID NO:43 for CDR-L1,
SEQ ID NO:44 for CDR-L2 and
SEQ ID NO:45 for CDR-L3,
or
SEQ ID NO:49 for CDR-L1,
SEQ ID NO:50 for CDR-L2 and
SEQ ID NO:51 for CDR-L3,
or
SEQ ID NO:55 for CDR-L1,
SEQ ID NO:38 for CDR-L2 and
SEQ ID NO:57 for CDR-L3,
or
SEQ ID NO:55 for CDR-L1,
SEQ ID NO:62 for CDR-L2 and
SEQ ID NO:63 for CDR-L3,
or
SEQ ID NO:55 for CDR-L1,
SEQ ID NO:68 for CDR-L2 and
SEQ ID NO:69 for CDR-L3,
or
SEQ ID NO:73 for CDR-L1,
SEQ ID NO:44 for CDR-L2 and
SEQ ID NO:75 for CDR-L3,
or
SEQ ID NO:79 for CDR-L1,
SEQ ID NO: 38 for CDR-L2 and
SEQ ID NO:81 for CDR-L3,
or
SEQ ID NO:85 for CDR-L1,
SEQ ID NO:86 for CDR-L2 and
SEQ ID NO:87 for CDR-L3,
or
SEQ ID NO:91 for CDR-L1,
SEQ ID NO:44 for CDR-L2 and
SEQ ID NO:93 for CDR-L3,
or
SEQ ID NO:97 for CDR-L1,
SEQ ID NO: 50 for CDR-L2 and
SEQ ID NO:99 for CDR-L3,
or
SEQ ID NO:103 for CDR-L1,
SEQ ID NO:50 for CDR-L2 and
SEQ ID NO:105 for CDR-L3,
or
SEQ ID NO:109 for CDR-L1,
SEQ ID NO:110 for CDR-L2 and
SEQ ID NO:111 for CDR-L3,
or
SEQ ID NO:115 for CDR-L1,
SEQ ID NO:50 for CDR-L2 and
SEQ ID NO:117 for CDR-L3
or a sequence having at least 60%, 70%, 80% such as at least 90%, 95% or 98% identity or similarity thereto.

In one embodiment, the present invention comprises a light chain, wherein the variable domain of the light chain comprises a variable domain as disclosed herein, for example from any heavy chain described.

In another embodiment, the antibody of the present invention comprises a light chain, wherein the variable domain of the light chain comprises a sequence having at least 60%, 70%, 80% identity or similarity, such as at least 90%, 95% or 98% identity or similarity to a heavy chain variable region disclosed herein.

In one embodiment there is provided a pair of variable domains, for example a heavy chain variable domain and a light chain variable domain. In one aspect there is provided a heavy and light chain variable domain pair which is a cognate pair. Examples of such variable domain sequences are provided in FIGS. 4-10.

The antibody molecules of the present invention comprise a complementary light chain or a complementary heavy chain, respectively.

In one embodiment the heavy and light chain are a natural pairing, that is to say are derived from the same antibody, for example as shown in a single table herein.

In one embodiment the heavy and the light chain have a non-natural pairing.

One antibody provided by the present invention is referred to herein as antibody 932 shown in FIG. 6 or 983 shown in FIG. 7 or 1080 shown in FIGS. 10 and 11. Antibody 932 comprises the heavy chain variable region amino acid sequence given in SEQ ID NO:140 and the light chain variable region amino acid sequence given in SEQ ID NO:139.

Antibody 983 comprises the heavy chain variable region amino acid sequence given in SEQ ID NO:148 and the light chain variable region amino acid sequence given in SEQ ID NO:147.

Antibody 1080 comprises the heavy chain variable region amino acid sequence given in SEQ ID NO:176 and the light chain variable region amino acid sequence given in SEQ ID NO:175.

In a further aspect the invention also provides a nucleotide sequence encoding an antibody or fragment thereof according to the present disclosure. Examples of such sequences are provided in FIGS. 4-13.

In one embodiment the heavy chain variable region of antibody 932 is encoded by the DNA sequence given in SEQ ID NO:138 and the light chain variable region is encoded by the DNA sequence given in SEQ ID NO:137.

In one embodiment the heavy chain variable region of antibody 983 is encoded by the DNA sequence given in SEQ ID NO:146 and the light chain variable region is encoded by the DNA sequence given in SEQ ID NO:145.

In one embodiment the heavy chain variable region of antibody 1080 is encoded by the DNA sequence given in SEQ ID NO:176 and the light chain variable region is encoded by the sequence given in SEQ ID NO:175.

Also provided by the present invention is a CDR-grafted (or humanised) anti-Na$_v$1.7 antibody characterised in that the antibody is functionally modifying to Na$_v$1.7. In one embodiment one or more of the CDRs in the CDR-grafted antibody molecule have been obtained from the rabbit antibodies 932 and/or 983 and/or 1080. The CDRs of rabbit antibody are provided herein. As used herein, the term 'CDR-grafted antibody molecule' refers to an antibody molecule wherein the heavy and/or light chain contains one or more CDRs (including, if desired, one or more modified CDRs) from a donor antibody (e.g. a rat or rabbit antibody as described herein) grafted into a heavy and/or light chain variable region framework of an acceptor antibody (e.g. a human antibody). For a review, see Vaughan et al, Nature Biotechnology, 16, 535-539, 1998.

When the CDRs are grafted, any appropriate acceptor variable region framework sequence may be used having regard to the class/type of the donor antibody from which the CDRs are derived, including rat, rabbit, mouse, primate and human framework regions. Preferably, the CDR-grafted antibody of the present invention has a variable domain comprising human acceptor framework regions as well as one or more of the CDRs derived from the donor antibody as referred to herein. Thus, provided is a CDR-grafted antibody wherein the variable domain comprises human acceptor framework regions and non-human, preferably rat, mouse or rabbit donor CDRs.

Examples of human frameworks which can be used in the present invention are KOL, NEWM, REI, EU, TUR, TEI, LAY and POM (Kabat et al., supra). For example, KOL and NEWM can be used for the heavy chain, REI can be used for the light chain and EU, LAY and POM can be used for both the heavy chain and the light chain. Alternatively, human germline sequences may be used; these are available at: http://vbase.mrc-cpe.cam.ac.uk/. In a further alternative a database of affinity matured human V region sequences may be used as a framework.

In a CDR-grafted antibody of the present invention, the acceptor heavy and light chains do not necessarily need to be derived from the same antibody and may, if desired, comprise composite chains having framework regions derived from different chains.

Also, in a CDR-grafted antibody of the present invention, the framework regions need not have exactly the same sequence as those of the acceptor antibody. For instance, unusual residues may be changed to more frequently-occurring residues for that acceptor chain class or type. Alternatively, selected residues in the acceptor framework regions may be changed so that they correspond to the residue found at the same position in the donor antibody (see Reichmann et al., 1998, Nature, 332, 323-324). Such changes should be kept to the minimum necessary to recover the affinity of the donor antibody. A protocol for selecting residues in the acceptor framework regions which may need to be changed is set forth in WO 91/09967.

Donor residues are residues from the donor antibody, i.e. the antibody from which the CDRs were originally derived, which may in one embodiment of the present invention be either of the rat, mouse or rabbit antibodies may be incorporated into the final antibody or fragment as required.

In one embodiment, the antibody, or fragment such as a Fab or Fab' fragment is a monoclonal, fully human, humanized or chimeric antibody fragment. In one embodiment the antibody, Fab or Fab' fragments are fully human or humanised.

Antibodies for use in the present invention include whole antibodies of any suitable class for example, IgA, IgD, IgE, IgG or IgM or subclass such as IgG1, IgG2, IgG3 or IgG4. and functionally active fragments or derivatives thereof and may be, but are not limited to, monoclonal, humanised, fully human or chimeric antibodies.

Antibodies for use in the present invention may therefore comprise a complete antibody molecule having full length heavy and light chains or a fragment thereof and may be, but are not limited to Fab, modified Fab, Fab', F(ab')$_2$, Fv, single domain antibodies (such as VH, VL, VHH, IgNAR V domains), scFv, bi, tri or tetra-valent antibodies, Bis-scFv, diabodies, triabodies, tetrabodies and epitope-binding fragments of any of the above (see for example Holliger and Hudson, 2005, Nature Biotech. 23(9):1126-1136; Adair and Lawson, 2005, Drug Design Reviews-Online 2(3), 209-217). The methods for creating and manufacturing these antibody fragments are well known in the art (see for example Verma et al., 1998, Journal of Immunological Methods, 216, 165-181). Other antibody fragments for use in the present invention include the Fab and Fab' fragments described in International patent applications WO2005/003169, WO2005/003170 and WO2005/003171. Other antibody fragments for use in the present invention include Fab-Fv and Fab-dsFv fragments described in WO2010/035012 and antibody fragments comprising those fragments. Multi-valent antibodies may comprise multiple specificities or may be monospecific (see for example WO 92/22853 and WO05/113605).

In one example the antibodies for use in the present invention may be derived from a camelid, such as a camel or llama. Camelids possess a functional class of antibodies devoid of light chains, referred to as heavy chain antibodies (Hamers et al., 1993, Nature, 363, 446-448; Muyldermans, et al., 2001, Trends. Biochem. Sci. 26, 230-235). The antigen-combining site of these heavy-chain antibodies is limited to only three hypervariable loops (H1-H3) provided by the N-terminal variable domain (VHH). The first crystal structures of VHHs revealed that the H1 and H2 loops are not restricted to the known canonical structure classes defined for conventional antibodies (Decanniere, et al., 2000, J. Mol. Biol, 300, 83-91). The H3 loops of VHHs are on average longer than those of conventional antibodies (Nguyen et al., 2001, Adv. Immunol., 79, 261-296). A large fraction of dromedary heavy chain antibodies have a preference for binding into active sites of enzymes against which they are raised (Lauwereys et al., 1998, EMBO J, 17, 3512-3520). In one case, the H3 loop was shown to protrude from the remaining paratope and insert in the active site of the hen egg white lysozyme (Desmyter et al., 1996, Nat. Struct. Biol. 3, 803-811 and De Genst et al., 2006, PNAS, 103, 12, 4586-4591 and WO97049805).

It has been suggested that these loops can be displayed in other scaffolds and CDR libraries produced in those scaffolds (See for example WO03050531 and WO97049805).

In one example the antibodies for use in the present invention may be derived from a cartilaginous fish, such as a shark. Cartilaginous fish (sharks, skates, rays and chimeras) possess an atypical immunoglobulin isotype known as IgNAR. IgNAR is an H-chain homodimer that does not associate with light chain. Each H chain has one variable and five constant domains. IgNAR V domains (or V-NAR domains) carry a number of non canonical cysteines that enable classification into two closely related subtypes, I and II. Type II V regions have an additional cysteine in CDRs 1 and 3 which have been proposed to form a domain-constraining disulphide bond, akin to those observed in camelid VHH domains. The CDR3 would then adopt a more extended conformation and protrude from the antibody framework akin to the camelid VHH. Indeed, like the VHH domains described above, certain IgNAR CDR3 residues have also been demonstrated to be capable of binding in the hen egg white lysozyme active site (Stanfield et al., 2004, Science, 305, 1770-1773.

Examples of methods of producing VHH and IgNAR V domains are described in for example, Lauwereys et al, 1998, EMBO J. 1998, 17(13), 3512-20; Liu et al., 2007, BMC Biotechnol., 7, 78; Saerens et al., 2004, J. Biol. Chem., 279 (5), 51965-72.

In one embodiment the constant region employed, in the antibody or certain fragments thereof according to the disclosure, is a hybrid constant region or mutated constant region. Hybrid constant regions comprises portions or domains from two or more distinct constant regions, for example two or more distinct human constant regions.

Examples of hybrid constant regions include those disclosed in US2007/0041972, where at least CH1 and the hinge region are derived from one or more IgG2 antibodies and at least a portion of the CH2 and CH3 regions are derived from one or more IgG4 CH2 and CH3 regions. Eculizimumab (Alexion Pharmaceuticals) is a humanised anti-human C5 mAb for paroxysmal nocturnal hemoglobinuria comprising a hybrid constant region. It has a hybrid chain of IgG2 derived CH1 and hinge with IgG4 derived CH2 and CH3 domains. It does not bind FcγR nor does it activate complement. It also has low immunogenicity (low titers of anti-Eculizimumab antibodies detected in only 3 of 196 (3%) patients).

WO 2008/090958 discloses certain hybrid constant regions comprising a chain of CH1, hinge and CH2 from IgG1 and a CH3 domain from IgG3. The hybrid has a higher CDC activity than that of an IgG1 or IgG3 antibody and a protein A-binding activity equivalent to that of IgG1.

Further hybrid constant regions are disclosed in Tao et al., (S. L. Morrison's group) J. Exp. Med 173 1025-1028, 1991. This paper contains many IgG domain swaps from all classes but the key hybrids are g1g4 and g4g1, each joined in the CH2 domain. IgG (1-1-1/4-4) is completely unable to activate complement in contrast to IgG1. However, IgG(4-4-4/1-1) showed significant activity compared with IgG4 but was slightly impaired compared with IgG1. The key difference seems to be the hinge and many papers have since demonstrated that the hinge modulates but does not mediates complement activation.

Tao et al., (S. L. Morrison's group) J. Exp. Med 178 661-667, 1993 discloses structural features of human IgG that determine isotype-specific differences in complement activation. Ser331 (CH2) in IgG4 prevents C1q binding and complement activation. Mutagenesis of Ser331 to Pro in IgG4 and IgG (1-1-1/4-4) allows binding and activation but at a lower level than that of IgG1. Interestingly P331S in IgG1 allows binding but not activation.

Zucker et al., Canc Res 58 3905-3908 1998 employs Chimeric human-mouse IgG abs with shuffled constant region exons to demonstate that muliple domains contribute to in vivo half-life. In particular this article examines half-life of IgG (1-1-1/4-4) hybrid and others. In SCID mice, IgG (1-1-1/4-4) has a significantly longer half-life than IgG4 but slightly less than IgG1. IgG (4-4-4/1-1) has the longest half-life.

An example of a mutated constant region includes that employed in Abatacept, which is a fusion of human CTLA-4 with IgG1 hinge-Fc. The hinge was altered from CPPC to SPPS. The latter is O-gly. The mutated constant region does not mediate ADCC or CDC and has low immunogenicity (3% incidence).

The hinge is thought to potentially have a role in complement activiation. The functional hinge, deduced from crystallographic studies, extends from 216-237 of IgG1 and consists of EPKSCDKTHTCPPCPAPELLGG (SEQ ID NO: 206) upper, middle and lower hinge respectively. In one embodiment an antibody or fragment according to the disclosure comprises a functional hinge.

Mutations/modifications to the constant region may, for example result in increased stability, for example US 2004/0191265 discloses mutagenesis of IgG1 hinge, which increased the stability of an IgG by introducing one or more amino acid modifications in the hinge region at positions 233-239 or 249 of human IgG1. This provided reduced degradation upon heating to 55° C. for one week.

Alternatively, modification may be effected by making point mutations in labile amino acids (e.g., histidine or threonine) or reactive amino acids (e.g., lysine or glutamic acid) in the upper hinge portion (human IgG1 residues 226-243 and corresponding residues in other IgG subtypes and/or immunoglobulins from other species) and/or in the flanking CH1 and/or CH2 sequences (human IgG1 residue 249 and corresponding residues in other IgG subtypes and/or immunoglobulins from other species).

Monoclonal antibodies may be prepared by any method known in the art such as the hybridoma technique (Kohler & Milstein, Nature, 1975, 256, 495-497), the trioma technique, the human B-cell hybridoma technique (Kozbor et al., Immunology Today, 1983, 4, 72) and the EBV-hybridoma technique (Cole et al., "Monoclonal Antibodies and Cancer Therapy", pp. 77-96, Alan R. Liss, Inc., 1985).

Antibodies for use in the invention may also be generated using single lymphocyte antibody methods by cloning and expressing immunoglobulin variable region cDNAs generated from single lymphocytes selected for the production of specific antibodies by, for example, the methods described by Babcook, J. et al., Proc. Natl. Acad. Sci. USA, 1996, 93(15), 7843-7848, WO 92/02551, WO2004/051268 and WO2004/106377.

Humanized antibodies are antibody molecules derived from non-human species having one or more complementarity determining regions (CDRs) from the non-human species and a framework region from a human immunoglobulin molecule (see, for example, U.S. Pat. No. 5,585,089). Such antibodies may further comprise one or more donor residues derived from the non-human species.

The antibodies for use in the present invention can also be generated using various phage display methods known in the art and include those disclosed by Brinkman et al., J. Immunol. Methods, 1995, 182, 41-50; Ames et al., J. Immunol. Methods, 1995, 184, 177-186; Kettleborough et al. Eur. J. Immunol., 1994, 24, 952-958; Persic et al., Gene, 1997 187, 9-18; and Burton et al., Advances in Immunology, 1994, 57, 191-280; WO 90/02809; WO 91/10737; WO 92/01047; WO 92/18619; WO 93/11236; WO 95/15982; and WO 95/20401; and U.S. Pat. Nos. 5,698,426; 5,223,409; 5,403,484; 5,580, 717; 5,427,908; 5,750,753; 5,821,047; 5,571,698; 5,427,908; 5,516,637; 5,780,225; 5,658,727; 5,733,743; and 5,969,108. Also, transgenic mice, or other organisms, including other mammals, may be used to generate humanized antibodies.

Fully human antibodies are those antibodies in which the variable regions and the constant regions (where present) of both the heavy and the light chains are all of human origin, or substantially identical to sequences of human origin, not necessarily from the same antibody. Examples of fully human antibodies may include antibodies produced for example by the phage display methods described above and antibodies produced by mice in which the murine immunoglobulin variable and/or constant region genes have been replaced by their human counterparts eg. as described in general terms in EP0546073 B1, U.S. Pat. No. 5,545,806, U.S. Pat. No. 5,569, 825, U.S. Pat. No. 5,625,126, U.S. Pat. No. 5,633,425, U.S. Pat. No. 5,661,016, U.S. Pat. No. 5,770,429, EP 0438474 B1 and EP0463151 B1.

The antibody or fragment for use in the present invention may be obtained from any whole antibody, especially a whole monoclonal antibody, using any suitable enzymatic cleavage and/or digestion techniques, for example by treatment with pepsin. Alternatively, or in addition the antibody starting material may be prepared by the use of recombinant DNA techniques involving the manipulation and re-expression of DNA encoding antibody variable and/or constant regions. Standard molecular biology techniques may be used to modify, add or delete amino acids or domains as desired. Any alterations to the variable or constant regions are still encompassed by the terms 'variable' and 'constant' regions as used herein.

The antibody fragment "starting material" may be obtained from any species including for example mouse, rat, rabbit, hamster, shark, camel, llama, goat or human. Parts of the antibody fragment may be obtained from more than one species, for example the antibody fragments may be chimeric. In one example, the constant regions are from one species and the variable regions from another. The antibody fragment starting material may also be modified. In another example, the variable region of the antibody fragment has been created using recombinant DNA engineering techniques. Such engineered versions include those created for example from natural antibody variable regions by insertions, deletions or changes in or to the amino acid sequences of the natural antibodies. Particular examples of this type include those engineered variable region domains containing at least one CDR and, optionally, one or more framework amino acids from one antibody and the remainder of the variable region domain from a second antibody. The methods for creating and manufacturing these antibody fragments are well known in the art (see for example, Boss et al., U.S. Pat. No. 4,816,397; Cabilly et al., U.S. Pat. No. 6,331,415; Shrader et al., WO 92/02551; Ward et al., 1989, Nature, 341, 544; Orlandi et al., 1989, Proc. Natl. Acad. Sci. USA, 86, 3833; Riechmann et al., 1988, Nature, 322, 323; Bird et al, 1988, Science, 242, 423; Queen et al., U.S. Pat. No. 5,585,089; Adair, WO91/09967; Mountain and Adair, 1992, Biotechnol. Genet. Eng. Rev, 10, 1-142; Verma et al., 1998, Journal of Immunological Methods, 216, 165-181).

Thus in one embodiment constant region domains may be human IgA, IgD, IgE, IgG or IgM domains. In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required. It will be appreciated that sequence variants of these constant region domains may also be used. For example IgG4 molecules in which the serine at position 241 has been changed to proline as described in Angal et al., Molecular Immunology, 1993, 30 (1), 105-108 may be used. It will also be understood by one skilled in the art that antibodies may undergo a variety of posttranslational modifications. The type and extent of these modifications often depends on the host cell line used to express the antibody as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, R J. *Journal of Chromatography* 705:129-134, 1995).

In one embodiment the antibody or fragment light chain comprises a CL domain, either kappa or lambda.

The term 'antibody' or fragment as used herein may also include binding agents which comprise one or more CDRs incorporated into a biocompatible framework structure. In one example, the biocompatible framework structure comprises a polypeptide or portion thereof that is sufficient to form a conformationally stable structural support, or framework, or scaffold, which is able to display one or more sequences of amino acids that bind to an antigen (e.g. CDRs, a variable region etc.) in a localised surface region. Such structures can be a naturally occurring polypeptide or polypeptide 'fold' (a structural motif), or can have one or more modifications, such as additions, deletions or substitutions of amino acids, relative to a naturally occurring polypeptide or fold. These scaffolds can be derived from a polypeptide of any species (or of more than one species), such as a human, other mammal, other vertebrate, invertebrate, plant, bacteria or virus.

Typically the biocompatible framework structures are based on protein scaffolds or skeletons other than immunoglobulin domains. For example, those based on fibronectin, ankyrin, lipocalin, neocarzinostain, cytochrome b, CP1 zinc finger, PST1, coiled coil, LACI-D1, Z domain and tendramisat domains may be used (See for example, Nygren and Uhlen, 1997, Current Opinion in Structural Biology, 7, 463-469).

In one embodiment the CDRs, may be grafted or engineered into an alternative type of scaffold, for example a fibronectin or actin-binding repeats.

In one embodiment the antibody or fragment comprises an effector molecule, such as a polymer, toxin including biotoxins such as venom or chemical inhibitor conjugated thereto.

Biotoxins and venom are natural modulators, such as blockers of cell signalling. When conjugated to an antibody or fragment according to the invention then they can be used to augment the functional effect on the ion channel, whilst maintaining the selectivity provided by the antibody. Tarantula venom peptide ProTxII has, for example be shown to selectively inhibit Na$_v$1.7, see for example Mol Pharmacol 74:1476-1484, 2008. In one embodiment the toxin is botulinum toxin, for example botulinum toxin A. Other toxins include tetrodotoxin and saxitoxin.

In one embodiment the antibody or fragment is conjugated to an aptamer. Aptamers are single stranded oligonucleotide sequences that adopt secondary and tertiary structures and that are able to bind and modulate protein activity. The conjugation of such structures to antibodies will lead to a target specific modulation of the ion channel (direct effect).

In one embodiment the antibody or fragment is conjugated to chemical inhibitor such as a synthetic chemical inhibitor of an ion channel. Examples of chemical inhibitors include compounds of formula (I):

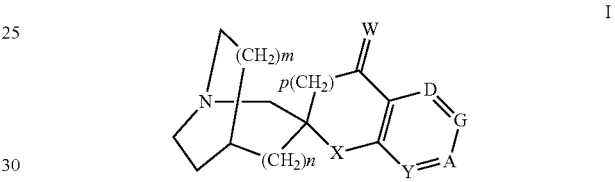

I wherein n is 0 or 1;
m is 0 or 1;
p is 0 or 1;
Y is CH, N or NO
X is oxygen or sulfur;
W is oxygen, H$_2$ or F$_2$;
A is N or C(R$^2$);
G is N or C(R$^3$);
D is N or C(R$^4$);
with the proviso that no more than one of A, G, and D is nitrogen but at least one of Y, A, G, and D is nitrogen or NO;
R$^1$ is hydrogen or C$_1$-C$_4$ alkyl;
R$^2$, R$^3$, and R$^4$ are independently hydrogen, halogen, C$_1$-C$_4$ alkyl, C$_2$-C$_4$ alkenyl, C$_2$-C$_4$ alkynyl, aryl, heteroaryl, OH, OC$_1$-C$_4$ alkyl, CO$_2$R$^1$, —CN, —NO$_2$, —NR$^5$R$^6$, —CF$_3$, —OSO$_2$CF$_3$, or R$^2$ and R$^3$, or R$^3$ and R$^4$, respectively, may together form another six membered aromatic or heteroaromatic ring sharing A and G, or G and D, respectively containing between zero and two nitrogen atoms, and substituted with one to two of the following substituents: independently hydrogen, halogen, C$_1$-C$_4$ alkyl, C$_2$-C$_4$ alkenyl, C$_2$-C$_4$ alkynyl, aryl, heteroaryl, OH, OC$_1$-C$_4$ alkyl, CO$_2$R$^1$, —CN, —NO$_2$, —NR$^5$R$^6$, —CF$_3$, OSO$_2$CF$_3$;
R$^5$ and R$^6$ are independently hydrogen, C$_1$-C$_4$ alkyl, C(O)R$^7$, C(O)NHR$^8$, C(O)O R$^9$, SO$_2$R$^{10}$ or may together be (CH$_2$)$_j$Q (CH$_2$)$_k$ where Q is O, S, NR$^{11}$, or a bond;
j is 2 to 7;
k is 0 to 2;
R$^7$, R$^8$, R$^9$, R$^{10}$, and R$^{11}$ are independently C$_1$-C$_4$ alkyl, aryl, or heteroaryl, or an enantiomer thereof, and the pharmaceutically acceptable salts thereof is a potent ligand for nicotinic acetylcholine receptors.
See EP0996622.

Bioorg Med Chem (2003) 11: 2099-113. R A Hill, S Rudra, B Peng, D S Roane, J K Bounds, Y g, A Adloo, T Lu, discloses certain hydroxyl substituted sulfonylureas as inhibitors.

4,4-Diisothiocyanatostilbene-2,2'-disulfonic acid (DIDS) has been used as an anion-transport inhibitor.

The following are also chemical inhibitors of Na$_v$1.7

| | FRET-based Assay (μM) | | | Electrophysiology (μM) | |
|---|---|---|---|---|---|
| | hNav1.5 | hNav1.7 | hNav1.8 | hNav1.5 | hNav1.7 |
| 1 | 0.02 | 0.03 | 0.27 | 0.17 | 0.37 |
| 2 | 0.18 | 0.03 | 0.30 | 4.30 | 0.55 |

The compound labeled 2 in the table above N—[(R)-1-(R)-7-chloro-1-isopropyl-2-oxo-2,3,4,5-tetrahydro-1H-benzo[b]azepine-3-ylcarbamoyl)-2-(2-fluorophenyl)-ethyl]-4-fluoro-2-trifluoromethyl-benzamide is discussed in a paper by McGowan et al Anesthesia and Analgesia Vol 109, No. 3, September 2009 (entitled A Peripherally Acting Na$_v$1.7 Sodium Channel Blocker Reverses Hyperalgesia and Allodynia on Rat Models of Inflammatory and Neuropathic Pain).

Tarnawa et al (2007) (Blockers of voltage-gated sodium channels for the treatment of central nervous system diseases, *Recent Patents on CNS Drug Discovery*, 2:57) reviewed the more recent medicinal chemistry of sodium channel blockers. Several old drugs such as lidocaine, mexiletine, carbamazepine, phenyloin, lamotrigine and newly developed drugs such as lacosamide, oxcarbazepine, crobenetine, ralfinamide are sodium channel blockers that have proved to be effective in the treatment of various types of chronic pain in animal models, and some of them are used clinically also. Some other examples of chemical modulators of voltage-gated sodium channels are listed below:

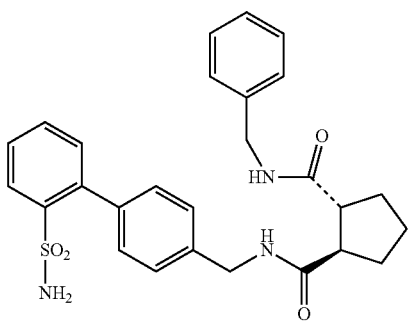

(44)

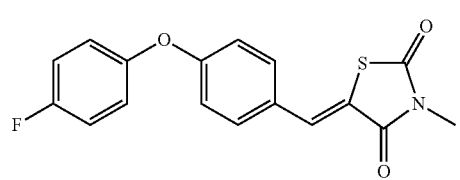

(45)

-continued

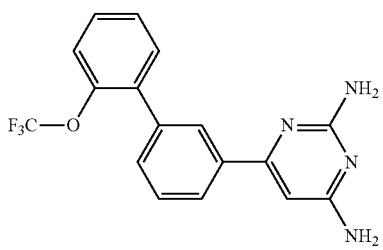
(46)

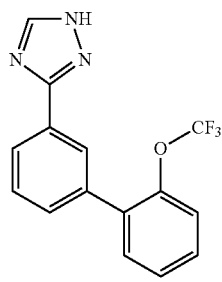
(47)

FIG. 15a). Compounds with a combination of aromatic and heteroaromatic rings, patented by Merck.

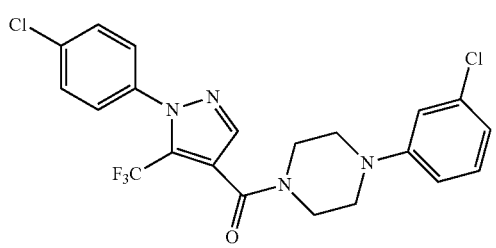
(52)

FIG. (16). Biarylcarboxamide compounds patented by Atkinson.

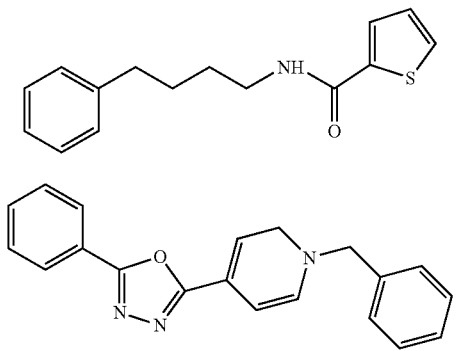
(53)

(54)

FIG. (17). Compounds with a combination of aromatic and heteroaromatic rings, patented by Ehring

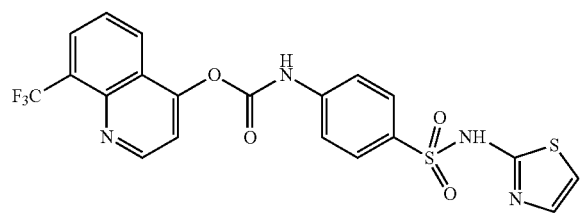
(60)

-continued

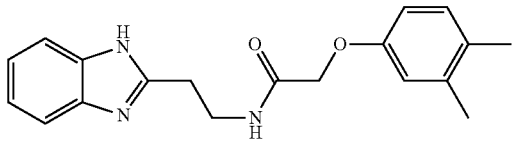
(61)

FIG. (18b). Compounds with combined aromatic and heteroaromatic rings patented by Vertex.

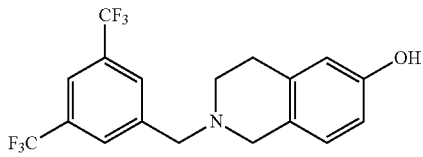
(62)

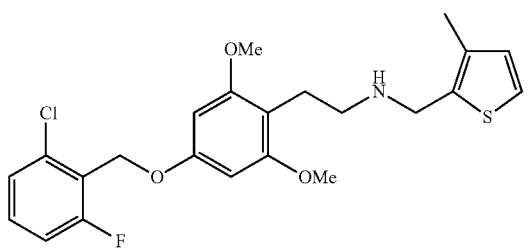
(63)

FIG. (19). Compounds with combined aromatic and heteroaromatic rings patented by Ionix.

Other references describing chemical modulators of voltage-gated sodium channels:

Anger et al. (2001) J. Med. Chem. 44(2):115; Hoyt et al. (2007), Bioorg. Med. Chem. Lett. 17:6172; Yang et al. (2004), J. Med. Chem. 47:1547; Benes et al. (1999) J. Med. Chem. 42:2582

U.S. Pat. No. 7,456,187 discloses certain potassium channel inhibitors of formula:

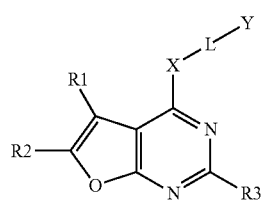

Wherein $R_1$ is aryl, heteroaryl, cycloalkyl or alkyl;

$R_1$ is H, alkyl, nitro, —$CO_2R_7$, $CONR_4R_5$ or halo;

$R_3$ is H, $NR_4R_5$, $NC(O)R_8$, halo, trifluoromethyl, alkyl, nitrile or alkoxy;

$R_4$ and $R_5$ may be the same or different, and may be H, alkyl, aryl, heteroaryl or cycloalkyl; or $R_4$ and $R_5$ may together form a saturated, unsaturated or partially saturated 4 to 7 member ring, wherein said ring may optionally comprise one or more further heteroatoms selected from N, O or S;

X is O, S or $NR_6$;

$R_6$ is H or alkyl;

$R_7$ is hydrogen, methyl or ethyl;

$R_8$ is methyl or ethyl;

L is $(CH_2)_n$, where n is 1, 2 or 3; and

Y is aryl, a heterocyclic group, alkyl, alkenyl or cycloalkyl; or pharmaceutically acceptable salts thereof.

Bioorganic and Medical Chemistry Letters Vol 19, Issue 11, 1 Jun. 2009 pages 3063-3066 discloses certain inhibitors of formula:
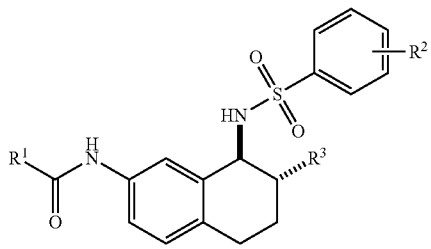
more specifically:
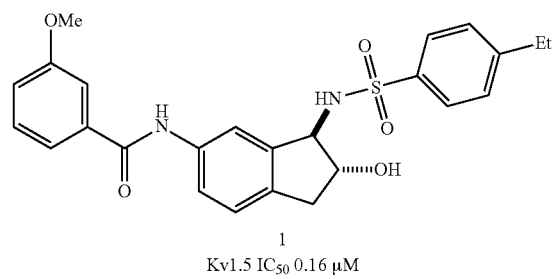
1
Kv1.5 IC$_{50}$ 0.16 μM
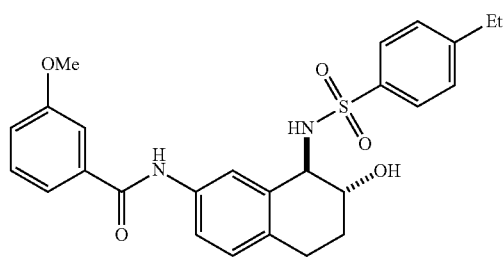
2a
Kv1.5 IC$_{50}$ 0.44 μM
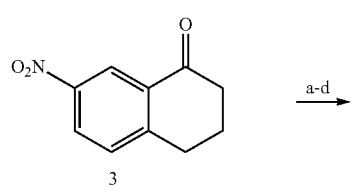
3
a-d →
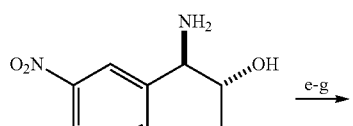
4
e-g →
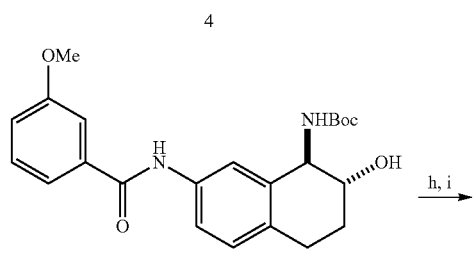
5
h, i →
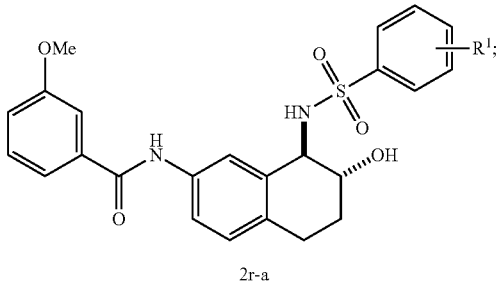
2r-a
4 —a, b→
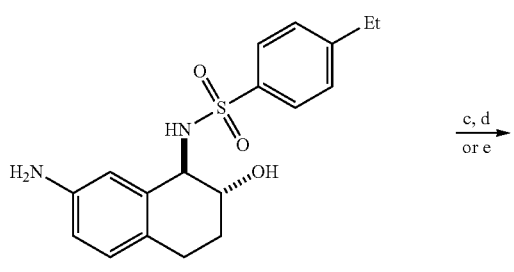
6
—c, d or e→
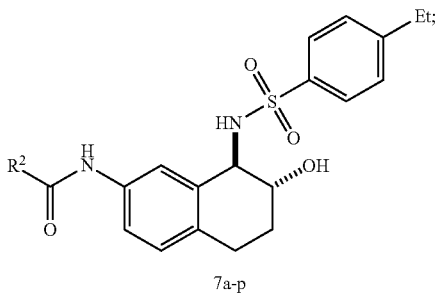
7a-p
6 —a-c→
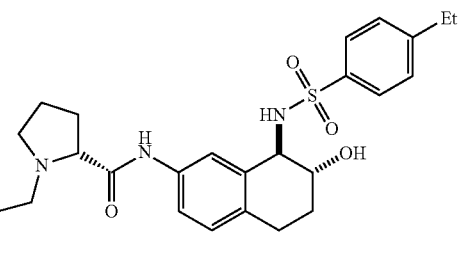
11a-l
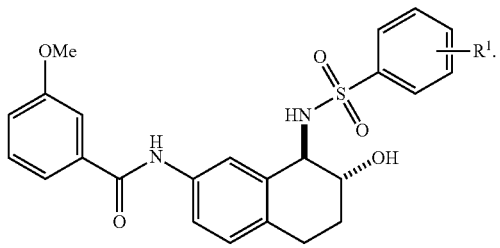
2r-a In one embodiment the entity conjugated to the antibody or fragment changes the overall charge of the molecule.

In one embodiment the overall charge is neutral.

In one embodiment the overall charge is negative.

In one embodiment the overall charge is positive.

The term effector molecule as used herein includes, for example, antineoplastic agents, drugs, toxins, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

Examples of effector molecules may include cytotoxins or cytotoxic agents including any agent that is detrimental to (e.g. kills) cells. Examples include combrestatins, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Effector molecules may also include, but are not limited to, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Other effector molecules may include chelated radionuclides such as $^{111}$In and $^{90}$Y, Lu$^{177}$, Bismuth$^{213}$, Californium$^{252}$, Iridium$^{192}$ and Tungsten$^{188}$/Rhenium$^{188}$; or drugs such as but not limited to, alkylphosphocholines, topoisomerase I inhibitors, taxoids and suramin.

Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, pseudomonas exotoxin, or diphtheria toxin.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

In another example the effector molecule may increase the half-life of the antibody in vivo, and/or reduce immunogenicity of the antibody and/or enhance the delivery of an antibody across an epithelial barrier to the immune system. Examples of suitable effector molecules of this type include polymers, albumin, albumin binding proteins or albumin binding compounds such as those described in WO05/117984.

Where the effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Specific optional substituents which may be present on the above-mentioned synthetic polymers include one or more hydroxy, methyl or methoxy groups.

Specific examples of synthetic polymers include optionally substituted straight or branched chain poly(propyleneglycol) poly(vinylalcohol) or derivatives thereof, especially optionally substituted poly(ethyleneglycol) such as methoxypoly(ethyleneglycol) or derivatives thereof.

Suitable polymers include a polyalkylene polymer, such as a poly(ethyleneglycol) or, especially, a methoxypoly(ethyleneglycol) or a derivative thereof, and especially with a molecular weight in the range from about 15000 Da to about 40000 Da.

The size of the polymer may be varied as desired, but will generally be in an average molecular weight range from 500 Da to 50000 Da, for example from 5000 to 40000 Da such as from 20000 to 40000 Da. The polymer size may in particular be selected on the basis of the intended use of the product for example ability to localize to certain tissues such as tumors or extend circulating half-life (for review see Chapman, 2002, Advanced Drug Delivery Reviews, 54, 531-545). Thus, for example, where the product is intended to leave the circulation and penetrate tissue, for example for use in the treatment of a tumour, it may be advantageous to use a small molecular weight polymer, for example with a molecular weight of around 5000 Da. For applications where the product remains in the circulation, it may be advantageous to use a higher molecular weight polymer, for example having a molecular weight in the range from 20000 Da to 40000 Da.

In one embodiment the PEG employed is releasable PEG, for example as supplied by Enzon pharmaceuticals.

In one example antibodies for use in the present invention are attached to poly(ethyleneglycol) (PEG) moieties. In one particular example the antibody is an antibody fragment and the PEG molecules may be attached through any available amino acid side-chain or terminal amino acid functional group located in the antibody fragment, for example any free amino, imino, thiol, hydroxyl or carboxyl group. Such amino acids may occur naturally in the antibody fragment or may be engineered into the fragment using recombinant DNA methods (see for example U.S. Pat. No. 5,219,996; U.S. Pat. No. 5,667,425; WO98/25971). In one example the antibody molecule of the present invention is a modified Fab fragment wherein the modification is the addition to the C-terminal end of its heavy chain one or more amino acids to allow the attachment of an effector molecule. Suitably, the additional amino acids form a modified hinge region containing one or more cysteine residues to which the effector molecule may be attached. Multiple sites can be used to attach two or more PEG molecules.

In one embodiment the Fab or Fab' is PEGylated with one or two PEG molecules.

In one embodiment a PEG molecule is linked to a cysteine 171 in the light chain, for example see WO2008/038024 incorporated herein by reference.

In one the Fab or Fab' is PEGylated through a surface accessible cysteine.

Suitably PEG molecules are covalently linked through a thiol group of at least one cysteine residue located in the fusion protein. Each polymer molecule attached to the fusion protein may be covalently linked to the sulfur atom of a cysteine residue located in the protein. The covalent linkage will generally be a disulphide bond or, in particular, a sulfur-carbon bond. Where a thiol group is used as the point of attachment appropriately activated PEG molecules, for example thiol selective derivatives such as maleimides and cysteine derivatives may be used. An activated PEG molecule may be used as the starting material in the preparation of polymer-fusion protein containing molecules as described above. The activated PEG molecule may be any polymer containing a thiol reactive group such as an α-halocarboxylic acid or ester, e.g. iodoacetamide, an imide, e.g. maleimide, a vinyl sulphone or a disulphide. Such starting materials may be obtained commercially (for example from Nektar, formerly Shearwater Polymers Inc., Huntsville, Ala., USA) or may be prepared from commercially available starting materials using conventional chemical procedures. Particular PEG molecules include 20K methoxy-PEG-amine (obtainable from Nektar, formerly Shearwater; Rapp Polymere; and SunBio) and M-PEG-SPA (obtainable from Nektar, formerly Shearwater).

Effector molecules such a PEG molecules may be attached to antibodies or by a number of different methods, including through aldehyde sugars or more commonly through any available amino acid side-chain or terminal amino acid functional group located in the antibody fragment, for example any free amino, imino, thiol, hydroxyl or carboxyl group. The site of attachment of effector molecules can be either random or site specific.

Random attachment is often achieved through amino acids such as lysine and this results in effector molecules, such as PEG molecules, being attached at a number of sites throughout the antibody fragment depending on the position of the lysines. While this has been successful in some cases the exact location and number of effector molecules, such as PEG molecules, attached cannot be controlled and this can lead to loss of activity for example if too few are attached and/or loss of affinity if for example they interfere with the antigen binding site (Chapman 2002 Advanced Drug Delivery Reviews, 54, 531-545). As a result, controlled site specific attachment of effector molecules, such as PEG molecules, is usually the method of choice.

Site specific attachment of effector molecules, such as PEG molecules, is most commonly achieved by attachment to cysteine residues since such residues are relatively uncommon in antibody fragments. Antibody hinges are popular regions for site specific attachment since these contain cysteine residues and are remote from other regions of the fusion protein likely to be involved in antigen binding. Suitable hinges either occur naturally in the fragment or may be created using recombinant DNA techniques (See for example U.S. Pat. No. 5,677,425; WO98/25971; Leong et al., 2001 Cytokine, 16, 106-119; Chapman et al., 1999 Nature Biotechnology, 17, 780-783). Alternatively, or in addition, site-specific cysteines may also be engineered into the antibody fragment for example to create surface exposed cysteine(s) for effector molecule attachment (U.S. Pat. No. 5,219,996).

Thus in one embodiment the PEG molecule is attached to a surface exposed cysteine.

A surface exposed cysteine (free cysteine) as employed herein is intended to refer to cysteine, that when the protein is in a "natual" folded conformation, is accessible for conjugating an effector molecule, such as a PEG molecule thereto. Examples of how to engineer free cysteines of this type are also provided in U.S. Pat. No. 7,521,541.

Specific naturally occurring polymers include lactose, amylose, dextran, glycogen or derivatives thereof.

"Derivatives" as used herein is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the fusion protein and the polymer.

The present invention also provides isolated DNA encoding an antibody described herein or a fragment thereof of a heavy or light chain thereof.

In a further aspect there is provided a vector comprising said DNA.

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

In a further aspect there is provided a host cell comprising said vector and/or DNA.

Any suitable host cell/vector system may be used for expression of the DNA sequences encoding the fusion protein molecule of the present invention. Bacterial, for example $E.\ coli$, and other microbial systems may be used or eukaryotic, for example mammalian, host cell expression systems may also be used. Suitable mammalian host cells include CHO, myeloma or hybridoma cells.

The present invention also provides a process for the production of an antibody or fragment thereof according to the present invention comprising culturing a host cell containing a vector (and/or DNA) of the present invention under conditions suitable for leading to expression of protein from DNA encoding the antibody or fragment thereof, and isolating the same.

For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

In one aspect there is provided a method of generating antibodies employing peptides whose sequence are derived from the extracellular regions of $Na_v1.7$. Such peptides, hereinafter referred to as $Na_v1.7$ peptides, are used both in immunization protocols to raise polyclonal antibodies to $Na_v1.7$ and/or in screening or panning protocols to select specific anti-$Na_v1.7$ antibodies. In one example the peptides are used for immunization and screening to produce clonal antibodies e.g. antibodies derived from a single B-cell or hybridoma. In one example the peptides may be used purely for screening where no immunization is required, for example screening or panning of phage display libraries.

The $Na_v1.7$ peptide may comprise at least part of an extracellular sequence of the $Na_v1.7$ ion channel wherein the extracellular sequence is an E1 region, E2 region or E3 region and may be derived from the A domain, B domain, C domain or D domain of $Na_v1.7$. In a preferred embodiment the $Na_v1.7$ peptide comprises at least a part of an E1 or E3 extracellular region derived from the A domain, B domain, C domain or D domain of the Na$_v$1.7 ion channel. In a further preferred embodiment the Na$_v$1.7 peptide comprises at least a part of an E1 or E3 extracellular region derived from the A domain or the B domain of the Na$_v$1.7 ion channel. Preferably the Na$_v$1.7 peptide comprises at least a part of the AE3 extracellular region or the BE1 extracellular region. One embodiment uses Na$_v$1.7 peptides that correspond to discrete sequences of the aforementioned extracellular regions where there is maximum dissimilarity to other Na$_v$1 isoforms. Based on the amino acid sequence numbering of the Na$_v$1.7 sequence deposited in the Swiss Prot database as human protein SCN9A (accession no. Q15858), these sequences are as follows:

273 to 308, 314 to 322, 326 to 336, 764 to 777, 1215 to 1227, 1354 to 1388, 1391 to 1397, 1406 to 1413, 1416 to 1426, 1533 to 1548, 1598 to 1604, 1670 to 1679, and/or 1708 to 1730.

Accordingly, suitable peptides may be designed that fall within one or more of these regions. In one example a peptide of use in the invention consists of a sequence selected from the group consisting of 273 to 308, 314 to 322, 326 to 336, 764 to 777, 1215 to 1227, 1354 to 1388, 1391 to 1397, 1406 to 1413, 1416 to 1426, 1533 to 1548, 1598 to 1604, 1670 to 1679, and 1708 to 1730 of the Na$_v$1.7 sequence deposited in the Swiss Prot database as human protein SCN9A (accession no. Q15858). In one example the peptide consists of sequence within the a sequence selected from the group consisting of 273 to 308, 314 to 322, 326 to 336, 764 to 777, 1215 to 1227, 1354 to 1388, 1391 to 1397, 1406 to 1413, 1416 to 1426, 1533 to 1548, 1598 to 1604, 1670 to 1679, and 1708 to 1730 of the Na$_v$1.7 sequence deposited in the Swiss Prot database as human protein SCN9A (accession no. Q15858).

In one example, suitable peptides for use in the present invention may be designed by comparing the amino acid sequence of Nav1.7 to other family members to identify unique residues specific for Nav1.7. Particular regions of interest such as the extracellular domains may be used in such a comparison. Peptides can then be designed based on the unique residues identified. Preferably the peptide contains at least one unique residue for Nav1.7. In this context unique refers to an amino acid residue which is specific for Nav 1.7 when the amino acid sequence of Nav1.7 is compared to at least one other, preferably all other family members for which sequences are available. In one embodiment the peptide contains two unique residues. In one embodiment the peptide contains three or four or five or six or seven or eight or nine or ten or eleven or twelve unique residues.

If desired, Kyte Doolittle plots may be used to support the choice of peptide used. By employing a Kyte Doolittle plot it is possible to determine which peptides will comprise the highest number of the most hydrophilic residues i.e. those which are more likely to be solvent exposed.

In one example the unique residue(s) are away from the site of conjugation.

In one example unique residues for Nav1.7 are identified by amino acid sequence alignment with other available family members, i.e Nav1.1, Nav 1.2, Nav 1.3, Nav 1.4, Nav 1.5, Nav 1.6, Nav 1.8 and Nav 1.9.

The following Nav1.7 residues are unique to Nav1.7 compared to other family members i.e Nav1.1, Nav 1.2, Nav 1.3, Nav 1.4, Nav 1.5, Nav 1.6, Nav 1.8 and Nav 1.9: N146, F276, S279, L280, E281, L286, M290, N291, T292, L293, S295, E296, D298, F299, R300, K301, F317, T319, T329, I333, K773, R1218, I1224, S1357, P1360, A1361, Q1363, P1365, R1367, F1371, S1377, N1379, L1385, T1409, I1410, V1419, K1423, K1536, E1537, G1538, H1542, E1545, T1601, D1673, N1676, K1718 and E1727.

Accordingly, a suitable peptide of Nav1.7 for use in the present invention may comprise at least one of the following residues in the peptide sequence: N146, F276, S279, L280, E281, L286, M290, N291, T292, L293, S295, E296, D298, F299, R300, K301, F317, T319, T329, I333, K773, R1218, I1224, S1357, P1360, A1361, Q1363, P1365, R1367, F1371, S1377, N1379, L1385, T1409, I1410, V1419, K1423, K1536, E1537, G1538, H1542, E1545, T1601, D1673, N1676, K1718 and E1727.

In one embodiment the peptide may comprise at least 5 consecutive amino acids incorporating one or more of the unique Nav1.7 residues identified above.

Examples of such peptides are described herein below, with the exception of peptide BE3 (SEQ ID NO:217) which has been designed based on the loss of function mutation described herein above.

The selected peptides may be conventional linear peptides or cyclic peptides and comprise at least 4 consecutive amino acids from the above sequences. In either case the peptide is designed to include a single functional group that is used for subsequent conjugation, such as by covalent attachment, to carrier protein or reporter group, for example a macromolecular carrier such as a xenogenic protein. The said functional group may be a side chain thiol of a cysteine residue, a C-terminal carboxyl or side chain carboxyl of an aspartic acid or glutamic acid residue or primary amine of an N-terminal amino group or lysine side chain residue.

If the peptide does not contain an aspartate, glutamate or lysine residue and is capped at the N-terminal, then the unique functional group may be the C-terminal carboxylic acid which may be derivatized directly for coupling to the carrier via amide chemistry.

If the peptide does not contain a lysine residue then the unique functional group may be the N-terminal amino group which can be derivatized to introduce a further reactive group such as a maleimide.

If the peptide contains a single cysteine residue then the side chain thiol may be the unique functional group which can be coupled to the carrier via maleimide chemistry.

A unique functional group may be incorporated by an additional residue (either natural or non-natural amino acid) e.g. a cysteine, at either terminus to allow specific coupling.

The amino acid residue bearing the said functional group may correspond to the native Na$_v$1.7 sequence or may be additional to the native Na$_v$1.7 sequence. The position of this residue in the Na$_v$1.7 peptide sequence may be at either terminus of the sequence or at any internal position.

In one embodiment the peptide is a linear peptide, for example, containing any of the following sequences, wherein the domain A, B, C or D and the extracellular loop E1, E2 or E3, from which the peptide is derived is denoted in brackets. The cysteines which are underlined in the peptides are non-naturally occurring cysteine residues in the ion channel. The cysteine residues in the following peptides may be used to attach a carrier protein.

| | | |
|---|---|---|
| CFRNSLENN, | (AE3) | (SEQ ID NO: 207) |
| CINTTDGSRFPASQVP, | (CE3) | (SEQ ID NO: 208) |
| CNVSQNVR, | (CE3) | (SEQ ID NO: 209) |
| VNVDKQPC, | (CE3) | (SEQ ID NO: 210) |
| EKEGQSQHMTEC, | (DE1) | (SEQ ID NO: 211) |
| CKKEDGIND, | (DE3) | (SEQ ID NO: 212) |
| CDPKKVHP, and/or | (DE3) | (SEQ ID NO: 213) |
| CFSTDSGQ. | (AE3) | (SEQ ID NO: 214) |

In one embodiment of the present invention the Na$_v$1.7 peptide has an amino acid sequence selected from the group consisting of SEQ ID NOs: 207 to 214. In a preferred embodiment, the Na$_v$1.7 peptide has an amino acid sequence selected from the group consisting of SEQ ID NOs: 207-213.

These sequences may be capped at either N-terminal or C-terminal with for example an Naacetyl or amide group respectively.

In one aspect there is provided a method of generating an antibody employing a cyclic peptide.

A cyclic peptide as employed herein is a peptide where a sequence of amino acids are joined by a bond, such as a disulfide bond, thereby forming a loop or circle with no discernable start and/or finish. The cyclic peptide may be formed from a corresponding linear peptide by various means such as but not limited to the following: C-terminal carboxyl group ligation to the N-terminal alpha amino group to form a peptide bond; alternatively side chain carboxyl groups (of aspartic or glutamic acid residues) may be ligated to the side chain amino group of lysine or the N-terminal alpha amino group or the C-terminal carboxyl group may be ligated to the side chain amino group of lysine; disulphide bond formation between side chains thiols of two cysteine residue separated from each other by at least three residues in the linear sequence. It may be desirable to form the "ring completing bond" in an area of overlap in the linear sequence. Area of overlap as employed herein is intended to refer to where there is a repeat of two or more amino acids occurring in the sequence. Thus a sequence of overlap as employed herein is intended to refer to where there is some commonality in the sequence, for example at least two, such as 3 or 4 amino acids are located in the same order in the sequence in two separate locations. These regions of overlap can be aligned and ligated such that an amino acid in one location replaces the corresponding amino acid in the second location to form the cyclised peptide.

Thus in one embodiment the peptide is cyclised by forming an amide bond.

In one embodiment the peptide is cyclised by forming a disulfide bond.

In one embodiment the sequence is ligated in a region of overlap in the linear sequence.

Cyclic peptides may be synthesized using any suitable method known in the art. In one embodiment the cyclic peptide is synthesized using protecting groups to prevent reactions of the amino acid side chains (Barlos, K.; Gatos, D.; Kutsogianni, S.; Papaphotiou, G.; Poulos, C.; Tsegenidis, T. Int. J. Pept. Protein Res. 1991, Vol 38, Issue 6 p 562-568) followed by cyclization and removal of the protecting groups (Kessler H et al., 1989, Computer Aided Drug Design, p 461-484; Dekker M et al, 1990, J. Peptide Research, 35, p 287-300; Gurrath M. et al., 1992, Eur. J. Biochem., 210, 911-921; Izumiya N. et al., 1981, Biopolymers, 20, 1785-1791; Brady S. F. et al., 1983, in Peptides, Structure and Function, Proceedings of the Eighth American Peptide Symposium, Ed. V. J. Hruby and D. H. Rick, pp. 127-130, Pierce Chemical Company, Rockford, Ill.; He J. X. et al., 1994, Lett. Peptide Sci., 1, 25-30).

Surprisingly functionally modifying antibodies can be generated employing a very short cyclic peptide sequence, for example containing only 5, 6, 7, 8, 9, 10, 11, 12, 13, 4, 15, 16, 17, 18 or 19 amino acids. This may be due the rigidity provided by cyclising the peptide.

In one embodiment the cyclised peptide comprising a fragment of at least 5 consecutive amino acids from NAV1.7, for example is selected from the following, wherein the domain A, B, C or D and the extracellular loop E1, E2 or E3, from which the peptide is derived is denoted in brackets:

| | | |
|---|---|---|
| CTLESIMNTLESEEDFRKY; | (AE3) | (SEQ ID NO: 215) |
| CPMTEEFKN, | (BE1) | (SEQ ID NO: 216) |
| CTLPRWHMNDD | (BE3) | (SEQ ID NO: 217) |
| CIERKKTIKI, | (CE1) | (SEQ ID NO: 218) |
| CEKEGQSQHMTE, | (DE1) | (SEQ ID NO: 219) |
| DDCTLPRWHMN, and/or | (BE3) | (SEQ ID NO: 220) |
| CFSTDSGQ. | (AE3) | (SEQ ID NO: 221) |

In one embodiment of the present invention the Na$_v$1.7 peptide has an amino acid sequence selected from the group consisting of SEQ ID NOs:215 to 221. In a preferred embodiment, the Na$_v$1.7 peptide has an amino acid sequence selected from the group consisting of SEQ ID NOs: 215 to 218.

In one embodiment the present invention provides a method of generating a functionally modifying antibody to Nav1.7 comprising immunizing a host with a peptide comprising an extracellular sequence of Nav1.7. In one example the peptide is linear. In one example the peptide is cyclic.

In one embodiment the present invention provides a method of generating a functionally modifying antibody to Nav1.7 comprising immunizing a host with a cyclic peptide selected from the group consisting of SEQ ID NO:215, SEQ ID NO:216, SEQ ID NO:217, SEQ ID NO:218 and SEQ ID NO:215.

In one embodiment the present invention provides a method of generating a functionally modifying antibody to Nav1.7 comprising immunizing a host with a cyclic peptide selected from the group consisting of SEQ ID NO:215, SEQ ID NO:216 and SEQ ID NO:218.

In one embodiment the present invention provides a method of generating a functionally modifying antibody to Nav1.7 comprising immunizing a host with a linear peptide selected from the group consisting of SEQ ID NO:207, SEQ ID NO:208, SEQ ID NO:209, SEQ ID NO:210, SEQ ID NO:211, SEQ ID NO:212, SEQ ID NO:213 and SEQ ID NO:222.

To prepare immunogens for the purpose of raising anti-Nav1.7 antibodies in a host animal each peptide requires covalent conjugation to a carrier protein. The carrier protein is selected on the basis of its 'foreignness' to the host species; thus for immunization of rabbits or rodents examples of suitable carrier proteins are keyhole limpet hemocyanin (KLH), ovalbumin (OVA) and bovine serum albumun (BSA). Each of the above peptides, whether linear or cyclic, may be conjugated through the cysteine thiol to one of each of the above proteins, where the lysine side chain amino groups of the latter have been covalently modified with a maleimide functionality to yield respectively:

KLH-maleimide,
Ovalbumin-maleimide, or
BSA-maleimide.

The present disclosure explicitly envisages each one of the peptides described herein in separate conjugations with each one of the carriers listed above, i.e. 45 different molecules are specifically provided for immunizing a host, for example KLH-CEKEGQSQHMTE (cyclic) (SEQ ID NO: 219) or BSA-CEKEGQSQHMTE (cyclic) (SEQ ID NO: 219). Accordingly, any of the peptides having an amino acid sequence selected from SEQ ID NOs: 207 to 221 may be conjugated with each of the carrier proteins listed above.

As described above, the carrier protein may be conjugated through a unique functional group such as a cysteine residue. However, any alternative naturally occurring or non-naturally occurring residue may be used in place of a cysteine residue in order to conjugate the peptide to the carrier protein. An example of a non-naturally occurring residue which may be used in place of cysteine is a homocysteine residue, which is a homologue of cysteine which further comprises an additional methylene group in the side chain. Accordingly, any of the peptides having an amino acid sequence selected from SEQ ID NOs: 207 to 221, which comprise a cysteine residue may be modified to replace the cysteine residue with an alternative suitable naturally occurring or non-naturally occurring residue for conjugation to the carrier protein, such as a homocysteine residue.

The present disclosure also extends to the novel peptides disclosed herein and compositions comprising same. In one embodiment of the present invention provides a $Na_v1.7$ peptide having an amino acid sequence selected from the group consisting of SEQ ID NOs:215 to 222. In a preferred embodiment, the $Na_v1.7$ peptide has an amino acid sequence selected from the group consisting of SEQ ID NO: 208, SEQ ID NO: 211, SEQ ID NO: 215, SEQ ID NO: 216, SEQ ID NO: 218 and SEQ ID NO: 222.

Generally between 0.001 and 1 mg of each peptide-carrier protein are required for each immunization dose per host animal.

Alternative immunogens suitable for raising function modifying antibodies to $Na_v1.7$ include: full length human $Na_v1.7$, truncations of $Na_v1.7$ including individual sub-domains and truncations of sub-domains; chimeric molecules with regions of $Na_v1.7$ fused to regions other transmembrane proteins to aid expression or present extracellular loops to the immune system and mutations of $Na_v1.7$ to constrain regions of $Na_v1.7$ in a desired conformation.

These immunogens may be expressed in mammalian cells for direct cell immunization or purification of protein for immunization.

These immunogens may be expressed in *E. coli* or cell-free expression systems for purification of protein for immunization.

Purified protein may be integrated into lipid vesicles for immunisation.

These $Na_v1.7$ versions may also be generated as lipoparticles for immunization.

In addition any of the above immunogens can be utilized as screening tools for identifying function-modifying antibodies.

Thus in one aspect there is provided a method of generating antibodies in a host by immunizing, for example with at least one $Na_v1.7$ peptide-carrier protein conjugate or several different $Na_v1.7$ peptides conjugated separately or as a mixture conjugated to the same carrier protein.

In one embodiment the method involves one, two, three, four or five immunizations.

In one embodiment the method involves at least two, such as two or three immunizations with the respective conjugates peptide(s).

In one embodiment the second immunization employs a different conjugate, wherein the peptide(s) is (are) common but the carrier protein is different to the carrier protein employed in the first immunization.

Thus in one embodiment the third immunization employs a different conjugate wherein the peptide(s) is (are) common to that of the first and second immunization, but the carrier protein is different to that employed in the first and/or second immunization. Unwanted antibody specificities against the carrier protein may in this way be minimized.

Suitable carrier protein combinations for sequential immunization include, KLH and Ovalbumin and BSA in any order.

Varying the carrier may be advantageous in optimizing the response to the peptide.

Each immunization will generally also include the administration of an adjuvant to stimulate immune responses. Suitable adjuvants include Freud's complete or incomplete adjuvant, and adjuvants comprising, alum, QS21, MPL and/or CPG.

The method may further comprises a step of separate antibodies or antibody producing cells from the host.

In one embodiment the host is a rabbit.

The aforementioned $Na_v1.7$ peptides may also be conjugated to a reporter group. The reporter group may for instance be biotin, a fluorescent group or enzyme tag, or any group which will allow detection or isolation of anti-$Na_v1.7$ antibodies. Reporter group-$Na_v1.7$ peptide conjugates may be used to screen the resulting polyclonal sera and monoclonal antibodies. For example, a screening ELISA may comprise streptavidin coated microwells and captured biotinylated peptide. Titrations of immune sera over this would result in peptide specific antibody binding to the surface, which in turn could be revealed by a fourth anti-species (such as anti-rabbit) IgG-peroxidase layer.

Reporter group-$Na_v1.7$ peptide conjugates may also be used to isolate specific $Na_v1.7$ antibody like modalities by library based techniques such as phage panning.

The method may also include a further purification step, for example to provide polyclonal or monoclonal antibodies.

The methods may also comprise the step of producing recombinant monoclonal antibodies derived from said immunizations.

Before monoclonal antibodies can be prepared recombinantly part, such as the variable regions, or all of the antibody may need to be cloned and/or sequenced.

The disclosure also extends to antibody producing cells and antibodies obtainable or obtained from the method herein.

The disclosure also extends to an antibody or suitable antibody fragment obtainable or obtained employing the method herein.

Accordingly the present invention also provides an anti-Nav1.7 antibody or binding fragment thereof which after binding the ion channel is functionally modifying thereto wherein the antibody binds to one or more $Na_v1.7$ peptides having an amino acid sequence selected from the group consisting of SEQ ID NOs:215 to 221. In a preferred embodiment, the antibody or binding fragment binds to one of more of the $Na_v1.7$ peptides selected from the group consisting of SEQ ID NOs: 208, SEQ ID NO: 211, SEQ ID NO: 215, SEQ ID NO: 216, SEQ ID NO: 218 and SEQ ID NO: 222.

In one embodiment the present invention provides an anti-Nav1.7 antibody or binding fragment thereof which after binding the ion channel is functionally modifying thereto wherein the antibody binds to one or more $Na_v1.7$ peptides falling within or a peptide consisting of sequences 273 to 308, 314 to 322, 326 to 336, 764 to 777, 1215 to 1227, 1354 to 1388, 1391 to 1397, 1406 to 1413, 1416 to 1426, 1533 to 1548, 1598 to 1604, 1670 to 1679, or 1708 to 1730, based on the amino acid sequence numbering of the $Na_v1.7$ sequence deposited in the Swiss Prot database as human protein SCN9A (accession no. Q15858).

The disclosure also includes pharmaceutical compositions comprising antibodies or fragments herein.

The pharmaceutical compositions suitably comprise a therapeutically effective amount of the antibody of the invention. The term "therapeutically effective amount" as used herein refers to an amount of a therapeutic agent needed to treat, ameliorate or prevent a targeted disease or condition, or to exhibit a detectable therapeutic or preventative effect. For any antibody, the therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgement of the clinician. Generally, a therapeutically effective amount will be from 0.01 mg/kg to 50 mg/kg, for example 0.1 mg/kg to 20 mg/kg. Pharmaceutical compositions may be conveniently presented in unit dose forms containing a predetermined amount of an active agent of the invention per dose.

Compositions may be administered individually to a patient or may be administered in combination (e.g. simultaneously, sequentially or separately) with other agents, drugs or hormones.

The dose at which the antibody or fragment of the present invention is administered depends on the nature of the condition to be treated, the extent of the disease and/or symptoms present and on whether the antibody or fragment is being used prophylactically or to treat an existing condition.

The frequency of dose will depend on the half-life of the antibody molecule and the duration of its effect. If the antibody molecule has a short half-life (e.g. 2 to 10 hours) it may be necessary to give one or more doses per day. Alternatively, if the antibody molecule has a long half life (e.g. 2 to 15 days) it may only be necessary to give a dosage once per day, once per week or even once every 1 or 2 months.

The pharmaceutically acceptable carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Suitable forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. Alternatively, the antibody molecule may be in dry form, for reconstitution before use with an appropriate sterile liquid.

Once formulated, the compositions of the invention can be administered directly to the subject. The subjects to be treated can be animals. However, in one or more embodiments the compositions are adapted for administration to human subjects.

Suitably in formulations according to the present disclosure, the pH of the final formulation is not similar to the value of the isoelectric point of the antibody or fragment, for example if the pH of the formulation is 7 then a pI of from 8-9 or above may be appropriate. Whilst not wishing to be bound by theory it is thought that this may ultimately provide a final formulation with improved stability, for example the antibody or fragment remains in solution.

The pharmaceutical compositions of this invention may be administered by any number of routes including, but not limited to, oral, intravenous, intramuscular, intra-arterial, intramedullary, intrathecal, intraventricular, transdermal, transcutaneous (for example, see WO98/20734), subcutaneous, intraperitoneal, intranasal, enteral, topical, sublingual, intravaginal or rectal routes. Hyposprays may also be used to administer the pharmaceutical compositions of the invention. Typically, the therapeutic compositions may be prepared as injectables, either as liquid solutions or suspensions.

Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

It will be appreciated that the active ingredient in the composition will be a protein molecule. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

A thorough discussion of pharmaceutically acceptable carriers is available in Remington's Pharmaceutical Sciences (Mack Publishing Company, N.J. 1991).

In one embodiment the formulation is provided as a formulation for topical administrations including inhalation.

Suitable inhalable preparations include inhalable powders, metering aerosols containing propellant gases or inhalable solutions free from propellant gases. Inhalable powders according to the disclosure containing the active substance may consist solely of the abovementioned active substances or of a mixture of the abovementioned active substances with physiologically acceptable excipient.

These inhalable powders may include monosaccharides (e.g. glucose or arabinose), disaccharides (e.g. lactose, saccharose, maltose), oligo- and polysaccharides (e.g. dextranes), polyalcohols (e.g. sorbitol, mannitol, xylitol), salts (e.g. sodium chloride, calcium carbonate) or mixtures of these with one another. Mono- or disaccharides are suitably used, the use of lactose or glucose, particularly but not exclusively in the form of their hydrates.

Particles for deposition in the lung require a particle size less than 10 microns, such as 1-9 microns for example from 0.1 to 5 µm, in particular from 1 to 5 µm. The particle size of the active ingredient (such as the antibody or fragment) is of primary importance.

The propellent gases which can be used to prepare the inhalable aerosols are known in the art. Suitable propellent gases are selected from among hydrocarbons such as n-propane, n-butane or isobutane and halohydrocarbons such as chlorinated and/or fluorinated derivatives of methane, ethane, propane, butane, cyclopropane or cyclobutane. The abovementioned propellent gases may be used on their own or in mixtures thereof.

Particularly suitable propellent gases are halogenated alkane derivatives selected from among TG 11, TG 12, TG 134a and TG227. Of the abovementioned halogenated hydrocarbons, TG134a (1,1,1,2-tetrafluoroethane) and TG227 (1,1,1,2,3,3,3-heptafluoropropane) and mixtures thereof are particularly suitable.

The propellent-gas-containing inhalable aerosols may also contain other ingredients such as cosolvents, stabilisers, surface-active agents (surfactants), antioxidants, lubricants and means for adjusting the pH. All these ingredients are known in the art.

The propellant-gas-containing inhalable aerosols according to the invention may contain up to 5% by weight of active substance. Aerosols according to the invention contain, for example, 0.002 to 5% by weight, 0.01 to 3% by weight, 0.015 to 2% by weight, 0.1 to 2% by weight, 0.5 to 2% by weight or 0.5 to 1% by weight of active ingredient.

Alternatively topical administrations to the lung may also be by administration of a liquid solution or suspension formulation, for example employing a device such as a nebulizer, for example, a nebulizer connected to a compressor (e.g., the Pari LC-Jet Plus® nebulizer connected to a Pari Master® compressor manufactured by Pari Respiratory Equipment, Inc., Richmond, Va.).

The antibody or fragment of the invention can be delivered dispersed in a solvent, e.g., in the form of a solution or a suspension. It can be suspended in an appropriate physiological solution, e.g., saline or other pharmacologically acceptable solvent or a buffered solution. Buffered solutions known in the art may contain 0.05 mg to 0.15 mg disodium edetate, 8.0 mg to 9.0 mg NaCl, 0.15 mg to 0.25 mg polysorbate, 0.25 mg to 0.30 mg anhydrous citric acid, and 0.45 mg to 0.55 mg sodium citrate per 1 ml of water so as to achieve a pH of about 4.0 to 5.0. A suspension can employ, for example, lyophilised antibody.

The therapeutic suspensions or solution formulations can also contain one or more excipients. Excipients are well known in the art and include buffers (e.g., citrate buffer, phosphate buffer, acetate buffer and bicarbonate buffer), amino acids, urea, alcohols, ascorbic acid, phospholipids, proteins (e.g., serum albumin), EDTA, sodium chloride, liposomes, mannitol, sorbitol, and glycerol. Solutions or suspensions can be encapsulated in liposomes or biodegradable microspheres. The formulation will generally be provided in a substantially sterile form employing sterile manufacture processes.

This may include production and sterilization by filtration of the buffered solvent/solution used for the for the formulation, aseptic suspension of the antibody in the sterile buffered solvent solution, and dispensing of the formulation into sterile receptacles by methods familiar to those of ordinary skill in the art.

Nebulizable formulation according to the present disclosure may be provided, for example, as single dose units (e.g., sealed plastic containers or vials) packed in foil envelopes. Each vial contains a unit dose in a volume, e.g., 2 ml, of solvent/solution buffer.

The fusion protein molecule of the present disclosure are thought to be suitable for delivery via nebulisation.

The antibodies and fragments of the present disclosure may be suitable for treating pain, for example neuropathic pain including painful diabetic neuropathy (PDN), post-herpetic neuropathy (PHN) or trigeminal neuralgia (TN). Other causes of neuropathic pain include spinal cord injuries, multiple sclerosis, phantom limb pain, post-stroke pain and HIV-associated pain. Conditions such as chronic back pain, osteoarthritis and cancer may also result in the generation of neuropathic-related pain and thus are potentially suitable for treatment with an antibody or fragment according to the present disclosure.

In one embodiment the anti-$Na_v1.7$ antibodies or fragments according the invention are suitable for the treatment or prophylaxis of pain, including somatic pain, visceral pain, neuropathic pain, nociceptive pain, acute pain, chronic pain, breakthrough pain and/or inflammatory pain.

In one embodiment anti-$Na_v1.7$ antibodies or fragments according the invention are suitable for the treatment or prophylaxis of one or more of the following pain types: allodynia, anaesthesia dolorosa, anginal pain, breakthrough pain, complex regional pain syndrome I, complex regional pain syndrome II, hyperalgesia, hyperpathia, idiopathic pain, malignant pain, paresthesia, phantom limb pain, psychogenic pain.

In one embodiment the anti-$Na_v1.7$ antibody or fragment according to the disclosure is useful in the treatment of asthma, airway hyper-reactivity in asthma, chronic cough, for example in asthma and/or chronic obstructive airways.

In one embodiment the anti-$Na_v1.7$ antibody or fragment according to the disclosure is useful in the treatment inflammation, osteoarthritis, rheumatoid arthritis and/or pain associated with any of the same.

In one embodiment the anti-$Na_v1.7$ antibody or fragment according to the disclosure is useful in the treatment of pain associated with acute injuries, for examples wounds such as lacerations, incisions, burns, bullet and/or shrapnel injuries.

As discussed the anti-$Na_v1.7$ antibody or fragment according the present disclosure is likely to be useful in the treatment of pain, such as acute pain and chronic pain, neuropathic pain, nociceptive pain, visceral pain, back pain and pain associated with disease and degeneration.

The pain may result from one or more causes, including, but not restricted to peripheral neuropathy, central neuropathy, nerve compression or entrapment syndromes such as carpal tunnel syndrome, tarsus tunnel syndrome, ulnar nerve entrapment, compression radiculopathy, lumbar spinal stenosis, sciatic nerve compression, spinal root compression, intercostal neuralgia, compression radiculopathy and radicular low back pain, spinal root lesions, back pain, neuritis, automimmune diseases, postoperative pain, dental pain, direct trauma, inflammation, HIV infection, small pox infection, herpes infection, toxic exposure, invasive cancer, chemotherapy, radiotherapy, hormonal therapy, foreign bodies, burns, congenital defect, phantom limb pain, rheumatoid arthritis, osteoarthritis, fracture pain, gout pain, fibromyalgias, multiple sclerosis, pain associated with diarrhea, irritable bowel syndrome, migraine, encephalitis, diabetes, chronic alcoholism, hypothyroidism, uremia and vitamin deficiencies. Thus the anti-$Na_v1.7$ antibody or fragment according to the present disclosure may be useful in the treatment or amelioration of symptoms of one or more of the above indications.

In one embodiment an antibody or fragment according to the present disclosure is employed as a standard in an assay for screening for $Na_v1.7$ inhibitors.

Comprising in the context of the present specification is intended to meaning including.

Where technically appropriate embodiments of the invention may be combined.

Embodiments are described herein as comprising certain features/elements. The disclosure also extends to separate embodiments consisting or consisting essentially of said features/elements.

The present invention is further described by way of illustration only in the following examples, which refer to the accompanying Figures, in which:

Examples

Therapeutic Antibody Generation/Selection

Peptides were supplied by Peptide Protein Research Ltd., Fareham, U.K., and linear peptides were synthesized by Fmoc solid phase peptide chemistry according to the method of Atherton and Sheppard (1989). *Solid Phase peptide synthesis: a practical approach*. Oxford, England: IRL Press. N to C terminal cyclic peptides were synthesised as side chain protected peptides according to the method of Barbs et al Int. J. Pept. Protein Res. 1991 and cyclisation was carried out in solution phase followed by side chain deprotection according to the method of Kessler H et al., 1989, in Computer-aided drug design, methods and applications, Ed. T. J. Perun and C. L. Probst, pp. 461-484, Marcel Dekker, New-York; Toniolo C., 1990, Int. J. Pept. Protein Res., 35, 287-300; Gurrath M. et al., 1992, Eur. J. Biochem., 210, 911-921; Izumiya N. et al., 1981, Biopolymers, 20, 1785-1791; Brady S. F. et al., 1983, in Peptides, Structure and Function, Proceedings of the Eighth American Peptide Symposium, Ed. V. J. Hruby and D. H. Rick, pp. 127-130, Pierce Chemical Company, Rockford, Ill.; He J. X. et al., 1994, Lett. Peptide Sci., 1, 25-30.

Rabbits were immunised with combinations of human $Na_v1.7$ peptides conjugated to either KLH, OVA or BSA (Table 1). Following 5 subcutaneous immunisations (KLH, OVA, BSA, KLH, OVA), animals were sacrificed and PBMC, spleen and bone marrow harvested. Sera was tested for binding to human biotinylated peptide in ELISA.

TABLE 1

$Na_v1.7$ peptide immunogens

| Rabbit | Peptides | Peptide Sequence |
|---|---|---|
| 3821 and 3822 | A31, A32 | A31 - Nα-acetyl-CFRNSLENN-amide (SEQ ID NO: 207)<br>A32 - CTLESIMNTLESEEDFRKY (cyclic) (SEQ ID NO: 215) |
| 3823 and 3824 | B11, B31 | B11 - CPMTEEFKN (cyclic) (SEQ ID NO: 216)<br>B31 - CTLPRWHMNDD (cyclic) (SEQ ID NO: 217) |
| 5825 and 5826 | C11, C31, C32, C33 | C11 - CIERKKTIKI (cyclic) (SEQ ID NO: 218)<br>C31 - Nα-acetyl-CINTTDGSRFPASQVP-amide (SEQ ID NO: 208)<br>C32 - Nα-acetyl-CNVSQNVR-amide (SEQ ID NO: 209)<br>C33 - Nα-acetyl-VNVDKQPC-amide (SEQ ID NO: 210) |
| 5827 and 5828 | D11, D31, D32 | D11 - Nα-acetyl-EKEGQSQHMTEC-amide (SEQ ID NO: 211)<br>D31 - Nα-acetyl-CKKEDGIND-amide (SEQ ID NO: 212)<br>D32 - Nα-acetyl-CDPKKVHP-amide (SEQ ID NO: 213) |

Table 1 shows immunised rabbit number, peptide combination employed for immunisation and peptide sequence. A31 and A32 are peptides from loop E3 in domain A. B11 is a peptide from loop E1 in domain B. B31 is a peptide from loop E3 in domain B. C11 is a peptide from loop E1 in domain C. C31, C32 and C33 are peptides from loop E3 in domain C. D11 is a peptide from loop E1 in domain D. D31 and D32 are peptide loops from E3 in domain D.

SLAM was performed using substantially the methods described in Tickle et al. 2009 (JALA, Vol. 14, number 5, p303-307). Briefly, SLAM cultures were set up using rabbit splenocytes or PBMC and supernatants were first screened for their ability to bind biotinylated peptide in a bead-based assay in the FMAT. This was a homogeneous assay using biotinylated human peptide bound to streptavidin beads (Bangs Laboratories) and revealing binding using a goat anti-rabbit Fc-Cy5 conjugate (Jackson immunoResearch). Positives from this screen were then put through a negative screen to identify non-specific antibodies. This used streptavidin beads with no peptide or with an irrelevant peptide, revealing binding with a goat anti-rabbit Fc-Cy5 conjugate (Jackson ImmunoResearch), to identify the peptide specific binders.

From 10 SLAM experiments, a number of A32-specific, B11-specific, C11-specific, D11-specific and C31-specific antibody-containing wells were identified using the screens described above.

Single B cell isolation via the fluorescent foci method and subsequent variable region gene cloning from a number of these wells successfully yielded heavy and light chain variable region gene pairs following reverse transcription (RT)-PCR. These V-region genes were cloned as rabbit IgG1 full-length antibodies and re-expressed in a HEK-293 transient expression system.

Sequence analysis of cloned v-regions revealed the presence of a number of unique families of anti-human A32-specific, anti-human B11-specific and C31-specific $Na_v1.7$ antibody (see table 2 below). DNA and amino acid sequences of these antibodies are shown in FIGS. 4-13. Antibodies were expressed in a transient CHO system and subsequently purified to allow further characterisation in vitro and in vivo.

TABLE 2

| UCB antibody number | Rabbit number | Peptide specificity |
|---|---|---|
| CA167_00915 | 3822 | A32 |
| CA167_00914 | 3822 | A32 |
| CA167_00933 | 3822 | A32 |
| CA167_00932 | 3822 | A32 |
| CA167_00931 | 3822 | A32 |
| CA167_00930 | 3822 | A32 |
| CA167_00983 | 3824 | B11 |
| CA167_00984 | 3824 | B11 |
| CA167_00985 | 3824 | B11 |
| CA167_01080 | 3824 | B11 |
| CA167_01081 | 3824 | B11 |
| CA167_01082 | 3824 | B11 |
| CA167_01083 | 3824 | B11 |
| CA167_01084 | 3824 | B11 |
| CA167_01085 | 3824 | B11 |
| CA167_01086 | 3824 | B11 |
| CA167_01059 | 5825 | C31 |
| CA167_01060 | 5825 | C31 |
| CA167_01066 | 5825 | C31 |
| CA167_01068 | 5825 | C31 |

FIGS. 4-13 show sequences for anti-$Na_v1.7$ antibodies. The immunised rabbit number that the antibodies were derived from and their peptide specificities are detailed.

Procedure for h $Na_v1.7$ Recording for Antibody Testing Solutions and Antibodies Handling Extracellular solution contained (in mM): 130 NaCl, 4 KCl, 1.5 $CaCl_2$, 1 $MgCl_2$, 30 glucose, 10 HEPES (pH 7.4 with Tris-Base, and 300 to 305 mOsmolar). Intracellular solution contained (in mM): 5 NaCl, 115 CsF, 20 CsCl, 110 HEPES, 10 EGTA free acid (pH 7.2 with CsOH, and 290 to 295 mOsmolar) and was either made fresh or kept frozen. Extracellular and intracellular solutions were filtered prior to use.

Antibodies were directly diluted in extracellular solution and were freshly (no more than 15 min) prepared before transfer to a 96-well polypropylene compound plate (Sarsted, #83.1835.500). For the experiments using selective peptide, antibodies and peptides, at equal concentrations, were preincubated at least 30-min at 4° C. prior Patch Clamp experiments.

Cell Preparation

HEK293 cells stably expressing the human $Na_v1.7$ channel (type IX voltage-gated sodium channel alpha subunit) were purchased from Upstate (Upstate, Millipore, cat.#CYL3011). Cells were cultured in T-75 (BD BioCoat™ Collagen I Cellware, Becton Dickinson Labware, Bedford, Mass., #356485) flasks coated with collagen type I using standard culture medium DMEM-F12 with-Glutamine (Invitrogen, #11320) containing 10% FBS (Lonza, #DE14-802F), 1% penicillin+streptomycin (Lonza, DE17-603E), 1% non essential amino acids (Lonza, BE13-114E) and 400 µg/ml G418 (GIBCO, #10131-027). Cells were plated at a density of 15,000 cells/cm2 or 8,000 cells/cm2 density for 2 or 3 days respectively before being used on PatchXpress® 7000A (Axon instrument, new part of MDS Analytical Technologies). Cells confluence never exceeded 90%. The day of the experiment, cells were harvested using Accumax (Sigma, A7089). Briefly, cells were washed twice in PBS (Lonza, #BE12-516F) without calcium and magnesium, and a 1:4 dilution of Accumax solution was added and incubated for 1.5 to 2-min at 37° C. DMEM-F12 with 15 mMHEPES and L-glutamine (Lonza, #BE12-719F) containing 10% FBS (recovery media) was added to quench Accumax digestion. The cells were subsequently centrifuged at 1,000 rpm for 5-min in 50 ml falcon tube and pellets are resuspended in 10 ml of recovery media. Cells are counted (CoulterZ2) and suspended at ~0.1 million cells/ml and transferred to a 15 ml screw-cap tube for minimum 90 minutes at room temperature. Cells were then centrifuged for 60-s at 1,000 rpm. The pellet was gently resuspended in 1,000 µl extracellular solution and centrifuged a second time for 30-s at 1,000 rpm. Pellet was resuspended in 150 µL extracellular solution and immediately tested on the PatchXpress®.

PatchXpress® Procedures

The AVIVA Biosciences SealChip16™ electrode arrays (purchased from Axon Instruments, Union City, Calif.) were manually placed in the holder of the PatchXpress® system and automatically prepared for application of the cells. Intracellular solution was injected into the bottom of each chamber, and extracellular solution was perfused into the top of the chambers through the 16-nozzle wash station. Throughout this period, the pressure controller maintained a positive pressure (+10 mmHg) from the intracellular side to keep the hole free of debris. Cells were triturated by the integrated Cavro pipetting robot prior to addition of 4 µl (containing 10K-30K cells) to each well.

PatchXpress® h $Na_v1.7$ Assay

After 10-s, the pressure was switched from +4 to −30 mmHg to attract suspended cells to each of the 16 holes (electrodes). Seal formation was achieved by repeating negative pressure ramp from −1 to −35 mmHg at a rate of 1.6 mmHg/s every 36-s until a Giga Ohm Seal was obtained and verified for 20-s. Whole-cell access was achieved by rupturing the patch of membrane over the hole using a ramp increase in negative pressure from −40 to −150 mmHg at a rate of 7.5 mmHg/s with a pipette potential of −80 mV. After whole cell configuration cells are washed with extracellular solution for 66-s to remove the excess cells in the well. The cell was allowed to dialyze for 5 min, during which the access resistance was monitored. From the time of whole-cell break-in to the end of the experiment, the cells were held at −80 mV between voltage protocols. A time course protocol was applied to assess the antibody potencies on sodium current elicited by a depolarizing step from −80 mV to 0 mV for 20 milliseconds at 10 seconds interval. Whole cell compensation was automatically made before each trial starts and electrical access resistance (Ra) was corrected by 65%. Linear leak substraction was performed online using a P/N leak subtraction protocol (N=4) at the holding of −80 mV.

After a stabilizing period (up to 10 min), a negative control solution (extracellular solution) was applied for 5-min, followed by two doses of antibodies. The interval between both additions of the same concentration of compound to a well was ~11-s. Antibody solution (45 µL) was added online (30 µL/s) at the desired concentration with permanent aspiration. Currents were monitored continuously during the 18-min exposure to the antibody.

Data Analysis

Cells were not analyzed if:
(1) the membrane resistance was initially <200 MOhm,
(2) current amplitude <200 pA,
(3) an access resistance no greater then 20 MOhm and
(4) no real stabilized current after negative control addition.

The current amplitude was measured using DataXpress2 software (Axon instruments) and rundown current correction was performed by linear or exponential fitting method on the measurement associated with the last 10-15 data points after the washout period and the last 10-15 data point after the negative control addition. Current was normalized by the mean current corrected amplitude prior antibody addition. Current inhibition was estimated by the residual response after 18-min antibodies application. Data is given below in Table 3.

TABLE 3

Inhibition of Nav1.7 currents expressed in HEK cells.

| Antibody | Peptide | Concentration (ug/ml) | Nav1.7 inhibition (%) |
|---|---|---|---|
| CA167_00914 | A32 | 25 | 28 |
| CA167_00915 | A32 | 25 | 26 |
| CA167_00931 | A32 | 2.5 | 9 |
| CA167_00932 | A32 | 25 | 27 |
| CA167_00933 | A32 | 25 | 8 |
| CA167_00983 | B11 | 25 | 41 |
| CA167_00984 | B11 | 25 | 9 |
| CA167_00985 | B11 | 25 | 12 |
| CA167_01059 | C31 | 25 | −5 |
| CA167_01060 | C31 | 25 | 21 |
| CA167_01066 | C31 | 25 | 28 |
| CA167_01068 | C31 | 25 | −7 |
| CA167_01080 | B11 | 25 | 46 |
| CA167_01081 | B11 | 25 | 33 |
| CA167_01082 | B11 | 25 | 10 |
| CA167_01083 | B11 | 25 | 16 |
| CA167_01084 | B11 | 25 | 27 |
| CA167_01085 | B11 | 25 | 27 |
| CA167_01086 | B11 | 25 | 31 |
| R3822_A32 | A32 | 25 | 53 |
| R3824_B11 | B11 | 25 | 68 |
| R5825_C11 | C11 | 25 | 20 |

FIG. 1

FIG. 1 shows the functional effects of selected antibodies (at 25 µg/ml), in the presence or absence of specific peptide, on human Nav1.7 currents expressed in HEK cells. Nav1.7 currents were recorded by automated Patch Clamp using a repetitive stimulation protocol and data are presented as the normalized Nav1.7 current after the last stimulation. Selected antibodies were incubated in the presence of the specific peptide (25 μg/ml) for 30 minutes at 4° C. and then transferred to the PatchXpress system for Nav1.7 current recordings. The presence of the peptide systematically reverses the inhibitory effect of the antibody thus indicating that inhibition of Nav1.7 currents is mediated by a specific interaction of antibodies with the Nav1.7 extracellular loops.

FIG. 3F (a)

Automated Patch Clamp analysis of recombinant human Nav1.7 channels expressed in HEK cells. 983 monoclonal antibody produces a dose-dependent inhibition of Nav1.7 currents. Data points represent the normalized peak current amplitudes after application of a repeated voltage step protocol (end point) in the presence of antibody.

FIG. 3F (b)

Automated Patch Clamp analysis of recombinant human Nav1.7 channels expressed in HEK cells. 1080 monoclonal antibody produces a dose-dependent inhibition of Nav1.7 currents. Data points represent the normalized peak current amplitudes after application of a repeated voltage step protocol (end point) in the presence of antibody.

FIG. 3G

Automated Patch Clamp analysis of recombinant rat Nav1.7 channels expressed in HEK cells. 983 monoclonal antibody produces a dose-dependent inhibition of Nav1.7 currents. 1080 monoclonal antibody produces a ~26% inhibition of Nav1.7 currents at 25 μg/ml. Data points represent the normalized peak current amplitudes after application of a repeated voltage step protocol (end point) in the presence of antibody.

FIG. 3H

Kinetics of human Nav1.7 inhibition by 983 monoclonal antibody. HEK cells expressing recombinant human Nav1.7 channels are stimulated with a voltage step protocol at 0.1 Hz for ~20 minutes. Data points represent the normalized peak current amplitudes (run down corrected) of Nav1.7 channels recorded every 10 seconds. Nav1.7 currents are reduced in the presence of the antibody (25 μg/ml) but only when repeated activation of the channel at 0.1 Hz is maintained. Stimulation of Nav1.7 channels only at the end of the protocol (and after incubation of antibody) does not produce an inhibition of the Nav1.7 current. Data suggest that specific inhibition by 983 monoclonal antibody requires repetitive activation (channel cycling) of the Nav1.7 channel protein.

Dorsal Route Ganglion In Vitro Testing

Primary Culture Preparation

Dorsal Root Ganglia were isolated from 1-2 wild-type rat pups, aged between postnatal day 1 and 3. Ganglia were washed in PBS after dissection and immediately placed into a DMEM (Lonza, #BE12-604F) solution containing 2 mg/ml collagenase (Sigma-Aldrich, #C2674) and incubated at 37° C. for approximately 45 minutes for enzymatic digestion. Collagenase solution was removed and replaced with DMEM supplemented with 10% Fetal Bovine Serum (Lonza, #DE14802F), 0.5 mM L-Glutamine (Lonza, #BE17-605E), 1% Penicillin/Streptomycin (Lonza, #BE17-603E) and 20 ng/ml nerve growth factor (NGF, Invitrogen). Ganglia were then mechanically triturated, centrifuged at 1000 g for 5 minutes, and resuspended in the same culture medium. Dissociated cells were counted and diluted to a suspension of 100,000-120,000 cells/ml on glass coverslips precoated with 50 μg/ml poly-D-lysine (Sigma) and 30 μg/ml laminin (Invitrogen) and incubated at 37° C., 5% $CO_2$ until ready for use.

Primary Culture Electrophysiology

Dissociated DRG were taken for use no more than two days in vitro (DIV) following preparation. Cells were visualized on an Olympus BX50WI upright microscope with an Ikegami ICD-42B CCD camera. Electrophysiological recordings were acquired using 5 khz digital sampling and filtered at 3 dB at a 3 khz frequency on an Axopatch 1D (Molecular Devices) amplifier and converted to a digital signal using a Digidata 1322A analog-to-digital converter (Molecular Devices). All recordings were acquired using pClamp 10 software (Molecular Devices) and subsequently analyzed in Clampfit 10 (Molecular Devices). Recording electrodes were pulled from borosilicate glass pipettes on a Sutter p-97 horizontal pipette puller to a final resistance of 4.5-6 MΩ and filled with an internal solution containing (in mM): 140 K-Methansulfonate, 5 NaCl, 1 $CaCl_2$, 2 $MgCl_2$, 11 EGTA, 10 HEPES, 2 Mg-ATP, and 1 L1-GTP; pH was adjusted to 7.2 with Tris-base, and osmolality was adjusted to 310 mOsm with sucrose. Bath solution contained (in mM): 130 NaCl, 25 glucose, 10 HEPES, 4 KCl, 2 $CaCl_2$, 1 $MgCl_2$, 1.25 $NaPO_4$; pH was adjusted to 7.35 with NaOH and osmolality was adjusted to 310 mOsm with sucrose. The liquid junction potential was calculated to be 14.2 mV, all reported voltages have been corrected to compensate.

After formation of a tight seal (>1 GΩ) by release of positive pressure and manual suction in voltage clamp mode, capacitative currents were compensated and the command voltage was set to −70 mV. The cell membrane was ruptured and the cell allowed to dialyze intracellular solution for 5 minutes. Whole cell parameters were recorded after dialysis. Cells were rejected if whole cell capacitance was >35 pF or a stable access resistance less than 3× electrode resistance could not be achieved. The amplifier was switched to current clamp mode and the resting membrane potential was recorded. The cell was then injected with a series of 1.5 s duration, depolarizing current steps of increasing amplitude intended to evoke an action potential (AP) or train of APs. Cells that could not fire more than a single AP during a single step after depolarizing to a maximum of −35 mV were rejected.

Cells were subsequently treated either with control or antibody solutions by fast bath perfusion directly on to the recorded cell for 90 seconds to sufficiently fill the recording chamber, at which point both perfusion and aspiration were halted. The previous series of depolarizing current steps were repeatedly administered at two minute intervals over a period of 40 minutes, typically with a delay of 1.5 s between individual steps to allow for membrane repolarization. Occasionally a constant current was injected if the resting membrane potential (RMP) adjusted over the course of the experiment in order to maintain a constant RMP of −65 mV. Cells whose RMP deviated more than 20% in either the positive or negative direction or whose holding current changed more than 100 pA during the course of the experiment were rejected. Individual holding currents and injected currents for each step were noted individually for each cell, as well as any electrophysiological parameters that were changed during the course of the experiment.

Data Analysis

Action Potentials (AP) were manually counted for each depolarizing step and the total number of evoked APs were summed for each time point. The number of APs at each time point were normalized in Microsoft Excel 2003 to the number of evoked APs at time=0 and plotted as a function of time using Graphpad Prism 5.0 software. Each plotted data point represents the mean value of all recorded cells under the specified experimental condition, with error bars representing the calculated standard error.

Figure 3A:
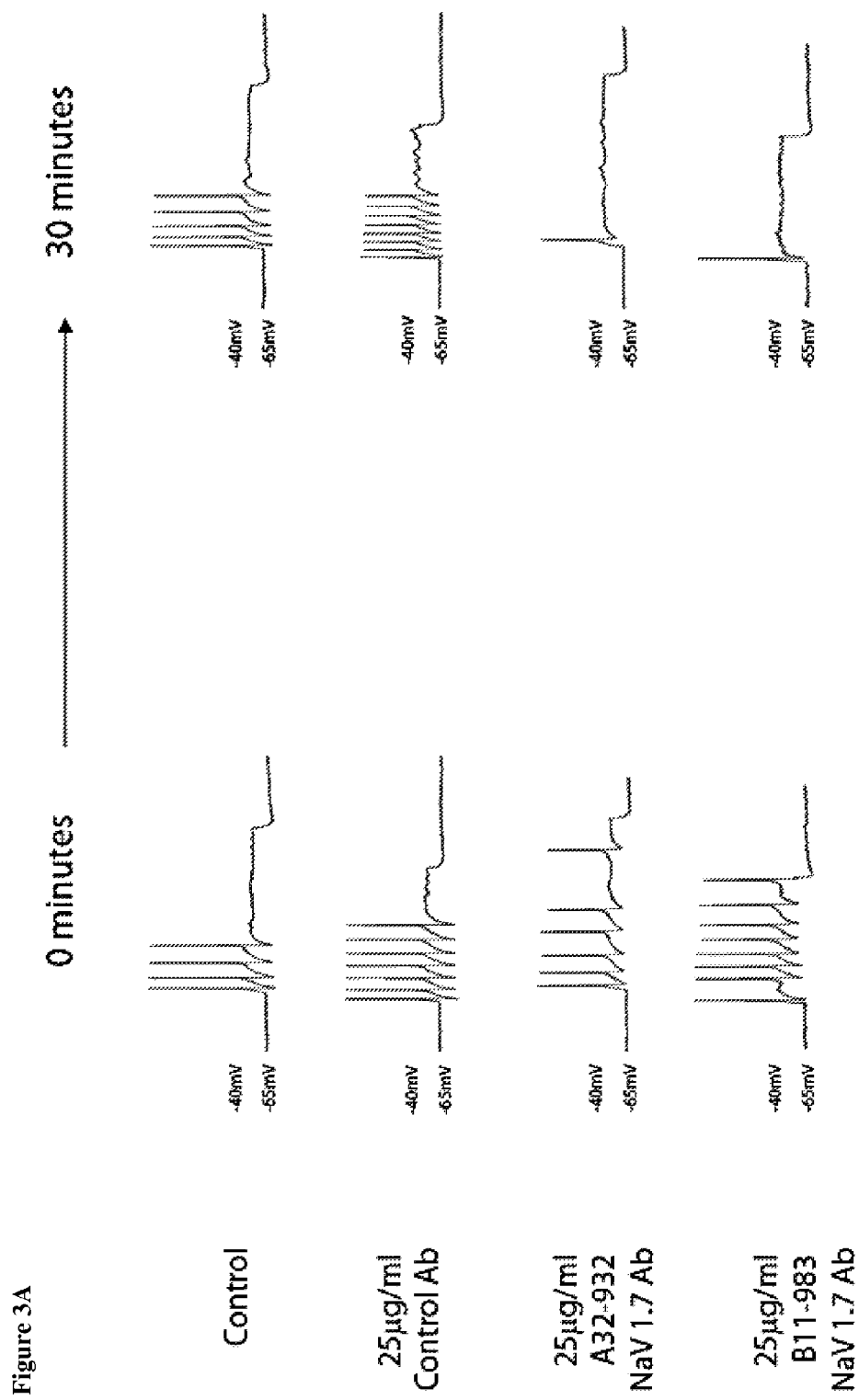
FIG. 3A shows that the 932 and 983 anti-Na$_v$1.7 monoclonal antibodies reduce electrically induced DRG spike frequency in vitro.

FIG. 3A Current clamp traces of evoked action potentials from representative DRG neurons before (time=0) and following (time=30 minutes) treatment.

Figure 3B:
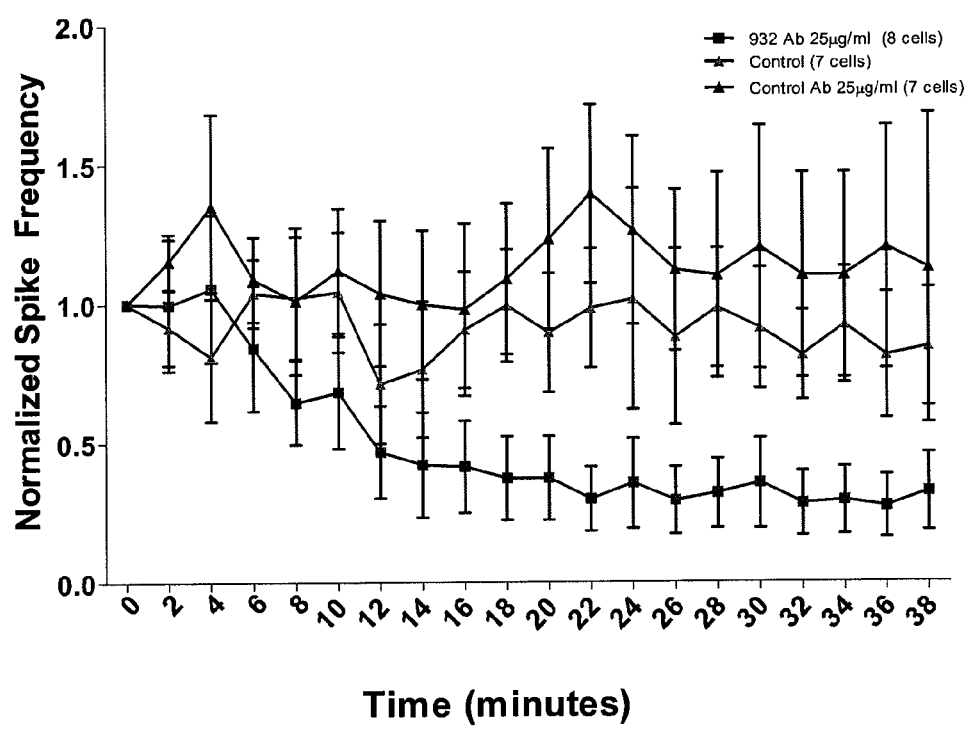
FIG. 3B shows that anti-Na$_v$1.7 monoclonal antibody 932 reduces electrically induced DRG spike frequency in vitro.

FIG. 3B The antibody 932 (25 μg/ml) significantly reduced the number of evoked action potentials compared with vehicle or control antibody treated controls following antibody administration at time=2 minutes.

Figure 3C:
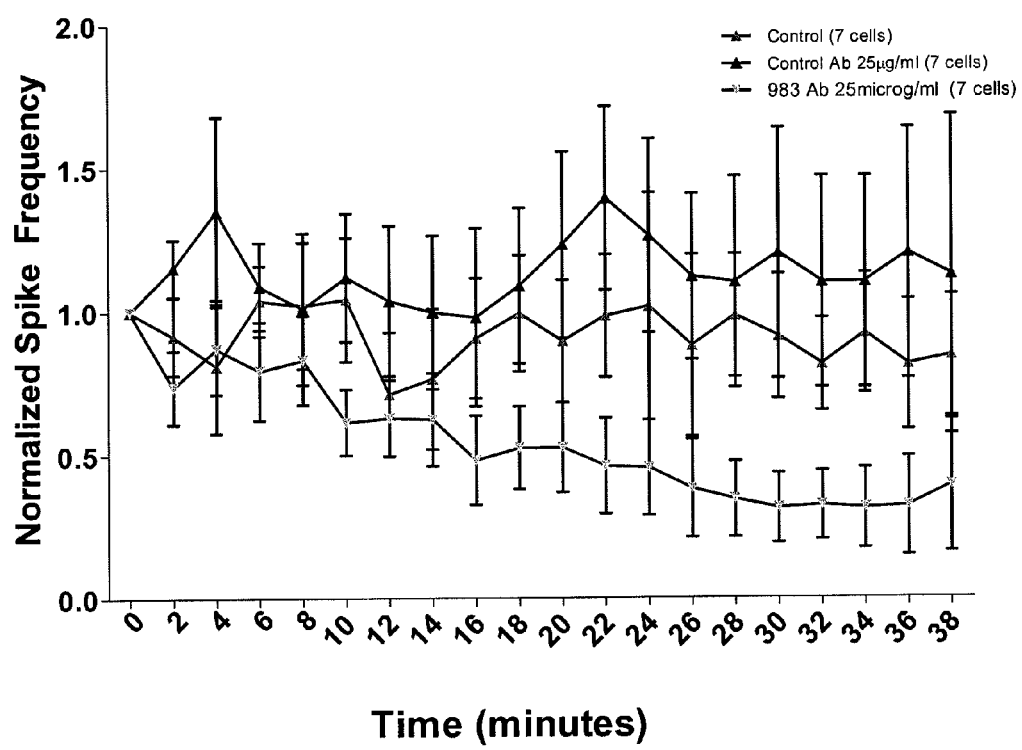
FIG. 3C shows that anti-Na$_v$1.7 monoclonal antibody 983 reduces electrically induced DRG spike frequency in vitro

FIG. 3C: The antibody 983 (25 μg/ml) significantly reduced the number of evoked action potentials compared with vehicle or control antibody treated controls following antibody administration at time=2 minutes.

FIG. 3E

Electrophysiology (current clamp recordings) investigations on action potential firing in cultured rat dorsal root ganglion (DRG) neurons. 1080 monoclonal antibody, at a dose of 25 μg/ml, reduces the electrically induced spike frequency of DRG neurons. Data points represent the normalized spike frequency compared to initial frequency observed at time 0 before antibody application.

Serum Concentration-Time Profile for Antibody 932

Antibody 932 was administered to three male Sprague Dawley rats in a single sub-cutaneous dose at 10 mg/kg. At 1, 3, 8, 24, 48, 72, 103 and 168 hours after dosing, blood samples were taken from the lateral tail vein under light anaesthesia. Serum was separated and stored at −20° C. until analysed. The serum samples were analysed by ELISA (enzyme-linked immunosorbent assay) to quantify the levels of the antibody (932). In the ELISA, microtitre plates were coated with AffiniPure F(ab')2 Fragment Goat Anti-Rabbit IgG. Samples were incubated, then revealed using Peroxidase-conjugated AffiniPure F(ab')2 Fragment Goat Anti-Rabbit IgG. The samples were developed using a TMB peroxidise substrate system and the absorbance at 450 nm was compared to a standard curve. If necessary, samples were diluted into the range for the standard curve. The mean concentration time profile was then plotted ±SEM (n=3).

Figure 3D:
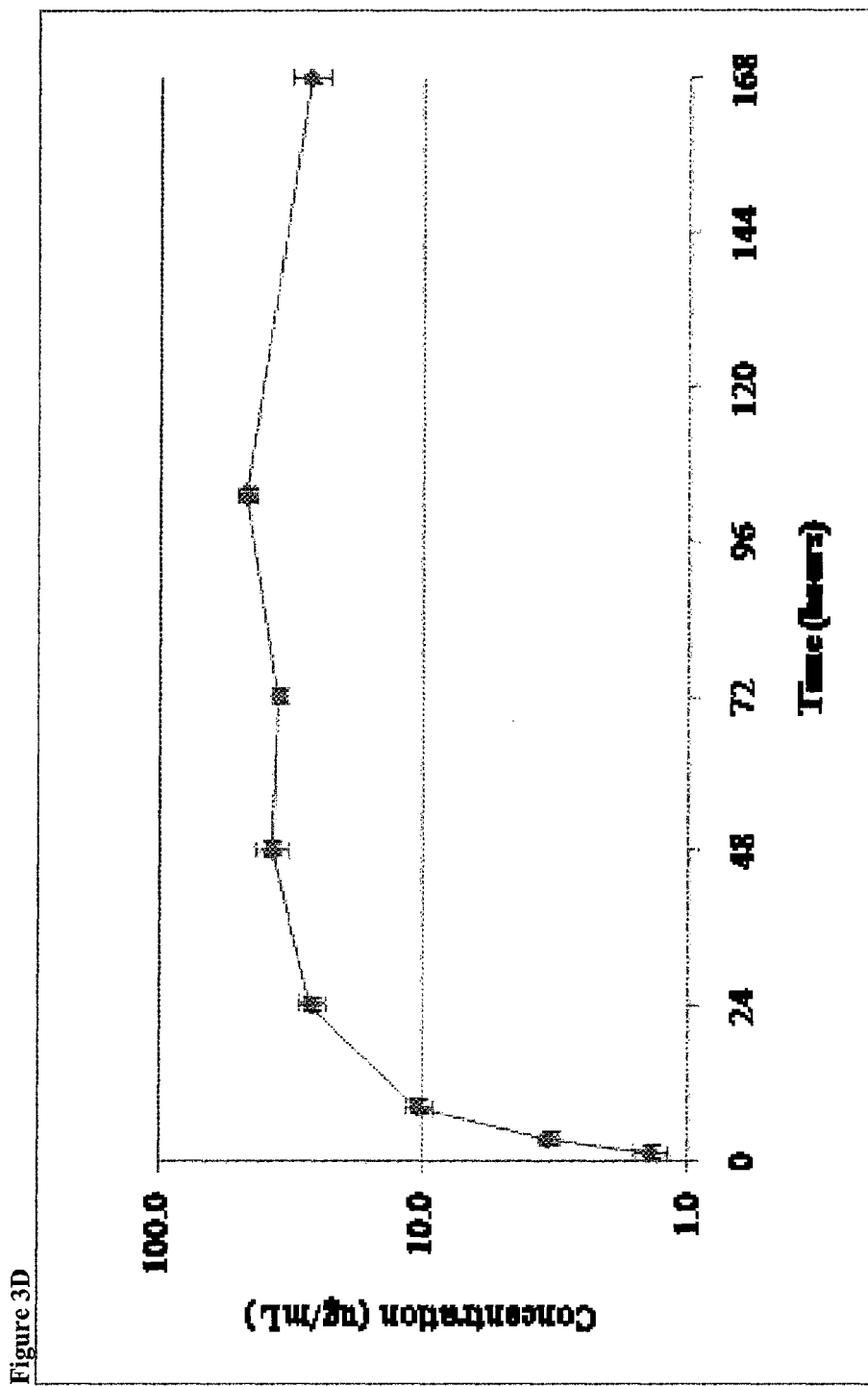
FIG. 3D shows serum concentration-time profile for antibody 932 in male Sprague Dawley rats following a single 10 mg/kg sub-cutaneous dose.
Figure 3E:
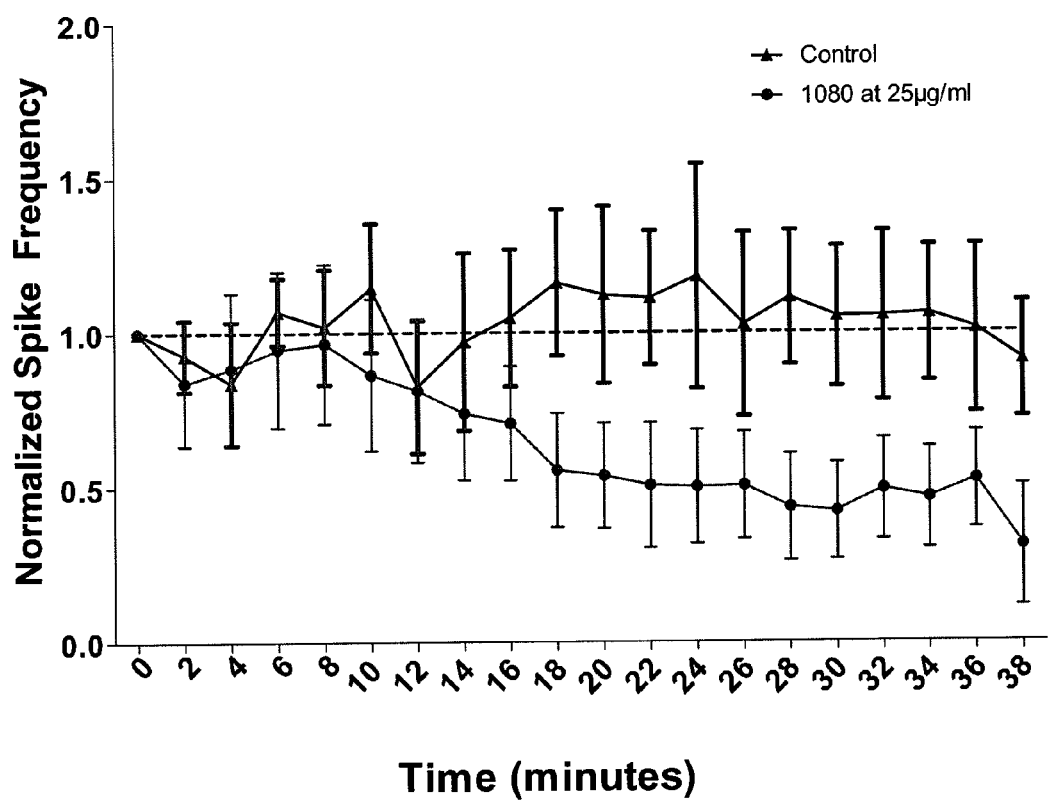
FIG. 3E shows that anti-Na$_v$1.7 monoclonal antibody 1080 reduces electrically induced DRG spike frequency in vitro FIG. 3Fa shows automated Patch Clamp analysis of recombinant human Nav1.7 channels expressed in HEK cells. 983 monoclonal antibody produces a dose-dependent inhibition of Nav1.7 currents.
Figure 3F:
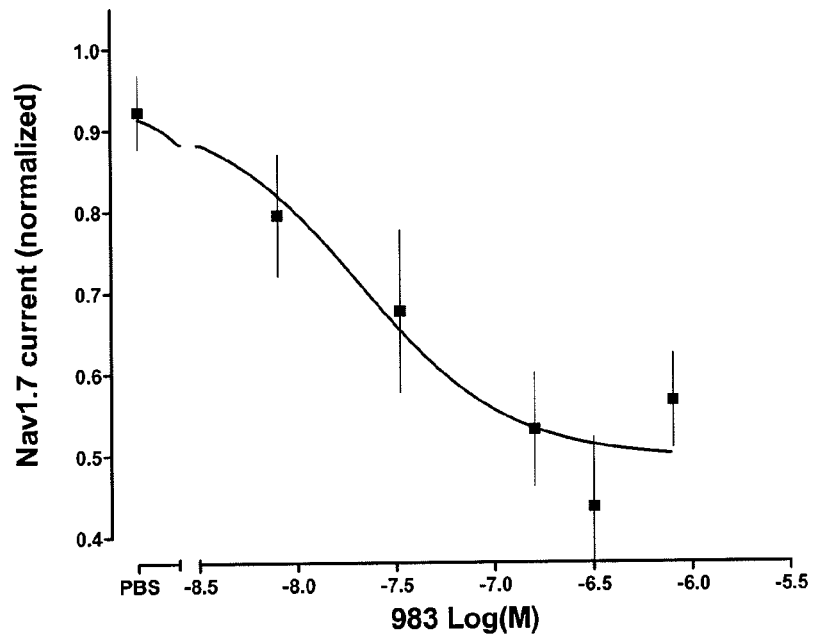
FIG. 3Fb shows automated Patch Clamp analysis of recombinant human Nav1.7 channels expressed in HEK cells. 1080 monoclonal antibody produces a dose-dependent inhibition of Nav1.7 currents.
Figure 3F:
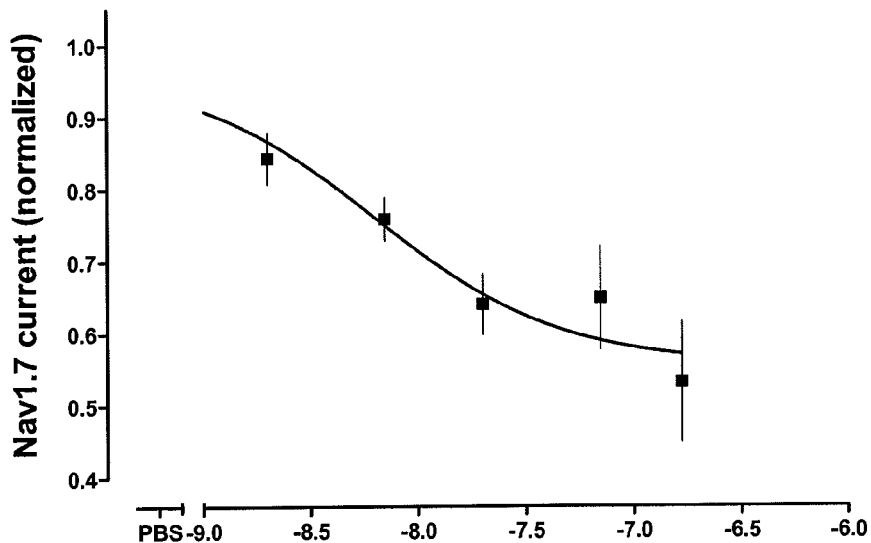
Figure 3G:
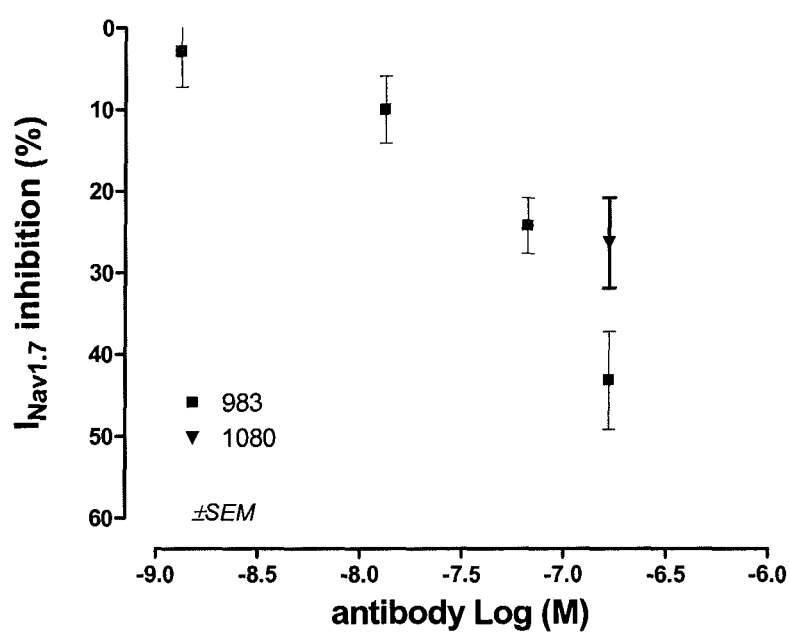
FIG. 3G shows automated Patch Clamp analysis of recombinant rat Nav1.7 channels expressed in HEK cells. 983 monoclonal antibody produces a dose-dependent inhibition of Nav1.7 currents. 1080 monoclonal antibody produces a ~26% inhibition of Nav1.7 currents at 25 µg/ml.
Figure 3H:
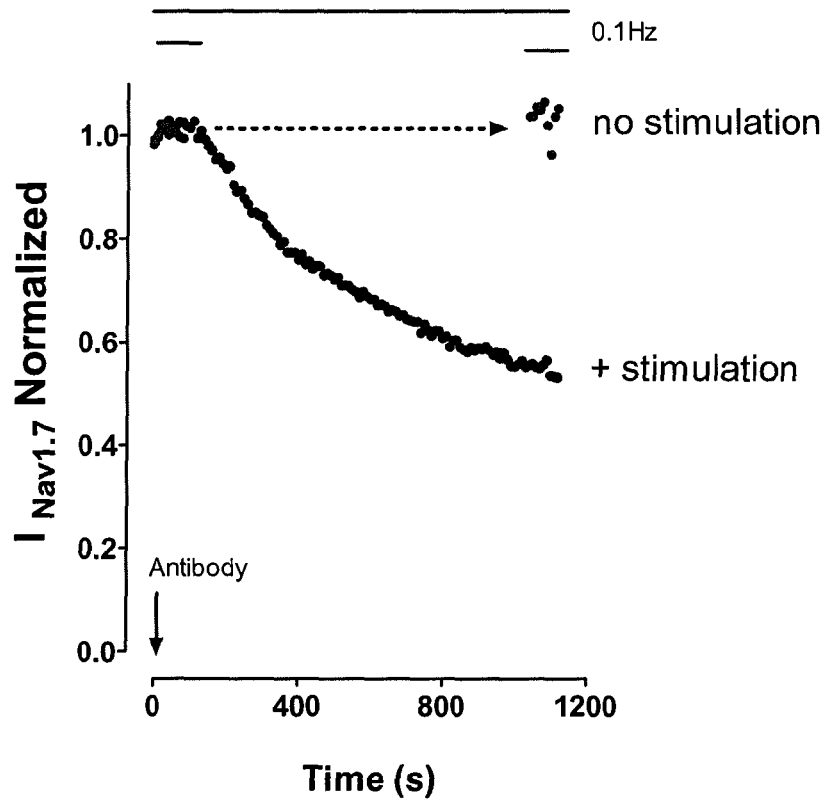
FIG. 3H Kinetics of human Nav1.7 inhibition by 983 monoclonal antibody.

FIG. 3D Serum concentration-time profile for antibody 932 in male Sprague Dawley rats following a single 10 mg/kg sub-cutaneous dose.

Isoform and Species Selectivity for 983 and 1080

TABLE 4

El peptides used for Nav isoform and species selectivity studies

| Peptide Name | Ion channel | Sequence |
| --- | --- | --- |
| B11 human | Nav 1.7 | PMTEEFKN (SEQ ID NO: 222) |
| B11 mouse | Nav 1.7 | PMTDEFKN (SEQ ID NO: 223) |
| B11.1 | Nav 1.1 | Cyclo[biotinyl-PEG-cysEHYPMTDHFNN] (SEQ ID NO: 224) |
| B11.2/3 | Nav 1.2 and 1.3 | Cyclo[biotinyl-PEG-cysEHYPMTEQFSS] (SEQ ID NO: 225) |

TABLE 4-continued

El peptides used for Nav isoform and species selectivity studies

| Peptide Name | Ion channel | Sequence |
| --- | --- | --- |
| B11.4 | Nav 1.4 | Cyclo[biotinyl-PEG-cysEHYPMTEHFDN] (SEQ ID NO: 226) |
| B11.5 | Nav 1.5 | Cyclo[biotinyl-PEG-cysEHYNMTSEFEE] (SEQ ID NO: 227) |
| B11.6 | Nav 1.6 | Cyclo[biotinyl-PEG-cysEHHPMTPQFEH] (SEQ ID NO: 228) |
| B11.7 | Nav 1.7 | Cyclo[biotinyl-PEG-cysPMTEEFKN] (SEQ ID NO: 216) |
| B11.8 | Nav 1.8 | Cyclo[biotinyl-PEG-cysEHHGMSPTFEA] (SEQ ID NO: 229) |
| B11.9 | Nav 1.9 | Cyclo[biotinyl-PEG-cysEHHKMEASFEK] (SEQ ID NO: 230) |

Peptide Binding ELISA

Nunc 96 well plates were coated overnight at 4° C. in 5 ug/ml Streptavidin (Jackson 016-000-114) 100 ul/well in carbonate coating buffer. Plates were washed four times in PBS/tween and 200 ul/well of block (1% BSA in PBS) was added for 1 hour at RT. Plates were washed four times in PBS/tween and 100 ul/well of biotinylated peptide at 5 ug/ml was added for 1 hour at RT. Plates were washed four times in PBS/tween and 100 ul/well of antibody added (starting at 10 ug/ml diluting in block in half logs down the plate) for 1 hour at RT. Plates were washed four times in PBS/tween and 100 ul/ml goat anti rabbit Fc HRP (Jackson 111-036-046) added for 1 hour at RT. Plates were washed four times in PBS/tween and 100 ul/well TMB (3,3',5,5' Tetramethylbenzidine) solution added. 50 ul/well of NaF was added to stop reaction and absorbance read at 630 nm.

Figure 3I:
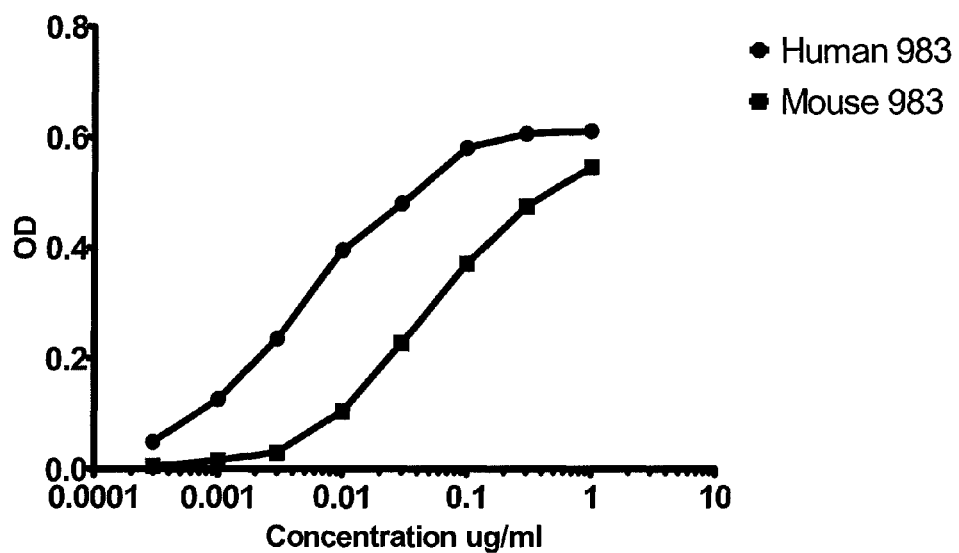
FIG. 3I shows (a) antibody 983 binding to Human and Mouse domain B loop E1 peptide (b) antibody 1080 binding to human and mouse domain B loop E1 peptide.
Figure 3I:
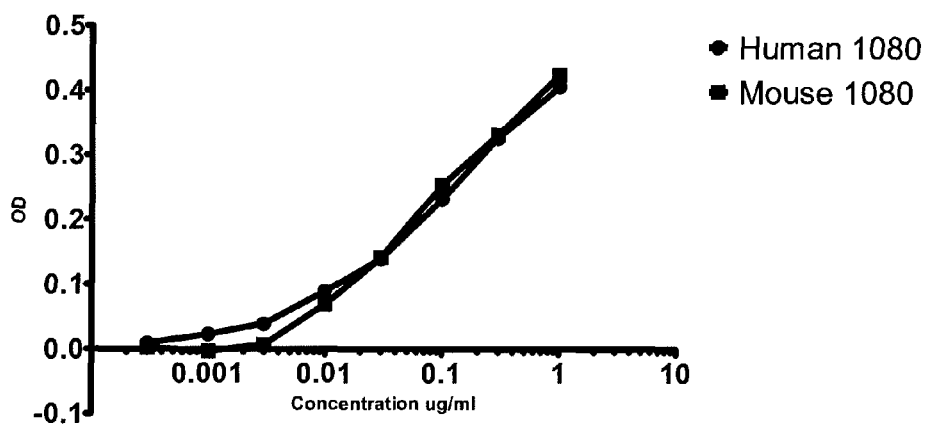

FIG. 3I shows (a) antibody 983 binding to Human and Mouse domain B loop El peptide B11 (Table 4) and (b) antibody 1080 binding to human and mouse domain B loop El peptide B11 (Table 4).

Figure 3J:
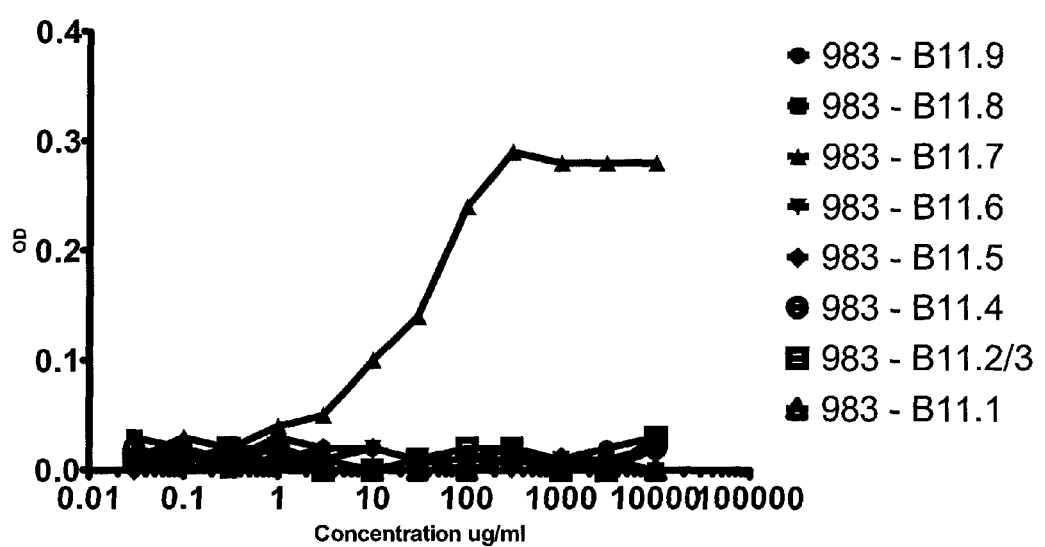
FIG. 3J shows ELISA data for antibody 983 specific binding to Nav 1.7 peptide

FIG. 3J shows ELISA data for antibody 983 binding to various cyclic Nav ion channel peptides Table 4.

Figure 3K:
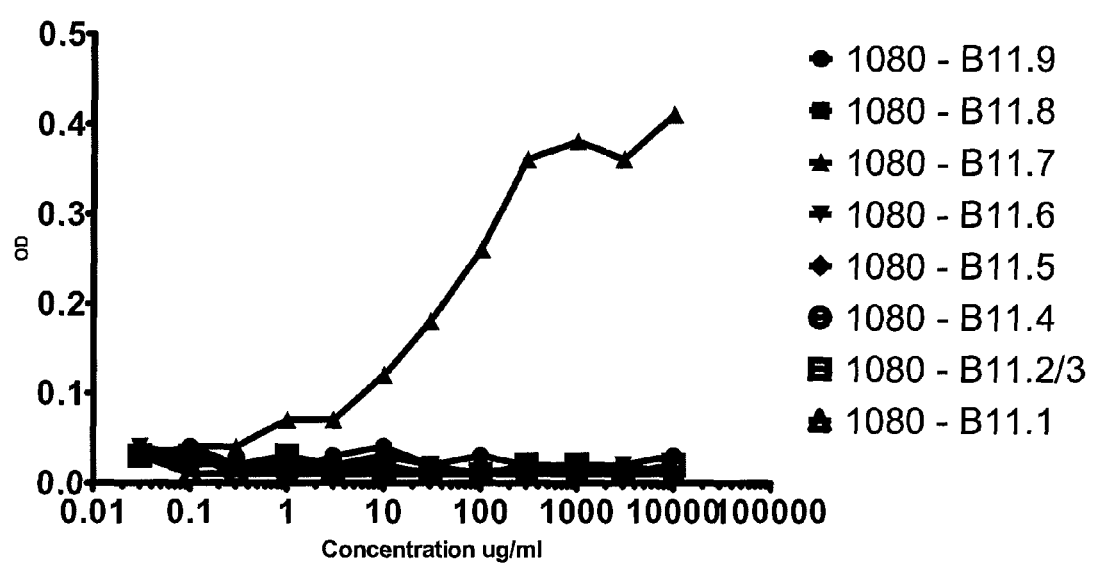
FIG. 3K shows ELISA data for antibody 1080 specific binding to Nav 1.7 peptide.

FIG. 3K ELISA data for antibody 1080 binding to various cyclic Nav ion channel peptides Table 4.

Specific binding in both cases was only observed for the B11.7 peptide and no binding to equivalent loops from the other Nav ion channels was observed.

The foregoing examples are meant to illustrate the invention, not limit it in any way. Modification within the spirit and scope of the invention disclosed herein are included. All references cited herein are hereby incorporated in their entireties.

We claim:

1. An isolated DNA encoding the heavy and/or light chain(s) of an anti-$Na_v1.7$ antibody or binding fragment thereof which, after binding the $Na_v1.7$ ion channel, is functionally modifying thereto such that the activity of the ion channel is reduced at least 5 percent in an in vitro assay, wherein the anti-$Na_v1.7$ antibody binds loop E3 in domain A, loop E1 in domain B, or loop E3 in domain C of $Na_v1.7$.

2. The isolated DNA of claim 1, wherein the variable domain of the heavy chain comprises CDRs having the sequence given in SEQ ID NO:28 for CDR-H1, SEQ ID NO 29 for CDR-H2 and SEQ ID NO 30 for CDR-H3; or SEQ ID NO:40 for CDR-H1, SEQ ID No:41 for CDR-H2 and SEQ ID NO 42 for CDR-H3; or SEQ ID NO:82 for CDR-H1, SEQ ID NO:83 for CDR-H2 and SEQ ID NO:84 for CDR-H3.

3. The isolated DNA of claim 1, wherein the variable domain of the light chain comprises CDRs having the sequence given in SEQ ID NO:25 for CDR-L1, SEQ ID NO:26 for CDR-L2 and SEQ ID NO: 27 for CDR-L3; or SEQ ID NO:37 for CDR-L1, SEQ ID NO; 38 for CDR-L2 and SEQ ID NO: 39 for CDR-L3; or SEQ ID NO:79 for CDR-L1, SEQ ID NO:38 for CDR-L2 and SEQ ID NO:81 for CDR-L3.

4. A cloning or expression vector comprising one or more DNA sequences according to claim 1, 2, or 3.

5. A host cell comprising one or more cloning or expression vectors according to claim 4.

6. A process for the production of an antibody having binding specificity for human Nav1.7, comprising culturing the host cell of claim 5 and isolating the antibody.

* * * * *

SEQUENCE LISTING

<160> NUMBER OF SEQ ID NOS: 230

<210> SEQ ID NO 1
<211> LENGTH: 11
<212> TYPE: PRT
<213> ORGANISM: artificial sequence
<220> FEATURE:
<223> OTHER INFORMATION: derived from rabbit

<400> SEQUENCE: 1

Gln Ala Ser Glu Ser Ile Gly Thr Ala Leu Ala
1               5                   10

```
<210> SEQ ID NO 2
<211> LENGTH: 7
<212> TYPE: PRT
<213> ORGANISM: artificial sequence
<220> FEATURE:
<223> OTHER INFORMATION: derived from rabbit

<400> SEQUENCE: 2

Lys Ala Ser Thr Leu Glu Ser
1               5

<210> SEQ ID NO 3
<211> LENGTH: 12
<212> TYPE: PRT
<213> ORGANISM: artificial sequence
<220> FEATURE:
<223> OTHER INFORMATION: derived from rabbit

<400> SEQUENCE: 3

Gln Gln Gly Glu Thr Ala Asn Arg Ile Asp Asn Ala
1               5                   10

<210> SEQ ID NO 4
<211> LENGTH: 5
<212> TYPE: PRT
<213> ORGANISM: artificial sequence
<220> FEATURE:
<223> OTHER INFORMATION: derived from rabbit

<400> SEQUENCE: 4

Arg Asn Ala Met Thr
1               5

<210> SEQ ID NO 5
<211> LENGTH: 16
<212> TYPE: PRT
<213> ORGANISM: artificial sequence
<220> FEATURE:
<223> OTHER INFORMATION: derived from rabbit

<400> SEQUENCE: 5

Tyr Ile Asn Thr Arg Gly Asp Thr Ser Tyr Ala Asn Trp Ala Lys Gly
1               5                   10                  15

<210> SEQ ID NO 6
<211> LENGTH: 7
<212> TYPE: PRT
<213> ORGANISM: artificial sequence
<220> FEATURE:
<223> OTHER INFORMATION: derived from rabbit

<400> SEQUENCE: 6

Gly Tyr Asn Pro Cys Lys Leu
1               5

<210> SEQ ID NO 7
<211> LENGTH: 11
<212> TYPE: PRT
<213> ORGANISM: artificial sequence
<220> FEATURE:
<223> OTHER INFORMATION: derived from rabbit

<400> SEQUENCE: 7

Gln Ala Ser Glu Ser Ile Asn Thr Ala Leu Ala
1               5                   10
```

```
<210> SEQ ID NO 8
<211> LENGTH: 7
<212> TYPE: PRT
<213> ORGANISM: artificial sequence
<220> FEATURE:
<223> OTHER INFORMATION: derived from rabbit

<400> SEQUENCE: 8

Ala Ala Ser Asp Leu Ala Ser
1               5

<210> SEQ ID NO 9
<211> LENGTH: 12
<212> TYPE: PRT
<213> ORGANISM: artificial sequence
<220> FEATURE:
<223> OTHER INFORMATION: derived from rabbit

<400> SEQUENCE: 9

Gln Gln Gly Tyr Thr Ala Asn Asn Ile Asp Asn Ala
1               5                   10

<210> SEQ ID NO 10

<400> SEQUENCE: 10

000

<210> SEQ ID NO 11
<211> LENGTH: 16
<212> TYPE: PRT
<213> ORGANISM: artificial sequence
<220> FEATURE:
<223> OTHER INFORMATION: derived from rabbit

<400> SEQUENCE: 11

Tyr Ile Asn Thr Arg Gly Gly Ala Ser Tyr Ala Asn Trp Ala Lys Gly
1               5                   10                  15

<210> SEQ ID NO 12

<400> SEQUENCE: 12

000

<210> SEQ ID NO 13
<211> LENGTH: 13
<212> TYPE: PRT
<213> ORGANISM: artificial sequence
<220> FEATURE:
<223> OTHER INFORMATION: derived from rabbit

<400> SEQUENCE: 13

Gln Ser Ser Gln Asn Val Val Asn Asn Asn Trp Phe Ser
1               5                   10

<210> SEQ ID NO 14
<211> LENGTH: 7
<212> TYPE: PRT
<213> ORGANISM: artificial sequence
<220> FEATURE:
<223> OTHER INFORMATION: derived from rabbit

<400> SEQUENCE: 14

Phe Val Ser Lys Leu Ala Ser
1               5
```

```
<210> SEQ ID NO 15
<211> LENGTH: 10
<212> TYPE: PRT
<213> ORGANISM: artificial sequence
<220> FEATURE:
<223> OTHER INFORMATION: derived from rabbit

<400> SEQUENCE: 15

Gly Gly Gly Tyr Ser Asp Asn Ile Tyr Ala
1               5                   10

<210> SEQ ID NO 16
<211> LENGTH: 5
<212> TYPE: PRT
<213> ORGANISM: artificial sequence
<220> FEATURE:
<223> OTHER INFORMATION: derived from rabbit

<400> SEQUENCE: 16

Tyr Tyr Ala Ile Ser
1               5

<210> SEQ ID NO 17
<211> LENGTH: 16
<212> TYPE: PRT
<213> ORGANISM: artificial sequence
<220> FEATURE:
<223> OTHER INFORMATION: derived from rabbit

<400> SEQUENCE: 17

Ile Ile Gly Ser Ser Gly Arg Thr Tyr Tyr Ala Ser Trp Ala Lys Gly
1               5                   10                  15

<210> SEQ ID NO 18
<211> LENGTH: 9
<212> TYPE: PRT
<213> ORGANISM: artificial sequence
<220> FEATURE:
<223> OTHER INFORMATION: derived from rabbit

<400> SEQUENCE: 18

Gly Gly Pro Thr Ser Ser Pro Ser Leu
1               5

<210> SEQ ID NO 19
<211> LENGTH: 13
<212> TYPE: PRT
<213> ORGANISM: artificial sequence
<220> FEATURE:
<223> OTHER INFORMATION: derived from rabbit

<400> SEQUENCE: 19

Gln Ala Ser Gln Ser Val Tyr Gly Thr Asn Arg Leu Ser
1               5                   10

<210> SEQ ID NO 20
<211> LENGTH: 7
<212> TYPE: PRT
<213> ORGANISM: artificial sequence
<220> FEATURE:
<223> OTHER INFORMATION: derived from rabbit

<400> SEQUENCE: 20

Gly Ala Ser Thr Leu Thr Ser
1               5

<210> SEQ ID NO 21
```

```
<211> LENGTH: 14
<212> TYPE: PRT
<213> ORGANISM: artificial sequence
<220> FEATURE:
<223> OTHER INFORMATION: derived from rabbit

<400> SEQUENCE: 21

Leu Gly Gly Trp Phe Glu Ser Ser Ser Ser Leu Asp Trp Ala
1               5                   10

<210> SEQ ID NO 22
<211> LENGTH: 5
<212> TYPE: PRT
<213> ORGANISM: artificial sequence
<220> FEATURE:
<223> OTHER INFORMATION: derived from rabbit

<400> SEQUENCE: 22

Arg Asn Ala Met Gly
1               5

<210> SEQ ID NO 23
<211> LENGTH: 16
<212> TYPE: PRT
<213> ORGANISM: artificial sequence
<220> FEATURE:
<223> OTHER INFORMATION: derived from rabbit

<400> SEQUENCE: 23

His Ile Ala Ser Arg Gly Asn Ile Trp Phe Arg Asn Trp Ala Lys Gly
1               5                   10                  15

<210> SEQ ID NO 24
<211> LENGTH: 12
<212> TYPE: PRT
<213> ORGANISM: artificial sequence
<220> FEATURE:
<223> OTHER INFORMATION: derived from rabbit

<400> SEQUENCE: 24

Phe Leu Val Val Ser Gly Val Gly Thr Phe Asp Pro
1               5                   10

<210> SEQ ID NO 25
<211> LENGTH: 13
<212> TYPE: PRT
<213> ORGANISM: artificial sequence
<220> FEATURE:
<223> OTHER INFORMATION: derived from rabbit

<400> SEQUENCE: 25

Gln Ser Ser Gln Ser Val Tyr Asn Asn Asn Glu Phe Ser
1               5                   10

<210> SEQ ID NO 26
<211> LENGTH: 7
<212> TYPE: PRT
<213> ORGANISM: artificial sequence
<220> FEATURE:
<223> OTHER INFORMATION: derived from rabbit

<400> SEQUENCE: 26

Asp Ala Ser Lys Leu Ala Ser
1               5

<210> SEQ ID NO 27
<211> LENGTH: 12
```

```
<212> TYPE: PRT
<213> ORGANISM: artificial sequence
<220> FEATURE:
<223> OTHER INFORMATION: derived from rabbit

<400> SEQUENCE: 27

Leu Gly Gly Tyr Asn Asp Asp Thr Asn Arg Trp Ala
1               5                   10

<210> SEQ ID NO 28
<211> LENGTH: 5
<212> TYPE: PRT
<213> ORGANISM: artificial sequence
<220> FEATURE:
<223> OTHER INFORMATION: derived from rabbit

<400> SEQUENCE: 28

Arg Tyr Trp Met Ser
1               5

<210> SEQ ID NO 29
<211> LENGTH: 17
<212> TYPE: PRT
<213> ORGANISM: artificial sequence
<220> FEATURE:
<223> OTHER INFORMATION: derived from rabbit

<400> SEQUENCE: 29

Asn Ile Gly Gly Gly Ser Gly Ser Thr Leu Tyr Ala Pro Trp Ala Lys
1               5                   10                  15

Gly

<210> SEQ ID NO 30
<211> LENGTH: 12
<212> TYPE: PRT
<213> ORGANISM: artificial sequence
<220> FEATURE:
<223> OTHER INFORMATION: derived from rabbit

<400> SEQUENCE: 30

Tyr Val Lys Asn Gly Gly Gly Tyr Arg Leu Asp Leu
1               5                   10

<210> SEQ ID NO 31
<211> LENGTH: 13
<212> TYPE: PRT
<213> ORGANISM: artificial sequence
<220> FEATURE:
<223> OTHER INFORMATION: derived from rabbit

<400> SEQUENCE: 31

Gln Ala Ser Glu Ser Val Ala Asn Asn Asn Trp Leu Ala
1               5                   10

<210> SEQ ID NO 32
<211> LENGTH: 7
<212> TYPE: PRT
<213> ORGANISM: artificial sequence
<220> FEATURE:
<223> OTHER INFORMATION: derived from rabbit

<400> SEQUENCE: 32

Lys Ala Ser Thr Leu Ala Ser
1               5

<210> SEQ ID NO 33
```

```
<211> LENGTH: 12
<212> TYPE: PRT
<213> ORGANISM: artificial sequence
<220> FEATURE:
<223> OTHER INFORMATION: derived from rabbit

<400> SEQUENCE: 33

Ala Gly Tyr Lys Ser Ser Thr Thr Asp Ala Val Ala
1               5                   10

<210> SEQ ID NO 34
<211> LENGTH: 5
<212> TYPE: PRT
<213> ORGANISM: artificial sequence
<220> FEATURE:
<223> OTHER INFORMATION: derived from rabbit

<400> SEQUENCE: 34

Ser Tyr Ala Ile Ser
1               5

<210> SEQ ID NO 35
<211> LENGTH: 17
<212> TYPE: PRT
<213> ORGANISM: artificial sequence
<220> FEATURE:
<223> OTHER INFORMATION: derived from rabbit

<400> SEQUENCE: 35

Phe Ile Asn Thr Ile Thr Gly Gly Thr Asn Tyr Ala Ser Trp Ala Lys
1               5                   10                  15

Ser

<210> SEQ ID NO 36
<211> LENGTH: 7
<212> TYPE: PRT
<213> ORGANISM: artificial sequence
<220> FEATURE:
<223> OTHER INFORMATION: derived from rabbit

<400> SEQUENCE: 36

Ser Gly Ala Tyr Phe Asp Leu
1               5

<210> SEQ ID NO 37
<211> LENGTH: 13
<212> TYPE: PRT
<213> ORGANISM: artificial sequence
<220> FEATURE:
<223> OTHER INFORMATION: derived from rabbit

<400> SEQUENCE: 37

Gln Ser Ser Gln Ser Val Tyr Lys Asn Asn Asp Leu Ala
1               5                   10

<210> SEQ ID NO 38
<211> LENGTH: 7
<212> TYPE: PRT
<213> ORGANISM: artificial sequence
<220> FEATURE:
<223> OTHER INFORMATION: derived from rabbit

<400> SEQUENCE: 38

Tyr Ala Ser Thr Leu Ala Ser
1               5
```

```
<210> SEQ ID NO 39
<211> LENGTH: 13
<212> TYPE: PRT
<213> ORGANISM: artificial sequence
<220> FEATURE:
<223> OTHER INFORMATION: derived from rabbit

<400> SEQUENCE: 39

Leu Gly Ser Tyr Asp Cys Ser Ser Ala Asp Cys Asn Ala
1               5                   10

<210> SEQ ID NO 40
<211> LENGTH: 5
<212> TYPE: PRT
<213> ORGANISM: artificial sequence
<220> FEATURE:
<223> OTHER INFORMATION: derived from rabbit

<400> SEQUENCE: 40

Asn Tyr Ala Met Ser
1               5

<210> SEQ ID NO 41
<211> LENGTH: 16
<212> TYPE: PRT
<213> ORGANISM: artificial sequence
<220> FEATURE:
<223> OTHER INFORMATION: derived from rabbit

<400> SEQUENCE: 41

Ile Ile Gly Lys Ser Gly Ser Thr Ala Tyr Ala Ser Trp Ala Lys Gly
1               5                   10                  15

<210> SEQ ID NO 42
<211> LENGTH: 4
<212> TYPE: PRT
<213> ORGANISM: artificial sequence
<220> FEATURE:
<223> OTHER INFORMATION: derived from rabbit

<400> SEQUENCE: 42

Phe Val Leu Leu
1

<210> SEQ ID NO 43
<211> LENGTH: 13
<212> TYPE: PRT
<213> ORGANISM: artificial sequence
<220> FEATURE:
<223> OTHER INFORMATION: derived from rabbit

<400> SEQUENCE: 43

Gln Ser Ser Gln Ser Val Asn Asn Asn Phe Leu Ser
1               5                   10

<210> SEQ ID NO 44
<211> LENGTH: 7
<212> TYPE: PRT
<213> ORGANISM: artificial sequence
<220> FEATURE:
<223> OTHER INFORMATION: derived from rabbit

<400> SEQUENCE: 44

Arg Ala Ser Thr Leu Ala Ser
1               5

<210> SEQ ID NO 45
```

<211> LENGTH: 10
<212> TYPE: PRT
<213> ORGANISM: artificial sequence
<220> FEATURE:
<223> OTHER INFORMATION: derived from rabbit

<400> SEQUENCE: 45

Ala Gly Gly Tyr Ser Gly Asn Ile Tyr Ala
1               5                   10

<210> SEQ ID NO 46
<211> LENGTH: 5
<212> TYPE: PRT
<213> ORGANISM: artificial sequence
<220> FEATURE:
<223> OTHER INFORMATION: derived from rabbit

<400> SEQUENCE: 46

Asp Tyr Ile Ile Asn
1               5

<210> SEQ ID NO 47
<211> LENGTH: 16
<212> TYPE: PRT
<213> ORGANISM: artificial sequence
<220> FEATURE:
<223> OTHER INFORMATION: derived from rabbit

<400> SEQUENCE: 47

Ile Met Gly Thr Ser Gly Thr Ala Tyr Tyr Ala Ser Trp Ala Lys Gly
1               5                   10                  15

<210> SEQ ID NO 48
<211> LENGTH: 8
<212> TYPE: PRT
<213> ORGANISM: artificial sequence
<220> FEATURE:
<223> OTHER INFORMATION: derived from rabbit

<400> SEQUENCE: 48

Gly Gly Val Ala Thr Ser Asn Phe
1               5

<210> SEQ ID NO 49
<211> LENGTH: 13
<212> TYPE: PRT
<213> ORGANISM: artificial sequence
<220> FEATURE:
<223> OTHER INFORMATION: derived from rabbit

<400> SEQUENCE: 49

Gln Ser Ser Gln Ser Val Tyr Gly Asn Asn Trp Leu Gly
1               5                   10

<210> SEQ ID NO 50
<211> LENGTH: 7
<212> TYPE: PRT
<213> ORGANISM: artificial sequence
<220> FEATURE:
<223> OTHER INFORMATION: derived from rabbit

<400> SEQUENCE: 50

Ser Ala Ser Thr Leu Ala Ser
1               5

<210> SEQ ID NO 51
<211> LENGTH: 10

```
<212> TYPE: PRT
<213> ORGANISM: artificial sequence
<220> FEATURE:
<223> OTHER INFORMATION: derived from rabbit

<400> SEQUENCE: 51

Val Gly Gly Tyr Ser Gly Asn Ile His Val
1               5                   10

<210> SEQ ID NO 52
<211> LENGTH: 5
<212> TYPE: PRT
<213> ORGANISM: artificial sequence
<220> FEATURE:
<223> OTHER INFORMATION: derived from rabbit

<400> SEQUENCE: 52

Asp Tyr Asp Met Ser
1               5

<210> SEQ ID NO 53
<211> LENGTH: 16
<212> TYPE: PRT
<213> ORGANISM: artificial sequence
<220> FEATURE:
<223> OTHER INFORMATION: derived from rabbit

<400> SEQUENCE: 53

Thr Ile Tyr Val Ser Gly Asn Thr Tyr Tyr Ala Thr Trp Ala Lys Gly
1               5                   10                  15

<210> SEQ ID NO 54
<211> LENGTH: 9
<212> TYPE: PRT
<213> ORGANISM: artificial sequence
<220> FEATURE:
<223> OTHER INFORMATION: derived from rabbit

<400> SEQUENCE: 54

Ala Val Pro Gly Ser Gly Lys Gly Leu
1               5

<210> SEQ ID NO 55
<211> LENGTH: 13
<212> TYPE: PRT
<213> ORGANISM: artificial sequence
<220> FEATURE:
<223> OTHER INFORMATION: derived from rabbit

<400> SEQUENCE: 55

Gln Ala Ser Gln Ser Leu Tyr Asn Lys Lys Asn Leu Ala
1               5                   10

<210> SEQ ID NO 56

<400> SEQUENCE: 56

000

<210> SEQ ID NO 57
<211> LENGTH: 13
<212> TYPE: PRT
<213> ORGANISM: artificial sequence
<220> FEATURE:
<223> OTHER INFORMATION: derived from rabbit

<400> SEQUENCE: 57
```

```
Gln Gly Glu Phe Ser Cys Ser Ser Val Asp Cys Val Ala
1               5                   10
```

<210> SEQ ID NO 58
<211> LENGTH: 5
<212> TYPE: PRT
<213> ORGANISM: artificial sequence
<220> FEATURE:
<223> OTHER INFORMATION: derived from rabbit

<400> SEQUENCE: 58

```
Ser Tyr Ala Met Thr
1               5
```

<210> SEQ ID NO 59
<211> LENGTH: 15
<212> TYPE: PRT
<213> ORGANISM: artificial sequence
<220> FEATURE:
<223> OTHER INFORMATION: derived from rabbit

<400> SEQUENCE: 59

```
Ile Ile Tyr Ala Ser Asp Thr Tyr Tyr Thr Ser Trp Ala Lys Gly
1               5                   10                  15
```

<210> SEQ ID NO 60
<211> LENGTH: 11
<212> TYPE: PRT
<213> ORGANISM: artificial sequence
<220> FEATURE:
<223> OTHER INFORMATION: derived from rabbit

<400> SEQUENCE: 60

```
Gly Asp Ser Thr Ser Gly Phe His Leu Thr Leu
1               5                   10
```

<210> SEQ ID NO 61

<400> SEQUENCE: 61

000

<210> SEQ ID NO 62
<211> LENGTH: 7
<212> TYPE: PRT
<213> ORGANISM: artificial sequence
<220> FEATURE:
<223> OTHER INFORMATION: derived from rabbit

<400> SEQUENCE: 62

```
Phe Ala Ser Thr Leu Ala Ser
1               5
```

<210> SEQ ID NO 63
<211> LENGTH: 13
<212> TYPE: PRT
<213> ORGANISM: artificial sequence
<220> FEATURE:
<223> OTHER INFORMATION: derived from rabbit

<400> SEQUENCE: 63

```
Gln Gly Glu Phe Ile Cys Ser Ser Gly Asp Cys Val Ala
1               5                   10
```

<210> SEQ ID NO 64

<400> SEQUENCE: 64

```
<210> SEQ ID NO 65
<211> LENGTH: 16
<212> TYPE: PRT
<213> ORGANISM: artificial sequence
<220> FEATURE:
<223> OTHER INFORMATION: derived from rabbit

<400> SEQUENCE: 65

Ile Ile Tyr Gly Thr Glu Thr Ile Tyr Tyr Ala Thr Arg Ala Lys Gly
1               5                   10                  15

<210> SEQ ID NO 66

<400> SEQUENCE: 66

000

<210> SEQ ID NO 67

<400> SEQUENCE: 67

000

<210> SEQ ID NO 68
<211> LENGTH: 7
<212> TYPE: PRT
<213> ORGANISM: artificial sequence
<220> FEATURE:
<223> OTHER INFORMATION: derived from rabbit

<400> SEQUENCE: 68

Phe Thr Ser Thr Leu Ala Ser
1               5

<210> SEQ ID NO 69
<211> LENGTH: 13
<212> TYPE: PRT
<213> ORGANISM: artificial sequence
<220> FEATURE:
<223> OTHER INFORMATION: derived from rabbit

<400> SEQUENCE: 69

Gln Gly Glu Phe Ser Cys Ser Ser Gly Asp Cys Leu Ala
1               5                   10

<210> SEQ ID NO 70

<400> SEQUENCE: 70

000

<210> SEQ ID NO 71
<211> LENGTH: 16
<212> TYPE: PRT
<213> ORGANISM: artificial sequence
<220> FEATURE:
<223> OTHER INFORMATION: derived from rabbit

<400> SEQUENCE: 71

Ile Ile Tyr Gly Thr Glu Leu Thr Tyr Tyr Ala Thr Trp Ala Lys Gly
1               5                   10                  15

<210> SEQ ID NO 72
<211> LENGTH: 11
```

```
<212> TYPE: PRT
<213> ORGANISM: artificial sequence
<220> FEATURE:
<223> OTHER INFORMATION: derived from rabbit

<400> SEQUENCE: 72

Gly Asp Ala Thr Ser Gly Phe His Leu Thr Leu
1               5                   10

<210> SEQ ID NO 73
<211> LENGTH: 11
<212> TYPE: PRT
<213> ORGANISM: artificial sequence
<220> FEATURE:
<223> OTHER INFORMATION: derived from rabbit

<400> SEQUENCE: 73

Gln Ala Ser Gln Thr Ile Tyr Ser Gly Leu Ala
1               5                   10

<210> SEQ ID NO 74

<400> SEQUENCE: 74

000

<210> SEQ ID NO 75
<211> LENGTH: 12
<212> TYPE: PRT
<213> ORGANISM: artificial sequence
<220> FEATURE:
<223> OTHER INFORMATION: derived from rabbit

<400> SEQUENCE: 75

Gln Val Gly Gly Tyr Gly Val Ser Tyr Asp His Ala
1               5                   10

<210> SEQ ID NO 76
<211> LENGTH: 6
<212> TYPE: PRT
<213> ORGANISM: artificial sequence
<220> FEATURE:
<223> OTHER INFORMATION: derived from rabbit

<400> SEQUENCE: 76

Ser Ser Tyr Trp Ile Cys
1               5

<210> SEQ ID NO 77
<211> LENGTH: 18
<212> TYPE: PRT
<213> ORGANISM: artificial sequence
<220> FEATURE:
<223> OTHER INFORMATION: derived from rabbit

<400> SEQUENCE: 77

Cys Ile Tyr Gly Gly Ser Ile Asn Ile Ile Asn Tyr Ala Ser Trp Ala
1               5                   10                  15

Lys Gly

<210> SEQ ID NO 78
<211> LENGTH: 13
<212> TYPE: PRT
<213> ORGANISM: artificial sequence
<220> FEATURE:
<223> OTHER INFORMATION: derived from rabbit
```

<400> SEQUENCE: 78

Val Gln Gly Gly Asn Ser Gly Gly Trp Tyr Phe Asp Leu
1               5                   10

<210> SEQ ID NO 79
<211> LENGTH: 13
<212> TYPE: PRT
<213> ORGANISM: artificial sequence
<220> FEATURE:
<223> OTHER INFORMATION: derived from rabbit

<400> SEQUENCE: 79

Gln Ser Ser Gln Ser Val Trp Lys Asn Asn Asp Leu Ser
1               5                   10

<210> SEQ ID NO 80

<400> SEQUENCE: 80

000

<210> SEQ ID NO 81
<211> LENGTH: 13
<212> TYPE: PRT
<213> ORGANISM: artificial sequence
<220> FEATURE:
<223> OTHER INFORMATION: derived from rabbit

<400> SEQUENCE: 81

Val Gly Ser Tyr Asp Cys Ser Ser Ala Asp Cys Asn Ala
1               5                   10

<210> SEQ ID NO 82
<211> LENGTH: 5
<212> TYPE: PRT
<213> ORGANISM: artificial sequence
<220> FEATURE:
<223> OTHER INFORMATION: derived from rabbit

<400> SEQUENCE: 82

Lys Trp Pro Met Thr
1               5

<210> SEQ ID NO 83
<211> LENGTH: 16
<212> TYPE: PRT
<213> ORGANISM: artificial sequence
<220> FEATURE:
<223> OTHER INFORMATION: derived from rabbit

<400> SEQUENCE: 83

Ile Ile Gly Arg Ser Gly Ser Thr Asn Tyr Ala Ser Trp Ala Lys Gly
1               5                   10                  15

<210> SEQ ID NO 84
<211> LENGTH: 7
<212> TYPE: PRT
<213> ORGANISM: artificial sequence
<220> FEATURE:
<223> OTHER INFORMATION: derived from rabbit

<400> SEQUENCE: 84

Gly Gly Ser Tyr Tyr Asp Leu
1               5

<210> SEQ ID NO 85

<211> LENGTH: 13
<212> TYPE: PRT
<213> ORGANISM: artificial sequence
<220> FEATURE:
<223> OTHER INFORMATION: derived from rabbit

<400> SEQUENCE: 85

Gln Ser Ser Gln Ser Val Asp Asn Asn Asn Tyr Leu Ser
1               5                   10

<210> SEQ ID NO 86
<211> LENGTH: 7
<212> TYPE: PRT
<213> ORGANISM: artificial sequence
<220> FEATURE:
<223> OTHER INFORMATION: derived from rabbit

<400> SEQUENCE: 86

Asp Ala Ser Asp Leu Ala Ser
1               5

<210> SEQ ID NO 87
<211> LENGTH: 13
<212> TYPE: PRT
<213> ORGANISM: artificial sequence
<220> FEATURE:
<223> OTHER INFORMATION: derived from rabbit

<400> SEQUENCE: 87

Ala Gly Gly Tyr Ile Thr Ser Ser Asp Ile Phe Tyr Asp
1               5                   10

<210> SEQ ID NO 88
<211> LENGTH: 5
<212> TYPE: PRT
<213> ORGANISM: artificial sequence
<220> FEATURE:
<223> OTHER INFORMATION: derived from rabbit

<400> SEQUENCE: 88

Thr Tyr Ala Met Ser
1               5

<210> SEQ ID NO 89
<211> LENGTH: 16
<212> TYPE: PRT
<213> ORGANISM: artificial sequence
<220> FEATURE:
<223> OTHER INFORMATION: derived from rabbit

<400> SEQUENCE: 89

Ile Val Gly Lys Ser Gly Ile Ile Lys Tyr Ala Ser Trp Ala Lys Gly
1               5                   10                  15

<210> SEQ ID NO 90
<211> LENGTH: 4
<212> TYPE: PRT
<213> ORGANISM: artificial sequence
<220> FEATURE:
<223> OTHER INFORMATION: derived from rabbit

<400> SEQUENCE: 90

Leu Trp Ser Leu
1

<210> SEQ ID NO 91
<211> LENGTH: 11

```
<212> TYPE: PRT
<213> ORGANISM: artificial sequence
<220> FEATURE:
<223> OTHER INFORMATION: derived from rabbit

<400> SEQUENCE: 91

Gln Ala Ser Gln Ser Ile Ser Asn Trp Leu Ala
1               5                   10

<210> SEQ ID NO 92

<400> SEQUENCE: 92

000

<210> SEQ ID NO 93
<211> LENGTH: 12
<212> TYPE: PRT
<213> ORGANISM: artificial sequence
<220> FEATURE:
<223> OTHER INFORMATION: derived from rabbit

<400> SEQUENCE: 93

Gln Ser Asp Tyr Gly Ile Asp Thr Tyr Gly Ser Ala
1               5                   10

<210> SEQ ID NO 94

<400> SEQUENCE: 94

000

<210> SEQ ID NO 95
<211> LENGTH: 16
<212> TYPE: PRT
<213> ORGANISM: artificial sequence
<220> FEATURE:
<223> OTHER INFORMATION: derived from rabbit

<400> SEQUENCE: 95

Met Val Arg Arg Ser Gly Thr Thr Tyr Tyr Ala Ser Trp Ala Lys Gly
1               5                   10                  15

<210> SEQ ID NO 96
<211> LENGTH: 14
<212> TYPE: PRT
<213> ORGANISM: artificial sequence
<220> FEATURE:
<223> OTHER INFORMATION: derived from rabbit

<400> SEQUENCE: 96

Cys Asp Asn Ser Ala Gly Asp Trp Ser Tyr Gly Met Asp Leu
1               5                   10

<210> SEQ ID NO 97
<211> LENGTH: 13
<212> TYPE: PRT
<213> ORGANISM: artificial sequence
<220> FEATURE:
<223> OTHER INFORMATION: derived from rabbit

<400> SEQUENCE: 97

Gln Ala Ser Gln Ser Val Tyr Gln Asn Asn Tyr Leu Ala
1               5                   10

<210> SEQ ID NO 98
```

<210> SEQ ID NO 99
<211> LENGTH: 13
<212> TYPE: PRT
<213> ORGANISM: artificial sequence
<220> FEATURE:
<223> OTHER INFORMATION: derived from rabbit

<400> SEQUENCE: 99

Leu Gly Ala Tyr Asp Cys Ser Gly Val Asp Cys Ser Ala
1               5                   10

<210> SEQ ID NO 100
<211> LENGTH: 5
<212> TYPE: PRT
<213> ORGANISM: artificial sequence
<220> FEATURE:
<223> OTHER INFORMATION: derived from rabbit

<400> SEQUENCE: 100

Thr Asn Ala Met Ile
1               5

<210> SEQ ID NO 101
<211> LENGTH: 16
<212> TYPE: PRT
<213> ORGANISM: artificial sequence
<220> FEATURE:
<223> OTHER INFORMATION: derived from rabbit

<400> SEQUENCE: 101

Val Ile Ala Gly Ser Gly Ser Thr Ser Tyr Ala Ser Trp Ala Lys Gly
1               5                   10                  15

<210> SEQ ID NO 102
<211> LENGTH: 10
<212> TYPE: PRT
<213> ORGANISM: artificial sequence
<220> FEATURE:
<223> OTHER INFORMATION: derived from rabbit

<400> SEQUENCE: 102

Gly Gly Trp Val Ser Gly Pro Glu Ser Leu
1               5                   10

<210> SEQ ID NO 103
<211> LENGTH: 13
<212> TYPE: PRT
<213> ORGANISM: artificial sequence
<220> FEATURE:
<223> OTHER INFORMATION: derived from rabbit

<400> SEQUENCE: 103

Gln Ser Ser Pro Ser Val Tyr Gly Asn Asn Trp Leu Gly
1               5                   10

<210> SEQ ID NO 104

<400> SEQUENCE: 104

000

<210> SEQ ID NO 105
<211> LENGTH: 10

```
<212> TYPE: PRT
<213> ORGANISM: artificial sequence
<220> FEATURE:
<223> OTHER INFORMATION: derived from rabbit

<400> SEQUENCE: 105

Ala Gly Gly Tyr Ser Gly Asn Ile His Val
1               5                   10

<210> SEQ ID NO 106
<211> LENGTH: 5
<212> TYPE: PRT
<213> ORGANISM: artificial sequence
<220> FEATURE:
<223> OTHER INFORMATION: derived from rabbit

<400> SEQUENCE: 106

Asn Tyr Asp Met Thr
1               5

<210> SEQ ID NO 107
<211> LENGTH: 16
<212> TYPE: PRT
<213> ORGANISM: artificial sequence
<220> FEATURE:
<223> OTHER INFORMATION: derived from rabbit

<400> SEQUENCE: 107

Ser Ile Phe Val Ser Gly Asn Ile Tyr Tyr Ala Ser Trp Ala Lys Gly
1               5                   10                  15

<210> SEQ ID NO 108
<211> LENGTH: 9
<212> TYPE: PRT
<213> ORGANISM: artificial sequence
<220> FEATURE:
<223> OTHER INFORMATION: derived from rabbit

<400> SEQUENCE: 108

Ala Ile Leu Gly Ser Ser Lys Gly Leu
1               5

<210> SEQ ID NO 109
<211> LENGTH: 11
<212> TYPE: PRT
<213> ORGANISM: artificial sequence
<220> FEATURE:
<223> OTHER INFORMATION: derived from rabbit

<400> SEQUENCE: 109

Gln Ala Ser Gln Ser Ile Tyr Ser Tyr Leu Ala
1               5                   10

<210> SEQ ID NO 110
<211> LENGTH: 7
<212> TYPE: PRT
<213> ORGANISM: artificial sequence
<220> FEATURE:
<223> OTHER INFORMATION: derived from rabbit

<400> SEQUENCE: 110

Ser Ala Ser Tyr Leu Ala Ser
1               5

<210> SEQ ID NO 111
<211> LENGTH: 12
<212> TYPE: PRT
```

```
<213> ORGANISM: artificial sequence
<220> FEATURE:
<223> OTHER INFORMATION: derived from rabbit

<400> SEQUENCE: 111

Gln His Gly Tyr Ile Ser Gly Asn Val Asp Asn Ala
1               5                   10

<210> SEQ ID NO 112
<211> LENGTH: 5
<212> TYPE: PRT
<213> ORGANISM: artificial sequence
<220> FEATURE:
<223> OTHER INFORMATION: derived from rabbit

<400> SEQUENCE: 112

Ile Tyr Asp Met Ser
1               5

<210> SEQ ID NO 113
<211> LENGTH: 16
<212> TYPE: PRT
<213> ORGANISM: artificial sequence
<220> FEATURE:
<223> OTHER INFORMATION: derived from rabbit

<400> SEQUENCE: 113

Ser Ile Tyr Val Ser Gly Asn Ile Tyr Tyr Ala Ser Trp Ala Lys Gly
1               5                   10                  15

<210> SEQ ID NO 114
<211> LENGTH: 9
<212> TYPE: PRT
<213> ORGANISM: artificial sequence
<220> FEATURE:
<223> OTHER INFORMATION: derived from rabbit

<400> SEQUENCE: 114

Ala Val Pro Gly Ser Ser Lys Gly Leu
1               5

<210> SEQ ID NO 115
<211> LENGTH: 12
<212> TYPE: PRT
<213> ORGANISM: artificial sequence
<220> FEATURE:
<223> OTHER INFORMATION: derived from rabbit

<400> SEQUENCE: 115

Gln Ser Ser Gln Ser Ile Tyr Thr Asn Tyr Leu Ser
1               5                   10

<210> SEQ ID NO 116

<400> SEQUENCE: 116

000

<210> SEQ ID NO 117
<211> LENGTH: 10
<212> TYPE: PRT
<213> ORGANISM: artificial sequence
<220> FEATURE:
<223> OTHER INFORMATION: derived from rabbit

<400> SEQUENCE: 117

Gln Ala Tyr Phe Thr Gly Glu Ile Phe Pro
```

<210> SEQ ID NO 118
<211> LENGTH: 5
<212> TYPE: PRT
<213> ORGANISM: artificial sequence
<220> FEATURE:
<223> OTHER INFORMATION: derived from rabbit

<400> SEQUENCE: 118

Asn Tyr His Met Gly
1               5

<210> SEQ ID NO 119
<211> LENGTH: 16
<212> TYPE: PRT
<213> ORGANISM: artificial sequence
<220> FEATURE:
<223> OTHER INFORMATION: derived from rabbit

<400> SEQUENCE: 119

Phe Ile Thr Arg Gly Gly Thr Thr Tyr Tyr Ala Ser Trp Ala Lys Gly
1               5                   10                  15

<210> SEQ ID NO 120
<211> LENGTH: 9
<212> TYPE: PRT
<213> ORGANISM: artificial sequence
<220> FEATURE:
<223> OTHER INFORMATION: derived from rabbit

<400> SEQUENCE: 120

Gly Ser Gly Ala Ser Gly Phe Tyr Leu
1               5

<210> SEQ ID NO 121
<211> LENGTH: 330
<212> TYPE: DNA
<213> ORGANISM: artificial sequence
<220> FEATURE:
<223> OTHER INFORMATION: derived from rabbit

<400> SEQUENCE: 121
gcctatgata tgacccagac tccagcctct gtggaggtag ctgtgggagg cacagtcacc      60
atcaattgcc aggccagtga gagcattggc actgcattag cctggtatca gcagaaacca     120
gggcagcctc ccaagctcct gatctacaag gcatccactc tggaatctgg ggtcccatcg     180
cggttcaaag gcgtggatc tgggacacag ttcactctca ccatcagcgg cgtgcagtgt     240
gacgatgctg ccacttacta ctgtcaacag ggtgaaactg caaatagaat tgataatgct     300
ttcggcggag ggaccgaggt ggtcgtcaaa                                      330

<210> SEQ ID NO 122
<211> LENGTH: 333
<212> TYPE: DNA
<213> ORGANISM: artificial sequence
<220> FEATURE:
<223> OTHER INFORMATION: derived from rabbit

<400> SEQUENCE: 122
cagtcggtgg aggagtccgg gggtcgcctg gtcacgcctg ggacacccct gacactcacc      60
tgcacagtct ctggaatcga cctcagtcgc aatgcaatga cctgggtccg ccaggctcca     120
gggaaggggc tggaatacat cgcatacatt aatactaggg gtgacacatc ctacgcgaac     180

```
tgggcgaaag gccgattcac catctccaaa acctcgacca cggtggatct gaaaatgacc      240
agtctgacaa ccgaggacac ggccacctat ttctgtgttc atggttataa tccctgtaag      300
ttgtggggcc aaggcaccct ggtcaccgtc tcg                                   333
```

<210> SEQ ID NO 123
<211> LENGTH: 110
<212> TYPE: PRT
<213> ORGANISM: artificial sequence
<220> FEATURE:
<223> OTHER INFORMATION: derived from rabbit

<400> SEQUENCE: 123

```
Ala Tyr Asp Met Thr Gln Thr Pro Ala Ser Val Glu Val Ala Val Gly
1               5                   10                  15

Gly Thr Val Thr Ile Asn Cys Gln Ala Ser Glu Ser Ile Gly Thr Ala
            20                  25                  30

Leu Ala Trp Tyr Gln Gln Lys Pro Gly Gln Pro Pro Lys Leu Leu Ile
        35                  40                  45

Tyr Lys Ala Ser Thr Leu Glu Ser Gly Val Pro Ser Arg Phe Lys Gly
    50                  55                  60

Gly Gly Ser Gly Thr Gln Phe Thr Leu Thr Ile Ser Gly Val Gln Cys
65                  70                  75                  80

Asp Asp Ala Ala Thr Tyr Tyr Cys Gln Gln Gly Glu Thr Ala Asn Arg
                85                  90                  95

Ile Asp Asn Ala Phe Gly Gly Gly Thr Glu Val Val Val Lys
            100                 105                 110
```

<210> SEQ ID NO 124
<211> LENGTH: 111
<212> TYPE: PRT
<213> ORGANISM: artificial sequence
<220> FEATURE:
<223> OTHER INFORMATION: derived from rabbit

<400> SEQUENCE: 124

```
Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Arg Asn Ala
            20                  25                  30

Met Thr Trp Val Arg Gln Ala Pro Gly Lys Gly Leu Glu Tyr Ile Ala
        35                  40                  45

Tyr Ile Asn Thr Arg Gly Asp Thr Ser Tyr Ala Asn Trp Ala Lys Gly
    50                  55                  60

Arg Phe Thr Ile Ser Lys Thr Ser Thr Thr Val Asp Leu Lys Met Thr
65                  70                  75                  80

Ser Leu Thr Thr Glu Asp Thr Ala Thr Tyr Phe Cys Val His Gly Tyr
                85                  90                  95

Asn Pro Cys Lys Leu Trp Gly Gln Gly Thr Leu Val Thr Val Ser
            100                 105                 110
```

<210> SEQ ID NO 125
<211> LENGTH: 330
<212> TYPE: DNA
<213> ORGANISM: artificial sequence
<220> FEATURE:
<223> OTHER INFORMATION: derived from rabbit

<400> SEQUENCE: 125

```
gcctatgata tgacccagac tccagcctct gtggaggtag ctgtgggagg cacagtcacc      60
```

```
atcaattgcc aggccagtga gagcattaac actgcattag cctggtatca gcagaaacca    120
ggacagcctc ccaaggtcct gatctatgct gcctccgatc tggcatctgg ggtcccatcg    180
cggttcaaag gcagtggatc tgggaaacag ttcactctca ccatcagcgg cgtgcagtgt    240
gccgatgctg ccacttacta ctgtcaacag ggttatactg caaataatat tgataatgct    300
ttcggcggag ggaccgaggt ggtcgtcaaa                                     330
```

<210> SEQ ID NO 126
<211> LENGTH: 333
<212> TYPE: DNA
<213> ORGANISM: artificial sequence
<220> FEATURE:
<223> OTHER INFORMATION: derived from rabbit

<400> SEQUENCE: 126

```
cagtcggtgg aggagtccgg gggtcgcctg gtcgcgcctg gacacccct gacactcacc      60 tgcacagtct ctggaatcga cctcagtagg aatgcaatga cctgggtccg ccaggctcca    120
gggaaggggc tggaatacat cgcatatatt aatactaggg gtggcgcatc ctacgcgaac    180
tgggcgaaag ccgattcac catctccaaa acctcgacca cggtggatct gaaaatgacc     240
agtctgacag cttcagacac ggccacctat ttctgtgtca atggttataa cccctgtaag    300
ttgtggggcc cggggaccct cgtcaccgtc tcg                                 333
```

<210> SEQ ID NO 127
<211> LENGTH: 110
<212> TYPE: PRT
<213> ORGANISM: artificial sequence
<220> FEATURE:
<223> OTHER INFORMATION: derived from rabbit

<400> SEQUENCE: 127

Ala Tyr Asp Met Thr Gln Thr Pro Ala Ser Val Glu Val Ala Val Gly
1               5                   10                  15

Gly Thr Val Thr Ile Asn Cys Gln Ala Ser Glu Ser Ile Asn Thr Ala
            20                  25                  30

Leu Ala Trp Tyr Gln Gln Lys Pro Gly Gln Pro Pro Lys Val Leu Ile
        35                  40                  45

Tyr Ala Ala Ser Asp Leu Ala Ser Gly Val Pro Ser Arg Phe Lys Gly
    50                  55                  60

Ser Gly Ser Gly Lys Gln Phe Thr Leu Thr Ile Ser Gly Val Gln Cys
65                  70                  75                  80

Ala Asp Ala Ala Thr Tyr Tyr Cys Gln Gln Gly Tyr Thr Ala Asn Asn
                85                  90                  95

Ile Asp Asn Ala Phe Gly Gly Gly Thr Glu Val Val Val Lys
            100                 105                 110

<210> SEQ ID NO 128
<211> LENGTH: 111
<212> TYPE: PRT
<213> ORGANISM: artificial sequence
<220> FEATURE:
<223> OTHER INFORMATION: derived from rabbit

<400> SEQUENCE: 128

Gln Ser Val Glu Glu Ser Gly Gly Arg Leu Val Ala Pro Gly Thr Pro
1               5                   10                  15

Leu Thr Leu Thr Cys Thr Val Ser Gly Ile Asp Leu Ser Arg Asn Ala
            20                  25                  30

Met Thr Trp Val Arg Gln Ala Pro Gly Lys Gly Leu Glu Tyr Ile Ala
            35                  40                  45

Tyr Ile Asn Thr Arg Gly Gly Ala Ser Tyr Ala Asn Trp Ala Lys Gly
         50                  55                  60

Arg Phe Thr Ile Ser Lys Thr Ser Thr Thr Val Asp Leu Lys Met Thr
 65                  70                  75                  80

Ser Leu Thr Ala Ser Asp Thr Ala Thr Tyr Phe Cys Val Asn Gly Tyr
                 85                  90                  95

Asn Pro Cys Lys Leu Trp Gly Pro Gly Thr Leu Val Thr Val Ser
                100                 105                 110

<210> SEQ ID NO 129
<211> LENGTH: 330
<212> TYPE: DNA
<213> ORGANISM: artificial sequence
<220> FEATURE:
<223> OTHER INFORMATION: derived from rabbit

<400> SEQUENCE: 129
gcccaagtgc tgacccagac tccatcttcc acgtctgcag ctgtgggagg cacagtcacc      60
atcaattgcc agtccagtca gaatgttgtt aataacaact ggttctcctg gtttcagcag     120
aaaccagggc agcctcccaa ggtcctgatc tatttttgtat ccaaactggc atctggggtc    180
ccatcgcggt ttaaaggcag tggatctggg acacagttca ctctcaccat cagcgacctg     240
gagtgtgacg atgctgccac ttattattgt ggaggcggtt atagtgataa tatttatgcg     300
ttcggcggag ggaccgaggt ggtcgtcgaa                                      330

<210> SEQ ID NO 130
<211> LENGTH: 339
<212> TYPE: DNA
<213> ORGANISM: artificial sequence
<220> FEATURE:
<223> OTHER INFORMATION: derived from rabbit

<400> SEQUENCE: 130
cagtcggtgg aggagtccgg gggtcgcctg gtcacgcctg ggacacccct ggcactcacc      60
tgcacagtct ctggaatcga cctcagttac tatgcaataa gctgggtccg ccaggctcca     120
gggaaggggc tggaatacat cggaatcatt ggtagtagtg gtagaacata ctacgcgagc     180
tgggcgaaag gccgattcac catctccaaa acctcgacca cggtggatct gaaaatgacc     240
agtctgacaa ccgaagacac ggccacctat ttctgtgtca ggggtggtcc tacttctagt     300
cctagtttgt ggggccaagg caccctcgtc accgtctcg                            339

<210> SEQ ID NO 131
<211> LENGTH: 110
<212> TYPE: PRT
<213> ORGANISM: artificial sequence
<220> FEATURE:
<223> OTHER INFORMATION: derived from rabbit

<400> SEQUENCE: 131

Ala Gln Val Leu Thr Gln Thr Pro Ser Ser Thr Ser Ala Ala Val Gly
 1               5                  10                  15

Gly Thr Val Thr Ile Asn Cys Gln Ser Ser Gln Asn Val Val Asn Asn
                 20                  25                  30

Asn Trp Phe Ser Trp Phe Gln Gln Lys Pro Gly Gln Pro Pro Lys Val
            35                  40                  45

```
Leu Ile Tyr Phe Val Ser Lys Leu Ala Ser Gly Val Pro Ser Arg Phe
 50                  55                  60
Lys Gly Ser Gly Ser Gly Thr Gln Phe Thr Leu Thr Ile Ser Asp Leu
 65                  70                  75                  80
Glu Cys Asp Asp Ala Ala Thr Tyr Tyr Cys Gly Gly Gly Tyr Ser Asp
                 85                  90                  95
Asn Ile Tyr Ala Phe Gly Gly Gly Thr Glu Val Val Val Glu
            100                 105                 110
```

<210> SEQ ID NO 132
<211> LENGTH: 113
<212> TYPE: PRT
<213> ORGANISM: artificial sequence
<220> FEATURE:
<223> OTHER INFORMATION: derived from rabbit

<400> SEQUENCE: 132

```
Gln Ser Val Glu Glu Ser Gly Gly Arg Leu Val Thr Pro Gly Thr Pro
 1                   5                  10                  15
Leu Ala Leu Thr Cys Thr Val Ser Gly Ile Asp Leu Ser Tyr Tyr Ala
                 20                  25                  30
Ile Ser Trp Val Arg Gln Ala Pro Gly Lys Gly Leu Glu Tyr Ile Gly
             35                  40                  45
Ile Ile Gly Ser Ser Gly Arg Thr Tyr Tyr Ala Ser Trp Ala Lys Gly
 50                  55                  60
Arg Phe Thr Ile Ser Lys Thr Ser Thr Val Asp Leu Lys Met Thr
 65                  70                  75                  80
Ser Leu Thr Thr Glu Asp Thr Ala Thr Tyr Phe Cys Val Arg Gly Gly
                 85                  90                  95
Pro Thr Ser Ser Pro Ser Leu Trp Gly Gln Gly Thr Leu Val Thr Val
            100                 105                 110
Ser
```

<210> SEQ ID NO 133
<211> LENGTH: 342
<212> TYPE: DNA
<213> ORGANISM: artificial sequence
<220> FEATURE:
<223> OTHER INFORMATION: derived from rabbit

<400> SEQUENCE: 133

```
gacatcgtga tgacccagac tccatcctcc gtgtctgcag ctgtgggagg cacagtcacc    60
atcaattgcc aggccagtca gagtgtttat gggaccaacc gtttatcctg gtatcagcag   120
aaaccagggc agcgtcccaa gctcctgatc tatggtgcat ccactctgac atctggggtc   180
ccatcgcggt tcaaaggcag tggatctggg acacagttca ctctcaccat cagtggcgtg   240
cagtgtgatg atgctgccac ttactactgt ctaggcggtt ggtttgaaag tagtagtagt   300
cttgattggg ctttcggcgg agggaccgag gtggtcgtcg aa                     342
```

<210> SEQ ID NO 134
<211> LENGTH: 348
<212> TYPE: DNA
<213> ORGANISM: artificial sequence
<220> FEATURE:
<223> OTHER INFORMATION: derived from rabbit

<400> SEQUENCE: 134

```
cagtcggtgg aggagtccgg gggtcgcctg gtcgcgcctg ggacaccct gacactcacc    60
```

```
tgtacagtct ctggaatcga cctcagtaga aatgcaatgg gctgggtccg ccaggctcca    120 gagaagggc tggaatacat cggccatatt gcgagtcgtg gtaacatatg gttcaggaac    180
tgggcgaaag gccgattcac cgtctccaaa acctcgacca cggtggatct aaaaatcacc    240
agtccgacaa ccgaggacac ggccacctat ttctgtggca gatttcttgt agtatctggg    300
gtggggactt tgatccctg gggccagggg accctcgtca ccgtctcg              348
```

<210> SEQ ID NO 135
<211> LENGTH: 114
<212> TYPE: PRT
<213> ORGANISM: artificial sequence
<220> FEATURE:
<223> OTHER INFORMATION: derived from rabbit

<400> SEQUENCE: 135

```
Asp Ile Val Met Thr Gln Thr Pro Ser Ser Val Ser Ala Ala Val Gly
1               5                   10                  15

Gly Thr Val Thr Ile Asn Cys Gln Ala Ser Gln Ser Val Tyr Gly Thr
            20                  25                  30

Asn Arg Leu Ser Trp Tyr Gln Gln Lys Pro Gly Gln Arg Pro Lys Leu
        35                  40                  45

Leu Ile Tyr Gly Ala Ser Thr Leu Thr Ser Gly Val Pro Ser Arg Phe
    50                  55                  60

Lys Gly Ser Gly Ser Gly Thr Gln Phe Thr Leu Thr Ile Ser Gly Val
65                  70                  75                  80

Gln Cys Asp Asp Ala Ala Thr Tyr Tyr Cys Leu Gly Gly Trp Phe Glu
                85                  90                  95

Ser Ser Ser Ser Leu Asp Trp Ala Phe Gly Gly Gly Thr Glu Val Val
            100                 105                 110

Val Glu
```

<210> SEQ ID NO 136
<211> LENGTH: 116
<212> TYPE: PRT
<213> ORGANISM: artificial sequence
<220> FEATURE:
<223> OTHER INFORMATION: derived from rabbit

<400> SEQUENCE: 136

```
Gln Ser Val Glu Glu Ser Gly Gly Arg Leu Val Ala Pro Gly Thr Pro
1               5                   10                  15

Leu Thr Leu Thr Cys Thr Val Ser Gly Ile Asp Leu Ser Arg Asn Ala
            20                  25                  30

Met Gly Trp Val Arg Gln Ala Pro Glu Lys Gly Leu Glu Tyr Ile Gly
        35                  40                  45

His Ile Ala Ser Arg Gly Asn Ile Trp Phe Arg Asn Trp Ala Lys Gly
    50                  55                  60

Arg Phe Thr Val Ser Lys Thr Ser Thr Val Asp Leu Lys Ile Thr
65                  70                  75                  80

Ser Pro Thr Thr Glu Asp Thr Ala Thr Tyr Phe Cys Gly Arg Phe Leu
                85                  90                  95

Val Val Ser Gly Val Gly Thr Phe Asp Pro Trp Gly Gln Gly Thr Leu
            100                 105                 110

Val Thr Val Ser
        115
```

<210> SEQ ID NO 137

<211> LENGTH: 336
<212> TYPE: DNA
<213> ORGANISM: artificial sequence
<220> FEATURE:
<223> OTHER INFORMATION: derived from rabbit

<400> SEQUENCE: 137

```
gcagccgtgc tgacccagac tccatcgtcc gtgtctgcag ctgtgggagg cacagtcacc    60
atcaagtgcc agtccagtca gagtgtttat aataacaacg aatttttcctg gtatcagcag   120
aaaccagggc agcctcccaa gctcctgatc tatgatgcat ccaaattggc atctggggtc   180
ccatcgcggt tcagcggcag tggatctggg acacagttca ctctcaccat cagcggcgtg   240
cagtgtgacg atgttgccac ttattactgt ctaggcggtt ataatgatga tactaataga   300
tgggctttcg gcggagggac cgaggtggtg gtcgaa                              336
```

<210> SEQ ID NO 138
<211> LENGTH: 351
<212> TYPE: DNA
<213> ORGANISM: artificial sequence
<220> FEATURE:
<223> OTHER INFORMATION: derived from rabbit

<400> SEQUENCE: 138

```
cagtcgctgg aggagtccgg gggtcgcctg gtcacgcctg gacacccct gacactcacc    60
tgcacagtct ctggattctc cctcagtcgc tactggatga gctgggtccg ccaggctcca   120
gggaaggggc tggagtggat cggaaacatt ggtggtggta gtggtagtac attatacgcg   180
ccctgggcaa aaggccgatc caccatctcc aaaacctcga ccacggtgga tctgaaaatc   240
accagtccga caaccgagga cacggccacc tatttctgtg cagatatgt taaaaatggt   300
ggtggttatc ggttggatct ttggggccca gggaccctgg tcaccgtctc g            351
```

<210> SEQ ID NO 139
<211> LENGTH: 112
<212> TYPE: PRT
<213> ORGANISM: artificial sequence
<220> FEATURE:
<223> OTHER INFORMATION: derived from rabbit

<400> SEQUENCE: 139

```
Ala Ala Val Leu Thr Gln Thr Pro Ser Ser Val Ser Ala Ala Val Gly
 1               5                  10                  15

Gly Thr Val Thr Ile Lys Cys Gln Ser Ser Gln Ser Val Tyr Asn Asn
             20                  25                  30

Asn Glu Phe Ser Trp Tyr Gln Gln Lys Pro Gly Gln Pro Pro Lys Leu
         35                  40                  45

Leu Ile Tyr Asp Ala Ser Lys Leu Ala Ser Gly Val Pro Ser Arg Phe
     50                  55                  60

Ser Gly Ser Gly Ser Gly Thr Gln Phe Thr Leu Thr Ile Ser Gly Val
 65                  70                  75                  80

Gln Cys Asp Asp Val Ala Thr Tyr Tyr Cys Leu Gly Gly Tyr Asn Asp
                 85                  90                  95

Asp Thr Asn Arg Trp Ala Phe Gly Gly Gly Thr Glu Val Val Val Glu
            100                 105                 110
```

<210> SEQ ID NO 140
<211> LENGTH: 117
<212> TYPE: PRT
<213> ORGANISM: artificial sequence
<220> FEATURE:

<223> OTHER INFORMATION: derived from rabbit

<400> SEQUENCE: 140

Gln Ser Leu Glu Glu Ser Gly Gly Arg Leu Val Thr Pro Gly Thr Pro
1               5                   10                  15
Leu Thr Leu Thr Cys Thr Val Ser Gly Phe Ser Leu Ser Arg Tyr Trp
            20                  25                  30
Met Ser Trp Val Arg Gln Ala Pro Gly Lys Gly Leu Glu Trp Ile Gly
        35                  40                  45
Asn Ile Gly Gly Gly Ser Gly Ser Thr Leu Tyr Ala Pro Trp Ala Lys
    50                  55                  60
Gly Arg Ser Thr Ile Ser Lys Thr Ser Thr Thr Val Asp Leu Lys Ile
65                  70                  75                  80
Thr Ser Pro Thr Thr Glu Asp Thr Ala Thr Tyr Phe Cys Gly Arg Tyr
                85                  90                  95
Val Lys Asn Gly Gly Gly Tyr Arg Leu Asp Leu Trp Gly Pro Gly Thr
                100                 105                 110
Leu Val Thr Val Ser
        115

<210> SEQ ID NO 141
<211> LENGTH: 336
<212> TYPE: DNA
<213> ORGANISM: artificial sequence
<220> FEATURE:
<223> OTHER INFORMATION: derived from rabbit

<400> SEQUENCE: 141
gccatcgtga tgacccagac tccatcttcc aagtctgtcc ctgtgggaga cacagtcacc      60
atcaattgcc aggccagtga gagtgttgct aataacaact ggttagcctg gtttcaacag     120
aaaccagggc agcctcccaa gctcctgatc tacaaggcat ccactctggc atctggggtc     180
tcatcgcggt ttaaaggcag tggatctggg acacagttca ctctcaccat cggcgatgtg     240
gtgtgtgacg atgctgccac ttactattgt gcaggatata aaagtagtac tactgatgct     300
gttgctttcg gcggagggac cgaggtggtg gtcaaa                                336

<210> SEQ ID NO 142
<211> LENGTH: 342
<212> TYPE: DNA
<213> ORGANISM: artificial sequence
<220> FEATURE:
<223> OTHER INFORMATION: derived from rabbit

<400> SEQUENCE: 142
cagtcagtga aggagtccga gggaggtctc ttcaagccaa cggataccct gacactcacc      60
tgcacagtct ctggattctc cctcagtagc tatgcaataa gctgggtccg ccaggctcca     120
gggaacgggc tggaatggat cggattcatt aacactatta ctggtggcac aaactacgcg     180
agctgggcga aaagccgatc caccatcacc agaaacacca cgataacac ggtgactctg      240
aaaatgacca gtctgacagc cgcggacacg gccacgtatt tctgtgcgag aagtggtgcc     300
tactttgact gtgggggccc aggcaccctg gtcaccgtct cg                         342

<210> SEQ ID NO 143
<211> LENGTH: 112
<212> TYPE: PRT
<213> ORGANISM: artificial sequence
<220> FEATURE:
<223> OTHER INFORMATION: derived from rabbit

<400> SEQUENCE: 143

Ala Ile Val Met Thr Gln Thr Pro Ser Ser Lys Ser Val Pro Val Gly
1               5                   10                  15

Asp Thr Val Thr Ile Asn Cys Gln Ala Ser Glu Ser Val Ala Asn Asn
            20                  25                  30

Asn Trp Leu Ala Trp Phe Gln Gln Lys Pro Gly Gln Pro Pro Lys Leu
        35                  40                  45

Leu Ile Tyr Lys Ala Ser Thr Leu Ala Ser Gly Val Ser Ser Arg Phe
    50                  55                  60

Lys Gly Ser Gly Ser Gly Thr Gln Phe Thr Leu Thr Ile Gly Asp Val
65                  70                  75                  80

Val Cys Asp Asp Ala Ala Thr Tyr Tyr Cys Ala Gly Tyr Lys Ser Ser
                85                  90                  95

Thr Thr Asp Ala Val Ala Phe Gly Gly Gly Thr Glu Val Val Val Lys
            100                 105                 110

<210> SEQ ID NO 144
<211> LENGTH: 114
<212> TYPE: PRT
<213> ORGANISM: artificial sequence
<220> FEATURE:
<223> OTHER INFORMATION: derived from rabbit

<400> SEQUENCE: 144

Gln Ser Val Lys Glu Ser Glu Gly Gly Leu Phe Lys Pro Thr Asp Thr
1               5                   10                  15

Leu Thr Leu Thr Cys Thr Val Ser Gly Phe Ser Leu Ser Ser Tyr Ala
            20                  25                  30

Ile Ser Trp Val Arg Gln Ala Pro Gly Asn Gly Leu Glu Trp Ile Gly
        35                  40                  45

Phe Ile Asn Thr Ile Thr Gly Gly Thr Asn Tyr Ala Ser Trp Ala Lys
    50                  55                  60

Ser Arg Ser Thr Ile Thr Arg Asn Thr Asn Asp Asn Thr Val Thr Leu
65                  70                  75                  80

Lys Met Thr Ser Leu Thr Ala Ala Asp Thr Ala Thr Tyr Phe Cys Ala
                85                  90                  95

Arg Ser Gly Ala Tyr Phe Asp Leu Trp Gly Pro Gly Thr Leu Val Thr
            100                 105                 110

Val Ser

<210> SEQ ID NO 145
<211> LENGTH: 339
<212> TYPE: DNA
<213> ORGANISM: artificial sequence
<220> FEATURE:
<223> OTHER INFORMATION: derived from rabbit

<400> SEQUENCE: 145
gcccaagtgc tgacccagac tgcatccccc gtgtctgcgg ctgttggagg cacagtcacc      60
atcaattgcc agtccagtca gagtgtttat aagaacaacg acttagcctg gtatcagcag     120
aaaccagggc agcctcccaa gctcctgatc tattatgcat ccactctggc atctggggtc     180
tcatcgcggt tcaaaggcag tggatctggg acagagttca ctctcaccat cagcgacgcg     240
cagtgtgacg atgctgccac ttactactgt ctaggtagtt atgattgtag tagtgctgat     300
tgtaatgctt tcggcggagg gaccaaggtg gtcgtcaaa                            339

<210> SEQ ID NO 146
<211> LENGTH: 324
<212> TYPE: DNA
<213> ORGANISM: artificial sequence
<220> FEATURE:
<223> OTHER INFORMATION: derived from rabbit

<400> SEQUENCE: 146

```
cagtcggtgg aggagtccgg gggtcgcctg gtcacgcctg ggacacccct gacactcacc      60
tgcacagtct ctggattctc cctcagtaac tatgcaatga gttgggtccg ccaggctcca     120
gggaaggggc tggaatggat cggaatcatt ggtaaaagtg gtagtacggc ctacgcgagc     180
tgggcgaaag gccgattcac catctccaga acctcgacca cggtggatct ggaaatcacc     240
agtccgacaa ccgaggacac ggccacctat ttctgtgtca gatttgtgct cttgtggggc     300
ccggggaccc tcgtcaccgt ctcg                                            324
```

<210> SEQ ID NO 147
<211> LENGTH: 113
<212> TYPE: PRT
<213> ORGANISM: artificial sequence
<220> FEATURE:
<223> OTHER INFORMATION: derived from rabbit

<400> SEQUENCE: 147

Ala Gln Val Leu Thr Gln Thr Ala Ser Pro Val Ser Ala Ala Val Gly
1               5                   10                  15

Gly Thr Val Thr Ile Asn Cys Gln Ser Ser Gln Ser Val Tyr Lys Asn
            20                  25                  30

Asn Asp Leu Ala Trp Tyr Gln Gln Lys Pro Gly Gln Pro Pro Lys Leu
        35                  40                  45

Leu Ile Tyr Tyr Ala Ser Thr Leu Ala Ser Gly Val Ser Ser Arg Phe
    50                  55                  60

Lys Gly Ser Gly Ser Gly Thr Glu Phe Thr Leu Thr Ile Ser Asp Ala
65                  70                  75                  80

Gln Cys Asp Asp Ala Ala Thr Tyr Tyr Cys Leu Gly Ser Tyr Asp Cys
                85                  90                  95

Ser Ser Ala Asp Cys Asn Ala Phe Gly Gly Thr Lys Val Val Val
            100                 105                 110

Lys

<210> SEQ ID NO 148
<211> LENGTH: 108
<212> TYPE: PRT
<213> ORGANISM: artificial sequence
<220> FEATURE:
<223> OTHER INFORMATION: derived from rabbit

<400> SEQUENCE: 148

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Asn Tyr Ala
            20                  25                  30

Met Ser Trp Val Arg Gln Ala Pro Gly Lys Gly Leu Glu Trp Ile Gly
        35                  40                  45

Ile Ile Gly Lys Ser Gly Ser Thr Ala Tyr Ala Ser Trp Ala Lys Gly
    50                  55                  60

Arg Phe Thr Ile Ser Arg Thr Ser Thr Thr Val Asp Leu Glu Ile Thr
65                  70                  75                  80

Ser Pro Thr Thr Glu Asp Thr Ala Thr Tyr Phe Cys Val Arg Phe Val
                85                  90                  95

Leu Leu Trp Gly Pro Gly Thr Leu Val Thr Val Ser
            100                 105

<210> SEQ ID NO 149
<211> LENGTH: 330
<212> TYPE: DNA
<213> ORGANISM: artificial sequence
<220> FEATURE:
<223> OTHER INFORMATION: derived from rabbit

<400> SEQUENCE: 149
gcgcaagtgc tgacccagac tccatcctcc gtgtctgcag ctgtgggagg cacagtcacc      60
atcaattgcc agtccagtca gagtgttaat aacaacaact tcttatcctg gtatcagcag     120
aaaccagggc agcctcccaa gcaactgatc tacagggctt ccactctggc atctggggtc     180
ccatcgcggt tcaaaggcag tggatctggg acacagttca ctctcaccat cagcgacgtg     240
cagtgtgacg atgctgccac ttacttctgt gcaggcggtt atagtggtaa tatttatgct     300
ttcggcggag ggaccgaggt ggtggtcgaa                                      330

<210> SEQ ID NO 150
<211> LENGTH: 339
<212> TYPE: DNA
<213> ORGANISM: artificial sequence
<220> FEATURE:
<223> OTHER INFORMATION: derived from rabbit

<400> SEQUENCE: 150
cagtcggtgg aggagtccgg gggtcgcctg gtcacgcctg gacacccct gacactcacc       60 tgcacagtct ctgaattctc cctcagtgac tatataataa actgggtccg ccaggctcca     120
gggaaggggc tggaatggat cgggatcatg ggtactagtg gtaccgcata ctacgcgagc     180
tgggcgaaag gccgattcac catctccaaa acctcgtcga ccacggtgga tctgagaatg     240
accagtctga caaccgagga cacggccacc tatttctgtg ccagagggg tgttgctact     300 tctaatttct ggggccaagg caccctggtc accgtctcg                            339

<210> SEQ ID NO 151
<211> LENGTH: 110
<212> TYPE: PRT
<213> ORGANISM: artificial sequence
<220> FEATURE:
<223> OTHER INFORMATION: derived from rabbit

<400> SEQUENCE: 151

Ala Gln Val Leu Thr Gln Thr Pro Ser Ser Val Ser Ala Ala Val Gly
1               5                   10                  15

Gly Thr Val Thr Ile Asn Cys Gln Ser Ser Gln Ser Val Asn Asn Asn
            20                  25                  30

Asn Phe Leu Ser Trp Tyr Gln Gln Lys Pro Gly Gln Pro Pro Lys Gln
        35                  40                  45

Leu Ile Tyr Arg Ala Ser Thr Leu Ala Ser Gly Val Pro Ser Arg Phe
    50                  55                  60

Lys Gly Ser Gly Ser Gly Thr Gln Phe Thr Leu Thr Ile Ser Asp Val
65                  70                  75                  80

Gln Cys Asp Asp Ala Ala Thr Tyr Phe Cys Ala Gly Gly Tyr Ser Gly
                85                  90                  95

```
Asn Ile Tyr Ala Phe Gly Gly Gly Thr Glu Val Val Val Glu
            100                 105                 110
```

```
<210> SEQ ID NO 152
<211> LENGTH: 113
<212> TYPE: PRT
<213> ORGANISM: artificial sequence
<220> FEATURE:
<223> OTHER INFORMATION: derived from rabbit

<400> SEQUENCE: 152

Gln Ser Val Glu Glu Ser Gly Gly Arg Leu Val Thr Pro Gly Thr Pro
1               5                   10                  15

Leu Thr Leu Thr Cys Thr Val Ser Glu Phe Ser Leu Ser Asp Tyr Ile
            20                  25                  30

Ile Asn Trp Val Arg Gln Ala Pro Gly Lys Gly Leu Glu Trp Ile Gly
        35                  40                  45

Ile Met Gly Thr Ser Gly Thr Ala Tyr Tyr Ala Ser Trp Ala Lys Gly
    50                  55                  60

Arg Phe Thr Ile Ser Lys Thr Ser Thr Thr Val Asp Leu Arg Met
65                  70                  75                  80

Thr Ser Leu Thr Thr Glu Asp Thr Ala Thr Tyr Phe Cys Ala Arg Gly
                85                  90                  95

Gly Val Ala Thr Ser Asn Phe Trp Gly Gln Gly Thr Leu Val Thr Val
            100                 105                 110

Ser
```

```
<210> SEQ ID NO 153
<211> LENGTH: 330
<212> TYPE: DNA
<213> ORGANISM: artificial sequence
<220> FEATURE:
<223> OTHER INFORMATION: derived from rabbit

<400> SEQUENCE: 153
gcccaagtgc tgacccagac tgcatcccct gtgtctgcag ctgtgggagg cacagtcacc      60
atcaattgtc agtccagtca gagcgtttat ggtaacaatt ggttaggctg gtatcagcag     120
aaaccagggc agcctcccaa gctcctgatc tattctgcat ctactctggc atctggggtc     180
ccatcgcggt tcagtggcag tggatctggg acacagttca ctctcaccat cagcgacctg     240
gagtgtgacg atggtgccac ttactattgt gtaggcgggt atagtggtaa tattcatgtt     300
ttcggcggag ggaccaaggt ggtggtcgaa                                      330
```

```
<210> SEQ ID NO 154
<211> LENGTH: 339
<212> TYPE: DNA
<213> ORGANISM: artificial sequence
<220> FEATURE:
<223> OTHER INFORMATION: derived from rabbit

<400> SEQUENCE: 154
cagtcggtgg aggagtccgg gggtcgcctg gtcacgcctg ggacacccct gacactcacc      60
tgcacagtct ctggattctc cctcaacgac tacgacatga gctgggtccg ccaggctcca     120
gggaaggggc tggaatggat cacaaccatt tatgttagtg gtaacacata ctacgcgacc     180
tgggcgaaag gccgattcac catctccaaa acctcgacca cggtggatct gaaaatgacc     240
agtccgacag ccgaggacac ggccacctat ttctgtgcca gagcggttcc tggtagtggt     300 aagggggttgt ggggcccggg caccctcgtc accgtctcg                           339
```

<210> SEQ ID NO 155
<211> LENGTH: 110
<212> TYPE: PRT
<213> ORGANISM: artificial sequence
<220> FEATURE:
<223> OTHER INFORMATION: derived from rabbit

<400> SEQUENCE: 155

Ala Gln Val Leu Thr Gln Thr Ala Ser Pro Val Ser Ala Ala Val Gly
1               5                   10                  15

Gly Thr Val Thr Ile Asn Cys Gln Ser Ser Gln Ser Val Tyr Gly Asn
            20                  25                  30

Asn Trp Leu Gly Trp Tyr Gln Gln Lys Pro Gly Gln Pro Pro Lys Leu
        35                  40                  45

Leu Ile Tyr Ser Ala Ser Thr Leu Ala Ser Gly Val Pro Ser Arg Phe
    50                  55                  60

Ser Gly Ser Gly Ser Gly Thr Gln Phe Thr Leu Thr Ile Ser Asp Leu
65                  70                  75                  80

Glu Cys Asp Asp Gly Ala Thr Tyr Tyr Cys Val Gly Tyr Ser Gly
                85                  90                  95

Asn Ile His Val Phe Gly Gly Gly Thr Lys Val Val Val Glu
            100                 105                 110

<210> SEQ ID NO 156
<211> LENGTH: 113
<212> TYPE: PRT
<213> ORGANISM: artificial sequence
<220> FEATURE:
<223> OTHER INFORMATION: derived from rabbit

<400> SEQUENCE: 156

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Asn Asp Tyr Asp
            20                  25                  30

Met Ser Trp Val Arg Gln Ala Pro Gly Lys Gly Leu Glu Trp Ile Thr
        35                  40                  45

Thr Ile Tyr Val Ser Gly Asn Thr Tyr Tyr Ala Thr Trp Ala Lys Gly
    50                  55                  60

Arg Phe Thr Ile Ser Lys Thr Ser Thr Thr Val Asp Leu Lys Met Thr
65                  70                  75                  80

Ser Pro Thr Ala Glu Asp Thr Ala Thr Tyr Phe Cys Ala Arg Ala Val
                85                  90                  95

Pro Gly Ser Gly Lys Gly Leu Trp Gly Pro Gly Thr Leu Val Thr Val
            100                 105                 110

Ser

<210> SEQ ID NO 157
<211> LENGTH: 339
<212> TYPE: DNA
<213> ORGANISM: artificial sequence
<220> FEATURE:
<223> OTHER INFORMATION: derived from rabbit

<400> SEQUENCE: 157
gcccaagtgc tgacccagac tccatcctcc gtgtctgcag ctgtgggagg cacagtcacc      60
atcaactgcc aggccagtca gagtctttat aataagaaaa atttagcctg gtatcagcag     120

```
aaaccagggc agcctcccaa actccttatc tattatgcat ccactctggc atctggggtc      180
tcatcgcggt tcaaaggcag tggatctggg acacagttta ctctcaccat cagcggcgtg      240
cagtgtgacg atgctgccac ttactattgt caaggcgaat ttagttgcag cagtgttgat      300
tgtgttgctt cggcggagg gaccaaggtg gtcgtcaaa                              339

<210> SEQ ID NO 158
<211> LENGTH: 342
<212> TYPE: DNA
<213> ORGANISM: artificial sequence
<220> FEATURE:
<223> OTHER INFORMATION: derived from rabbit

<400> SEQUENCE: 158
cagtcgctgg aggagtccgg gggtcgcctg gtaacgcctg gaggatccct gacactcacc       60
tgcacagtct ctggaatcga cctcagtagc tatgcaatga cctgggtccg ccaggctcca      120
gggaaggggc tggaatggat cggaatcatt tatgctagtg atacatacta cacgagctgg      180
gcgaaaggcc gattcaccat ctccaaaacc tcgaccacgg tggatctcaa aatcaccagt      240
ccgacaaccg aggacacggc catttatttc tgtgccagag gagattctac tagtggtttt      300
catttgactt tgtggggcca gggggaccctg gtcaccgtct cg                       342

<210> SEQ ID NO 159
<211> LENGTH: 113
<212> TYPE: PRT
<213> ORGANISM: artificial sequence
<220> FEATURE:
<223> OTHER INFORMATION: derived from rabbit

<400> SEQUENCE: 159

Ala Gln Val Leu Thr Gln Thr Pro Ser Ser Val Ser Ala Ala Val Gly
1               5                   10                  15

Gly Thr Val Thr Ile Asn Cys Gln Ala Ser Gln Ser Leu Tyr Asn Lys
            20                  25                  30

Lys Asn Leu Ala Trp Tyr Gln Gln Lys Pro Gly Gln Pro Pro Lys Leu
        35                  40                  45

Leu Ile Tyr Tyr Ala Ser Thr Leu Ala Ser Gly Val Ser Ser Arg Phe
    50                  55                  60

Lys Gly Ser Gly Ser Gly Thr Gln Phe Thr Leu Thr Ile Ser Gly Val
65                  70                  75                  80

Gln Cys Asp Asp Ala Ala Thr Tyr Tyr Cys Gln Gly Glu Phe Ser Cys
                85                  90                  95

Ser Ser Val Asp Cys Val Ala Phe Gly Gly Gly Thr Lys Val Val Val
                100                 105                 110

Lys

<210> SEQ ID NO 160
<211> LENGTH: 114
<212> TYPE: PRT
<213> ORGANISM: artificial sequence
<220> FEATURE:
<223> OTHER INFORMATION: derived from rabbit

<400> SEQUENCE: 160

Gln Ser Leu Glu Glu Ser Gly Gly Arg Leu Val Thr Pro Gly Gly Ser
1               5                   10                  15

Leu Thr Leu Thr Cys Thr Val Ser Gly Ile Asp Leu Ser Ser Tyr Ala
            20                  25                  30
```

```
Met Thr Trp Val Arg Gln Ala Pro Gly Lys Gly Leu Glu Trp Ile Gly
            35                  40                  45

Ile Ile Tyr Ala Ser Asp Thr Tyr Tyr Thr Ser Trp Ala Lys Gly Arg
 50                  55                  60

Phe Thr Ile Ser Lys Thr Ser Thr Thr Val Asp Leu Lys Ile Thr Ser
 65                  70                  75                  80

Pro Thr Thr Glu Asp Thr Ala Ile Tyr Phe Cys Ala Arg Gly Asp Ser
                 85                  90                  95

Thr Ser Gly Phe His Leu Thr Leu Trp Gly Gln Gly Thr Leu Val Thr
            100                 105                 110

Val Ser

<210> SEQ ID NO 161
<211> LENGTH: 339
<212> TYPE: DNA
<213> ORGANISM: artificial sequence
<220> FEATURE:
<223> OTHER INFORMATION: derived from rabbit

<400> SEQUENCE: 161
gcccaagtgc tgacccagac tccatcctcc gtgtctgcaa ctgtgggagg cacagtcacc     60
atcaactgcc aggccagtca gagtctttat aataagaaaa atttagcctg gtatcaacag    120
aaaccagggc agcctcccaa gctcctgatc tattttgcat ccactctggc atctggggtc    180
tcatcgcggt tcaaaggcag tggatctggg acacagttca ctctcaccat cagcgacgtg    240
cagtgtgacg atgctgccac ttactattgt cagggcgagt ttatttgcag cagtggtgat    300
tgtgttgctt tcggcggagg gaccaaggtg gtggtcaaa                           339

<210> SEQ ID NO 162
<211> LENGTH: 345
<212> TYPE: DNA
<213> ORGANISM: artificial sequence
<220> FEATURE:
<223> OTHER INFORMATION: derived from rabbit

<400> SEQUENCE: 162
cagtcgctgg aggagtccgg gggtcgcctg ataacgcctg aggatccct gacactcacc      60 tgtacagtct ctggattcga cctcagtagc tatgcaatga cctgggtccg ccaggctcca    120
gggaaggggc tggagtggat cggaatcatt tatggtacta gaccatata ctacgcgacc    180 agggcgaaag gccgattcac catctccaaa gcctcgacca cggtggatct caaaatcacc    240
agtccgacaa ccgaggacac ggccatttat ttctgtgcca gaggagattc tactagtggt    300
tttcatttga ctttgtgggg cccgggcacc ctcgtcaccg tctcg                    345

<210> SEQ ID NO 163
<211> LENGTH: 113
<212> TYPE: PRT
<213> ORGANISM: artificial sequence
<220> FEATURE:
<223> OTHER INFORMATION: derived from rabbit

<400> SEQUENCE: 163

Ala Gln Val Leu Thr Gln Thr Pro Ser Ser Val Ser Ala Thr Val Gly
  1               5                  10                  15

Gly Thr Val Thr Ile Asn Cys Gln Ala Ser Gln Ser Leu Tyr Asn Lys
                 20                  25                  30

Lys Asn Leu Ala Trp Tyr Gln Gln Lys Pro Gly Gln Pro Pro Lys Leu
             35                  40                  45
```

Leu Ile Tyr Phe Ala Ser Thr Leu Ala Ser Gly Val Ser Arg Phe
            50                  55                  60

Lys Gly Ser Gly Ser Gly Thr Gln Phe Thr Leu Thr Ile Ser Asp Val
 65                  70                  75                  80

Gln Cys Asp Asp Ala Ala Thr Tyr Tyr Cys Gln Gly Glu Phe Ile Cys
                85                  90                  95

Ser Ser Gly Asp Cys Val Ala Phe Gly Gly Gly Thr Lys Val Val Val
            100                 105                 110

Lys

<210> SEQ ID NO 164
<211> LENGTH: 115
<212> TYPE: PRT
<213> ORGANISM: artificial sequence
<220> FEATURE:
<223> OTHER INFORMATION: derived from rabbit

<400> SEQUENCE: 164

Gln Ser Leu Glu Glu Ser Gly Gly Arg Leu Ile Thr Pro Gly Gly Ser
 1               5                  10                  15

Leu Thr Leu Thr Cys Thr Val Ser Gly Phe Asp Leu Ser Ser Tyr Ala
            20                  25                  30

Met Thr Trp Val Arg Gln Ala Pro Gly Lys Gly Leu Glu Trp Ile Gly
        35                  40                  45

Ile Ile Tyr Gly Thr Glu Thr Ile Tyr Tyr Ala Thr Arg Ala Lys Gly
    50                  55                  60

Arg Phe Thr Ile Ser Lys Ala Ser Thr Thr Val Asp Leu Lys Ile Thr
 65                  70                  75                  80

Ser Pro Thr Thr Glu Asp Thr Ala Ile Tyr Phe Cys Ala Arg Gly Asp
                85                  90                  95

Ser Thr Ser Gly Phe His Leu Thr Leu Trp Gly Pro Gly Thr Leu Val
            100                 105                 110

Thr Val Ser
        115

<210> SEQ ID NO 165
<211> LENGTH: 339
<212> TYPE: DNA
<213> ORGANISM: artificial sequence
<220> FEATURE:
<223> OTHER INFORMATION: derived from rabbit

<400> SEQUENCE: 165
gcccaagtgc tgacccagac tccatcctcc gtgtctgcag ctgtgggagg cacagtcacc      60
atcaattgcc aggccagtca gagtctttat aataagaaaa atttggcctg gtatcagcag     120
aaaccagggc agcctcccaa gctcctgatg ttctttacgt ccactctggc atctgggatc     180
tcgtcgcggt tcaaaggcag tggatctggg acacagttca ctctcaccat cagcggcgtg     240
cagtgtgacg atgctgccac ttactattgt caaggcgaat ttagttgtag cagtggtgat     300
tgtcttgctt tcggcggagg gaccaaggtg gtcgtcaaa                            339

<210> SEQ ID NO 166
<211> LENGTH: 345
<212> TYPE: DNA
<213> ORGANISM: artificial sequence
<220> FEATURE:
<223> OTHER INFORMATION: derived from rabbit

<400> SEQUENCE: 166

```
cagtcggtgg aggagtccgg cggtcgcctg gtaactcctg gaggatccct gacactcacc      60
tgcaccgtct ctggattcga cctcagtagc tatgcaatga cctgggtccg ccaggctcca     120
gggaaggggc tggagtggat cggaatcatt tatggtactg aactcacata ctacgcgacc     180
tgggcgaaag ccgattcac catctccgaa acctcgacca cggtggatct caaactcacc     240
agtccgacaa ccgaggacac ggccatttat ttctgtgcca gaggagatgc tactagtggt     300
tttcatttga cgttgtgggg cccggggacc ctcgtcaccg tctcg                     345
```

<210> SEQ ID NO 167
<211> LENGTH: 113
<212> TYPE: PRT
<213> ORGANISM: artificial sequence
<220> FEATURE:
<223> OTHER INFORMATION: derived from rabbit

<400> SEQUENCE: 167

Ala Gln Val Leu Thr Gln Thr Pro Ser Ser Val Ser Ala Ala Val Gly
1               5                   10                  15

Gly Thr Val Thr Ile Asn Cys Gln Ala Ser Gln Ser Leu Tyr Asn Lys
            20                  25                  30

Lys Asn Leu Ala Trp Tyr Gln Gln Lys Pro Gly Gln Pro Pro Lys Leu
        35                  40                  45

Leu Met Phe Phe Thr Ser Thr Leu Ala Ser Gly Ile Ser Ser Arg Phe
    50                  55                  60

Lys Gly Ser Gly Ser Gly Thr Gln Phe Thr Leu Thr Ile Ser Gly Val
65                  70                  75                  80

Gln Cys Asp Asp Ala Ala Thr Tyr Tyr Cys Gln Gly Glu Phe Ser Cys
                85                  90                  95

Ser Ser Gly Asp Cys Leu Ala Phe Gly Gly Gly Thr Lys Val Val Val
            100                 105                 110

Lys

<210> SEQ ID NO 168
<211> LENGTH: 115
<212> TYPE: PRT
<213> ORGANISM: artificial sequence
<220> FEATURE:
<223> OTHER INFORMATION: derived from rabbit

<400> SEQUENCE: 168

Gln Ser Val Glu Glu Ser Gly Gly Arg Leu Val Thr Pro Gly Gly Ser
1               5                   10                  15

Leu Thr Leu Thr Cys Thr Val Ser Gly Phe Asp Leu Ser Ser Tyr Ala
            20                  25                  30

Met Thr Trp Val Arg Gln Ala Pro Gly Lys Gly Leu Glu Trp Ile Gly
        35                  40                  45

Ile Ile Tyr Gly Thr Glu Leu Thr Tyr Tyr Ala Thr Trp Ala Lys Gly
    50                  55                  60

Arg Phe Thr Ile Ser Glu Thr Ser Thr Val Asp Leu Lys Leu Thr
65                  70                  75                  80

Ser Pro Thr Thr Glu Asp Thr Ala Ile Tyr Phe Cys Ala Arg Gly Asp
                85                  90                  95

Ala Thr Ser Gly Phe His Leu Thr Leu Trp Gly Pro Gly Thr Leu Val
            100                 105                 110

Thr Val Ser

<210> SEQ ID NO 169
<211> LENGTH: 330
<212> TYPE: DNA
<213> ORGANISM: artificial sequence
<220> FEATURE:
<223> OTHER INFORMATION: derived from rabbit

<400> SEQUENCE: 169

```
gctcaagtgc tgacccagac tccagcctcc gtgtctgaac ctgtgggagg cacagtcacc    60
atcaagtgcc aggccagtca gaccatttat agtggtttag cctggtatca gcagaaacca   120
gggcagcctc ccaagctcct gatctacagg gcatccactc tggcatctgg ggtctcatcg   180
cggttcaaag gcagtggatc tgggacagag ttcattctca ccatcagcga cctggagtgt   240
ggcgatgctg ccacttacta ctgtcaagtt ggtggttatg gtgttagtta tgaccatgct   300
ttcggcggag ggaccaaggt ggtcgtcaaa                                     330
```

<210> SEQ ID NO 170
<211> LENGTH: 366
<212> TYPE: DNA
<213> ORGANISM: artificial sequence
<220> FEATURE:
<223> OTHER INFORMATION: derived from rabbit

<400> SEQUENCE: 170

```
caggaacagc tggaggagtc cggggggaggc ctggtccagc ctgagggatc cctgacactc    60
acctgcacag cttctggatt ctccttcagt agcagctact ggatatgttg ggtccgccag   120
gctccaggga aggggctgga attgatcgca tgcatttatg gtggtagtat taatattatt   180
aactacgcga gctgggcgaa aggccgattc accatctcca aaacctcgtc gaccacggtg   240
actctgcgaa tgaccagtct gacagccgcg gacacggcca ccaatttctg tgcgagagta   300
cagggtggta atagtggtgg ttggtacttt gacttgtggg gcccaggcac cctcgtcacc   360
gtctcg                                                              366
```

<210> SEQ ID NO 171
<211> LENGTH: 110
<212> TYPE: PRT
<213> ORGANISM: artificial sequence
<220> FEATURE:
<223> OTHER INFORMATION: derived from rabbit

<400> SEQUENCE: 171

```
Ala Gln Val Leu Thr Gln Thr Pro Ala Ser Val Ser Glu Pro Val Gly
1               5                   10                  15
Gly Thr Val Thr Ile Lys Cys Gln Ala Ser Gln Thr Ile Tyr Ser Gly
            20                  25                  30
Leu Ala Trp Tyr Gln Gln Lys Pro Gly Gln Pro Pro Lys Leu Leu Ile
        35                  40                  45
Tyr Arg Ala Ser Thr Leu Ala Ser Gly Val Ser Ser Arg Phe Lys Gly
    50                  55                  60
Ser Gly Ser Gly Thr Glu Phe Ile Leu Thr Ile Ser Asp Leu Glu Cys
65                  70                  75                  80
Gly Asp Ala Ala Thr Tyr Tyr Cys Gln Val Gly Gly Tyr Gly Val Ser
                85                  90                  95
Tyr Asp His Ala Phe Gly Gly Gly Thr Lys Val Val Val Lys
            100                 105                 110
```

<210> SEQ ID NO 172
<211> LENGTH: 122
<212> TYPE: PRT
<213> ORGANISM: artificial sequence
<220> FEATURE:
<223> OTHER INFORMATION: derived from rabbit

<400> SEQUENCE: 172

```
Gln Glu Gln Leu Glu Glu Ser Gly Gly Gly Leu Val Gln Pro Glu Gly
1               5                   10                  15

Ser Leu Thr Leu Thr Cys Thr Ala Ser Gly Phe Ser Phe Ser Ser Ser
            20                  25                  30

Tyr Trp Ile Cys Trp Val Arg Gln Ala Pro Gly Lys Gly Leu Glu Leu
        35                  40                  45

Ile Ala Cys Ile Tyr Gly Gly Ser Ile Asn Ile Asn Tyr Ala Ser
    50                  55                  60

Trp Ala Lys Gly Arg Phe Thr Ile Ser Lys Thr Ser Ser Thr Thr Val
65                  70                  75                  80

Thr Leu Arg Met Thr Ser Leu Thr Ala Ala Asp Thr Ala Thr Asn Phe
                85                  90                  95

Cys Ala Arg Val Gln Gly Gly Asn Ser Gly Gly Trp Tyr Phe Asp Leu
            100                 105                 110

Trp Gly Pro Gly Thr Leu Val Thr Val Ser
        115                 120
```

<210> SEQ ID NO 173
<211> LENGTH: 339
<212> TYPE: DNA
<213> ORGANISM: artificial sequence
<220> FEATURE:
<223> OTHER INFORMATION: derived from rabbit

<400> SEQUENCE: 173

```
gcccaagtgc tgacccagac tgcatcgccc gtgtctgcag ctgtgggaaa cacagtcacc    60
atcacttgcc agtccagtca gagtgtttgg aagaataacg acttatcctg gtatcagcag   120
aaactagggc agcctcccaa gctcctgatc tattatgcat ccactctggc atctggggtc   180
tcatcgcggt tcaaagccag tggatctggg acacagttca ctctcaccat cagcgacgtg   240
caatgtgacg atgctggcac ttactactgt gtaggcagtt atgattgtag tagtgctgat   300
tgtaatgctt tcggcggagg gaccaaggtg gtcgtcaaa                          339
```

<210> SEQ ID NO 174
<211> LENGTH: 333
<212> TYPE: DNA
<213> ORGANISM: artificial sequence
<220> FEATURE:
<223> OTHER INFORMATION: derived from rabbit

<400> SEQUENCE: 174

```
cagtcgctgg aggagtccgg gggtcgcctg gtcacgccgg agacacccct gacactcacc    60
tgcacagcct ctggaatcga cctcagtaag tggccaatga cctgggtccg ccaggctcca   120
gggaagggac tggagtggat cggaattatt ggtaggagtg gtagcacgaa ttacgcgagc   180
tgggcgaaag gccgattcac catctccaaa acctcgacca cggtggatct gaaaatgacc   240
agtccgacaa ccgaggacac ggccacttat ttctgtgcca gaggtggtag ttattatgat   300
ttgtggggcc aggggaccct ggtcaccgtc tcg                                333
```

<210> SEQ ID NO 175
<211> LENGTH: 113
<212> TYPE: PRT
<213> ORGANISM: artificial sequence
<220> FEATURE:
<223> OTHER INFORMATION: derived from rabbit

<400> SEQUENCE: 175

```
Ala Gln Val Leu Thr Gln Thr Ala Ser Pro Val Ser Ala Ala Val Gly
1               5                   10                  15

Asn Thr Val Thr Ile Thr Cys Gln Ser Ser Gln Ser Val Trp Lys Asn
            20                  25                  30

Asn Asp Leu Ser Trp Tyr Gln Gln Lys Leu Gly Gln Pro Pro Lys Leu
        35                  40                  45

Leu Ile Tyr Tyr Ala Ser Thr Leu Ala Ser Gly Val Ser Ser Arg Phe
    50                  55                  60

Lys Ala Ser Gly Ser Gly Thr Gln Phe Thr Leu Thr Ile Ser Asp Val
65                  70                  75                  80

Gln Cys Asp Asp Ala Gly Thr Tyr Tyr Cys Val Gly Ser Tyr Asp Cys
                85                  90                  95

Ser Ser Ala Asp Cys Asn Ala Phe Gly Gly Gly Thr Lys Val Val Val
            100                 105                 110

Lys
```

<210> SEQ ID NO 176
<211> LENGTH: 111
<212> TYPE: PRT
<213> ORGANISM: artificial sequence
<220> FEATURE:
<223> OTHER INFORMATION: derived from rabbit

<400> SEQUENCE: 176

```
Gln Ser Leu Glu Glu Ser Gly Gly Arg Leu Val Thr Pro Glu Thr Pro
1               5                   10                  15

Leu Thr Leu Thr Cys Thr Ala Ser Gly Ile Asp Leu Ser Lys Trp Pro
            20                  25                  30

Met Thr Trp Val Arg Gln Ala Pro Gly Lys Gly Leu Glu Trp Ile Gly
        35                  40                  45

Ile Ile Gly Arg Ser Gly Ser Thr Asn Tyr Ala Ser Trp Ala Lys Gly
    50                  55                  60

Arg Phe Thr Ile Ser Lys Thr Ser Thr Thr Val Asp Leu Lys Met Thr
65                  70                  75                  80

Ser Pro Thr Thr Glu Asp Thr Ala Thr Tyr Phe Cys Ala Arg Gly Gly
                85                  90                  95

Ser Tyr Tyr Asp Leu Trp Gly Gln Gly Thr Leu Val Thr Val Ser
            100                 105                 110
```

<210> SEQ ID NO 177
<211> LENGTH: 339
<212> TYPE: DNA
<213> ORGANISM: artificial sequence
<220> FEATURE:
<223> OTHER INFORMATION: derived from rabbit

<400> SEQUENCE: 177

```
gccgccgtgc tgacccagac tccatctccc gtgtctgcag ctgtgggagg cacagtcagc      60
atcagttgcc agtccagtca gagtgttgat aataacaact acttatcctg gtatcagcag     120
aaaccagggc agcctcccaa gctcctgatc tatgatgcat ccgatctggc atctggggtc     180
```

```
ccatcgcggt tcaaaggcag tggatctggg acacagttca ctctcaccat cagcgacgtg      240
cagtgtgacg atgctgccac ttactactgt gcaggcggtt atataactag tagtgatatt      300
ttttatgatt tcggcggagg gaccaaggtg gtggtcaaa                             339
```

<210> SEQ ID NO 178
<211> LENGTH: 324
<212> TYPE: DNA
<213> ORGANISM: artificial sequence
<220> FEATURE:
<223> OTHER INFORMATION: derived from rabbit

<400> SEQUENCE: 178

```
cagtcggtgg aggagtccgg gggtcgcctg gtcacgcctg ggacacccct gacactcacc      60
tgcacagtct ctggattctc cctcagtacc tatgcaatga gctgggtccg ccaggctcca      120
gggaaggggc tggaatggat cggaatcgtt ggaaagagtg gtattataaa gtacgcgagc      180
tgggcgaaag gccggttcac catctccaaa acctcgacca cggtggatct gaaaatgacc      240
agtctgacaa ccgaggacac ggccatttat ttctgtgcca gactatggag cttgtggggc      300
caagggaccc tcgtcaccgt ctcg                                             324
```

<210> SEQ ID NO 179
<211> LENGTH: 113
<212> TYPE: PRT
<213> ORGANISM: artificial sequence
<220> FEATURE:
<223> OTHER INFORMATION: derived from rabbit

<400> SEQUENCE: 179

```
Ala Ala Val Leu Thr Gln Thr Pro Ser Pro Val Ser Ala Ala Val Gly
1               5                   10                  15

Gly Thr Val Ser Ile Ser Cys Gln Ser Ser Gln Ser Val Asp Asn Asn
            20                  25                  30

Asn Tyr Leu Ser Trp Tyr Gln Gln Lys Pro Gly Gln Pro Pro Lys Leu
        35                  40                  45

Leu Ile Tyr Asp Ala Ser Asp Leu Ala Ser Gly Val Pro Ser Arg Phe
    50                  55                  60

Lys Gly Ser Gly Ser Gly Thr Gln Phe Thr Leu Thr Ile Ser Asp Val
65                  70                  75                  80

Gln Cys Asp Asp Ala Ala Thr Tyr Tyr Cys Ala Gly Gly Tyr Ile Thr
                85                  90                  95

Ser Ser Asp Ile Phe Tyr Asp Phe Gly Gly Gly Thr Lys Val Val Val
            100                 105                 110

Lys
```

<210> SEQ ID NO 180
<211> LENGTH: 108
<212> TYPE: PRT
<213> ORGANISM: artificial sequence
<220> FEATURE:
<223> OTHER INFORMATION: derived from rabbit

<400> SEQUENCE: 180

```
Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Thr Tyr Ala
            20                  25                  30

Met Ser Trp Val Arg Gln Ala Pro Gly Lys Gly Leu Glu Trp Ile Gly
        35                  40                  45
```

Ile Val Gly Lys Ser Gly Ile Ile Lys Tyr Ala Ser Trp Ala Lys Gly
    50                  55                  60

Arg Phe Thr Ile Ser Lys Thr Ser Thr Thr Val Asp Leu Lys Met Thr
 65                  70                  75                  80

Ser Leu Thr Thr Glu Asp Thr Ala Ile Tyr Phe Cys Ala Arg Leu Trp
                 85                  90                  95

Ser Leu Trp Gly Gln Gly Thr Leu Val Thr Val Ser
            100                 105

<210> SEQ ID NO 181
<211> LENGTH: 330
<212> TYPE: DNA
<213> ORGANISM: artificial sequence
<220> FEATURE:
<223> OTHER INFORMATION: derived from rabbit

<400> SEQUENCE: 181
gacattgtga tgacccagac tccagcctcc gtgtctgaac ctgtgggagg cacagtcacc    60
atcaagtgcc aggccagtca gagcattagc aactggttag cctggtatca gcagaaacca   120
gggcagcctc ccaagctcct gatctacagg catccactc tggcatctgg ggtctcatcg    180
cggttcaaag gcagtggatc tgggacagag ttcactctca ccatcagcga cctggagtgt   240
gccgatgctg ccacttacta ctgtcaaagc gattatggta tagatactta tggaagtgct   300
ttcggcggag ggaccaaggt ggtggtcaaa                                    330

<210> SEQ ID NO 182
<211> LENGTH: 354
<212> TYPE: DNA
<213> ORGANISM: artificial sequence
<220> FEATURE:
<223> OTHER INFORMATION: derived from rabbit

<400> SEQUENCE: 182
cagtcgctgg aggagtcccg gggtcgcctg gtcacgcctg gacacccct gacactcacc     60 tgcacagtct ctggaatcga cctcagtagt tatgcaatga cctgggtccg ccaggctcca   120
gggaaggggc tggaatggat cggaatggtt cgtcgtagtg gtaccacata ctacgcgagc   180
tgggcgaaag gccgattcac catctccaaa acctcgacca cggtggatct gaaaatcatc   240
agtccgacaa ccgaggacac ggccacctat ttctgtgcca gatgtgataa tagtgctggt   300
gactggagtt acggcatgga cctctggggc cggggacccc tggtcaccgt ctcg         354

<210> SEQ ID NO 183
<211> LENGTH: 110
<212> TYPE: PRT
<213> ORGANISM: artificial sequence
<220> FEATURE:
<223> OTHER INFORMATION: derived from rabbit

<400> SEQUENCE: 183

Asp Ile Val Met Thr Gln Thr Pro Ala Ser Val Ser Glu Pro Val Gly
 1               5                  10                  15

Gly Thr Val Thr Ile Lys Cys Gln Ala Ser Gln Ser Ile Ser Asn Trp
                20                  25                  30

Leu Ala Trp Tyr Gln Gln Lys Pro Gly Gln Pro Pro Lys Leu Leu Ile
            35                  40                  45

Tyr Arg Ala Ser Thr Leu Ala Ser Gly Val Ser Arg Phe Lys Gly
    50                  55                  60

Ser Gly Ser Gly Thr Glu Phe Thr Leu Thr Ile Ser Asp Leu Glu Cys
 65                  70                  75                  80

Ala Asp Ala Ala Thr Tyr Tyr Cys Gln Ser Asp Tyr Gly Ile Asp Thr
                 85                  90                  95

Tyr Gly Ser Ala Phe Gly Gly Gly Thr Lys Val Val Val Lys
            100                 105                 110

<210> SEQ ID NO 184
<211> LENGTH: 118
<212> TYPE: PRT
<213> ORGANISM: artificial sequence
<220> FEATURE:
<223> OTHER INFORMATION: derived from rabbit

<400> SEQUENCE: 184

Gln Ser Leu Glu Glu Ser Arg Gly Arg Leu Val Thr Pro Gly Thr Pro
1               5                   10                  15

Leu Thr Leu Thr Cys Thr Val Ser Gly Ile Asp Leu Ser Ser Tyr Ala
            20                  25                  30

Met Thr Trp Val Arg Gln Ala Pro Gly Lys Gly Leu Glu Trp Ile Gly
        35                  40                  45

Met Val Arg Arg Ser Gly Thr Thr Tyr Tyr Ala Ser Trp Ala Lys Gly
    50                  55                  60

Arg Phe Thr Ile Ser Lys Thr Ser Thr Thr Val Asp Leu Lys Ile Ile
65                  70                  75                  80

Ser Pro Thr Thr Glu Asp Thr Ala Thr Tyr Phe Cys Ala Arg Cys Asp
                85                  90                  95

Asn Ser Ala Gly Asp Trp Ser Tyr Gly Met Asp Leu Trp Gly Pro Gly
            100                 105                 110

Thr Leu Val Thr Val Ser
        115

<210> SEQ ID NO 185
<211> LENGTH: 339
<212> TYPE: DNA
<213> ORGANISM: artificial sequence
<220> FEATURE:
<223> OTHER INFORMATION: derived from rabbit

<400> SEQUENCE: 185
gcccaagtgc tgacccagac tgcatcgccc gtgtctgcag ctgtgggaag cacagtcacc      60
atcaattgcc aggccagtca gagtgtttat cagaacaact acttagcctg gtttcagcag     120
aaaccagggc agcctcccaa gcgcctgatc tattctgcat ccactctggc atctggggtc     180
tcatcgcggt tcaaaggcag tggatctggg acacagttca ctctcaccat cagcgacgtg     240
cagtgtgacg atgctgccac ttattactgt ctgggcgcct atgattgtag tggtgttgat     300
tgtagtgctt tcggcggagg gaccaaggtg gtcgtcaaa                            339

<210> SEQ ID NO 186
<211> LENGTH: 342
<212> TYPE: DNA
<213> ORGANISM: artificial sequence
<220> FEATURE:
<223> OTHER INFORMATION: derived from rabbit

<400> SEQUENCE: 186
cagtcggtgg aggagtccgg gggtcgcctg gtcacgcctg gacacccct gacactcacc       60 tgcaccgtct ctggattctc cctcagtacc aatgcaatga tctgggtccg ccaggctcca    120

```
gggaaggggc tggaatatat cggtgtgatt gctggtagtg gtagcacatc ttacgcgagc    180
tgggcgaaag gccgattcac catctccaaa acctcgacca cggtggatct gaaaatcacc    240
agtccgacaa ccgaggacac ggccacctat ttctgtgcca gagggggttg ggttagtggt    300
ccggagagct tgtggggcca aggcaccctc gtcaccgtct cg                      342
```

<210> SEQ ID NO 187
<211> LENGTH: 113
<212> TYPE: PRT
<213> ORGANISM: artificial sequence
<220> FEATURE:
<223> OTHER INFORMATION: derived from rabbit

<400> SEQUENCE: 187

```
Ala Gln Val Leu Thr Gln Thr Ala Ser Pro Val Ser Ala Ala Val Gly
1               5                   10                  15

Ser Thr Val Thr Ile Asn Cys Gln Ala Ser Gln Ser Val Tyr Gln Asn
            20                  25                  30

Asn Tyr Leu Ala Trp Phe Gln Gln Lys Pro Gly Gln Pro Pro Lys Arg
        35                  40                  45

Leu Ile Tyr Ser Ala Ser Thr Leu Ala Ser Gly Val Ser Ser Arg Phe
    50                  55                  60

Lys Gly Ser Gly Ser Gly Thr Gln Phe Thr Leu Thr Ile Ser Asp Val
65                  70                  75                  80

Gln Cys Asp Asp Ala Ala Thr Tyr Tyr Cys Leu Gly Ala Tyr Asp Cys
                85                  90                  95

Ser Gly Val Asp Cys Ser Ala Phe Gly Gly Gly Thr Lys Val Val Val
            100                 105                 110

Lys
```

<210> SEQ ID NO 188
<211> LENGTH: 114
<212> TYPE: PRT
<213> ORGANISM: artificial sequence
<220> FEATURE:
<223> OTHER INFORMATION: derived from rabbit

<400> SEQUENCE: 188

```
Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Thr Asn Ala
            20                  25                  30

Met Ile Trp Val Arg Gln Ala Pro Gly Lys Gly Leu Glu Tyr Ile Gly
        35                  40                  45

Val Ile Ala Gly Ser Gly Ser Thr Ser Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Gly Gly
                85                  90                  95

Trp Val Ser Gly Pro Glu Ser Leu Trp Gly Gln Gly Thr Leu Val Thr
            100                 105                 110

Val Ser
```

<210> SEQ ID NO 189
<211> LENGTH: 330
<212> TYPE: DNA
<213> ORGANISM: artificial sequence

```
<220> FEATURE:
<223> OTHER INFORMATION: derived from rabbit

<400> SEQUENCE: 189
gcccaagtgc tgacccagac tccatcttcc acgtctgcag ctgtgggagg cacagtcacc    60
atcagttgcc agtccagtcc gagtgtttat ggtaataact ggttaggctg gtatcagaag   120
aaaccagggc agcctcccaa gctcctgatc tattctgcat ccactctggc atctggggtc   180
tcatcgcggt ttaaaggcag tggatctggg acacagttca ctctcaccat cagcgacctg   240
gagtgtgacg atgctgccac ttactactgt gcaggcggtt atagtggtaa tattcatgtt   300
ttcggcggag ggaccaaggt ggtggtcaaa                                     330

<210> SEQ ID NO 190
<211> LENGTH: 339
<212> TYPE: DNA
<213> ORGANISM: artificial sequence
<220> FEATURE:
<223> OTHER INFORMATION: derived from rabbit

<400> SEQUENCE: 190
cagtcggtgg aggagtccgg gggtcgcctg gtcacgcctg gacacccct gacactcacc     60 tgcacagtct ctggattctc cctcaataac tacgacatga cctgggtccg ccaggctcca   120
gggaaggggc tggaatggat cggaagtatt tttgttagtg gtaatatata ctacgcgagc   180
tgggcgaaag gccgattcac catctccaaa acctcgacca cggtggatct gaaaatgacc   240
agtccgacaa ccgaggacac ggccacctat ttctgtgcca gagcaattct tggtagtagt   300
aaggggttgt ggggcccagg caccctggtc accgtctcg                          339

<210> SEQ ID NO 191
<211> LENGTH: 110
<212> TYPE: PRT
<213> ORGANISM: artificial sequence
<220> FEATURE:
<223> OTHER INFORMATION: derived from rabbit

<400> SEQUENCE: 191

Ala Gln Val Leu Thr Gln Thr Pro Ser Ser Thr Ser Ala Ala Val Gly
1               5                   10                  15

Gly Thr Val Thr Ile Ser Cys Gln Ser Ser Pro Ser Val Tyr Gly Asn
            20                  25                  30

Asn Trp Leu Gly Trp Tyr Gln Lys Lys Pro Gly Gln Pro Pro Lys Leu
        35                  40                  45

Leu Ile Tyr Ser Ala Ser Thr Leu Ala Ser Gly Val Ser Ser Arg Phe
    50                  55                  60

Lys Gly Ser Gly Ser Gly Thr Gln Phe Thr Leu Thr Ile Ser Asp Leu
65                  70                  75                  80

Glu Cys Asp Asp Ala Ala Thr Tyr Tyr Cys Ala Gly Gly Tyr Ser Gly
                85                  90                  95

Asn Ile His Val Phe Gly Gly Gly Thr Lys Val Val Val Lys
            100                 105                 110

<210> SEQ ID NO 192
<211> LENGTH: 113
<212> TYPE: PRT
<213> ORGANISM: artificial sequence
<220> FEATURE:
<223> OTHER INFORMATION: derived from rabbit

<400> SEQUENCE: 192
```

```
Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Asn Asn Tyr Asp
            20                  25                  30

Met Thr Trp Val Arg Gln Ala Pro Gly Lys Gly Leu Glu Trp Ile Gly
        35                  40                  45

Ser Ile Phe Val Ser Gly Asn Ile Tyr Tyr Ala Ser Trp Ala Lys Gly
        50                  55                  60

Arg Phe Thr Ile Ser Lys Thr Ser Thr Thr Val Asp Leu Lys Met Thr
65                  70                  75                  80

Ser Pro Thr Thr Glu Asp Thr Ala Thr Tyr Phe Cys Ala Arg Ala Ile
                85                  90                  95

Leu Gly Ser Ser Lys Gly Leu Trp Gly Pro Gly Thr Leu Val Thr Val
                100                 105                 110

Ser
```

```
<210> SEQ ID NO 193
<211> LENGTH: 330
<212> TYPE: DNA
<213> ORGANISM: artificial sequence
<220> FEATURE:
<223> OTHER INFORMATION: derived from rabbit

<400> SEQUENCE: 193
gcctatgata tgacccagac tccagcctct gtggaggtag ctgtgggagg cacagtcacc    60
atcaagtgcc aggccagtca gagcatttac agctatttag cctggtatca gcagaaacca   120
gggcagcctc ccaagctcct gatttattct gcatcctatc tagcatctgg ggtcccatcg   180
cggttcagcg gcagtggatc tgggacagag ttcactctca ccatcagcga cctggagtgt   240
gccgatgctg ccacttatta ctgtcaacac gggtacatta gtggtaatgt tgataatgct   300
ttcggcggag ggaccaaggt ggtcgtcaaa                                    330

<210> SEQ ID NO 194
<211> LENGTH: 339
<212> TYPE: DNA
<213> ORGANISM: artificial sequence
<220> FEATURE:
<223> OTHER INFORMATION: derived from rabbit

<400> SEQUENCE: 194
cagtcggtgg aggagtccgg gggtcgcctg gtcacgcctg gacacccct gacactcacc     60 tgcacagtct ctggattctc cctcagcatc tacgacatga gctgggtccg ccaggctcca   120
gggaaggggc tggaatggat cggatccatt tatgttagtg gtaatatata ctacgcgagc   180
tgggcgaaag gccgattcac catctccaaa acctcgacca cggtggatct gaaaatgacc   240
agtccgacaa ccgaggacac ggccacctat ttctgtgcca gagcggttcc tggtagtagt   300 aagggggttgt ggggccaggg gaccctcgtc accgtctcg                         339

<210> SEQ ID NO 195
<211> LENGTH: 110
<212> TYPE: PRT
<213> ORGANISM: artificial sequence
<220> FEATURE:
<223> OTHER INFORMATION: derived from rabbit

<400> SEQUENCE: 195

Ala Tyr Asp Met Thr Gln Thr Pro Ala Ser Val Glu Val Ala Val Gly
```

```
                1               5                   10                  15
            Gly Thr Val Thr Ile Lys Cys Gln Ala Ser Gln Ser Ile Tyr Ser Tyr
                            20                  25                  30

Leu Ala Trp Tyr Gln Gln Lys Pro Gly Gln Pro Pro Lys Leu Leu Ile
                        35                  40                  45

Tyr Ser Ala Ser Tyr Leu Ala Ser Gly Val Pro Ser Arg Phe Ser Gly
                    50                  55                  60

Ser Gly Ser Gly Thr Glu Phe Thr Leu Thr Ile Ser Asp Leu Glu Cys
            65                  70                  75                  80

Ala Asp Ala Ala Thr Tyr Tyr Cys Gln His Gly Tyr Ile Ser Gly Asn
                            85                  90                  95

Val Asp Asn Ala Phe Gly Gly Gly Thr Lys Val Val Val Lys
                            100                 105                 110

<210> SEQ ID NO 196
<211> LENGTH: 113
<212> TYPE: PRT
<213> ORGANISM: artificial sequence
<220> FEATURE:
<223> OTHER INFORMATION: derived from rabbit

<400> SEQUENCE: 196

Gln Ser Val Glu Glu Ser Gly Gly Arg Leu Val Thr Pro Gly Thr Pro
            1               5                   10                  15

Leu Thr Leu Thr Cys Thr Val Ser Gly Phe Ser Leu Ser Ile Tyr Asp
                            20                  25                  30

Met Ser Trp Val Arg Gln Ala Pro Gly Lys Gly Leu Glu Trp Ile Gly
                        35                  40                  45

Ser Ile Tyr Val Ser Gly Asn Ile Tyr Tyr Ala Ser Trp Ala Lys Gly
                    50                  55                  60

Arg Phe Thr Ile Ser Lys Thr Ser Thr Val Asp Leu Lys Met Thr
            65                  70                  75                  80

Ser Pro Thr Thr Glu Asp Thr Ala Thr Tyr Phe Cys Ala Arg Ala Val
                            85                  90                  95

Pro Gly Ser Ser Lys Gly Leu Trp Gly Gln Gly Thr Leu Val Thr Val
                            100                 105                 110

Ser

<210> SEQ ID NO 197
<211> LENGTH: 327
<212> TYPE: DNA
<213> ORGANISM: artificial sequence
<220> FEATURE:
<223> OTHER INFORMATION: derived from rabbit

<400> SEQUENCE: 197
gcgcaagtgc tgacccagac tccatcccct gtgtctgcag ctgtgggagg caaagtcacc        60
atcaattgcc agtccagtca gagtatttat actaactact tatcctggta tcagcagaaa       120
ccaggacagc ctcccaggct cctgatctat tctgcatcca ctctggcatc tggggtccca       180
tcgcggttca aaggcagtgg atctgggaca cagttcactc tcacaatcag cgaagtacag       240
tgtgacgatg ctgccactta ctactgtcaa gcctatttta ctggtgagat ttttcctttc       300
ggcggaggga ccaaggtggt cgtcaaa                                           327

<210> SEQ ID NO 198
<211> LENGTH: 342
<212> TYPE: DNA
```

<213> ORGANISM: artificial sequence
<220> FEATURE:
<223> OTHER INFORMATION: derived from rabbit

<400> SEQUENCE: 198

```
caggagcaac tgaaggagtc cggggggaggc ctggtaacgc ctggaggaac cctgacactc    60
acctgcaccg tctctggatt ctccctcgat aactaccaca tgggctgggt ccgccaggct   120
ccagggaagg ggctcaatta catcggattc attactcgtg gtggtaccac atactacgcg   180
agctgggcga agggccgatt caccatctcc aaaacctcga ccacggtgga tctgatgatc   240
accagtccga caaccgggga cacggccacc tatttctgtg ccagaggaag tggcgctagc   300
ggcttttact tgtggggccc aggcaccctg gtcaccgtct cg                       342
```

<210> SEQ ID NO 199
<211> LENGTH: 109
<212> TYPE: PRT
<213> ORGANISM: artificial sequence
<220> FEATURE:
<223> OTHER INFORMATION: derived from rabbit

<400> SEQUENCE: 199

```
Ala Gln Val Leu Thr Gln Thr Pro Ser Pro Val Ser Ala Ala Val Gly
1               5                   10                  15

Gly Lys Val Thr Ile Asn Cys Gln Ser Ser Gln Ser Ile Tyr Thr Asn
            20                  25                  30

Tyr Leu Ser Trp Tyr Gln Gln Lys Pro Gly Gln Pro Pro Arg Leu Leu
        35                  40                  45

Ile Tyr Ser Ala Ser Thr Leu Ala Ser Gly Val Pro Ser Arg Phe Lys
    50                  55                  60

Gly Ser Gly Ser Gly Thr Gln Phe Thr Leu Thr Ile Ser Glu Val Gln
65                  70                  75                  80

Cys Asp Asp Ala Ala Thr Tyr Tyr Cys Gln Ala Tyr Phe Thr Gly Glu
                85                  90                  95

Ile Phe Pro Phe Gly Gly Gly Thr Lys Val Val Val Lys
            100                 105
```

<210> SEQ ID NO 200
<211> LENGTH: 114
<212> TYPE: PRT
<213> ORGANISM: artificial sequence
<220> FEATURE:
<223> OTHER INFORMATION: derived from rabbit

<400> SEQUENCE: 200

```
Gln Glu Gln Leu Lys Glu Ser Gly Gly Gly Leu Val Thr Pro Gly Gly
1               5                   10                  15

Thr Leu Thr Leu Thr Cys Thr Val Ser Gly Phe Ser Leu Asp Asn Tyr
            20                  25                  30

His Met Gly Trp Val Arg Gln Ala Pro Gly Lys Gly Leu Asn Tyr Ile
        35                  40                  45

Gly Phe Ile Thr Arg Gly Gly Thr Thr Tyr Tyr Ala Ser Trp Ala Lys
    50                  55                  60

Gly Arg Phe Thr Ile Ser Lys Thr Ser Thr Val Asp Leu Met Ile
65                  70                  75                  80

Thr Ser Pro Thr Thr Gly Asp Thr Ala Thr Tyr Phe Cys Ala Arg Gly
                85                  90                  95

Ser Gly Ala Ser Gly Phe Tyr Leu Trp Gly Pro Gly Thr Leu Val Thr
            100                 105                 110
```

Val Ser

<210> SEQ ID NO 201
<211> LENGTH: 738
<212> TYPE: PRT
<213> ORGANISM: Homo sapiens

<400> SEQUENCE: 201

```
Met Ala Met Leu Pro Pro Gly Pro Gln Ser Phe Val His Phe Thr
1               5                   10                  15

Lys Gln Ser Leu Ala Leu Ile Glu Gln Arg Ile Ala Glu Arg Lys Ser
            20                  25                  30

Lys Glu Pro Lys Glu Glu Lys Asp Asp Asp Glu Ala Pro Lys
            35                  40                  45

Pro Ser Ser Asp Leu Glu Ala Gly Lys Gln Leu Pro Phe Ile Tyr Gly
    50                  55                  60

Asp Ile Pro Pro Gly Met Val Ser Glu Pro Leu Glu Asp Leu Asp Pro
65                  70                  75                  80

Tyr Tyr Ala Asp Lys Lys Thr Phe Ile Val Leu Asn Lys Gly Lys Thr
                85                  90                  95

Ile Phe Arg Phe Asn Ala Thr Pro Ala Leu Tyr Met Leu Ser Pro Phe
            100                 105                 110

Ser Pro Leu Arg Arg Ile Ser Ile Lys Ile Leu Val His Ser Leu Phe
    115                 120                 125

Ser Met Leu Ile Met Cys Thr Ile Leu Thr Asn Cys Ile Phe Met Thr
130                 135                 140

Met Asn Asn Pro Pro Asp Trp Thr Lys Asn Val Glu Tyr Thr Phe Thr
145                 150                 155                 160

Gly Ile Tyr Thr Phe Glu Ser Leu Val Lys Ile Leu Ala Arg Gly Phe
                165                 170                 175

Cys Val Gly Glu Phe Thr Phe Leu Arg Asp Pro Trp Asn Trp Leu Asp
            180                 185                 190

Phe Val Val Ile Val Phe Ala Tyr Leu Thr Glu Phe Val Asn Leu Gly
    195                 200                 205

Asn Val Ser Ala Leu Arg Thr Phe Arg Val Leu Arg Ala Leu Lys Thr
210                 215                 220

Ile Ser Val Ile Pro Gly Leu Lys Thr Ile Val Gly Ala Leu Ile Gln
225                 230                 235                 240

Ser Val Lys Lys Leu Ser Asp Val Met Ile Leu Thr Val Phe Cys Leu
                245                 250                 255

Ser Val Phe Ala Leu Ile Gly Leu Gln Leu Phe Met Gly Asn Leu Lys
            260                 265                 270

His Lys Cys Phe Arg Asn Ser Leu Glu Asn Asn Glu Thr Leu Glu Ser
    275                 280                 285

Ile Met Asn Thr Leu Glu Ser Glu Glu Asp Phe Arg Lys Tyr Phe Tyr
290                 295                 300

Tyr Leu Glu Gly Ser Lys Asp Ala Leu Leu Cys Gly Phe Ser Thr Asp
305                 310                 315                 320

Ser Gly Gln Cys Pro Glu Gly Tyr Thr Cys Val Lys Ile Gly Arg Asn
                325                 330                 335

Pro Asp Tyr Gly Tyr Thr Ser Phe Asp Thr Phe Ser Trp Ala Phe Leu
            340                 345                 350

Ala Leu Phe Arg Leu Met Thr Gln Asp Tyr Trp Glu Asn Leu Tyr Gln
    355                 360                 365
```

-continued

```
Gln Thr Leu Arg Ala Ala Gly Lys Thr Tyr Met Ile Phe Val Val
    370                 375                 380
Val Ile Phe Leu Gly Ser Phe Tyr Leu Ile Asn Leu Ile Leu Ala Val
385                 390                 395                 400
Val Ala Met Ala Tyr Glu Glu Gln Asn Gln Ala Asn Ile Glu Glu Ala
                405                 410                 415
Lys Gln Lys Glu Leu Glu Phe Gln Gln Met Leu Asp Arg Leu Lys Lys
            420                 425                 430
Glu Gln Glu Glu Ala Glu Ala Ile Ala Ala Ala Ala Glu Tyr Thr
        435                 440                 445
Ser Ile Arg Arg Ser Arg Ile Met Gly Leu Ser Glu Ser Ser Ser Glu
    450                 455                 460
Thr Ser Lys Leu Ser Ser Lys Ser Ala Lys Glu Arg Arg Asn Arg Arg
465                 470                 475                 480
Lys Lys Lys Asn Gln Lys Lys Leu Ser Ser Gly Glu Glu Lys Gly Asp
                485                 490                 495
Ala Glu Lys Leu Ser Lys Ser Glu Ser Glu Asp Ser Ile Arg Arg Lys
            500                 505                 510
Ser Phe His Leu Gly Val Glu Gly His Arg Arg Ala His Glu Lys Arg
        515                 520                 525
Leu Ser Thr Pro Asn Gln Ser Pro Leu Ser Ile Arg Gly Ser Leu Phe
    530                 535                 540
Ser Ala Arg Arg Ser Ser Arg Thr Ser Leu Phe Ser Phe Lys Gly Arg
545                 550                 555                 560
Gly Arg Asp Ile Gly Ser Glu Thr Glu Phe Ala Asp Asp Glu His Ser
                565                 570                 575
Ile Phe Gly Asp Asn Glu Ser Arg Arg Gly Ser Leu Phe Val Pro His
            580                 585                 590
Arg Pro Gln Glu Arg Arg Ser Ser Asn Ile Ser Gln Ala Ser Arg Ser
        595                 600                 605
Pro Pro Met Leu Pro Val Asn Gly Lys Met His Ser Ala Val Asp Cys
    610                 615                 620
Asn Gly Val Val Ser Leu Val Asp Gly Arg Ser Ala Leu Met Leu Pro
625                 630                 635                 640
Asn Gly Gln Leu Leu Pro Glu Val Ile Ile Asp Lys Ala Thr Ser Asp
                645                 650                 655
Asp Ser Gly Thr Thr Asn Gln Ile His Lys Lys Arg Arg Cys Ser Ser
            660                 665                 670
Tyr Leu Leu Ser Glu Asp Met Leu Asn Asp Pro Asn Leu Arg Gln Arg
        675                 680                 685
Ala Met Ser Arg Ala Ser Ile Leu Thr Asn Thr Val Glu Glu Leu Glu
    690                 695                 700
Glu Ser Arg Gln Lys Cys Pro Pro Trp Trp Tyr Arg Phe Ala His Lys
705                 710                 715                 720
Phe Leu Ile Trp Asn Cys Ser Pro Tyr Trp Ile Lys Phe Lys Lys Cys
                725                 730                 735
Ile Tyr

<210> SEQ ID NO 202
<211> LENGTH: 449
<212> TYPE: PRT
<213> ORGANISM: Homo sapiens

<400> SEQUENCE: 202
```

-continued

```
Phe Ile Val Met Asp Pro Phe Val Asp Leu Ala Ile Thr Ile Cys Ile
1               5                   10                  15
Val Leu Asn Thr Leu Phe Met Ala Met Glu His His Pro Met Thr Glu
                20                  25                  30
Glu Phe Lys Asn Val Leu Ala Ile Gly Asn Leu Val Phe Thr Gly Ile
            35                  40                  45
Phe Ala Ala Glu Met Val Leu Lys Leu Ile Ala Met Asp Pro Tyr Glu
50                  55                  60
Tyr Phe Gln Val Gly Trp Asn Ile Phe Asp Ser Leu Ile Val Thr Leu
65                      70                  75                  80
Ser Leu Val Glu Leu Phe Leu Ala Asp Val Glu Gly Leu Ser Val Leu
                85                  90                  95
Arg Ser Phe Arg Leu Leu Arg Val Phe Lys Leu Ala Lys Ser Trp Pro
                100                 105                 110
Thr Leu Asn Met Leu Ile Lys Ile Ile Gly Asn Ser Val Gly Ala Leu
                115                 120                 125
Gly Asn Leu Thr Leu Val Leu Ala Ile Ile Val Phe Ile Phe Ala Val
    130                 135                 140
Val Gly Met Gln Leu Phe Gly Lys Ser Tyr Lys Glu Cys Val Cys Lys
145                 150                 155                 160
Ile Asn Asp Asp Cys Thr Leu Pro Arg Trp His Met Asn Asp Phe Phe
                165                 170                 175
His Ser Phe Leu Ile Val Phe Arg Val Leu Cys Gly Glu Trp Ile Glu
                180                 185                 190
Thr Met Trp Asp Cys Met Glu Val Ala Gly Gln Ala Met Cys Leu Ile
                195                 200                 205
Val Tyr Met Met Val Met Val Ile Gly Asn Leu Val Val Leu Asn Leu
        210                 215                 220
Phe Leu Ala Leu Leu Leu Ser Ser Phe Ser Ser Asp Asn Leu Thr Ala
225                 230                 235                 240
Ile Glu Glu Asp Pro Asp Ala Asn Asn Leu Gln Ile Ala Val Thr Arg
                245                 250                 255
Ile Lys Lys Gly Ile Asn Tyr Val Lys Gln Thr Leu Arg Glu Phe Ile
                260                 265                 270
Leu Lys Ala Phe Ser Lys Lys Pro Lys Ile Ser Arg Glu Ile Arg Gln
            275                 280                 285
Ala Glu Asp Leu Asn Thr Lys Lys Glu Asn Tyr Ile Ser Asn His Thr
        290                 295                 300
Leu Ala Glu Met Ser Lys Gly His Asn Phe Leu Lys Glu Lys Asp Lys
305                 310                 315                 320
Ile Ser Gly Phe Gly Ser Ser Val Asp Lys His Leu Met Glu Asp Ser
                325                 330                 335
Asp Gly Gln Ser Phe Ile His Asn Pro Ser Leu Thr Val Thr Val Pro
            340                 345                 350
Ile Ala Pro Gly Glu Ser Asp Leu Glu Asn Met Asn Ala Glu Glu Leu
        355                 360                 365
Ser Ser Asp Ser Asp Ser Glu Tyr Ser Lys Val Arg Leu Asn Arg Ser
    370                 375                 380
Ser Ser Ser Glu Cys Ser Thr Val Asp Asn Pro Leu Pro Gly Glu Gly
385                 390                 395                 400
Glu Glu Ala Glu Ala Glu Pro Met Asn Ser Asp Glu Pro Glu Ala Cys
                405                 410                 415
```

```
Phe Thr Asp Gly Cys Val Arg Arg Phe Ser Cys Cys Gln Val Asn Ile
            420                 425                 430

Glu Ser Gly Lys Gly Lys Ile Trp Trp Asn Ile Arg Lys Thr Cys Tyr
        435                 440                 445

Lys

<210> SEQ ID NO 203
<211> LENGTH: 322
<212> TYPE: PRT
<213> ORGANISM: Homo sapiens

<400> SEQUENCE: 203

Ile Val Glu His Ser Trp Phe Glu Ser Phe Ile Val Leu Met Ile Leu
1               5                   10                  15

Leu Ser Ser Gly Ala Leu Ala Phe Glu Asp Ile Tyr Ile Glu Arg Lys
            20                  25                  30

Lys Thr Ile Lys Ile Ile Leu Glu Tyr Ala Asp Lys Ile Phe Thr Tyr
        35                  40                  45

Ile Phe Ile Leu Glu Met Leu Leu Lys Trp Ile Ala Tyr Gly Tyr Lys
    50                  55                  60

Thr Tyr Phe Thr Asn Ala Trp Cys Trp Leu Asp Phe Leu Ile Val Asp
65                  70                  75                  80

Val Ser Leu Val Thr Leu Val Ala Asn Thr Leu Gly Tyr Ser Asp Leu
                85                  90                  95

Gly Pro Ile Ser Leu Arg Thr Leu Arg Ala Leu Arg Pro Leu Arg Ala
            100                 105                 110

Leu Ser Arg Phe Glu Gly Met Arg Val Val Val Asn Ala Leu Ile Gly
        115                 120                 125

Ala Ile Pro Ser Ile Met Asn Val Leu Leu Val Cys Leu Ile Phe Trp
    130                 135                 140

Leu Ile Phe Ser Ile Met Gly Val Asn Leu Phe Ala Gly Lys Phe Tyr
145                 150                 155                 160

Glu Cys Ile Asn Thr Thr Asp Gly Ser Arg Phe Pro Ala Ser Gln Val
                165                 170                 175

Pro Asn Arg Ser Glu Cys Phe Ala Leu Met Asn Val Ser Gln Asn Val
            180                 185                 190

Arg Trp Lys Asn Leu Lys Val Asn Phe Asp Asn Val Gly Leu Gly Tyr
        195                 200                 205

Leu Ser Leu Leu Gln Val Ala Thr Phe Lys Gly Trp Thr Ile Ile Met
    210                 215                 220

Tyr Ala Ala Val Asp Ser Val Asn Val Asp Lys Gln Pro Lys Tyr Glu
225                 230                 235                 240

Tyr Ser Leu Tyr Met Tyr Ile Tyr Phe Val Phe Ile Ile Phe Gly
                245                 250                 255

Ser Phe Phe Thr Leu Asn Leu Phe Ile Gly Val Ile Ile Asp Asn Phe
            260                 265                 270

Asn Gln Gln Lys Lys Leu Gly Gly Gln Asp Ile Phe Met Thr Glu
        275                 280                 285

Glu Gln Lys Lys Tyr Tyr Asn Ala Met Lys Lys Leu Gly Ser Lys Lys
    290                 295                 300

Pro Gln Lys Pro Ile Pro Arg Pro Gly Asn Lys Ile Gln Gly Cys Ile
305                 310                 315                 320

Phe Asp
```

```
<210> SEQ ID NO 204
<211> LENGTH: 478
<212> TYPE: PRT
<213> ORGANISM: Homo sapiens

<400> SEQUENCE: 204

Leu Val Thr Asn Gln Ala Phe Asp Ile Ser Ile Met Val Leu Ile Cys
1               5                   10                  15

Leu Asn Met Val Thr Met Met Val Glu Lys Glu Gly Gln Ser Gln His
            20                  25                  30

Met Thr Glu Val Leu Tyr Trp Ile Asn Val Val Phe Ile Ile Leu Phe
        35                  40                  45

Thr Gly Glu Cys Val Leu Lys Leu Ile Ser Leu Arg His Tyr Tyr Phe
    50                  55                  60

Thr Val Gly Trp Asn Ile Phe Asp Phe Val Val Ile Ile Ser Ile
65                  70                  75                  80

Val Gly Met Phe Leu Ala Asp Leu Ile Glu Thr Tyr Phe Val Ser Pro
                85                  90                  95

Thr Leu Phe Arg Val Ile Arg Leu Ala Arg Ile Gly Arg Ile Leu Arg
            100                 105                 110

Leu Val Lys Gly Ala Lys Gly Ile Arg Thr Leu Leu Phe Ala Leu Met
        115                 120                 125

Met Ser Leu Pro Ala Leu Phe Asn Ile Gly Leu Leu Leu Phe Leu Val
130                 135                 140

Met Phe Ile Tyr Ala Ile Phe Gly Met Ser Asn Phe Ala Tyr Val Lys
145                 150                 155                 160

Lys Glu Asp Gly Ile Asn Asp Met Phe Asn Phe Glu Thr Phe Gly Asn
                165                 170                 175

Ser Met Ile Cys Leu Phe Gln Ile Thr Thr Ser Ala Gly Trp Asp Gly
            180                 185                 190

Leu Leu Ala Pro Ile Leu Asn Ser Lys Pro Pro Asp Cys Asp Pro Lys
        195                 200                 205

Lys Val His Pro Gly Ser Ser Val Glu Gly Asp Cys Gly Asn Pro Ser
210                 215                 220

Val Gly Ile Phe Tyr Phe Val Ser Tyr Ile Ile Ile Ser Phe Leu Val
225                 230                 235                 240

Val Val Asn Met Tyr Ile Ala Val Ile Leu Glu Asn Phe Ser Val Ala
                245                 250                 255

Thr Glu Glu Ser Thr Glu Pro Leu Ser Glu Asp Asp Phe Glu Met Phe
            260                 265                 270

Tyr Glu Val Trp Glu Lys Phe Asp Pro Asp Ala Thr Gln Phe Ile Glu
        275                 280                 285

Phe Ser Lys Leu Ser Asp Phe Ala Ala Ala Leu Asp Pro Pro Leu Leu
290                 295                 300

Ile Ala Lys Pro Asn Lys Val Gln Leu Ile Ala Met Asp Leu Pro Met
305                 310                 315                 320

Val Ser Gly Asp Arg Ile His Cys Leu Asp Ile Leu Phe Ala Phe Thr
                325                 330                 335

Lys Arg Val Leu Gly Glu Ser Gly Glu Met Asp Ser Leu Arg Ser Gln
            340                 345                 350

Met Glu Glu Arg Phe Met Ser Ala Asn Pro Ser Lys Val Ser Tyr Glu
        355                 360                 365

Pro Ile Thr Thr Thr Leu Lys Arg Lys Gln Glu Asp Val Ser Ala Thr
370                 375                 380
```

```
Val Ile Gln Arg Ala Tyr Arg Arg Tyr Arg Leu Arg Gln Asn Val Lys
385                 390                 395                 400

Asn Ile Ser Ser Ile Tyr Ile Lys Asp Gly Asp Arg Asp Asp Asp Leu
            405                 410                 415

Leu Asn Lys Lys Asp Met Ala Phe Asp Asn Val Asn Glu Asn Ser Ser
        420                 425                 430

Pro Glu Lys Thr Asp Ala Thr Ser Ser Thr Ser Pro Pro Ser Tyr
        435                 440                 445

Asp Ser Val Thr Lys Pro Lys Glu Lys Tyr Glu Gln Asp Arg Thr
450                 455                 460

Glu Lys Glu Asp Lys Gly Lys Asp Ser Lys Glu Ser Lys Lys
465                 470                 475

<210> SEQ ID NO 205
<211> LENGTH: 1987
<212> TYPE: PRT
<213> ORGANISM: Homo sapiens

<400> SEQUENCE: 205

Met Ala Met Leu Pro Pro Gly Pro Gln Ser Phe Val His Phe Thr
1               5                   10                  15

Lys Gln Ser Leu Ala Leu Ile Glu Gln Arg Ile Ala Glu Arg Lys Ser
            20                  25                  30

Lys Glu Pro Lys Glu Glu Lys Lys Asp Asp Asp Glu Gly Ala Pro Lys
        35                  40                  45

Pro Ser Ser Asp Leu Glu Ala Gly Lys Gln Leu Pro Phe Ile Tyr Gly
    50                  55                  60

Asp Ile Pro Pro Gly Met Val Ser Glu Pro Leu Glu Asp Leu Asp Pro
65                  70                  75                  80

Tyr Tyr Ala Asp Lys Lys Thr Phe Ile Val Leu Asn Lys Gly Lys Thr
                85                  90                  95

Ile Phe Arg Phe Asn Ala Thr Pro Ala Leu Tyr Met Leu Ser Pro Phe
            100                 105                 110

Ser Pro Leu Arg Arg Ile Ser Ile Lys Ile Leu Val His Ser Leu Phe
        115                 120                 125

Ser Met Leu Ile Met Cys Thr Ile Leu Thr Asn Cys Ile Phe Met Thr
    130                 135                 140

Met Asn Asn Pro Pro Asp Trp Thr Lys Asn Val Glu Tyr Thr Phe Thr
145                 150                 155                 160

Gly Ile Tyr Thr Phe Glu Ser Leu Val Lys Ile Leu Ala Arg Gly Phe
                165                 170                 175

Cys Val Gly Glu Phe Thr Phe Leu Arg Asp Pro Trp Asn Trp Leu Asp
            180                 185                 190

Phe Val Ile Val Phe Ala Tyr Leu Thr Glu Phe Val Asn Leu Gly
        195                 200                 205

Asn Val Ser Ala Leu Arg Thr Phe Arg Val Leu Arg Ala Leu Lys Thr
    210                 215                 220

Ile Ser Val Ile Pro Gly Leu Lys Thr Ile Val Gly Ala Leu Ile Gln
225                 230                 235                 240

Ser Val Lys Lys Leu Ser Asp Val Met Ile Leu Thr Val Phe Cys Leu
                245                 250                 255

Ser Val Phe Ala Leu Ile Gly Leu Gln Leu Phe Met Gly Asn Leu Lys
            260                 265                 270

His Lys Cys Phe Arg Asn Ser Leu Glu Asn Asn Glu Thr Leu Glu Ser
        275                 280                 285
```

-continued

```
Ile Met Asn Thr Leu Glu Ser Glu Glu Asp Phe Arg Lys Tyr Phe Tyr
    290                 295                 300

Tyr Leu Glu Gly Ser Lys Asp Ala Leu Leu Cys Gly Phe Ser Thr Asp
305                 310                 315                 320

Ser Gly Gln Cys Pro Glu Gly Tyr Thr Cys Val Lys Ile Gly Arg Asn
                325                 330                 335

Pro Asp Tyr Gly Tyr Thr Ser Phe Asp Thr Phe Ser Trp Ala Phe Leu
            340                 345                 350

Ala Leu Phe Arg Leu Met Thr Gln Asp Tyr Trp Glu Asn Leu Tyr Gln
        355                 360                 365

Gln Thr Leu Arg Ala Ala Gly Lys Thr Tyr Met Ile Phe Phe Val Val
    370                 375                 380

Val Ile Phe Leu Gly Ser Phe Tyr Leu Ile Asn Leu Ile Leu Ala Val
385                 390                 395                 400

Val Ala Met Ala Tyr Glu Glu Gln Asn Gln Ala Asn Ile Glu Glu Ala
                405                 410                 415

Lys Gln Lys Glu Leu Glu Phe Gln Gln Met Leu Asp Arg Leu Lys Lys
            420                 425                 430

Glu Gln Glu Glu Ala Glu Ala Ile Ala Ala Ala Ala Glu Tyr Thr
        435                 440                 445

Ser Ile Arg Arg Ser Arg Ile Met Gly Leu Ser Glu Ser Ser Ser Glu
    450                 455                 460

Thr Ser Lys Leu Ser Ser Lys Ser Ala Lys Glu Arg Arg Asn Arg Arg
465                 470                 475                 480

Lys Lys Lys Asn Gln Lys Lys Leu Ser Ser Gly Glu Glu Lys Gly Asp
                485                 490                 495

Ala Glu Lys Leu Ser Lys Ser Glu Ser Glu Asp Ser Ile Arg Arg Lys
            500                 505                 510

Ser Phe His Leu Gly Val Glu Gly His Arg Arg Ala His Glu Lys Arg
        515                 520                 525

Leu Ser Thr Pro Asn Gln Ser Pro Leu Ser Ile Arg Gly Ser Leu Phe
    530                 535                 540

Ser Ala Arg Arg Ser Ser Arg Thr Ser Leu Phe Ser Phe Lys Gly Arg
545                 550                 555                 560

Gly Arg Asp Ile Gly Ser Glu Thr Glu Phe Ala Asp Asp Glu His Ser
                565                 570                 575

Ile Phe Gly Asp Asn Glu Ser Arg Arg Gly Ser Leu Phe Val Pro His
            580                 585                 590

Arg Pro Gln Glu Arg Arg Ser Ser Asn Ile Ser Gln Ala Ser Arg Ser
        595                 600                 605

Pro Pro Met Leu Pro Val Asn Gly Lys Met His Ser Ala Val Asp Cys
    610                 615                 620

Asn Gly Val Val Ser Leu Val Asp Gly Arg Ser Ala Leu Met Leu Pro
625                 630                 635                 640

Asn Gly Gln Leu Leu Pro Glu Val Ile Ile Asp Lys Ala Thr Ser Asp
                645                 650                 655

Asp Ser Gly Thr Thr Asn Gln Ile His Lys Lys Arg Arg Cys Ser Ser
            660                 665                 670

Tyr Leu Leu Ser Glu Asp Met Leu Asn Asp Pro Asn Leu Arg Gln Arg
        675                 680                 685

Ala Met Ser Arg Ala Ser Ile Leu Thr Asn Thr Val Glu Glu Leu Glu
    690                 695                 700
```

```
Glu Ser Arg Gln Lys Cys Pro Pro Trp Trp Tyr Arg Phe Ala His Lys
705                 710                 715                 720

Phe Leu Ile Trp Asn Cys Ser Pro Tyr Trp Ile Lys Phe Lys Lys Cys
            725                 730                 735

Ile Tyr Phe Ile Val Met Asp Pro Phe Val Asp Leu Ala Ile Thr Ile
                740                 745                 750

Cys Ile Val Leu Asn Thr Leu Phe Met Ala Met Glu His His Pro Met
            755                 760                 765

Thr Glu Glu Phe Lys Asn Val Leu Ala Ile Gly Asn Leu Val Phe Thr
770                 775                 780

Gly Ile Phe Ala Ala Glu Met Val Leu Lys Leu Ile Ala Met Asp Pro
785                 790                 795                 800

Tyr Glu Tyr Phe Gln Val Gly Trp Asn Ile Phe Asp Ser Leu Ile Val
                805                 810                 815

Thr Leu Ser Leu Val Glu Leu Phe Leu Ala Asp Val Glu Gly Leu Ser
            820                 825                 830

Val Leu Arg Ser Phe Arg Leu Leu Arg Val Phe Lys Leu Ala Lys Ser
            835                 840                 845

Trp Pro Thr Leu Asn Met Leu Ile Lys Ile Ile Gly Asn Ser Val Gly
850                 855                 860

Ala Leu Gly Asn Leu Thr Leu Val Leu Ala Ile Ile Val Phe Ile Phe
865                 870                 875                 880

Ala Val Val Gly Met Gln Leu Phe Gly Lys Ser Tyr Lys Glu Cys Val
                885                 890                 895

Cys Lys Ile Asn Asp Asp Cys Thr Leu Pro Arg Trp His Met Asn Asp
            900                 905                 910

Phe Phe His Ser Phe Leu Ile Val Phe Arg Val Leu Cys Gly Glu Trp
            915                 920                 925

Ile Glu Thr Met Trp Asp Cys Met Glu Val Ala Gly Gln Ala Met Cys
            930                 935                 940

Leu Ile Val Tyr Met Met Val Met Val Ile Gly Asn Leu Val Val Leu
945                 950                 955                 960

Asn Leu Phe Leu Ala Leu Leu Leu Ser Ser Phe Ser Ser Asp Asn Leu
                965                 970                 975

Thr Ala Ile Glu Glu Asp Pro Asp Ala Asn Asn Leu Gln Ile Ala Val
            980                 985                 990

Thr Arg Ile Lys Lys Gly Ile Asn  Tyr Val Lys Gln Thr Leu Arg Glu
            995                 1000                1005

Phe Ile Leu Lys Ala Phe Ser Lys Lys Pro Lys Ile Ser Arg Glu
    1010                1015                1020

Ile Arg Gln Ala Glu Asp Leu Asn Thr Lys Lys Glu Asn Tyr Ile
    1025                1030                1035

Ser Asn His Thr Leu Ala Glu Met Ser Lys Gly His Asn Phe Leu
    1040                1045                1050

Lys Glu Lys Asp Lys Ile Ser Gly Phe Gly Ser Ser Val Asp Lys
    1055                1060                1065

His Leu Met Glu Asp Ser Asp Gly Gln Ser Phe Ile His Asn Pro
    1070                1075                1080

Ser Leu Thr Val Thr Val Pro Ile Ala Pro Gly Glu Ser Asp Leu
    1085                1090                1095

Glu Asn Met Asn Ala Glu Glu Leu Ser Ser Asp Ser Asp Ser Glu
    1100                1105                1110

Tyr Ser Lys Val Arg Leu Asn Arg Ser Ser Ser Ser Glu Cys Ser
```

```
                  1115                1120                1125
Thr  Val  Asp  Asn  Pro  Leu  Pro  Gly  Glu  Gly  Glu  Ala  Glu  Ala
                  1130                1135                1140

Glu  Pro  Met  Asn  Ser  Asp  Glu  Pro  Glu  Ala  Cys  Phe  Thr  Asp  Gly
                  1145                1150                1155

Cys  Val  Arg  Arg  Phe  Ser  Cys  Cys  Gln  Val  Asn  Ile  Glu  Ser  Gly
                  1160                1165                1170

Lys  Gly  Lys  Ile  Trp  Trp  Asn  Ile  Arg  Lys  Thr  Cys  Tyr  Lys  Ile
                  1175                1180                1185

Val  Glu  His  Ser  Trp  Phe  Glu  Ser  Phe  Ile  Val  Leu  Met  Ile  Leu
                  1190                1195                1200

Leu  Ser  Ser  Gly  Ala  Leu  Ala  Phe  Glu  Asp  Ile  Tyr  Ile  Glu  Arg
                  1205                1210                1215

Lys  Lys  Thr  Ile  Lys  Ile  Ile  Leu  Glu  Tyr  Ala  Asp  Lys  Ile  Phe
                  1220                1225                1230

Thr  Tyr  Ile  Phe  Ile  Leu  Glu  Met  Leu  Leu  Lys  Trp  Ile  Ala  Tyr
                  1235                1240                1245

Gly  Tyr  Lys  Thr  Tyr  Phe  Thr  Asn  Ala  Trp  Cys  Trp  Leu  Asp  Phe
                  1250                1255                1260

Leu  Ile  Val  Asp  Val  Ser  Leu  Val  Thr  Leu  Val  Ala  Asn  Thr  Leu
                  1265                1270                1275

Gly  Tyr  Ser  Asp  Leu  Gly  Pro  Ile  Ser  Leu  Arg  Thr  Leu  Arg  Ala
                  1280                1285                1290

Leu  Arg  Pro  Leu  Arg  Ala  Leu  Ser  Arg  Phe  Glu  Gly  Met  Arg  Val
                  1295                1300                1305

Val  Val  Asn  Ala  Leu  Ile  Gly  Ala  Ile  Pro  Ser  Ile  Met  Asn  Val
                  1310                1315                1320

Leu  Leu  Val  Cys  Leu  Ile  Phe  Trp  Leu  Ile  Phe  Ser  Ile  Met  Gly
                  1325                1330                1335

Val  Asn  Leu  Phe  Ala  Gly  Lys  Phe  Tyr  Glu  Cys  Ile  Asn  Thr  Thr
                  1340                1345                1350

Asp  Gly  Ser  Arg  Phe  Pro  Ala  Ser  Gln  Val  Pro  Asn  Arg  Ser  Glu
                  1355                1360                1365

Cys  Phe  Ala  Leu  Met  Asn  Val  Ser  Gln  Asn  Val  Arg  Trp  Lys  Asn
                  1370                1375                1380

Leu  Lys  Val  Asn  Phe  Asp  Asn  Val  Gly  Leu  Gly  Tyr  Leu  Ser  Leu
                  1385                1390                1395

Leu  Gln  Val  Ala  Thr  Phe  Lys  Gly  Trp  Thr  Ile  Ile  Met  Tyr  Ala
                  1400                1405                1410

Ala  Val  Asp  Ser  Val  Asn  Val  Asp  Lys  Gln  Pro  Lys  Tyr  Glu  Tyr
                  1415                1420                1425

Ser  Leu  Tyr  Met  Tyr  Ile  Tyr  Phe  Val  Val  Phe  Ile  Ile  Phe  Gly
                  1430                1435                1440

Ser  Phe  Phe  Thr  Leu  Asn  Leu  Phe  Ile  Gly  Val  Ile  Ile  Asp  Asn
                  1445                1450                1455

Phe  Asn  Gln  Gln  Lys  Lys  Lys  Leu  Gly  Gly  Gln  Asp  Ile  Phe  Met
                  1460                1465                1470

Thr  Glu  Glu  Gln  Lys  Lys  Tyr  Tyr  Asn  Ala  Met  Lys  Lys  Leu  Gly
                  1475                1480                1485

Ser  Lys  Lys  Pro  Gln  Lys  Pro  Ile  Pro  Arg  Pro  Gly  Asn  Lys  Ile
                  1490                1495                1500

Gln  Gly  Cys  Ile  Phe  Asp  Leu  Val  Thr  Asn  Gln  Ala  Phe  Asp  Ile
                  1505                1510                1515
```

```
Ser Ile Met Val Leu Ile Cys Leu Asn Met Val Thr Met Met Val
1520                1525                1530

Glu Lys Glu Gly Gln Ser Gln His Met Thr Glu Val Leu Tyr Trp
1535                1540                1545

Ile Asn Val Val Phe Ile Ile Leu Phe Thr Gly Glu Cys Val Leu
1550                1555                1560

Lys Leu Ile Ser Leu Arg His Tyr Tyr Phe Thr Val Gly Trp Asn
1565                1570                1575

Ile Phe Asp Phe Val Val Val Ile Ile Ser Ile Val Gly Met Phe
1580                1585                1590

Leu Ala Asp Leu Ile Glu Thr Tyr Phe Val Ser Pro Thr Leu Phe
1595                1600                1605

Arg Val Ile Arg Leu Ala Arg Ile Gly Arg Ile Leu Arg Leu Val
1610                1615                1620

Lys Gly Ala Lys Gly Ile Arg Thr Leu Leu Phe Ala Leu Met Met
1625                1630                1635

Ser Leu Pro Ala Leu Phe Asn Ile Gly Leu Leu Leu Phe Leu Val
1640                1645                1650

Met Phe Ile Tyr Ala Ile Phe Gly Met Ser Asn Phe Ala Tyr Val
1655                1660                1665

Lys Lys Glu Asp Gly Ile Asn Asp Met Phe Asn Phe Glu Thr Phe
1670                1675                1680

Gly Asn Ser Met Ile Cys Leu Phe Gln Ile Thr Thr Ser Ala Gly
1685                1690                1695

Trp Asp Gly Leu Leu Ala Pro Ile Leu Asn Ser Lys Pro Pro Asp
1700                1705                1710

Cys Asp Pro Lys Lys Val His Pro Gly Ser Ser Val Glu Gly Asp
1715                1720                1725

Cys Gly Asn Pro Ser Val Gly Ile Phe Tyr Phe Val Ser Tyr Ile
1730                1735                1740

Ile Ile Ser Phe Leu Val Val Val Asn Met Tyr Ile Ala Val Ile
1745                1750                1755

Leu Glu Asn Phe Ser Val Ala Thr Glu Glu Ser Thr Glu Pro Leu
1760                1765                1770

Ser Glu Asp Asp Phe Glu Met Phe Tyr Glu Val Trp Glu Lys Phe
1775                1780                1785

Asp Pro Asp Ala Thr Gln Phe Ile Glu Phe Ser Lys Leu Ser Asp
1790                1795                1800

Phe Ala Ala Ala Leu Asp Pro Pro Leu Leu Ile Ala Lys Pro Asn
1805                1810                1815

Lys Val Gln Leu Ile Ala Met Asp Leu Pro Met Val Ser Gly Asp
1820                1825                1830

Arg Ile His Cys Leu Asp Ile Leu Phe Ala Phe Thr Lys Arg Val
1835                1840                1845

Leu Gly Glu Ser Gly Glu Met Asp Ser Leu Arg Ser Gln Met Glu
1850                1855                1860

Glu Arg Phe Met Ser Ala Asn Pro Ser Lys Val Ser Tyr Glu Pro
1865                1870                1875

Ile Thr Thr Thr Leu Lys Arg Lys Gln Glu Asp Val Ser Ala Thr
1880                1885                1890

Val Ile Gln Arg Ala Tyr Arg Arg Tyr Arg Leu Arg Gln Asn Val
1895                1900                1905
```

Lys Asn Ile Ser Ser Ile Tyr Ile Lys Asp Gly Asp Arg Asp Asp
    1910                1915                1920

Asp Leu Leu Asn Lys Lys Asp Met Ala Phe Asp Asn Val Asn Glu
    1925                1930                1935

Asn Ser Ser Pro Glu Lys Thr Asp Ala Thr Ser Ser Thr Thr Ser
    1940                1945                1950

Pro Pro Ser Tyr Asp Ser Val Thr Lys Pro Asp Lys Glu Lys Tyr
    1955                1960                1965

Glu Gln Asp Arg Thr Glu Lys Glu Asp Lys Gly Lys Asp Ser Lys
    1970                1975                1980

Glu Ser Lys Lys
    1985

<210> SEQ ID NO 206
<211> LENGTH: 22
<212> TYPE: PRT
<213> ORGANISM: artificial sequence
<220> FEATURE:
<223> OTHER INFORMATION: derived from homosapiens IgG1 hinge

<400> SEQUENCE: 206

Glu Pro Lys Ser Cys Asp Lys Thr His Thr Cys Pro Pro Cys Pro Ala
1               5                   10                  15

Pro Glu Leu Leu Gly Gly
            20

<210> SEQ ID NO 207
<211> LENGTH: 9
<212> TYPE: PRT
<213> ORGANISM: artificial sequence
<220> FEATURE:
<223> OTHER INFORMATION: derived from homo sapiens Nav1.7

<400> SEQUENCE: 207

Cys Phe Arg Asn Ser Leu Glu Asn Asn
1               5

<210> SEQ ID NO 208
<211> LENGTH: 16
<212> TYPE: PRT
<213> ORGANISM: artificial sequence
<220> FEATURE:
<223> OTHER INFORMATION: derived from homo sapiens Nav1.7

<400> SEQUENCE: 208

Cys Ile Asn Thr Thr Asp Gly Ser Arg Phe Pro Ala Ser Gln Val Pro
1               5                   10                  15

<210> SEQ ID NO 209
<211> LENGTH: 8
<212> TYPE: PRT
<213> ORGANISM: artificial sequence
<220> FEATURE:
<223> OTHER INFORMATION: derived from homo sapiens Nav1.7

<400> SEQUENCE: 209

Cys Asn Val Ser Gln Asn Val Arg
1               5

<210> SEQ ID NO 210
<211> LENGTH: 8
<212> TYPE: PRT
<213> ORGANISM: artificial sequence

```
<220> FEATURE:
<223> OTHER INFORMATION: derived from homo sapiens Nav1.7

<400> SEQUENCE: 210

Val Asn Val Asp Lys Gln Pro Cys
1               5

<210> SEQ ID NO 211
<211> LENGTH: 12
<212> TYPE: PRT
<213> ORGANISM: artificial sequence
<220> FEATURE:
<223> OTHER INFORMATION: derived from homo sapiens Nav1.7

<400> SEQUENCE: 211

Glu Lys Glu Gly Gln Ser Gln His Met Thr Glu Cys
1               5                   10

<210> SEQ ID NO 212
<211> LENGTH: 9
<212> TYPE: PRT
<213> ORGANISM: artificial sequence
<220> FEATURE:
<223> OTHER INFORMATION: derived from homo sapiens Nav1.7

<400> SEQUENCE: 212

Cys Lys Lys Glu Asp Gly Ile Asn Asp
1               5

<210> SEQ ID NO 213
<211> LENGTH: 8
<212> TYPE: PRT
<213> ORGANISM: artificial sequence
<220> FEATURE:
<223> OTHER INFORMATION: derived from homo sapiens Nav1.7

<400> SEQUENCE: 213

Cys Asp Pro Lys Lys Val His Pro
1               5

<210> SEQ ID NO 214
<211> LENGTH: 8
<212> TYPE: PRT
<213> ORGANISM: artificial sequence
<220> FEATURE:
<223> OTHER INFORMATION: derived from homo sapiens Nav1.7

<400> SEQUENCE: 214

Cys Phe Ser Thr Asp Ser Gly Gln
1               5

<210> SEQ ID NO 215
<211> LENGTH: 19
<212> TYPE: PRT
<213> ORGANISM: artificial sequence
<220> FEATURE:
<223> OTHER INFORMATION: derived from homo sapiens Nav1.7

<400> SEQUENCE: 215

Cys Thr Leu Glu Ser Ile Met Asn Thr Leu Glu Ser Glu Glu Asp Phe
1               5                   10                  15

Arg Lys Tyr
```

```
<210> SEQ ID NO 216
<211> LENGTH: 9
<212> TYPE: PRT
<213> ORGANISM: artificial sequence
<220> FEATURE:
<223> OTHER INFORMATION: derived from homosapiens Nav1.7

<400> SEQUENCE: 216

Cys Pro Met Thr Glu Glu Phe Lys Asn
1               5

<210> SEQ ID NO 217
<211> LENGTH: 11
<212> TYPE: PRT
<213> ORGANISM: artificial sequence
<220> FEATURE:
<223> OTHER INFORMATION: derived from homo sapiens Nav1.7

<400> SEQUENCE: 217

Cys Thr Leu Pro Arg Trp His Met Asn Asp Asp
1               5                   10

<210> SEQ ID NO 218
<211> LENGTH: 10
<212> TYPE: PRT
<213> ORGANISM: artificial sequence
<220> FEATURE:
<223> OTHER INFORMATION: derived from homo sapiens Nav1.7

<400> SEQUENCE: 218

Cys Ile Glu Arg Lys Lys Thr Ile Lys Ile
1               5                   10

<210> SEQ ID NO 219
<211> LENGTH: 12
<212> TYPE: PRT
<213> ORGANISM: artificial sequence
<220> FEATURE:
<223> OTHER INFORMATION: derived from homo sapiens Nav1.7

<400> SEQUENCE: 219

Cys Glu Lys Glu Gly Gln Ser Gln His Met Thr Glu
1               5                   10

<210> SEQ ID NO 220
<211> LENGTH: 11
<212> TYPE: PRT
<213> ORGANISM: artificial sequence
<220> FEATURE:
<223> OTHER INFORMATION: derived from homo sapiens Nav1.7

<400> SEQUENCE: 220

Asp Asp Cys Thr Leu Pro Arg Trp His Met Asn
1               5                   10

<210> SEQ ID NO 221
<211> LENGTH: 8
<212> TYPE: PRT
<213> ORGANISM: artificial sequence
<220> FEATURE:
<223> OTHER INFORMATION: derived from homo sapiens Nav1.7

<400> SEQUENCE: 221

Cys Phe Ser Thr Asp Ser Gly Gln
1               5
```

```
<210> SEQ ID NO 222
<211> LENGTH: 8
<212> TYPE: PRT
<213> ORGANISM: artificial sequence
<220> FEATURE:
<223> OTHER INFORMATION: derived from homo sapiens Nav1.7

<400> SEQUENCE: 222

Pro Met Thr Glu Glu Phe Lys Asn
1               5

<210> SEQ ID NO 223
<211> LENGTH: 8
<212> TYPE: PRT
<213> ORGANISM: artificial sequence
<220> FEATURE:
<223> OTHER INFORMATION: derived from Mus musculus Nav1.7

<400> SEQUENCE: 223

Pro Met Thr Asp Glu Phe Lys Asn
1               5

<210> SEQ ID NO 224
<211> LENGTH: 12
<212> TYPE: PRT
<213> ORGANISM: artificial sequence
<220> FEATURE:
<223> OTHER INFORMATION: derived from homo sapiens Nav1.1

<400> SEQUENCE: 224

Cys Glu His Tyr Pro Met Thr Asp His Phe Asn Asn
1               5                   10

<210> SEQ ID NO 225
<211> LENGTH: 12
<212> TYPE: PRT
<213> ORGANISM: artificial sequence
<220> FEATURE:
<223> OTHER INFORMATION: derived from homo sapiens Nav1.2 and Nav1.3

<400> SEQUENCE: 225

Cys Glu His Tyr Pro Met Thr Glu Gln Phe Ser Ser
1               5                   10

<210> SEQ ID NO 226
<211> LENGTH: 12
<212> TYPE: PRT
<213> ORGANISM: artificial sequence
<220> FEATURE:
<223> OTHER INFORMATION: derived from homo sapiens Nav1.4

<400> SEQUENCE: 226

Cys Glu His Tyr Pro Met Thr Glu His Phe Asp Asn
1               5                   10

<210> SEQ ID NO 227
<211> LENGTH: 12
<212> TYPE: PRT
<213> ORGANISM: artificial sequence
<220> FEATURE:
<223> OTHER INFORMATION: derived from homo sapiens Nav1.5

<400> SEQUENCE: 227

Cys Glu His Tyr Asn Met Thr Ser Glu Phe Glu Glu
1               5                   10
```

-continued

```
<210> SEQ ID NO 228
<211> LENGTH: 12
<212> TYPE: PRT
<213> ORGANISM: artificial sequence
<220> FEATURE:
<223> OTHER INFORMATION: derived from homo sapiens Nav1.6

<400> SEQUENCE: 228

Cys Glu His His Pro Met Thr Pro Gln Phe Glu His
1               5                   10

<210> SEQ ID NO 229
<211> LENGTH: 12
<212> TYPE: PRT
<213> ORGANISM: artificial sequence
<220> FEATURE:
<223> OTHER INFORMATION: derived from homo sapiens Nav.18

<400> SEQUENCE: 229

Cys Glu His His Gly Met Ser Pro Thr Phe Glu Ala
1               5                   10

<210> SEQ ID NO 230
<211> LENGTH: 12
<212> TYPE: PRT
<213> ORGANISM: artificial sequence
<220> FEATURE:
<223> OTHER INFORMATION: derived from homo sapiens Nav1.9

<400> SEQUENCE: 230

Cys Glu His His Lys Met Glu Ala Ser Phe Glu Lys
1               5                   10
```